United States Patent [19]
Smith et al.

[11] Patent Number: 6,140,100
[45] Date of Patent: *Oct. 31, 2000

[54] CELL-TARGETING MOLECULE COMPRISING A MUTANT HUMAN CARBOXYPEPTIDASE A

[75] Inventors: Gary Keith Smith, Raleigh, N.C.; Todd Andrew Blumenkopf, Old Lyme, Conn.; Michael Cory, Chapel Hill, N.C.

[73] Assignee: Glaxo Wellcome Inc., Research Triangle Park, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/640,906

[22] PCT Filed: Nov. 11, 1994

[86] PCT No.: PCT/GB94/02483

§ 371 Date: May 9, 1996

§ 102(e) Date: May 9, 1996

[87] PCT Pub. No.: WO95/13095

PCT Pub. Date: May 18, 1995

[30] Foreign Application Priority Data

Nov. 12, 1993 [GB] United Kingdom .................. 9323429

[51] Int. Cl.[7] .............................. C12N 9/64; C12N 15/57; C12N 15/62; C12N 15/79

[52] U.S. Cl. ......................... 435/226; 435/69.1; 435/212; 435/252.3; 435/471; 536/23.2; 530/350; 530/391.1; 530/391.7; 424/943; 424/134.1

[58] Field of Search ..................................... 435/183, 212, 435/69.1, 471, 226, 252.3; 424/134.1, 94.3; 530/391.1, 391.7, 350; 536/23.2, 23.4

[56] References Cited

FOREIGN PATENT DOCUMENTS

| 0 382 411 | 8/1990 | European Pat. Off. . |
|---|---|---|
| 0 423 818 | 4/1991 | European Pat. Off. . |
| 0 633 029 | 1/1995 | European Pat. Off. . |
| 88 07378 | 10/1988 | WIPO . |
| 89 10140 | 11/1989 | WIPO . |
| 90 07929 | 7/1990 | WIPO . |
| 93 13806 | 7/1993 | WIPO . |

OTHER PUBLICATIONS

Olesen K. et al., "Altering Substrate Preference of Carboxypeptidase Y by a Novel Strategy of Mutagenesis Eliminating Wild Type Background", *Protein Engineering*, England, GB, 6(4), 409–415 (1993).

Phillips, Margaret A. et al., "Transition State Characterization: A New Approach Combining Inhibitor Analogues and Variation in Enzyme Structure", *Biochemistry*, Easton, PA, US, 31, 959–963, (1992).

Kuefner, Ulrike et al., "Carboxypeptidase–Mediated Release of Methotrezate From Methotrexate Alpha–Peptides", *Biochemistry*, Easton, PA, US, 28, 2288–2297 (1989).

*Primary Examiner*—Ponnathapura Achutamurthy
*Assistant Examiner*—William W. Moore
*Attorney, Agent, or Firm*—Frank P. Grassler; Virginia C. Bennett; Robert T. Hrubiec

[57] ABSTRACT

Conjugates of a cell targetting molecule and a mutant human carboxypeptidase A enzyme are provided. Suitable targetting molecules include antibodies, hormones, ligands, cytokines, antigens, oligonucleotides and peptidomimetics. Enzymes comprising a mutant human carboxypeptidase A enzyme are also provided.

12 Claims, 5 Drawing Sheets

* SITE OF hCPA MUTATIONS

CELL-TARGETING MOLECULE COMPRISING A MUTANT HUMAN CARBOXYPEPTIDASE A

This application is filed pursuant to 35 U.S.C. §371 as a United States National Phase Application of International Application No. PCT/GB94/02483 filed 11 Nov. 11, 1994 which claims priority from GB 9323429.2 filed Nov. 12, 1993.

FIELD OF THE INVENTION

The present invention relates to improvements in targetted enzyme prodrug therapy including antibody-directed enzyme prodrug therapy (ADEPT), it particularly relates to novel enzymes and prodrugs for use in ADEPT.

In the therapy of certain conditions it is preferable that a drug be delivered onto to a particular cellular subpopulation. For example the use of drugs in the treatment of cancer is limited by the inability of the cytotoxic drug to differentiate between cells exhibiting normal cell division and those exhibiting neoplastic division. Hence the therapy is not targeted to a clinically acceptable extent and healthy cells are exposed to cytotoxin. Conjugation of a drug to an antibody, preferably a monoclonal antibody (mAb), allows the targeting of the drug to a particular cellular subpopulation expressing the antigenic determinant to which the targetting antibody binds. However, factors, such as the inability of the conjugate to penetrate the relevant tissue, poor release of the drug from the antigen bound conjugate and the limitation placed on the amount of drug which can be delivered by the number of available antibody-binding sites, have limited the effectiveness of this approach.

BACKGROUND

Avoidance of such limitations led to the concept of targeting conjugates of antibodies and enzymes capable of converting relatively non-cytotoxic 'prodrugs' into low molecular weight cytotoxins at the antibody-binding site. This general concept was disclosed by Rose in European Patent application 84302218.7. Bagshawe and collaborators have referred to the concept as ADEPT, Antibody Directed Enzyme Prodrug Therapy. (Bagshawe K. D. et.al., Br. J. Cancer [1987] 56, 531–532, Bagshawe K. D. et al., Br. J. Cancer [1988] 50, 700–703 and WO 90/10140). In this way one conjugate could generate a proportionately larger amount of drug at the target site by repeated rounds of enzymatic catalysis of prodrug activation.

EP 382 411 describes ADEPT wherein a prodrug may be converted to a cytotoxic agent by enzymes including beta-lactamases isolated from various micro-organisms, L-pyroglutamate aminopeptidase, beta-galactosidase, D-amino acid peptidase, isoenzymes of alkaline phosphatase and various carboxypeptidases.

WO 91/11201 describes ADEPT wherein a prodrug may be enzymatically cleaved to generate cyanide by β-glycosidases or β-glucosidases, generally of plant origin.

EP 302 473 describes ADEPT wherein the enzyme alkaline phosphatase may be used to cleave novel prodrugs of mitomycin, penicillin V amidase may be used to cleave novel prodrugs of adriamycin, or cytosine deaminase may be used with the prodrug 5-fluorocytosine.

EP 484 870 describes ADEPT wherein β-lactamase may be used to activate a cephalosporin prodrug to yield a cytotoxic nitrogen mustard.

WO 88/07378 describes ADEPT wherein benzoic acid nitrogen mustard glutamides may be converted to the nitrogen mustard under the action of carboxypeptidases.

Vitols, K. S., et al, Pteridines 3, [1992], 125–126, discloses a number of MTX-amino acid prodrugs which may be activated by carboxypeptidase-mAb conjugates as part of ADEPT.

WO 91/09134 discloses bispecific hybrid mAbs for use in ADEPT wherein the mAb has specificities against both human cancer cell antigens and a prodrug-activating enzyme.

All previously disclosed methods of ADEPT may be divided into two categories: those which employ human enzymes and those which employ non-human (eg. bacterial) enzymes to activate the relevant prodrug. Both strategies retain inherent problems which limit their potential to provide effective therapy. Use of a human enzyme results in instability of the associated prodrug in vivo, as it may be activated at sites distant to the target site where endogenous human enzymatic activity may occur naturally. Clearly this will also have the highly undesirable effect of generating potentially cytotoxic compounds in non-targetted areas of the body with possibly lethal consequences. The use of a non-human enzyme permits the associated prodrug, which is only activated by the non-human enzymatic activity, to avoid activation by endogenous enzymes and so remain stable in vivo until converted to drug at the target site. However, such a non-human enzyme may elicit an immune response when introduced in vivo and antibodies generated to the enzyme will limit or destroy its ability to activate the prodrug.

WO 90/07929 identifies the desideratum of a non-endogenous catalytic activity being provided by a non-immunogenic enzyme but teaches only that this may be achieved by the use of "genetically conserved" enzymes or those from a "genetically similar species". However it is not taught how this may be accomplished.

It has now been found that the apparent conflict arising from the need to provide a prodrug which is stable in vivo and yet activated by a non-immunogenic enzyme may be resolved by generation of a mutant mammalian enzyme which retains catalytic activity but possesses a novel substrate specificity. The associated prodrug may be activated by the catalytic activity of the mutant enzyme but since the substrate specificity of the mutant enzyme is not a naturally occurring one, the prodrug remains stable in vivo until converted to drug at the target site. The ability to use a non-immunogenic enzyme according to the present invention provides the further advantage that repeated rounds of therapy may be administered. This is in contrast to known processes for ADEPT, in which the initial introduction of the enzyme to the system elicits an immune response which effectively precludes further treatment with the same enzyme as this will be removed from the body by an immune reaction 'primed' during the first round of therapy.

SUMMARY OF THE INVENTION

One aspect of the present invention provides a method of targetting a chemotherapeutic agent to a specific cell-type comprising the administration to a mammal of (i) an effective amount of a conjugate of a cell-type specific targetting molecule with a mutant mammalian enzyme capable of catalysing a functionally inactive precursor of a chemotherapeutic agent to its active form and (ii) an effective amount of the functionally inactive precursor of the chemotherapeutic agent which is refractory to endogenous catalysis to the chemotherapeutic agent.

Endogenous catalysis implies conversion of functionally inactive precursor of a chemotherapeutic agent to that chemotherapeutic agent by enzymes naturally present in vivo. Clearly, conversion occurring at the target site, catalysed by the targetted mutant mammalian enzyme, is not considered to be endogenous catalysis.

A further aspect of the present invention provides a method of treatment of a mammal requiring therapy for any of the conditions hereinafter described comprising the administration to the mammal of an effective amount of a cell-type specific targetting molecule conjugated with a mutant mammalian enzyme which is capable of catalysing a functionally inactive precursor of a drug to its active form in combination with an effective amount of a functionally inactive precursor of the drug which is refractory to endogenous catalysis.

DETAILED DESCRIPTION

Figure 1:
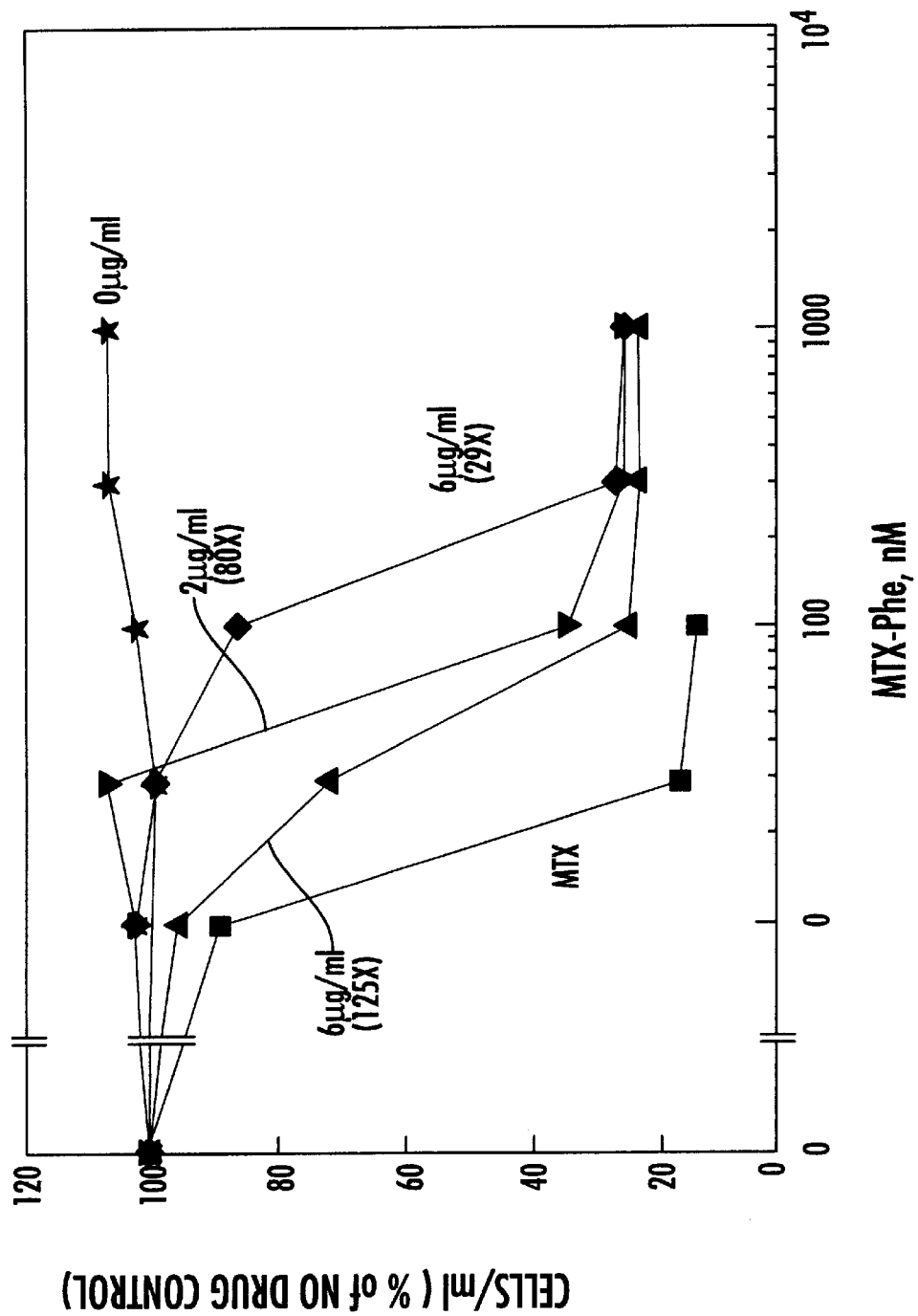
FIG. 1 graphs the inhibition of growth of Wein-133 B-cell lymphoma cells after incubation with a monoclonal antibody conjugate of wild-type human carboxypeptidase A, followed by incubation with varying concentrations of the prodrug MTX-phe.

A mutant human enzyme as used herein shall be taken to be any human enzyme with a sequence differing by at least one amino acid from the amino acid sequence or sequences of that enzyme in the patient to which the therapy is applied.

As used herein the term "cell-type" means any localised or dispersed population of cells possessing a common determinant essentially selective for a pathological state, for example, cancer cells expressing carcinoembryonic antigen, Tag-72, mucin, or the antigens recognised by the antibodies Ing-1, 17-1A, 323/A3, NR-LU-10, c174, PR.1A3, MOV18, G250, U36, E48, NR-CO-02 or any of the other antigens shown in Table 3.

The cell-type specific targetting molecule may be any molecule capable of being noncovalently or covalently linked or conjugated with the mutant enzyme and which can demonstrate a selectivity in its binding affinity for cell-surface markers. Such molecules include polyclonal and monoclonal antibodies, including bispecific antibodies in which one antibody arm noncovalently binds the mutant enzyme and the other performs the cell-type specific targetting (U. Sahin, et al, Cancer Research 50, 6944, 1990).

Alternative targetting molecules which may be linked to mutant mammalian enzymes to form conjugates include hormones, ligands, cytokines, antigens, oligonucleotides and peptidomimetics.

The choice of targetting molecule will depend upon the nature of the cells to be targetted but will most probably be an antibody and preferably a monoclonal antibody as mAbs produce the greatest selectivity.

A "chemotherapeutic agent" which may also be referred to herein as a "drug" includes any molecule which has activity in human therapy. Such chemotherapeutic agents include but are not limited to cytostatic or cytotoxic compounds used in the therapy of cancers or viral infections. A "functionally inactive precursor" which may also be referred to herein as a "prodrug" includes any compound which may be converted into a chemotherapeutic agent under the action of an enzyme. Such functionally inactive precursors may typically be converted to a chemotherapeutic agent by the enzymatic cleavage of the functionally inactive precursor to yield a chemotherapeutic agent and a "prodrug moiety". Such conversion from functionally inactive precursor to chemotherapeutic agent may also occur by enzymatically mediated isomerisation.

A functionally inactive precursor will generally not exhibit clinically significant levels of the therapeutic activity possessed by the chemotherapeutic agent into which it may be enzymatically converted having been chemically derivitized to decrease its normal pharmacological activity. The functionally inactive precursor of a cytotoxic chemotherapeutic agent will not itself exhibit clinically significant cytotoxicity and will be sufficiently stable in vivo such that during therapy, clinically significant level of cytotoxicity are largely only generated at the site of conversion of functionally inactive precursor to chemotherapeutic agent i.e. at the site to which the mutant enzyme has been targetted.

The mutant mammalian enzyme is preferably a wild-type mammalian enzyme with one or more mutations which generate novel substrate specificities without engendering a significant immunological response when administered during human therapy. A significant immunological response may be regarded as one which would preclude the clinical use of such an enzyme in human therapy.

The essential characteristic of a mutant mammalian enzyme of the present invention is the presence of a mutant substrate-binding site irrespective of the amino acid sequences flanking this mutant substrate-binding site. Hence a chimaeric enzyme comprising a mutant substrate-binding site and flanking sequences derived from one or more different enzymes is included with the definitions of a mutant mammalian enzyme of the present invention. Such a chimaeric enzyme may be generated by recombinant DNA technology and/or protein engineering.

Enzymes suitable for directed mutagenesis include any enzymes possessing a catalytic activity capable of converting a prodrug to a drug. Such catalytic activities include transferase, hydrolase, oxido-reductase, isomerase, lyase, or ligase. The directed mutagenesis will generate a novel substrate specificity but preserve the class of catalytic activity involved. For example a mutant isomerase of the present invention will possess a novel isomerase activity sufficiently different from the isomerase from which it was derived to ensure that prodrugs susceptible to activation by the mutant isomerase remain substantially stable in the presence of the isomerase from which the mutant enzyme was derived. As will be shown this dramatic shift in activity may be achieved by the alteration of as little as one residue at the catalytic site. The alteration of the minimum number of residues necessary to obtain the required shift in activity ensures continuity of enzyme structure and hence avoids negative immunological effects when the mutant enzyme is introduced to the body.

A preferred mutant enzyme of the present invention is mutant mammalian carboxypeptidase A (CPA). This enzyme has the general activity of cleaving carboxy-terminal aromatic and aliphatic amino acid residues and has been characterised in a diversity of species and tissue-specific variants. Particularly preferred mutant carboxypeptidases include mutants derived from human pancreatic carboxypeptidase A1 (Catasus L. et al., Biochem. J. 287, 299–303, 1992), human mast cell carboxypeptidase A (Reynolds D. S. et al. J. Clin. Invest. 89 273–282, 1992) and human pancreatic carboxypeptidase A2 (FIG. 9 hereinafter). It will be appreciated that the common characteristic of these carboxypeptidases is the presence of a CPA-like substrate-binding pocket and associated enzymatic activity irrespective of overall sequence or structure of the enzyme and that any enzyme possessing this CPA-like substrate-binding pocket is amenable to mutation to a mutant carboxypeptidase of the present invention.

In a particularly preferred embodiment of the present invention the mutant enzyme is mutant human pancreatic carboxypeptidase A1 or A2 (CPA1 or CPA2) and yet more preferably, CPA1 or CPA2 wherein amino acid substitutions are generated at one or more of residues 203, 210, 242, 244, 250, 253, 255, 267, 268, 269 and 305, of the amino acid sequences shown in Table 4 which represent the wild-type (w.t.) sequences of CPA1 and CPA2 respectively. Particularly preferred combinations of residue substitution include Gly at residues 250 and 268 when 253 and 255 are w.t.; Gly at 253 and 268 when 250 and 255 are w.t.; Gly at 250 and His at 268 when 253 and 255 are w.t.; Gly at 250 when 253, 255 and 268 are w.t.; Ala at 255 and His at 268 when 250 and 253 are w.t. and His at 268 when 250, 253 and 255 are w.t. The most preferred mutants are carboxypeptidase A1 or A2 mutants comprising a single substitution; Gly at 268.

The most preferred conjugate of the present invention comprises all or part of either of mAbs CAMPATH-1H®, 323/A3 or ING-1 and at least the substrate-binding domain of either of mutant mammalian enzymes CPA1 or CPA2 having glycine present at amino acid position 268 as described in Table 5.

Figure 2:
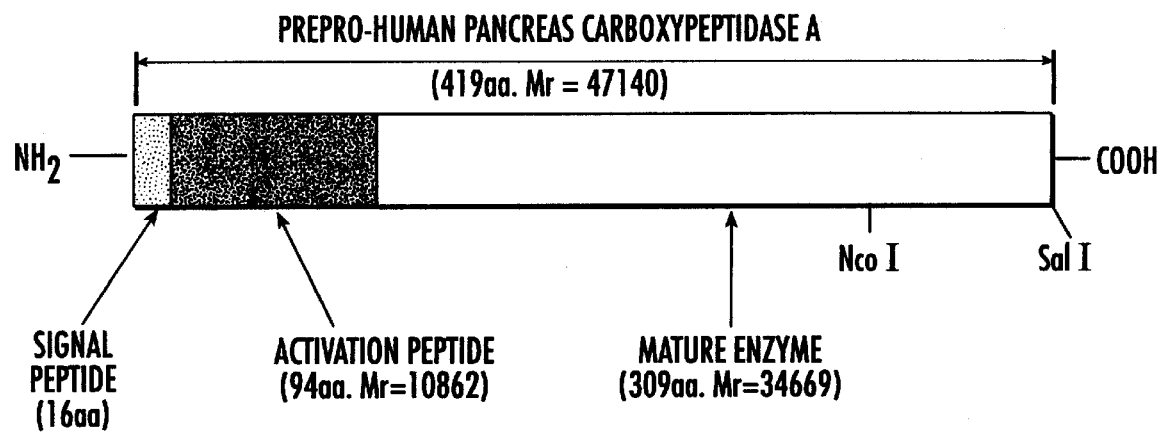
FIG. 2 diagrams the human pancreatic carboxypeptidase A preproenzyme, containing a signal peptide, activation peptide, and mature enzyme.

Human pancreatic carboxypeptidase A is expressed as a preproenzyme (FIG. 2) which is processed to a proenzyme and subsequently to the mature enzyme. Mutant carboxypeptidases of the present invention may be mutants of the preproenzyme, the proenzyme or of the mature enzyme but are preferably mutants of the mature enzyme. These mutants may be derived from either preproenzyme, the proenzyme or the mature enzyme but are preferably derived from the proenzyme. The mutated proenzyme (or preproenzyme) may then be converted to the corresponding mutant mature enzyme by standard methods such as trypsinisation.

A mutant enzyme of the present invention may be generated from the DNA or RNA source of any enzyme possessing the previously discussed activities by methods well known in the art of molecular biology and more particularly by the methods described hereinafter in the Examples.

The selection of the enzymatic activity and the primary sequence of a mutant enzyme of the present invention will clearly depend upon the nature of the relevant prodrug and, if a prodrug of the type which is activated by the removal of a prodrug moiety, on the precise structure of that moiety.

The substrate-binding or active site of the mutant enzyme must, unlike the corresponding non-mutant enzyme, be capable of interacting with the prodrug in such a way that enzymatic catalysis is facilitated. The ability of the mutant enzyme to perform this activity will depend upon subtle alterations in the 3-dimensional structure of the active site, which is in turn dependent upon the primary amino acid sequence of this region of the protein. Alterations of the primary sequence of an enzyme by standard techniques of protein engineering will allow the generation of an appropriate mutant enzyme for use according to the invention with a corresponding prodrug.

Novel prodrugs comprise those of formula (II)

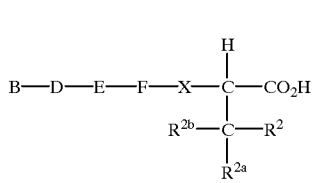

(II)

wherein,

X represents NH or O and $R^2$ represents $CO_2H$, $SO_3H$, $SO_2H$, $OSO_3H$, $PO_3H_2$, $OPO_3H_2$, $C_{1-6}$ alkyl esterified $CO_2H$, $C_{1-6}$ esterified $PO_3H_2$, $C_{4-12}$ alkyl, $C_{4-12}$ alkenyl, $C_{4-12}$ alkynyl, $C_{4-12}$ branched alkyl, $C_{1-8}$ alkyl or $C_{3-8}$ branched alkyl; substituted with $CO_2H$, $SO_3H$, $SO_2H$, $OSO_3H$, $PO_3H_2$, $OPO_3H_2$, $C_{1-6}$ alkyl esterified $CO_2H$, $C_{1-6}$ alkyl esterified $PO_3H_2$, hydroxyl, alkoxy, halo, haloalkyl, cyano or carboxamide; $C_{3-8}$ cycloalkyl, aryl or heteroaryl optionally substituted with $C_{1-8}$ alkyl, $C_{3-8}$ branched alkyl, $C_{3-8}$ cycloalkyl, $C_{3-6}$ alkenyl, $C_{2-6}$ alkynyl, $C_{4-6}$ cycloalkenyl, trisubstituted-silyl i.e. $(R^{13})(R^{14})(R^{15})Si$, where $R^{13}$, $R^{14}$, and $R^{15}$ are $C_{1-6}$ alkyl, $C_{3-6}$ branched alkyl, $C_{3-6}$ cycloalkyl, $C_{3-6}$ alkenyl, $C_{2-6}$ alkynyl, $C_{4-6}$ cycloalkenyl, aryl, or heteroaryl, and where $R^{13}$, $R^{14}$, and $R^{15}$ are each the same group or different groups (e.g. trimethylsilyl, tert-butyldimethylsilyl, cyclohexyldimethylsilyl, or phenyldimethylsilyl), aryl, $CO_2H$, $SO_3H$, $SO_2H$, $OSO_3H$, $PO_3H_2$, $OPO_3H_2$, $C_{1-6}$ alkyl esterified $CO_2H$, $C_{1-6}$ alkyl esterified $PO_3H_2$, carboxamide, hydroxyl, $C_{1-6}$ alkoxy, $C_{1-6}$ alkythio, mercapto, halo, haloalkyl, nitro or cyano, $R^{2a}$ and $R^{2b}$ represent H, hydroxy, mercapto, alkoxy, alkylthio, halo, cyano, $CO_2H$, $SO_3H$, $SO_2H$, $OSO_3H$, $PO_3H_2$, $OPO_3H_2$, $C_{1-6}$ alkyl esterified $CO_2H$, carboxamide, $C_{1-6}$ alkyl esterified $PO_3H_2$, cyclic $C_{2-6}$ [i.e., $R^{2a}$ and $R^{2b}$ together represent $(CH_2)_{2-6}$], trisubstituted-silyl i.e. $(R^{13})(R^{14})(R^{15})Si$, where $R^{13}$, $R^{14}$, and $R^{15}$ are $C_{1-6}$ alkyl, $C_{3-6}$ branched alkyl, $C_{3-6}$ cycloalkyl $C_{3-6}$ alkenyl, $C_{2-6}$ alkynyl, $C_{4-6}$ cycloalkenyl, aryl, or heteroaryl and where $R^{13}$, $R^{14}$, and $R^{15}$ could be the same group or different groups, e.g. trimethylsilyl, tert-butyldimethylsilyl, cyclohexyldimethylsilyl, or phenyldimethylsilyl; or $C_{1-6}$ alkyl or $C_{1-6}$ branched alkyl or $C_{1-6}$ cycloalkyl or aryl or heteroaryl optionally substituted with hydroxy, mercapto, $C_{1-C}$ alkoxy, $C_{1-6}$ alkylthio, halo, cyano, $CO_2H$, $SO_3H$, $SO_2H$, $OSO_3H$, nitro, $PO_3H_2$, $OPO_3H_2$, $C_{1-6}$ alkyl esterified $CO_2H$, carboxamide, $C_{1-6}$ alkyl esterified $PO_3H_2$, $C_{1-6}$ alkyl, $C_{1-6}$ branched alkyl, $C_{1-6}$ cycloalkyl, trisubstituted-silyl i.e. $(R^{13})(R^{14})(R^{15})Si$, where $R^{13}$, $R^{14}$, and $R^{15}$ are $C_{1-6}$ alkyl, $C_{3-6}$ branched alkyl, $C_{3-6}$ cycloalkyl, aryl, or heteroaryl, and where $R^{13}$, $R^{14}$, and $R^{15}$ could be the same group or different groups, e.g. trimethylsilyl, tertbutyldimethylsilyl or phenyldimethylsilyl; with the proviso that $R^{2a}$ and $R^{2b}$ are not both hydroxy or mercapto.

F comprises a moiety of formula (IV)

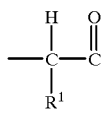

(IV)

wherein $R^1$ represents a group corresponding to the side chain of any α-amino acid for example, H, $C_{1-6}$ alkyl, $C_{1-6}$ alkenyl, $C_{1-6}$ alkynyl optionally substituted with $CO_2H$, $C_{1-6}$ alkyl esterified $CO_2H$, $OPO_3$, $PO_3H_2$, $C_{1-6}$ alkyl esterified $PO_3H_2$, halo, hydroxy, carboxamide, amino optionally substituted with $C_{1-6}$ alkyl, cyano or nitro, E represents

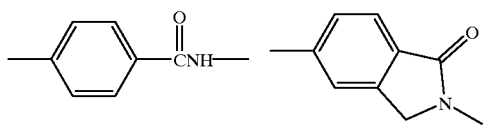

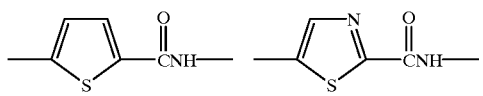

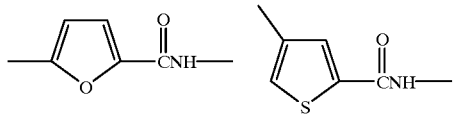

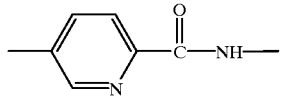

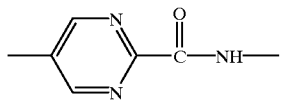

 where n = 3–6 or

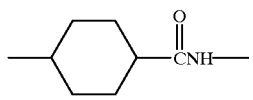

each of which may be optionally substituted with one or more of hydroxy, one or more of alkoxy, halo, or $C_{1-6}$ alkyl optionally substituted with one or more of hydroxy, $C_{1-6}$ alkoxy or halo.

D represents —$CH_2$—$CH(R^3)$—, —$CH_2$—$NR^3$—, —$NR^3$—$CH_2$—, —$CH_2S$— or —$CH_2O$— where $R^3$ is H, $C_{1-6}$ alkyl, allyl or propargyl, optionally substituted with one or more of $C_{1-6}$ alkoxy halo, hydroxy or cyano; and B represents

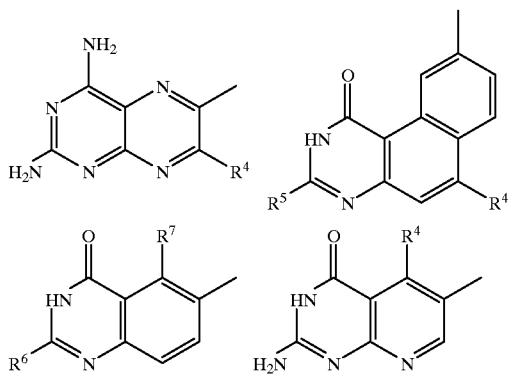

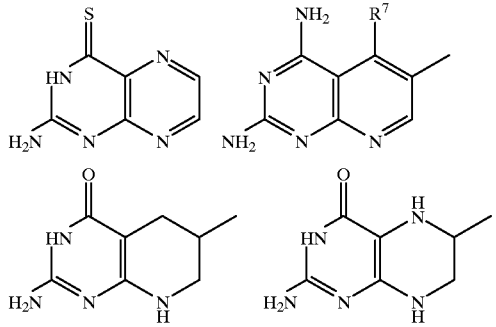

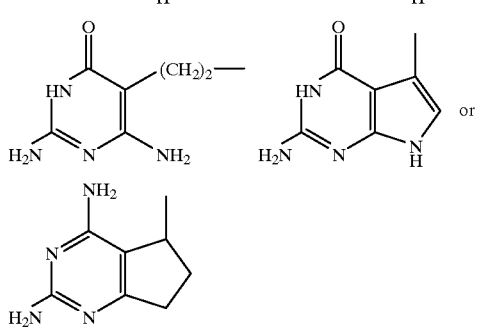

wherein, $R^4$ represents H, $C_{3-6}$ branched alkyl, $C_{3-6}$ cycloalkyl, or $C_{1-6}$ alkyl;

$R^5$ represents $C_{1-6}$ alkyl, $C_{3-6}$ branched alkyl, $C_{3-6}$ cycloalkyl, amino (optionally substituted with $C_{1-6}$ alkyl, $C_{1-6}$ alkanoyl or benzyl);

$R^6$ represents H, $C_{1-6}$ alkyl, $C_{3-6}$ branched alkyl, $C_{3-6}$ cycloalkyl, amino (optionally substituted with $C_{1-6}$ alkyl, $C_{1-6}$ alkanoyl or benzyl), $C_{1-6}$ alkoxyl or $C_{1-6}$ alkylthio; and $R^7$ represents H, $C_{1-6}$ alkyl, $C_{3-6}$ branched alkyl, $C_{3-6}$ cycloalkyl, halo $C_{1-6}$ alkyl or halo and salts N-oxides, solvates and physiologically functional derivatives thereof; with the proviso that the following compounds are not included within the definition of novel prodrugs although the use of these compounds in therapy does form one embodiment of the present invention;

N-(N-(4-(((2-amino-3,4-dihydro-4-oxo-6-quinazolinyl) methyl)(2-propynyl)amino)benzoyl)-L-glutam-1-yl)-L-glutamic acid, N-(4-(((2,4-diamino-6-pteridinyl)methyl)methylamino) benzoyl)-L-glutam-1-yl-L-glutamic acid, N-(4-(((2,4-diamino-6-pteridinyl)methyl)methylamino) benzoyl)-L-glutam-1-yl-L-aspartic acid, N-(4-(((2,4-diamino-6-pteridinyl)methyl)methylamino) benzoyl)-L-glutam-1-yl-L-phenylalanine, 4-bis(2-chloroethyl)amino)-phenylalanylphenylalanine and 4-bis(2-chloroethyl)amino)-phenylalanyl-3,5-dimethyl-4-methoxyphenylalanine In a preferred embodiment of prodrugs according to the present invention, X is NH;

$R^2$ is $C_{3-8}$ cycloalkyl or aryl substituted with $C_{1-8}$ alkyl, $C_{3-8}$ cycloalkyl, $C_{3-9}$ branched alkyl or trisubstituted-silyl i.e. $(R^{13})(R^{14})(R^{15})Si$, where $R^{13}$, $R^{14}$, and $R^{15}$ are $C_{1-6}$ alkyl, $C_{3-6}$ branched alkyl, $C_{3-6}$ cycloalkyl, aryl, or heteroaryl, and where $R^{13}$, $R^{14}$, and $R^{15}$ are each the same group or different groups (e.g. trimethylsilyl, tertbutyldimethylsilyl, cyclohexyldimethylsilyl, or phenyldimethylsilyl);

$R^{2a}$ and $R^{2b}$ are both H;

$R^1$ is H, $C_{1-6}$ alkyl, $CH_2CO_2H$, $CH_2CH_2CO_2H$ or $CH_2$, $CH_2CH_2NH_2$, E is

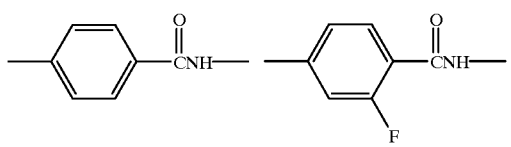

or

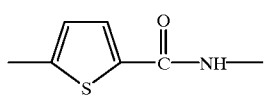

D is $-CH_2NH-$, $-CH_2N(CH_3)-$, $-CH_2N(CH_2C\equiv CH)-$, $-CH_2CH_2-$ or $-CH_2-CH(C_2H_5)-$ and B is

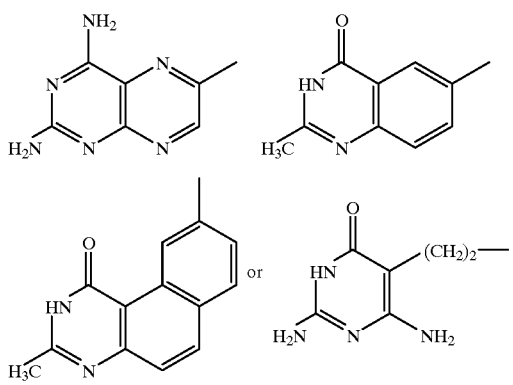

and salts, N-oxides, solvates and physiologically functional derivatives thereof.

In the most preferred embodiment of prodrugs according to the present invention, X is NH;

$R^2$ is phenyl or para-hydroxyphenyl substituted with cyclopentyl, cyclobutyl or tert-butyl. The cyclopentyl, cyclobutyl and tert-butyl groups may both be either ortho- or meta- but are preferably meta-, $R^{2a}$ and $R^{2b}$ are H, $R^1$ is $CH_2CH_2CO_2H$ E is

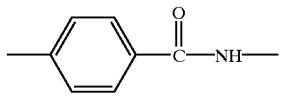

and B is

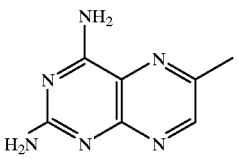

and salts, N-oxides, solvates and physiologically functional derivatives thereof.

Where chiral centres of prodrugs as defined above are present they may, independently, each be either in the S or R configuration or may be a mixture of the S and R configuration. Preferably they are in the S-configuration for 'F' and the chiral carbon of formula (II) adjacent to X.

A preferable prodrug for use according to the present invention is a prodrug of the cytotoxic agent melphalan (UK 750, 155) which is commercially available under the name Alkeran (T. M. The Wellcome Foundation Limited) and has the chemical name 4-[bis(2-chloroethyl)amino]-1-phenylalanine. Prodrugs of melphalan according to the present invention have the general formula

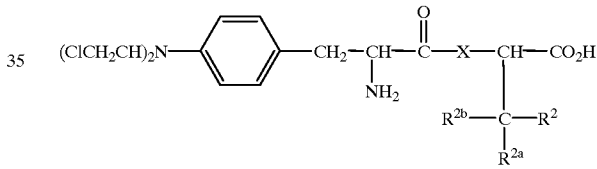

wherein $R^2$, $R^{2a}$, $R^{2b}$ and X are as herein defined.

The following are particularly preferred novel prodrugs according to the present invention:

N-((S)-4-carboxy-2-(5-(((1,2-dihydro-3-methyl-1-oxobenzo(F)quinazolin-9-yl)methyl)amino)-1-oxo-2-isoindolinyl)butanoyl)-L-phenylalanine, N-(4-(((2,4-diamino-6-pteridinyl)methyl)methylamino)benzoyl)-L-glutam-1-yl-2-cyclopentyl-L-phenylalanine, N-(4-(((2,4-diamino-6-pteridinyl)methyl)methylamino)benzoyl)-L-glutam-1-yl-3-cyclopentyl-L-phenylalanine, N-(4-(((2,4-diamino-6-pteridinyl)methyl)methylamino)benzoyl)-L-glutam-1-yl-3-cyclobutyl-L-phenylalanine, N-(4-(((2,4-diamino-6-pteridinyl)methyl)methylamino)benzoyl)-L-glutam-1-yl-3-trimethylsilyl-L-phenylalanine, N-(4-(((2,4-diamino-6-pteridinyl)methyl)methylamino)benzoyl)-L-glutam-1-yl-3-tert-butyl-L-phenylalanine, N-(4-((3-(2,4-diamino-1,6-dihydro-6-oxo-5-pyrimidinyl)propyl)amino)benzoyl)-L-glutam-1-yl-3-cyclopentyl-L-phenylalanine, N-(4-(((1,2-dihydro-3-methyl-1-oxobenzo(F)quinazolin-9-yl)methyl)amino)-2-fluorobenzoyl)-L-glutam-1-yl-3-cyclopentyl-L-phenylalanine, N-(4-(((2,4-diamino-6-pteridinyl-methyl)methylamino)
benzoyl)-L-glutam-1-yl-3-cyclopentyl-L-tyrosine, N-(4-(((2,4-diamino-6-pteridinyl)methyl)methylamino)
benzoyl)-L-glutam-1-yl-3,5-diiodo-L-tyrosine, N-(4-(((2,4-diamino-6-pteridinyl)methyl)methylamino)
benzoyl)-L-glutam-1-yl-2-cyclopentyl-L-tyrosine, (S)-3-(3-cyclopentyl-4-hydroxyphenyl)-2-((N-(4-(((2,4-
diamino-6-pteridinyl)methyl)methylamino)benzoyl)-
L-glutam-1-yl)oxy)propionic acid, N-(4-(((2,4-diamino-6-pteridinyl)methyl)methylamino)
benzoyl)-L-glutam-1-yl-3-tert-butyl-L-tyrosine and salts, N-oxides, solvates and physiologically functional derivatives thereof.

The most preferred prodrug according to the present invention is:

N-(4-(((2,4-diamino-6-pteridinyl)methyl)methylamino)
benzoyl)-L-glutam-1-yl-3-cyclopentyl-L-tyrosine.

Any chiral centers of any of the chemical structures on compounds described herein can be in the R and S configuration. Although these chiral centers of the chemical structures drawn hereinafter which are depicted in the preferred S-configuration, it is understood that the corresponding chemical structures having the chiral centers in the R-configuration as well as enantiomeric and diastereomeric mixtures of these compounds are also considered as being party of the invention.

A prodrug of formula (V), where B, D and E are as defined in formula (III), and X, $R^1$ and $R^2$ are as defined in formulas (IV) and (II),

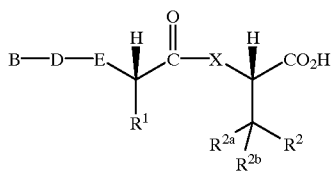

(V)

can be prepared by hydrolysis of an ester of formula (VI); where $R^8$ is alkyl, branched alkyl, or cycloalkyl group such as methyl, ethyl, tert-butyl or cyclohexyl; or an aryl group such as phenyl, 2,6-dimethylphenyl; benzyl (optionally substituted with halo, alkoxy, or alkyl groups such as methyl or tert-butyl); or 9-fluorenylmethyl (Fm); normally in the presence of a base, such as NaOH, LiOH; or, in the case where $R^8$ is Fm, diethylamine or piperidine; or in the presence of an acid such as HCl or trifluoroacetic acid; in a solvent or solvent mixture such as THF, nitromethane or THF:$H_2O$; at a temperature, for example 0° C. to reflux temperature, conveniently at room temperature; or in the present of an acid, such as HCl or trifluoroacetic acid;

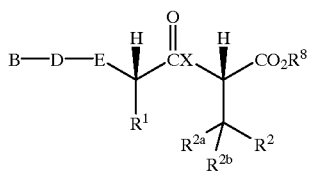

(VI)

in a solvent such as THF or nitromethane; at a temperature, for example 0° C. to reflux temperature, conveniently at room temperature; or by hydrogenolysis where $R^8$ is 9-fluorenylmethyl (Fm) or benzyl optionally substituted with alkyl groups such as methyl or tert-butyl using hydrogen at ambient or elevated pressure, for example between 1·75 kgcm$^{-2}$ and 7·0 kgcm$^{-2}$, conveniently at 3·5 kgcm$^{-2}$, in the presence of a catalyst such as palladium-on-carbon, in a polar solvent, for example methanol or ethanol, or a mixture of methanol and dichloromethane, at ambient temperature, or by methods which are known to anyone skilled in the art such as those methods described in Rylander, P. N., *Catalytic Hydrogenation in Organic Syntheses,* Academic Press: New York 1979, or in Rylander, P. N., *Hydrogenation Methods,* Academic Press: London, 1985, or in Bodanszky, M., et al., *The Practice of Peptide Synthesis,* Springer-Verlag: Berlin, 1984, which are incorporated herein by reference; or by oxidation where $R^8$ is phenyl or benzyl substituted with alkoxy (preferably in the 2-, 4-, or 6- position of the phenyl ring) optionally substituted with suitable alkyl groups such as methyl or tert-butyl, in the presence of a suitable oxidizing agent such as ceric ammonium nitrate or dichlorodicyanoquinone (DDQ) in a suitable solvent such as methanol, water, dichloromethane, or combinations thereof, by methods which are known to anyone skilled in the art such as those methods described in Heathcock, C. H., et.al., *Tetrahedron,* 1981, 37, 4087; or those methods described in Greene, T. W., et.al., *Protective Groups in Organic Synthesis, second edition,* John Wiley & Sons: New York, 1991, which are incorporated herein by reference; or where $R^8$ is 2-(trimethylsilyl)ethyl by reaction with a source of a suitable nucleophile such as potassium fluoride or tetrabutylammonium fluoride for which methods are known to anyone skilled in the art such as those methods described in Greene, T. W., et al., *Protective Groups in Organic Synthesis, second edition,* John Wiley & Sons: New York, 1991, or in Bodanszky, M., et.al., *the Practice of Peptide Synthesis,* Springer-Verlag: Berlin, 1984, or in Jones, J., *The Chemical Synthesis of Peptides,* Clarendon Press: Oxford, England, 1991, which are incorporated herein by reference; or where $R^8$ is a photoremovable group such as orthonitrophenyl by photolytic methods which are known to anyone skilled in the art such as those described in Cama, L. D., et.al., *J. Am. Chem. Soc.,* 1978, 100, 8006, or in Pillai, V. N. R., *Synthesis,* 1980, 1, or in Pillai, V. N. R., *Org. Photochem.,* 1987, 9, 225 which are incorporated herein by reference. Esters present on sidechains $R^1$ or $R^2$ may or may not be hydrolyzed in the same reaction utilised to hydrolyze $R^8$, depending on the choice of ester group and the reaction conditions.

Ester (VI) can be prepared by reaction of an amine of formula (VII) where $R^1$ is defined as in formula (IV), $R^2$ and X are defined as in formula (II), and $R^8$ is defined as in formula (VI); a carboxylic acid of formula (VIII),

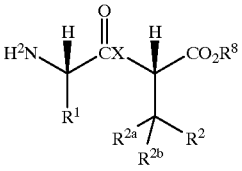

(VII)

B—D—G—CO$_2$H (VIII)

where B and D are as defined in hereinbefore and G represents a group (IX),

 (IX)

 (X)

where n=3–7, or 1,4-cyclohexyl(X) where the 1- and 4-substituents may either in the cis- or trans- configuration or mixtures of the two configurations, or an aromatic group chosen from the following:

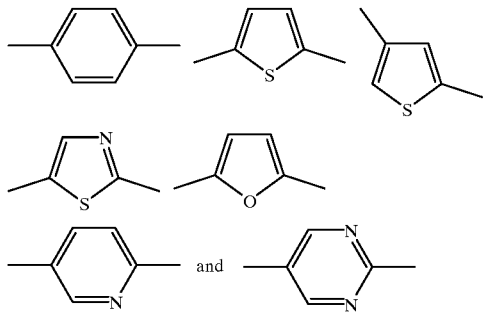

The reaction of amines of formula (VII) with carboxylic acids of formula (VIII) are carried out in the presence of a coupling agent; including but not limited to diethyl cyanophosphate (XI), 1-ethyl-3-(dimethylaminopropyl) carbodiimide (XII), or dicyclohexylcarbodiimide (XIIa), optionally in the presence of an activating group such as 1-hydroxybenzotriazole (HOBT), in a polar, aprotic solvent, conveniently N,N-dimethylformamide (DMF) or N,N-dimethylpropyleneurea (DMPU) at a temperature, for example 0° C. or 80° C.,

 (XI)

 (XII)

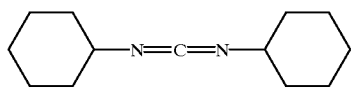 (XIIa)

conveniently at room temperature. Alternatively, an ester of formula (VI) can be prepared by treating a mixture of carboxylic acid (VIII) and a tertiary amine base; such as triethylamine, diisopropylethylamine, or N-methylmorpholine; in an aprotic solvent, such as DMF or DMPU; at a temperature from 0° C. to 25° C.; with a acylating agent, such as isobutyl chloroformate or ethyl chloroformate; followed by addition of amine (VII).

Several of the preferred carboxylic acids (VIII) can be purchased from commercial suppliers, eg. (XIII) can be purchased from Aldrich Chemical Co; or can be prepared via literature methods, eg. (XIV): De Graw, J I, et al, *J. Med Chem*, 1982, 25, 1227; Ibid, 1986, 29, 1056. (XV): Jones, T R, et al,: *J. Med Chem*, 1986, 29, 1114; Nair, M G, et al,: Ibid, 1986, 29, 1754; Ghazola, M, et al,: Ibid, 1986, 29, 1263; Acharya S. P. et.al., *J. Heterocyclic Chem*, 1975, 12, 1283. (XVI): Barnett, C J, et al, *Tetrahedron Lett*, 1989, 30, 6291. (XVII): Styles V L, et al,: *J. Med Chem*, 1990, 33, 561 Taylor, E.c., et al. *J. Med. Chem.* 1992, 32 1517: (XVIIa) and Bisset, G. M. F. et al *J. Med. Chem*, 1992 35 859;

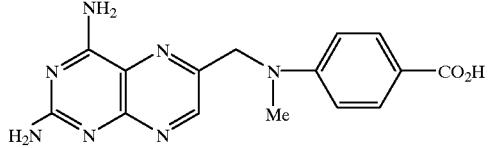 (XIII)

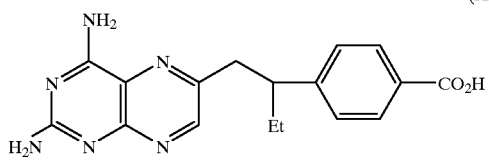 (XIV)

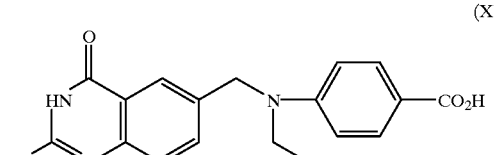 (XV)

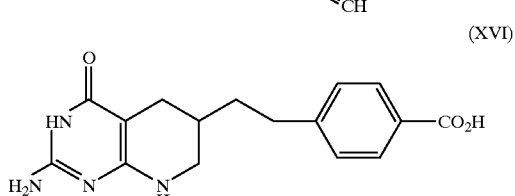 (XVI)

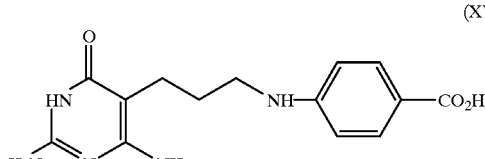 (XVII)

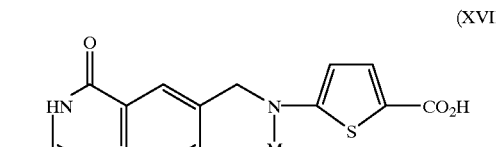 (XVIIa)

Carboxylic acids of formula (VIII) can be prepared by hydrolysis of esters of formula (XVIII), wherein B and D are as defined in formula (III), G is as defined in formula (VIII) and $R^9$ is a suitable group such as methyl, ethyl, or tert-butyl; normally in the presence of a suitable base, such as NaOH or LiOH; or a suitable acid, such as HCl or trifluoroacetic acid; in a suitable solvent or solvent mixture, such as THF, nitromethane, or THF:$H_2O$; at a temperature, for example from 0° C. to reflux temperature, conveniently at room temperature.

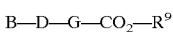 (XVIII)

For prodrugs where D in formula (III) or formula (XVIII) represents —$CH_2$—$NR^3$—, esters of formula (XVIII) can be prepared by:

(a) reaction of a compound of formula (XIX), where G is as defined in formula (VIII), $R^9$ is as defined in formula (XVIII), and $R^{10}$ represents $$R^{10}-G-CO_2R^9 \quad (XIX)$$

$NHR^3$ wherein $R^3$ is as defined in formula (III); and a compound of formula (XX)

$$K-R^{11} \quad (XX)$$

wherein $R^{11}$ is an aldehyde group or cyano group and K is a heterocyclic group such as those defined as B in formula (III) or a group such as (XXI) where Z=O, or a group such as defined as B in formula (III) or a group such as (XXI) where Z=O substituted with a suitable protecting group to provide a more suitable reactant, suitable groups including but not limited to N-pivaloyl, N-benzoyl, N-carbobenzyloxy (N-cbz), or N-tert-butoxycarbonyl (N-T-BOC). Such protecting groups can be removed at a later stage in the synthesis, where appropriate, using standard methods known to anyone skilled in the art such as those methods described in Green, T. W., et al., *Protective Groups in Organic Synthesis*, second edition, John Wiley & Sons: New York, 1991, which are incorporated herein by reference.

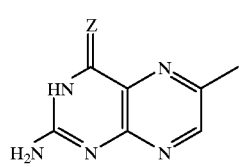

(XXI)

Esters of formula (XVIII) are prepared by reaction of (XVI) and (XX) in a solvent such as THF, DMPU, DMF, ethanol, or acetic acid at a temperature between 25° C. and 100° C., optionally with removal of water during the course of the reaction, followed by reduction with sodium cyanoborohydride or hydrogen gas in the presence of a suitable catalyst, such as Raney nickel, using standard reaction conditions known to anyone skilled in the art.

(b) reaction of a compound of formula (XIX), as defined in (a), with a compound of formula (XX), where K is as defined in (a) but $R^{11}$ is defined as $CH_2Y$, where Y is defined as a leaving group such as chloro, bromo, iodo, mesyl, or tosyl, in a suitable solvent such as THF, in the presence of a base such as $NaHCO_3$, $Na_2CO_3$, $K_2CO_3$, triethylamine, or diisopropylethylamine, at an elevated temperature, for example 50° C. to 150° C. and conveniently 80° C. to 120° C.

For prodrugs where D in formula (III) and formula (XVIII) represents $-NR^3-CH_2-$, esters of formula (XVIII) can be prepared by reaction of a compound of formula (XIX) where $R^{10}$ represents an aldehyde group and G is as defined in formula (VIII), and a compound of formula (XX), where K is as defined in formula (XX) and $R^{11}$ is defined as $HNR^3$ where $R^3$ is as defined in formula (III), in a solvent such as THF, DMF, DMPU, or acetic acid at a temperature between 25° C. and 100° C., optionally with removal of water during the course of the reaction, followed by reduction with sodium cyanoborohydride or hydrogen gas in the presence of a suitable catalyst, such as Raney nickel.

For prodrugs where D in formula (III) and formula (XVIII) represents $-CH_2O-$ or $-CH_2S-$ esters of formula (XVIII) are prepared by reaction of a compound of formula (XIX), where $R^9$ is as defined in formula (XVIII), G is as defined in formula (VIII), and $R^{10}$ is OH or SH; with a compound of formula (XX), where K is as defined in formula (XX) and $R^{11}$ is $CH_2Y$, where Y is defined as a leaving group such as chloro, bromo, iodo, mesyl, or tosyl; in a suitable solvent such as DMF, DMPU, or acetone; in the presence of a base such as triethylamine, diisopropylethylamine, cesium carbonate, cesium bicarbonate, sodium carbonate, or sodium bicarbonate, at a temperature from 25° C. to 80° C.

For prodrugs where D in formula (III) and formula (XVIII) represents $-CH_2CH_2-$, esters of formula (XVIII) are prepared by:

(a) reaction of a compound of formula (XX) where K is defined as in formula (XX) and where $R^{11}$ is $CH_2Br$, with triphenylphosphine in a polar solvent, for example a $C_{1-4}$ alkanol or glycol, conveniently methanol or ethanol, normally in the presence of a base, for example a metal alkoxide conveniently formed from the metal and the solvent, ie. sodium methoxide or sodium ethoxide at a temperature of 0° C. to reflux temperature; followed by addition of a compound of formula (XIX), where $R^9$ is as defined in formula (XVIII), G is as defined in formula (VIII), and $R^{10}$ is an aldehyde group; followed by reduction with hydrogen at elevated pressure, for example between 1·75 kgcm$^{-2}$ and 7·0 kgcm$^{-2}$, conveniently at 3·5 kgcm$^2$ in the presence of a suitable catalyst such as palladium-on-carbon, in a polar solvent, for example methanol or ethanol or a mixture of methanol and dichloromethane, at ambient temperature.

(b) reaction of a compound of formula (XIX) where $R^9$ is defined as in formula (XVIII) and G is defined as in formula (VIII), and $R^{10}$ is $CH_2Br$, with triphenylphosphine in a polar solvent, for example a $C_{1-4}$ alkanol or glycol, conveniently methanol or ethanol, normally in the presence of a base, for example a metal alkoxide conveniently formed from the metal and the solvent, ie. sodium methoxide or sodium ethoxide at a temperature of 0° C. to reflux temperature; followed by addition of a compound of formula (XX), where K is as defined in formula (XX), and $R^{11}$ is an aldehyde group; followed by reduction with hydrogen at elevated pressure, for example between 1·75 kgcm$^{-2}$ and 7·0 kgcm$^{-2}$, conveniently at 3·5 kgcm$^{-2}$, in the presence of a suitable catalyst such as palladium-on-carbon, in a polar solvent, for example methanol or ethanol or a mixture of methanol and dichloromethane, at ambient temperature.

(c) reaction of a compound of formula (XX), where K is defined as in formula (XX) and $R^{11}$ is chloro, bromo, or iodo; with a compound of formula (XIX), where $R^9$ is defined as in formula (XVIII), G is as defined in formula (VIII), and $R^{10}$ is a acetylene group C≡CH.

The reaction is carried out in the presence of a Pd(O) catalyst, conveniently tetrakis-(triphenylphosphine) palladium; and a base such as triethylamine or diisopropylethyl-amine; in a polar aprotic solvent such as DMF or DMPU; at a temperature of 25° C. to 50° C.; followed by reduction with hydrogen at elevated pressure, for example between 1.75 kgcm$^{-2}$ and 7.0 kgcm$^{-2}$, conveniently at 3.5 kgcm$^{-2}$, in the presence of a suitable catalyst such as palladium-on-carbon, in a polar solvent, for example methanol or ethanol or a mixture of methanol and dichloromethane, at ambient temperature.

For prodrugs where D in formula (III) and formula (XVIII) represents $-CH_2-CH(R^3)-$, $R^3$ is as defined in formula (III), esters of formula (XVIII) are prepared by reaction of a compound of formula (XX), where K is defined as in formula (XX) and where $R^{11}$ is $CH_2Br$, with tributylphosphine or triphenylphosphine in a polar solvent, for example a $C_{1-4}$ alkanol or glycol, conveniently methanol or ethanol, normally in the presence of a base, for example a metal alkoxide conveniently formed from the metal and the solvent, ie. sodium methoxide or sodium ethoxide, or in a solution of dimethyl sulfoxide and a base such as sodium hydride at a temperature from 25° C. to 80° C.; followed by addition of a compound of formula (XI), where $R^9$ is defined as in formula (XVIII), G is defined as in formula (VIII), and $R^{10}$ is a keto group —(CO)—$R^3$ where $R^3$ is defined as in formula (III); subsequently stirring the reaction mixture at a temperature from 25° C. to reflux temperature for an extended period from 4 to 96 hours, conveniently 24 to 48 hours; followed by reduction with hydrogen at elevated pressure, for example between 1.75 $kgcm^{-2}$ and 7.0 $kgcm^2$, conveniently at 3.5 $kgcm^{-2}$, in the presence of a suitable catalyst such as palladium-on-carbon or platinum oxide, in a polar solvent, for example methanol ethanol or acetic acid.

Compounds of formula (XX) where K is as defined above and $R^{11}$ is $CH_2Br$ can be prepared using methodology available to those skilled in the art. (Piper, J R et al, *J Org Chem*, 1977, 42, 208; Piper, J R et at, *J Med Chem*, 1986, 29, 1080; Oakes V, et al *J Chem Soc*, 1956, 4433Acharya, S P, et al, *J Heterocyclis Chem*, 1975 12, 1283; bird, O D et al in *Pteridine Chemistry*, Pfleiderer W & Taylor E C, Eds, Pergamon Press, Oxford, 1964, p. 417; Piper, J R, et al *J Heterocyclic Chem*, 1974, 279).

Compounds of formula (XX) where K is as defined above and $R^{11}$ is an aldehyde group can be prepared using methodology available to those skilled in the art. (Taylor, E C, et al, *J Org Chem*, 1983, 48, 4852; Arnold. A, et al, *Collect Czech Chem Commun*, 1960, 25, 1318; Beardsley, G P, et al *Proc Am Assoc Cancer Res*, 1986, 1027.)

Compounds of formula (XX) where K is as defined above and $R^{11}$ is a cyano group can be prepared using methodology available to those skilled in the art, (Elsager, E F, et al, *Lect Heterocyclic Chem*, 1974, 2, S-97; Davoll, J, et al, *J Chem Soc (C)*, 1970, 997; Jones, T, R., *Eur, J, Cancer*, 1981, 17, 11; Kondo, T., et,al., *Chem Lett.*, 1980, 559.

Compounds of formula (XX) where K is as defined above and $R^{11}$ is an amino group can be prepared using methodolgy available to those skilled in the art, (Hynes, J B, et al, *J Med Chem*, 1975, 18, 632, 1191; Davoll, J, et al, *J Med Chem*, 1972, 15, 837; Bernetti, R et al, *J Org Chem*, 1962, 27, 2863.)

Compounds of formula (XX) where K is as defined above and $R^{11}$ is a bromo, chloro, or iodo group can be prepared using methodology available to those skilled in the art, Taylor, E C, et al, *J Med Chem*, 1992, 35, 4450; Taylor, E C. et al, *J Org Chem*, 1989, 54, 3618; Jones, J H, et al, *J Med Chem*, 1968, 11, 322.)

Carboxylic acids of formula (VIII) where A is a group of formula (XXI) where Z=S, can be prepared from carboxylic acids of formula (VIII) where C is a group of formula (XXI) wherein Z=O, by reaction with a sulfurating agent such as $P_2S_5$ in a solvent such as pyridine at a temperature between 25° C. and reflux temperature.

Compounds of formula (XIX) where G is defined as in formula (VIII), $R^9$ is as defined in formula (XVIII), and $R^{10}$ is $NHR^3$ is as defined in formula (III) can be prepared from compounds of formula (XIX) where G and $R^9$ are as defined above and $R^{10}$ is $NH_2$ by reaction with a compound $R^3$—Y where Y is defined as a leaving group such as chloro, bromo, iodo, mesyl, or tosyl; in the presence of a suitable base such as 2,6-lutidine, in a polar aprotic solvent such as DMF or dimethylacetamide at an elevated temperature between 50° C. and 100° C.

Compounds of formula (XIX) where G is a phenyl or furyl group, $R^{10}$ is $NH_2$, and $R^9$ is defined as in formula (XVIII) can be obtained from commercial suppliers, or can be readily prepared from such compounds that are available from commercial suppliers using methods known to anyone skilled in the art. One such preferred compound of formula (XXII)

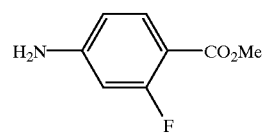

(XXII)

can be prepared by methods described by N Soundararajan and M S Platz. (soundararajan N et al, *J Org Chem*, 1990, 55, 2034.) One such preferred compound is of formula (XXIIa) and can be prepared by methods described in Mackay, D., *Can J. Chem*, 1966, 44, 2881: or in Paul, H., et al., *Arch, Pharm*, 1978, 52 538.

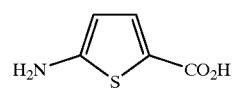

(XXIIa)

Compounds of formula (XIX) where G is a cyclohexyl group, $R^{10}$ is $NH_2$, and $R^9$ is as defined in formula (XVIII) can be obtained from commercial suppliers, or can be readily prepared using standard methods available to anyone skilled in the art, (Banfi, A, et al, *Synth Commun*, 198, 19, 1787; Krieg, R, et al, *J Prakt Chem*, 1987, 329, 1123; Johnston, T P, et al, *J Med Chem*, 1977, 20, 279.)

Compounds of formula (XIX) where G is a thienyl group, $R^{10}$ is $NH_2$, and $R^9$ is as defined in formula (XVIII) can be prepared by methodolgy available to anyone skilled in the art. (Goddard, C J, *J Heterocyclic Chem*, 1991, 28, 17Decroix, B, et al, *J Chem Res (S)*, 1978, 134; Paul, H, et al, *Arch Pharm*, 1978, 311, 679; Mackay, D, *Can J Chem*, 1966, 44, 2881.)

Compounds of formula (XIX) where G is a thiazole group, $R^{10}$ is $NH_2$, and $R^9$ is as defined in formula (XVIII) can be prepared from 5-nitrothiazole-2-carboxylic acid (Strehlke, P, *Chem Ber*, 1973, 106, 721) using esterification and reduction methods known to anyone skilled in the art.

Compounds of formula (XIX) where G is a pyridyl group, $R^{10}$ is $NH_2$, and $R^9$ is as defined in formula (XVIII) can be prepared using methodology available to anyone skilled in the art. (Dawson, M I, et al, *J Med Chem*, 1983, 26, 1282; Finch, N et al, *J Med Chem*, 1978, 21, 1269; Cooper, G H, et al, *J Chem Soc(C)*, 1971, 3257; Deady, L W, et al, *Aust J Chem*, 1971, 24, 385.)

Compounds of formula (XIX) where G is a pyrimidyl group, $R^{10}$ is $NH_2$, and $R^9$ is as defined in formula (XVIII) can be prepared using methods analogous to those described by P R Marsham, et al. (Marsham, P R, et al, *J Med Chem*, 1991, 34, 1594.)

General methods for synthesis of compounds of formula (VIII) are described in two recent reviews, (Palmer, D C, et al, *Prog Med Chem*, 1988, 25, 85; Rosowsky, A, *Prog Med Chem*, 1989, 26, 1.)

Esters of formula (VI) where E is defined as

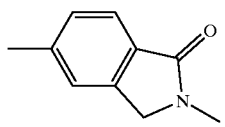

can be prepared by reaction of a compound of formula (XX) where $R^{11}$ is $CH_2Br$; and a compound of formula (XXIII) where $R^1$ is defined

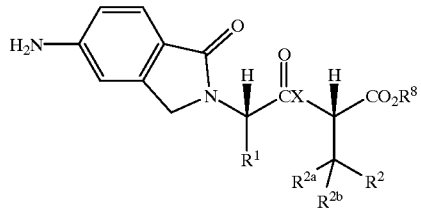

(XXIII)

as in formula (IV), $R^2$ and X are defined as in formula (II), and $R^8$ is defined as in formula (VI); in a polar solvent, such as DMF or DMPU; in the presence of a base, such as sodium bicarbonate, cesium bicarbonate, sodium carbonate or cesium carbonate; at an elevated temperature, for example form 50° C. to 100° C., conveniently at 100° C. Compounds of formula (XXIII) can be prepared from compounds of formula (VII) and a compound of formula (XXIV) by methods analgous to those described by

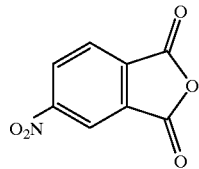

(XXIV)

W Pendergast, et al, (Pendergast, W, et al, *J Med Chem*, [1994], 37 p 838) or in patent application WO 01/19700 which is incorporated in its entirely by reference herein.

Compounds of formula (VII) can be prepared from compounds of formula (XXV), where $R^1$ is as defined in formula (IV), $R^2$ and X are as defined in formula (II), $R^8$ is as defined in formula (VI), and $R^{12}$ represents a suitable protecting group such as N-tert-butoxycarbonyl(N-t-Boc), or N-carbobenzyloxy (n-Cbz), for which methods are known to anyone skilled in the art such as those methods described in Greene, T. W., et al., *Protective Groups in Organis Synthesis, second edition*, John Wiley & Sons; New York, 1991, which are incorporated herein by reference.

Compounds of formula (XXV)

(XXV)

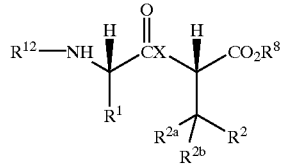

can be prepared by a reaction of carboxylic acid of formula (XXVI) and a compound of formula (XXVII), where X is defined as in formula (II); for compounds where X is NH, compounds of formula (XXV) can be prepared by reaction for a carboxylic acid of formula (XXVI) and an amine of formula (XXVII), where X is NH, in the presence of a suitable coupling agent such as 1-(3-dimethylaminopropyl)-3-ethylcarbodiimide or dicyclohexylcarbodiimide, in the presence of a suitable base such as N-methylmorpholine, in an aprotic solvent such as dichloromethane or DMF at 0° C. to 50° C. or by methods which are known to anyone skilled in the art such as those methods described in Bodanszky, M., et,al., *The Practice of Peptide Synthesis*, Springer-Verlag: Berlin, 1984, or in Jones, J., *The Chemical Synthesis of Peptides*, Clarendon Press: Oxford, England, 1991which are incorporated herein by reference.

(XXVI)

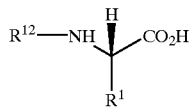

(XXVII)

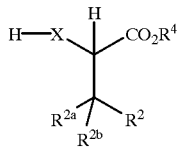

dichloromethane or DMF at 0° C. to 50° C. for which methods are known to anyone skilled in the art such as those methods described in Green, T. W., et.al., *Protective Groups in Organic Synthesis*, second edition John Wiley & Sons: New York 1991, which are incorporated herein by reference.

For compounds of formula (XXV) where X is O, compounds of formula (XXV) can be prepared by reaction of a carboxylic acid of formula (XXVI) with a suitable activating agent such as para-toluenesulfonyl chloride or benzene-sulfonyl chloride, in a suitable solvent such as pyridine or lutidine, at a temperature between 0° C. and 25° C.; followed by addition of an alcohol of formula (XXVII) where X is O.

(XXVIII)

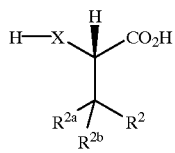

Esters of formula (XXVII), where X is defined as in formula (II), can be prepared from carboxylic acids of formula (XXVIII) using standard methods known to anyone skilled in the art for which methods are known to anyone skilled in the art such as those methods described in Green, T. W., et.al., *Protective Groups in Organic Synthesis*, second edition, John Wiley & Sons: New York, 1991, which are incorporated herein by reference.

Carboxylic acids of formula (XXVIII), where X is O, can be made from carboxylic acids of formula (XXVIII) where X is NH by methods analogous to those described by C Morin, et al, (Morin, C, et al, Synthesis, 1987, 479) and K Mori, et al (Mori, K, et al, *Tehrahedron*, 1982, 38, 3705).

Carboxylic acids of formula (XXVIII) where X is NH can be prepared from compounds of formula (XXIX); where W is a leaving group such as chloro, bromo, iodo, mesyl, or tosyl and $R^2$ is defined as in formula (II); by methods analogous to

WCH₂R² (XXIX)

described by R M Williams (Williams, R M, *Aldrichimica Acta*, 1992, 25, 11 and references cited therein), or by M J O'Donnell, et al, (O'Donnell, M J, et al, *J Am Chem Soc*, 1989, 111, 2353.)

Compounds of formula (XXIX), where W is a leaving group such as chloro, bromo, iodo, mesyl, or tosyl can be prepared from compounds of formula (XXIX) where W is a hydroxyl group for which methods are known to anyone skilled in the art such a those methods described in March, J., *Advanced Organic Chemistry, fourth edition*, John Wiley & Sons: New York, 1992, which are incorporated herein by reference.

Some of the preferred compounds of formula (XXIX) where $R^2$ is a phenyl group substituted with $C_{1-8}$ alkyl, $C_{3-8}$ branched alkyl, or $C_{3-8}$ cycloalkyl can be prepared by reaction of a compound of (XXIX) where W is a hydroxyl group, or a hydroxyl group with a suitable protecting group which can be attached and later removed where appropriate in the synthesis, by standard methods known to anyone skilled in the art, and $R^2$ is a phenyl group substituted with an iodo group or a bromo group; the reaction can proceed by addition of a suitable olefinic compound in the presence of a PD catalyst by methods analogous to those described by H A Dieck, et al, (Dieck, H A, et al, *J Am Chem Soc*, 1974, 96, 1133), followed by reduction with hydrogen gas in the presence of a suitable catalyst using standard condition known to anyone skilled on the art for which methods are known to anyone skilled in the art such as those methods described in Rylander, P. N., *Catalytic Hydrogenation in Organic Syntheses*, Academic Press: London, 1985, which are incorporated herein by reference; or the reaction can proceed by reaction with a suitable aklyllithium reagent such as n-butyllithium reagent, in an ethereal solvent such as THF, at a reduced temperature, for example −100° C. to −20° C., conveniently at −78° C., followed by addition of the resulting benzylonic alcohol group by methods analogous to those described by C T West, et al, (West C T, et al, *J Org Chem*, 1973, 38, 2675).

Some of the preferred compounds of formula (XXIX) where $R^2$ is a phenyl group substituted with a carboxyl or esterified carboxyl group can be prepared by reaction of a compound of formula (XXIX) where W is a hydroxyl group and $R^2$ is a phenyl group substituted with a bromo or iodo group, with carbon monoxide in a suitable alkanol solvent by methods analogous to those described by A Schoenber, et al, (Schoenber, A, et al, *J Org Chem*, 197, 39, 3318), followed by hydrolysis of the resulting ester, if desired, for which methods are known to anyone skilled in the art such as those methods described in Greene, T, W., et,al., *Protective Groups in Organic Synthesis, second edition*, John Wiley & Sons: New York, 1991, which are incorporated herein by reference.

Some of the preferred carboxylic acids of formula (XXVIII) where X is NH and $R^2$ is a para-hydroxphenyl) group substituted with $C_{1-8}$ alkyl, $C_{3-8}$ branched alkyl, or $C_{3-8}$ cycloalkyl can be prepared by reaction to tyrosine substituted on the phenyl ring with a bromo or an iodo group; where the amino and/or carboxyl groups can be optionally substituted with a suitable protecting group which can be attached and later removed where approppriated in the synthesis, for which methods are known to anyone skilled in the art such as those methods described in Greene, T. W., et.al., *Protective Groups in Organic Synthesis, second edition*, John Wiley & Sons: New York 1991which are incorporated herein by reference with a suitable olefinic compound in the presence of a Pd catalyst by methods analogous to those described by H A Dieck, et al, (Dieck, H A, et al, *J Am Chem Soc*, 1974, 96, 1133), followed by reduction with hydrogen gas in the presence of a suitable catalyst using standard conditions known to anyone skilled in the art.

Some of the preferred carboxylic acids of formula (XXVIII) where X is NH and $R^2$ is a para-hydroxyphenyl) group substituted with carboxyl or esterified carboxyl can be prepared by reaction to tyrosine substituted on the phenyl ring with a bromo or an iodo group; where the amino and/or carboxyl groups can be optionally substituted with a suitable protecting group which can be attached and later removed where appropriate in the synthesis, for which methods are known to anyone skilled in the art such as those methods described in Green, T. W., et. al., *Protective Groups in Organic Synthesis, second edition*, John Wiley & Sons: New York, 1991, which are incorporated herein by reference; with carbon monoxide in a suitable alkanol solvent by methods analogous to those described by (Schoenberg, A, et al, *J Org Chem*, 1974, 39, 3318), followed by hydrolysis of the resulting ester, if desired, by using standard methods known to anyone skilled in the art.

An alternate method for the synthesis of compounds of formula (VI) involves reaction of a compound of formula (XX), where K is as defined in formula (XX) and $R^{11}$ is an aldehyde group, a cyano group, $NHR^3$ where $R^3$ is as defined in formula (III), or a group $CH_2Y$ where Y is defined as a leaving group such as chloro, bromo, iodo, mesyl, or tosyl; with a compound of formula (XXX), where $R^1$ is as defined in formula (IV), G is as defined in formula (VIII), and $R^{10}$ is defined as Oh, SH, $NHR^3$ where $R^3$ is as defined in formula (III), or a group $CH_2Y$ where Y is a leaving group such as chloro, bromo, iodo, mesyl, or tosyl; by methods analogous to

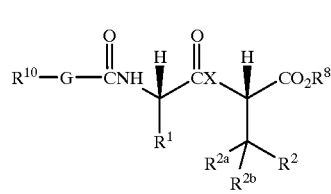

(XXX)

those described for the preparation of compounds of formula (XVIII) by reaction of compounds of formula (XX) with compounds of formula (XIX).

Compounds of formula (XXX) where $R^1$ is as defined in formula (IV), $R^2$ and X are as defined in formula (II), $R^8$ is as defined in formula (VI), G is defined as in formula (VIII), and $R^{10}$ is $CH_2Y$ where Y is a leaving group such as chloro, bromo, iodo, mesyl, or tosyl can be prepared from compounds of formula (XXX) where $R^1$, $R^2$, $R^8$, X and G are as defined above, and Where $R^{10}$ is $CH_2OH$ for which methods are known to anyone skilled in the art such as those methods described in March, J., *Advanced Organic Chemistry, fourth edition*, John Wiley & sons: New York, 1992which are incorporated herein by reference.

Compounds of formula (XXX), where $R^1$ is as defined in formula (IV), $R^2$ and X are as defined in formula (II), $R^8$ is as defined in formula (VI), G is as defined in formula (VIII), and $R^{10}$ is defined as OH, SH, $CH_2OH$, $NHR^3$ where $R^3$ is as defined in formula (III), an aldehyde group, or a keto group —(CO)—$R^3$ can be prepared from compounds of formula (VII), where $R^1$, $R^2$, $R^8$, and X are as defined above, with a compound of formula (XIX), where $R^9$ is hydrogen and $R^{10}$ is as defined above, by methods analogous to those described from the preparation of compounds of formula (VI) by reaction of compounds of formula (VII) with compounds of formula (VIII), In cases where $R^{10}$ is OH, SH, $CH_2OH$, $NHr^3$, it may be preferable to add a protecting group to $R^{10}$ prior to reaction with a compound of formula (VII), Such protecting groups can be added and can be removed at a later stage in the synthesis, for which methods are known to anyone skilled in the art such as those methods described in Green, T. W., et,al., *Protective Groups in Organic Synthesis, second edition*, John Wiley & Sons: New York, 1991, which are incorporated herein by reference.

Compounds of formula (XIX), where $R^9$ is hydrogen and $R^{10}$ is defined as OH, SH, $CH_2OH$, $NHR^3$ is as defined in formula (III), an aldehyde group, or a keto group —(CO)— $R^3$ above, can be prepared from compounds of formula (XIX), where $R^9$ is as defined in formula (XVIII) and $R^{10}$ is as defined above, for which methods are known to anyone skilled in the art such as those methods described in Green, T. W., et.al., *Protective Groups in Organic Synthesis, second edition*, John Wiley & Sons: New York, 1991, which are incorporated herein by reference.

Prodrugs of general structure (XXXI) where X and $R^2$ are as defined in formula (II) can be prepared from compounds of formula (XXXII)

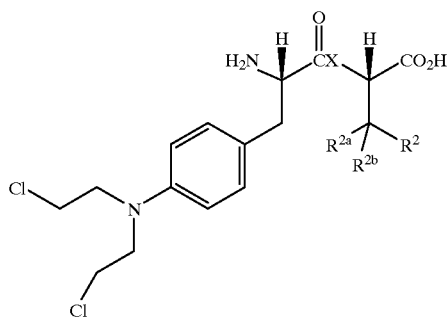

(XXXI)

wherein $R^{12}$ is as defined in formula (XXV), $R^2$ is as defined in formula (II), and $R^8$ is as defined in formula (VI), for which methods are known to anyone skilled in the art such as those methods described in Greene, T. W., et.al., *Protective Groups in Organic Synthesis, second edition*, John Wiley & Sons: New York, 1991, which are incorporated herein by reference.

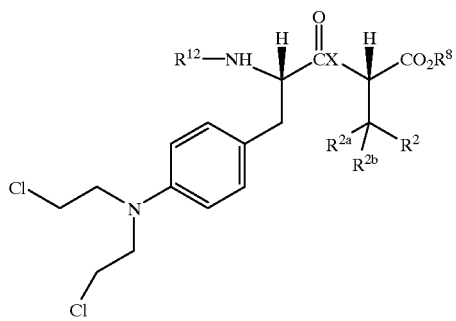

(XXXII)

Compounds of formula (XXXII) can be prepared by reaction of compounds of formula (XXXIII) where $R^{12}$ is as defined in formula (XXV);

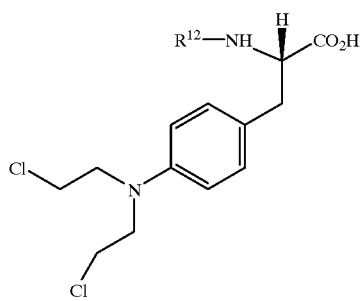

(XXXIII)

with compounds of formula (XXVII) where X is NH or O, $R^2$ is as defined in formula (II), and $R^8$ is as defined in formula (VI); using methods analogous to those described for the preparation of compounds of formula (XXV) from compounds of formulas (XXVI) and (XXVII).

Compounds of formula (XXXIII), where $R^{12}$ is a suitable protecting group as defined in formula (XXV), can be prepared for which methods are known to anyone skilled in the art such as those methods described in Green, T. W., et.al., *Protective Groups in Organic Synthesis, second edition*, John Wiley & Sons: New York, 1991, which are incorporated herein by reference; from melphalan (UK 750, 155) which is commercially available under the name Alkeran (T.M. The Wellcome Foundation Limited) and has the chemical name of 4-[bis(2-chloroethyl)amino]-1- phenylalanine.

The term protein engineering has come to mean the structurally directed modification of a protein to obtain a specific, desired new set of protein properties or, in this context, a precise enzymatic activity, Two approaches t modification of protein specificity and reactivity can be used. The differences in these approaches depend upon the chemical and structural information available for a specific enzyme. If no chemical structural information is known about a protein, random mutations can be introduced singly or in groups to determine the importance of specific amino acid residues using techniques well known in the art of molecular biology. However, a more directed approach using site directed mutagenesis, can be performed, if there is detailed chemical and structural information available on a protein. This involves only specific changes to amino acid residues that the chemical and structural data suggest are the residues critical to determination of the desired enzymatic activity, If 3-dimensional structural data are available, the methodolgy can be carried further to provide molecular models of proposed mutation. These models can provide estimates of the relative stability or reactivity of a specific site directed mutation.

Typically, in the computer-assisted protein engineering approach, computer models based upon x-ray crystallographic structures or models built, by homology model building, from x-ray structures of homologous proteins are used. In many cases the starting crystallographic structures can be obtained from the publicly available Brookhaven Protein Database.

Extensive studies of protein structure and the function of individual amino acids have allowed the classification of residues in respect of their importance in structure, stability, reactivity or catalysis. Many active site amino acid residues in proteins show unusual chemical reactivity, these chemical reactivities characterise the catalytic properties of proteins. This chemical reactivity aids in the identification of the active site and the non-reactive associated residues in the active site. Crystallographic studies in concert with chemical reactivity information can indicate distinctly the active site locations. Additionally, some proteins will crystallise with substrates or inhibitors in the active site. All of these pieces of structural information can be combined to enhance the focus of design efforts towards specific residues as candidates for site directed mutagenesis.

The specific desired change in protein reactivity can be obtained by specific changes in the amino acid at a given site of interest. Amino acid residues can be inserted, thus separating functional groups in space, or existing residues can be deleted, bringing functional groups closer together.

Additionally, changes in protein structure can be effected by changing the side chain or main chain torsion angles and the functional groups on the amino acid residues. These torsion angles can be changed by exchange, deletion or insertion of amino acid residues. If structural data are available, all these changes can be modelled using computer-assisted molecular modelling techniques. Forces interacting on the protein structures can be modelled in the computer using molecular mechanics or molecular dynamics force fields.

The space available for ligand binding within a protein can be modified by changes in the bulk of amino acid side chains. Mutating bulky residues, such as isoleucine or leucine, to alanin or glycine, can provide pockets within a ligand binding site without appreciable changing the hydrophobicity of the site. The opposite mutation can exclude bulky substrates from binding to a specific protein.

Mutation that involve changes in the functional groups of the amino acids that make up an active site can provide more drastic changes than bulk tolerance or steric changes. Examples of many of these types of changes are available in the literature (see, eg: Recktenwald, A, et al, J. Biotech, 1993, 28, 1–23 and references cited therein; and Lesk, A, et al, "Antibody engineering: A Practical Guide", Ed. C. A K. Borrebaeck et al 1991, 1–75). In systems with high quality structural data, specific hydrogen bonding groups can be inserted to improve the interaction of polar substrates. Replacing uncharged residues with arginine, lysine, or histidine inserts groups that could interact with negatively charged substrates. Replacing residues with glutamic acid or aspartic acid can provide interaction with positively charged substrates and thus change the specificity of an enzyme substrate interaction.

In a further aspect of the present invention there is provided a recombinant conjugate comprising a tragetting antibody as hereinbefore described and a mutant enzyme of the present invention; such recombinant conjugate having been expressed from a single DNA construct or translated from a single RNA transcript. Also included within the scope of the present invention are the corresponding DNA and RNA molecules encoding such a conjugate. Preferred embodiments of such a conjugate reflect a combination of the preferred embodiments for its two component activities as hereinbefore expressed.

Such recombinant conjugates may be produced by expression of fusion constructs, generated by joining, in vitro, fragments of DNA that separately encode the enzyme and all or a part of a mAb that confers antigen specificity (Pastan, I et al, (1986) Cell, 47, 641–648). Such fusions may be constructed by standard techniques of recombinant molecular biology in ways that place the substrate-binding or active site of the polypeptide at the amino terminus or the carboxy terminus and preferably at the amino terminus. The mAb portion of the construct may be designed so that a single chain species of the antibody is connected to the enzyme portion either with the variable light or the variable heavy domain at the 5'-end. In either case, the variable light and variable heavy gene regions will be connected with a synthetic DNA fragment encoding a peptide linker that achieves the correct spatial arrangement of the antibody variable regions. Such a synthetic DNA region connecting the antibody portion of the fusion construct to the enzyme portion may also be desirable. In other forms, the gene encoding the enzyme may be fused to the 5'-end of the variable region of the heavy or light chain gene that extends to form a Fab or F(ab')$_2$ species. Other variations of the heavy chain gene may be used to form the enzyme/antibody recombinant conjugate. Such variations may include natural heavy chain isotypes, modified full-length heavy chain genes of all antibody isotypes, and heavy with various deletions, specifically, deletion of the $C_{H2}$ domain may confer desirable pharmacokinetic properties. Alternatively, the fusion may produce a covalent bispecific antibody enzyme conjugate where one arm of the antibody is replaced by the enzyme in a fashion similar to but not limited to that described in De Sutter, K and Fiers, W. Mol Immunol 31 261 (1994), The term 'conjugate' as used herein includes such recombinant conjugates.

Antibodies designed to have particular cellular specificities may be generated in any way well known in the art. Fragments of antibodies generated by recombinant DNA technology may also be used as targetting molecules.

Although the preferred antibodies for use will be those expressed from natural or recombinant human derived cell-lines, it is also possible to exploit antibodies from other antibody producing mammalian cell-lines providing such antibodies are not immunogenic to an extent liable to interfere significantly with therapy or that the antibodies have been 'humanised' such that they no longer elicit an immune reaction in vivo. Such a humanized antibody may be a chimaeric antibody (Morrison et al P.N.A.S (1984), 81, 6851–6855; Boulianne et al, Nature, 1985, 314, 268–270 and Neuberger et al, Nature, 1985, 314, 268–70), or a CDR-grafted antibody (James et al, Nature, 1986, 321, 522–525Riechmann et al. Nature, 1988, 332, 323–327).

An antibody for use according to the present invention preferably is a monoclonal antibody or a fragment thereof. The antibody may therefore comprise a complete antibody, a (Fab')$_2$ fragment, a Fab' fragment, a Fab fragment, a light chain dimmer or a heavy chain dimmer or single chain species comprising the variable regions from heavy and light chains. The antibody may be an IgG such as IgG1, IgG2, IgG3, or IgG4; or IgM, IgA, IgE or IgD. The constant domain of the antibody heavy chain may be selected accordingly. The light chain constant domain may be a kappa or lambda constant domain.

The antibody may be a chimaeric antibody of the type described in WO 86/01533. A chimaeric antibody according to WO 86/01533 comprises an antigen binding region and a non-immunoglobulin region. The antigen binding region is an antibody light chain variable domain and/or heavy chain variable domain. Typically the chimaeric antibody comprises both light and heavy chain variable domains. The non-immunoglobin region is fused to the C-terminus of the antigen binding region. The non-immunoglobulin region is typically a non-immunoglobulin protein and is preferably an enzyme region. The tow regions of the chimaeric antibody may be connected via a cleavable linker sequence.

Antibodies of any of the classes referred to above may be raised against any antigen characteristic of and essentially limited to, a particular target. Such targets include all types of human pathogens cells expressing antigens as a consequence of transformation or viral infection, cells expressing particular histocompatability antigens, cells involved in inflammatory responses, blood clots which may be targetted by antibodies against fibrin, etc.

Preferred antibodies for use according to the invention, the antigens which they target and the associated indication are detailed in FIG. 8.

Particularly preferred antibodies for use according to the invention include CAMPATH 1H®, ING-1c174, PR1.A3, 323/A3, G250, MOV18, 17-1A, NR-LU-10, U326, NR-CO-OZ2 as well as antibodies targetting mucins or carcinoembryonic antigen.

For the treatment of humans when the targetting moiety is an antibody, it is preferred to use and antibody which does not carry with it the risk of the development of an immune reaction against the antibody itself. Accordingly whilst it is possible to use mouse or rat non-clonal antibodies it is preferred to use antibodies which have been produced by recombinant DNA technology and which have been engineered to reduce the risk of causing an immune reaction. Thus it is possible to use a chimaeric antibody in which the constant domains of a mouse or rat antibody have been replaced by the constant domains of a human antibody. However, it is preferred to use a humanised or CDR-grafted antibody for the treatment of humans, i.e. an antibody in which the complementary determining regions from a mouse or rat antibody are combined with framework regions and constant domains from one or more human antibodies.

In one preferred embodiment the method according to the invention is carried out using the CDR-grafted antibody CAMPATH-1H (see Riechmann et al *Nature*, 322, 323–327 (1988)). As noted above, the antibody CAMPATH-1H can be produced in rate myeloma cells as originally described or it can be produced in ay other expression system, particularly an expression system suitable for the production of a correctly folded, glycosylated, mammalian protein. High yields of CAMPATH-1H have been obtained by expression in a genetically manipulated CHO cell line (Page and Sydenham, *Biotechnology*, 9, 64–68 (1991)).

The conjugation of the tragetting molecule to the enzyme may be carried out in any appropriate way which will neither interfere with the binding specificity and capability of the tragetting molecule nor inhibit the catalytic activity of the enzyme. In the case of proteinic tragetting molecules the conjugation may be carried out either by direct covalent linkage following the generation of reactive groups by treatment with protein modifying agents or by these of homo or heterobifunctional cross-linking molecules.

Commercially available linkers with amino or hydrazide groups may be reacted with aldehydes generated by oxidation of the sugar moieties of glycoproteins and carbohydrates to from a Schiff's base (Sela M. et al, Conjugates of Antibodies with Cytotoxic Drugs. Immunoconjugates Antibody Conjugates in Radioimaging and Therapy of Cancer (C. -W. Vogel, ed.) 189–216, (1987)). Alternatively linkers may be reacted with amino, carboxyl or sulfhydryl groups of the antibody or enzyme. (Wawrzynczak P. E. et al, Methods for Preparing Immunotoxins: Effect of the Linkage on Activity & Stability In : Immunoconjugates: Antibody Conjugates in Radioimaging and therapy of Cancer (C. -W. Vogel, ed.) 78–85(1987)).

Covalent linkage may be obtained by the generation of sulfhydryl groups and, particularly in the case of antibodies, by reduction of disulfide bonds. Such free sulfhydryl groups may be reacted with haloalkyl groups, p-mercuribenzoate groups and groups capable of Michael-type addition reactions, such as maleimides or groups as per (Mitra et al, J Amer Chem Soc, 101, 3097–3110, 1979).

Another method for linking enzyme to antibody comprises utilising the epsilon amino groups of lysine. Reactive succinimide esters, cyclic thio esters or anhydrides may be used to introduce carbonyl functions which may react with the lysine amino group or to introduce a thiol reactive group such as those discussed herein. Alternatively, carbonyl functions may be activated with carbodimides to form carboxamide bonds or the lysine amino group may be reacted with methyl amidate esters to form an amindinium bond.

One particular utility of the present invention is its application it in vitro or in vivo diagnostics. For example, in vitro detection of a particular antigen may be achieved by exposing a diagnostic sample to a conjugate of the present invention comprising a tragetting moiety such as an antibody capable of binding to the antigen and subsequent exposure to a prodrug such as a methotrexate prodrug of the present invention, which may be catalysed to methotrexate by the enzyme of the conjugate if antigen is present and conjugate is bound to the antigen. Prodrug such as MTX may be detected by standard HPLC analysis, or by the coupled spectrophotometric assay described herein.

In vivo diagnostic applications of the present invention include its ability to be used in tumour imaging. Particularly preferred conjugates for use in this application include those comprising antibodies to a tumour associated antigen and a mutant enzyme capable of catalysing to methotrexate an MTX-prodrug labelled in the benzene right with $^{131}$I. Such a prodrug should be one which is otherwise refractory to endogenous catalysis. Conjugate and prodrug may be administered in a manner analogous to the therapeutic application of the invention and detection of the location of catalysed prodrug i.e. $^{131}$I MTX achieved using standard equipment for detection of radioisotopic decay.

Salts of prodrugs of the present invention include pharmaceutically acceptable base salts, derived from an appropriate base, such as alkali metal (e.g. sodium), alkaline earth metal (e.g. magnesium) slats, ammonium and NX+4 (wherein X is $C_{1-4}$ alkyl) salts. Suitable pharmaceutically acceptable salts also include, but are not limited to, those prepared from the following acids: hydrochloric, hydrobrimic, sulfuric, nitric, phosphoric, maleic, salicylic, p-toluene-sulfonic, tartaric, citric, acetic, trifluoroacetic methanesulfonic, formic, succinic, naphthalene-2- sulfonic, isethionic, lactobionic and benzenesulfonic. The pharmaceutically acceptable prodrug salts may be prepared in conventional manner for example by treatment with the appropriate base or acid.

In a method of treatment according to the present invention the means of administration of conjugate and of prodrug will depend upon the disease and its severity and will be at the discretion of the practicing physician. Both the conjugate and prodrug may be administered by the conventional methods well known to those skilled in the art including intravenously, intraperitoneally, intralymphatically, subcutaneously, intradermally, intramuscularly, orally or in the case of a tumour by direct injection into the tumour. Both the prodrug and the conjugate will preferably be administered intravenously as a bolus or by continuous infusion. Preferably the dose of conjugate administered is in the rage 0.1 to 100 mg per kg of bodyweight per day and most preferably between 1.0 and 40 mg per kg of bodyweight per day. The preferred dose of the prodrug administered is in the range 0.01 to 100 mg per kg of bodyweight per day and preferably between 1.0 and 50 mg per kg of bodyweight per day.

It is preferred that the conjugate of targetting molecule and mutant enzyme be administered to the patient prior to administration of the prodrug. The period between administration of conjugate and prodrug must be sufficient to permit targetting of the conjugate to the targetted cells and effective removal from the system of excess conjugate which has not bound to the targetted cells. Unbound conjugate must be effectively removed to avoid activation of the subsequently administered prodrug by unbound conjugate present at sites distant from the target cells. The period between administration of conjugate and prodrug is preferably between 0.5 days and 7 days but may be reduced by use of any known technique for the accelerated clearance of such conjugates from the system; particularly by delivery of an effective amount of anti-enzyme antibody, which binds to the mutant enzyme and in turn accelerates elimination, or by extra corporeal circulation (Nilsson, I M, et al, *Plasma ther, Transfus Technol*, 1984, 5, 127; Wallmark, A, et al, *Artificial Organs*, 1984, 8, 72) involving removal of the unbound conjugate by methods such as passage through a column of an appropriate affinity matrix. It may also be desirable to couple galactosyl residues to the conjugate to facilitate unbound conjugate clearance via hepatocyte lectins.

Conditions susceptible to therapy according the present invention will clearly include those for which there exists a known chemotherapeutic agent and a corresponding prodrug thereof as hereinbefore defined and which presents pathology specific feature permitting binding of a conjugate of the present invention. Such conditions include neoplastic and non-neoplatic cellular transformation, autoimmune disease, inflammatory disease and viral, bacterial, fungal, mycoplasmal or parasitic infection.

a method of treatment according to the present invention may further comprise the co-administration of a number of agents capable of increasing the efficiency of the therapy. For example, interferons are known to increase the level of expression of certain potential ADEPT target antigens and therefore administration of an appropriate interferon before administration of conjugate may increase level of conjugate binding to target cells.

It is further preferred that a combination of a prodrug of a purine synthesis inhibitor such as an inhibitor of glycineamide ribonucleotide transformylase (GAR TFase) or a prodrug of a pyrimidine synthesis inhibitor such as an inhibitor of thymidine synthase (TS) be administered in combination with a prodrug of a dithydrofolate (DHFR) inhibitor as part of such therapy (Galivan, J. et al, J. Biol. Chem. 264, 10685, 1989Ferguson, K. et al Cancer Chemother. Pharmacol. 23, 173, 1989), It is further preferred that a combination of a prodrug of purine synthesis inhibitor such as an inhibitor of GAR TFase or a prodrug of a pyrimidine synthesis inhibitor such as an inhibitor of TS be administered in combination with DHFR inhibitor, or that a combination of a purine synthesis inhibitor such as an inhibitor of GAR TFase or a pyrimidine synthesis inhibitor such as an inhibitor of TS be administered in combination with a prodrug of a DHFR inhibitor as part of such therapy.

A further aspect of the present invention comprises a method for the potentiation of any antiviral compound, the efficacy of which may be augmented by elevation of intracellular kinase activity.

According to a preferred embodiment of this further aspect of the present invention, a conjugate of the present invention comprising a targetting molecule capable of directing conjugate to a virally-infected cell and a prodrug of a folate antagonist which may be one or more of a thymidylate synthase (TS) inhibitor, dihydrofolate reductase (DFHR) inhibitor or GAR transformylase inhibitor is used to deliver high does of folate antagonist directly to the virally-infected cells of a patient who is undergoing therapy. As viral infection is associated with increased levels of DNA synthesis, it is proposed that the delivery of an inhibitor of DNA synthesis in combination with such an antiviral may prove therapeutic as the inhibition of DNA synthesis will increase the level of intracellular kinases available for phosphorylating the antiviral compound.

In a preferred embodiment of this further aspect of the invention, the anti-viral is an anti-herpes compound selected from acyclovir(GB 1523865), valacyclovir a(EP308065), famiciclovir EP182024), penciclovir (EP141927), foscarnet (GB1585615), iododeoxyuridine, 5-bromovinyl-2'-deoxyuridine (GB1601020), arabino-furanosyl-5-bromovinyl-2'deoxyuridine (EP0031128), benzimidazole nucleosides, 1-(β-D-arabinofuranosyl)-5-(1-propynyl)uracil (EP272065) and 2'-deoxy-5- ethyl-β-4'-thiouridine (EP409575), or is an anti-HIV compound selected from 2',3'-dideoxyinosine (EP206497), 2,'3'-dideoxycytidine (J. Org. Chem 32(3) 817 . 818(1967)), (2R, 5S)-5- fluoro-1-(2-(hydroxymethyl)-1,3-oxathiolan-5-yl)cytosine (US5210085), (2R,5S)-1-(2-(hydroxymethyl)-1,3-oxathiolan-5-yl)cytosine(EP0382526), 5-chloro-2',3',-dideoxy-3'-fluorouridine (EP0305117) and (1S,4R)-4-(2amino-6-(cyclopropylamino)-9H-purin-9- yl)-2-cyclopentent-1-methanol (EP0434450) or is the anti-influenza compound 9-(2-Deoxy-2fluoro-β-D-ribofuranosyl) guanine) (EP0417999).

In the most preferred embodiment of this further aspect of the invention, the antiviral compound is an anti-HIV compound such as zidovudine (EP196185), (Retrovir: registered trade mark of The Wellcome Foundation Limited), the conjugate comprises an antibody against an HIV-associated antigen such as GP210 and the prodrug is a prodrug of a TS inhibitor.

The present invention provides for the use of a novel prodrug of the present invention as hereinbefore defined, or a pharmaceutically acceptable, salt, solvate, N-oxide or physiologically functional derivative thereof, in therapy or in the preparation of a medicament for use in the treatment of any of the conditions hereinbefore described.

Also provided is the use of a mutant enzyme of the present invention, or a conjugate thereof as hereinbefore described, in therapy or in the preparation of medicament for use in the treatment of any of the conditions hereinbefore described.

Pharmaceutical formulations for mutant enzyme, antibody and prodrug may each include but are not limited to solutions, suspensions, tablets, powders, and other formulations known to those skilled in the art. The formulations may contain pharmaceutically acceptable stabilisers and carriers including human serum albumin or other proteins, pH buffering agents, and physiological or other nontoxic salts as well as non toxic solubilisers known to those skilled in the art. Preferably a pharmaceutical formulation of mutant enzyme and antibody will comprise conjugate in a sterile solution. A pharmaceutical formulation of prodrug will preferably comprise a sterile solution or a solid.

A yet further aspect of the present invention comprises a kit comprising a pharmaceutical formulation of conjugate and a pharmaceutical formulation of prodrug which may be converted to drug by the conjugate.

A yet further aspect of the present invention comprises the combination of a prodrug and a conjugate of the present invention as hereinbefore defined.

A yet further aspect of the present invention comprises the use of a novel prodrug as hereinbefore defined but excluding the previously stated proviso for use in the preparation of a medicament for use in the treatment of any of the conditions hereinbefore described.

A yet further aspect of the present invention comprises the use of a novel prodrug as hereinbefore defined but excluding the previously stated proviso, for use in the treatment of any of the conditions hereinbefore described.

A yet further aspect of the present invention comprises the use of a prodrug in the preparation of a medicament for use in the treatment of a patient who has previously been administered with a conjugate of the present invention as hereinbefore defined.

A further aspect of the invention comprises the cloned version of human carboxypeptidase A2 described herein as well as the DNA encoding carboxypeptidase A2.

A further aspect of the invention comprises any DNA sequence encoding a mutant enzyme for use according to the present invention and plasmids, expression vectors, and cell lines containing such DNA. Preferably such DNA encodes mutant carboxypeptidase A1 or A2 mutants as herein described and most preferable mutant carboxypeptidase A1 or A2 wherein position 268 is glycine.

A further aspect of the invention comprises any DNA sequence encoding a mutant enzyme for use according to the present invention and plasmids, expression vectors, and cell lines containing such DNA. Preferably such DNA encodes mutant carboxypeptidase A1 or A2 mutants as herein described and most preferable mutant carboxypeptidase A1 or A2 wherein position 268 is glycine.

A further aspect of the invention comprises DNA sequence encoding a conjugate according to the present invention and plasmids, expression vectors, and cell lines containing such DNA.

A yet further agreed aspect of the invention is a method of converting a prodrug to a drug which is cytotoxic to cells.

All references to alternatives herein, such as alternative patterns of chemical substitutions, shall be construed as inclusive and not as exclusive.

As used herein the term "halo" means fluoro, chloro, bromo or iodo.

The terms "aryl" means phenyl, naphthyl or anthracenyl optionally substituted by one or more halo, hydroxy, nitro, cyano, trifluoromethyl, $C_{1-6}$ alkyl, $C_{1-6}$ alkoxy or amino optionally substituted with $C_{1-6}$ alkyl.

The term "heteroaryl" means an aromatic monocyclic or bicyclic fused ring system comprising 5 to 10 carbon atoms wherein one or more ring atoms are independently selected from nitrogen, oxygen or suffer.

"Carboxamide" groups can be unsubsituted or substituted $C_{1-6}$ alkyl.

A mutant mammalian enzyme as used herein shall be taken to be any enzyme with a sequence differing by at least one amino acid from the amino acid sequence or sequences of that enzyme in the mammal to which the therapy is applied. Preferably the mammal to which the therapy is applied is a human patient and preferably the amino acid sequence of the mutant mammalian enzyme does not differ by more than 15% from the amino acid sequence or sequences of that enzyme in the mammal to which the therapy is applied.

All references hereinbefore and in the Claims hereinafter to residue numbers of amino acids relate to the residue number indicated in the Tables contained herein and not to the residue numbers given in the Sequence Listing herein which follows a different numbering convention.

EXPERIMENTAL PROCEDURES

General Comments

All solvents were reagent grade and were used without further purification. Anhydrous solvents were dispensed from Aldrich Sure Seal bottles using a dry syringe. Chemicals are reagent grade and were used without purification. The full name and address of the suppliers of the reagents is given when first cited. Thereafter, an abbreviated name is used.

$^1$H-NMR spectra were obtained using Varian XL-200 or XL-300 spectrometers at 200 and 300 MHz respectively. Chemical shifts are expressed in ppm downfield from tetramethylsilane. Spectral data are tabulated in order: multiplicity (s, singlet; d, doublet; t, triplet; q, quartet; m, multiplet; br, broad), number of hydrogens, coupling constant(s) in Hertz, descriptor. Chemical ionization (CI) mass spectra were performed by Oneida Research Services, Inc. Whitesboro, N.Y. 13492. Atmospheric pressure chemical ionization (APCI) mass spectra were obtained using a Fisons platform mass spectrometer. Fast atom bombardment (FAB) mass spectra were obtained using a VG Analytical 70SQ spectrometer. Ion spray mass spectra were obtained using a Sciex API III spectrometer. Elemental analysis were performed by Atlantic Microlabs, Inc., Atlanta, Ga. 30366. Reverse analyses phase analytical HPLC's were run on C18 analytical columns using a Waters HPLC system consisting of a 600E System Controller, a 715 UltraWisp sample processor, and a 991 Photodiode Array Detector. Semi-preparative HPLC's were run on a Regis column (C18, Prep-100-60-ODS-FEC, 10 mm packing, 25 cm×21.1 mm i.d.) using a similar system equipped with a manual injector.

Abbreviations used are: grams (g), milliliters (mL), liters (L), hours (h), minutes (min), room temperature (RT), calculated (calcd.), decomposition (dec.), molecular weight (mw), tetrahydrofuran (THF), dimethyl formamide (DMF), dimethyl sulphoxide (DMSO), 1,3-dimethyl-3,4,5,6-tetrahydro-2(1H)-pyrimidinone (DMPU), 1-ethyl-3-(dimethylaminopropyl)carbodiimide hydrochloride (EDC), dicyclohexylcarbdiimide (DCC), diethyl cyanophosphonate (DECP), (benzyloxy)carbonyl (Cbz), and trifluoroacetic acid (TFA).

Some examples prepared were very tenacious of water and/or other hydroxylic solvents (e.g. DMF), and/or were obtained as whole or partial salts of organic or inorganic acids (e.g. trifluoroacetic acid, hydrochloric acid). Such addends are indicated in the analytical data for appropriate examples; although these addends may not be indicated as part of the compound name, their presence in the isolated products is noted by the inclusion of salt and hydration data in the molecular formulas and analytical data in appropriate examples.

EXAMPLE 1

2-Fluoro-4-nitrobenzoic Acid

A 3L 3-necked flask equipped with a magnetic stirrer was charged with 25.00 g of 2-fluoro-4-nitrotoluene (Aldrich Chemical Co., Milwaukee, Wis., 53233), 1.65 L of 1 N NaOH, and 25.00 g of $KMnO_4$. The resulting mixture was heated to 95° C. with stirring. Additional 25.00 g portions of $KMnO_4$ were added after 1 h and 2 h. After stirring at 95° C. for an additional hour the reaction mixture was cooled to RT and filtered through celite to remove $MnO_2$. The filtrate was concentrated in vacuo to 500 mL and acidified to pH 2 by addition of concentrated $H_2SO_4$. A yellow-orange precipitate formed which was collected by vacuum filtration. The crude solid was dissolved in 300 mL of 1 N aqueous NaOH, acidified to pH 2 and the mixture extracted with $CH_2Cl_2$ (4×150 mL). The combined $CH_2Cl_2$ extracts were washed with 0.1 N aqueous HCl (2×100 mL), dried over anhydrous Na$_2$SO$_4$, and concentrated in vacuo to afford 12.44 g (42%) of 2-fluoro-4-nitrobenzoic acid as a yellow crystalline solid, m.p. 165–167° C.

EXAMPLE 2

Ethyl 2-fluoro-4-nitrobenzoate

To a dry 100 mL 3-necked flask equipped with a magnetic stirrer and a nitrogen inlet were added 3.00 g of 2-fluoro-4-nitrobenzoic acid, 3.00 g of NaHCO$_3$, and 20 mL of anhydrous dimethylacetamide. The suspension was treated with 3.50 mL of ethyl iodide and stirred at RT under N$_2$ for 18 h. The reaction mixture was filtered to remove solids and the filtrate concentrated in vacuo to give an orange residue which was dissolved in 100 mL of CH$_2$Cl$_2$. The solution was washed with saturated aqueous NaHCO$_3$ (3×50 mL), water (1×60 mL), and dried over anhydrous Na$_2$SO$_4$. Removal of drying agent by filtration and passage through a silica gel plus (3×5 cm) gave a light yellow solution which was concentrated in vacuo to afford 3.10 g (90%) of ethyl 2-fluoro-4-nitrobenzoate as a light yellow crystalline solid, m.p. 70–73° C.

EXAMPLE 3

Ethyl 4-amino-2-fluorobenzoate

To a 250 mL round bottomed flask equipped with a magnetic stirrer were added 3.00 g of ethyl 2-fluoro-4-nitrobenzoate and 100 mL of MeOH. The solution was deoxygenated by bubbling nitrogen through for 10 min and then treated with 2.00 g of Raney nickel (Raney 3200, Davison Chemical, Chattanooga, Tenn. 37406) which had been washed with water and EtOH. The solution was subjected to hydrogenation at 1 atm with stirring for 40 min. The flask was purged with nitrogen and the catalyst was removed by filtration. The filtrate was concentrated in vacuo to afford 2.40 g (93%) of ethyl-4-amino-2-fluorobenzoate as a tan crystalline solid, m.p. 110–112° C.

EXAMPLE 4

9-Bromomethyl-3-methylbenzo(f)quinazolin-1(2H)-one

To a 3L 3-necked flask equipped with a magnetic stirrer, a nitrogen inlet, and a reflux condenser were added 1.4 L of 1,2-dichloroethane. The solvent was heated to reflux and 10.00 g of 3,9-dimethylbenzo(f)-quinazolin-1(2H)-one (prepared according to the method described in International Patent Application WO 91/19700) were slowly added. This was followed by addition of 8.73 g of N-bromosuccinimide (Aldrich) and 1.00 g of benzoyl peroxide (Aldrich). After heating at reflux for 2 h the reaction mixture was cooled to room temperature and concentrated in vacuo. The residue was slurried with 60 mL of EtOH and the solid was collected by vacuum filtration. The product was washed with 50 mL of EtOH and dried in vacuo to afford 12.39 g of a light tan solid, m.p.>200° C. Analysis by $^1$H-NMR indicated a mixture consisting of 80% of 9-bromomethyl-3-methylbenzo(f) quinazolin-1(2H)-one and 20% of starting material. The material was carried on to the next step without further purification.
$^1$H-NMR: (300 MHz, DMSO-d$_6$) δ 9.86 (s,1H, aromatic CH), 8.28 (d, 1H, J=9.0, aromatic CH), 8.06 (d, 1H, J=8.4, aromatic CH), 7.72 (d, 1H, J=8.2, aromatic CH), 7.65 (d, 1H, J=8.8, aromatic CH), 4.94 (s, 2H, ArCH$_2$Br), 2.49 (s, 3H, CH$_3$).

EXAMPLE 5

Ethyl 4-(((1,2-dihydro-3-methyl-1-oxobenzo(f) quinazolin-9-yl)methyl)amino)-2-fluorobenzoate To a 500 mL 3-neck flask equipped with a magnetic stirrer, a nitrogen inlet, and a reflux condenser were added 5.00 g of 9-bromomethyl-3-methylbenzo(f)quinazolin-1 (2H)-one, 3.02 g of ethyl 4-amino-2-fluorobenzoate, 4.17 g of NaHCO$_3$, and 42 mL of anhydrous DMF. The reaction mixture was heated to 100° C. with stirring under nitrogen for 1.5 h.

After cooling to RT the mixture was filtered to remove solids and the crude product was deposited on 30 g of silicon gel by concentrating the filtrate in vacuo in the presence of silica gel. The product/silica gel mixture was applied to a column (360 g SiO$_2$) and purified by flash chromatography using MeOH—EtOAc gradient elution (EtOAc→2% MeOH—EtOAc). This afforded 3.50 g (65%) of ethyl 4-(((1, 2-dihydro-3-methyl-1-oxobenzo(f)quinazolin-9-yl)methyl) amino)-2-fluorobenzoate as a white powder. m.p. >200° C.
$^1$H-NMR: (300 MHz, DMSO-d$_6$) δ 12.54 (s,1H, NH), 9.85 (s, 1H, aromatic CH), 8.23 (d, 1H, J=8.7, aromatic CH), 8.01 (d, 1H, J=8.2, aromatic CH), 7.69–7.50 (m, 3H, aromatic CH), 6.52 (dd, 1H, J=1.8, 8.9; aromatic CH), 6.40 (dd; 1H; J=1.7, 14.7; aromatic CH), 4.58 (d, 2H, J=5.6, ArCH$_2$N), 4.19 (q, 2H, J=7.0, ethyl CH$_2$), 2.44 (s, 3H, CH$_3$), 1.24 (t, 3H, J=7.0, ethyl CH$_3$).

EXAMPLE 6

4-(((1,2-Dihydro-3-methyl-1-oxobenzo(f)quinazolin-9-yl)methyl)amino)-2-fluorobenzoic acid A 100 mL 3-necked flask equipped with a magnetic stirrer was charged with 0.200 g of ethyl 4-(((1,2-dihydro-3-methyl-1-oxobenzo(f)quinazolin-9-yl)methyl)amino)-2-fluorobenzoate, 18 mL of 1 N NaOH, and 20 mL of EtOH. After stirring overnight at RT, the solution was concentrated to 20 mL in vacuo and acidified to pH 2.5 by addition of concentrated HCl. The resulting precipitate was collected by vacuum filtration, washed with 15 mL of water, and dried in vacuo to afford 0.15 g (77%) of 4-(((1,2-dihydro-3-methyl-1-oxobenzo(f)quinazolin-9-yl)methyl)amino)-2-fluorobenzoic acid as a white powder, m.p. >250° C.
$^1$H-NMR: (300 MHz, DMSO-d$_6$) δ 13.20–12.30 (br s, 1H, COOH), 9.83 (s, 1H, aromatic CH), 8.24 (d, 1H, J=8.6, aromatic CH), 8.06 (d,1H, J=8.4, aromatic CH), 7.80–7.40 (m, 4H, aromatic CH), 6.51 (d, 1H, J=7.9, aromatic CH), 6.37 (d, 1H, J=14.2, aromatic CH), 4.60 (s, 2H, ArCH$_2$N), 2.48 (s, 3H, CH$_3$).

EXAMPLE 7

N-((Benzyloxy)carbonyl)-5-O-ethyl-L-glutamic Acid

A 2L 3-necked flask equipped with a magnetic stirrer and a thermometer was charged with 25.0 g of glutamic acid γ-ethyl ester (Sigma Chemical Co., St. Louis, Mo., 63178) and 1 L of distilled water. The solution was heated to 60° C. with stirring and treated with 30 g of NaHCO$_3$ followed by 25 mL of benzyl chloroformate (Aldrich). The flask was allowed to cool to RT and stirring was continued for 2 h. The mixture was extracted with ethyl ether (5×100 mL) and the ether extracts were discarded. The aqueous phase was acidified to a congo red end point by addition of concentrated aqueous HCl and the resulting emulsion was extracted with CH$_2$Cl$_2$ (5×100 mL). The combined CH$_2$Cl$_2$ extracts were washed with 0.05 N aqueous HCl (2×100 mL), dried over anhydrous $Na_2SO_4$, and concentrated in vacuo to a volume of 50 mL. The solution was chilled in an ice water bath and triturated with addition of 200 mL of pentane. The resulting solid was collected by vacuum filtration and dried in vacuo to afford 37.0 g (83%) of N-((benzyloxy)carbonyl)-5-O-ethyl-L-glutamic acid as a white powder, m.p. 82–84° C.

EXAMPLE 8

Ethyl 3-(1-naphthyl)-L-alaninate

To a 250 mL 3-necked flask equipped with a magnetic stirrer and a reflux condenser were added 3.00 g of 3-(1'-naphthyl)-L-alanine (Schweizerhall, Inc., Piscataway, N.J., 08854) and 75 mL of absolute EtOH. The suspension was acidified by bubbling HCl gas through until a clear solution was obtained and the solution was heated at reflux with stirring for 5 h. The solution was cooled to RT and concentrated in vacuo to give a white solid, which was suspended in 100 mL of 5% aqueous $NaHCO_3$ and extracted with EtOAc (3×60 mL). The combined EtOAc extracts were washed with 5% aqueous $NaHCO_3$(3×50 mL), water (1×50 mL), and dried over anhydrous $Na_2SO_4$. The drying agent was removed by filtration and the filtrate concentrated in vacuo to give an oil which was dissolved in 40 mL of ethyl ether. The ether solution was treated with 13.9 mL of 1 N ethereal HCl and the resulting precipitate was collected by vacuum filtration and dried in vacuo to afford 3.70 g (95%) of ethyl 3-(1-naphthyl)-L-alaninate HCl as a white powder, m.p. 182–184° C.

EXAMPLE 9

Ethyl N-((benzyloxy)carbonyl)-5-O-ethyl-L-glutam-1-yl-3-(1-naphthyl)-L-alaninate A 250 mL 3-necked flask equipped with a magnetic stirrer and a nitrogen inlet was charged with 3.70 g of ethyl 3-(1-naphthyl)-L-alaninate HCl, 4.09 g of N-((benzyloxy)carbonyl)-5-O-ethyl-L-glutamic acid, 60 mL of $CH_2Cl_2$, and 1.45 mL of N-methylmorpholine. The mixture was chilled to 0° C. in an ice bath, treated with 2.66 g of EDC (Aldrich) and stirred under nitrogen. After 1 h at 0° C. the solution was allowed to warm to RT and stirring was continued for an additional 3 h. The solution was concentrated in vacuo and the residue was dissolved in 100 mL of EtOAc. The EtOAc solution was washed with 10% aqueous citric acid (3×50 mL) followed by 5% aqueous $NaHCO_3$ (3×50 mL). The solution was dried over anhydrous $Na_2SO_4$, concentrated in vacuo to 20 mL and triturated with addition of 50 mL of pentane. The resulting solid was collected by vacuum filtration and dried in vacuo to afford 5.80 g (82%) of ethyl N-((benzyloxy)carbonyl)-5-O-ethyl-L-glutam-1-yl-3-(1-naphthyl)-L-alaninate as a white powder, m.p. 124–126° C.

EXAMPLE 10

Ethyl 5-O-ethyl-L-glutam-1-yl-3-(1-naphthyl)-L-alaninate

A 500 mL Parr bottle was charged with 0.19 g of 10% Pd(C) and 60 mL of absolute EtOH under nitrogen. The catalyst-solvent mixture was deoxygenated by bubbling nitrogen through for 5 minutes and then treated with 0.14 mL of acetyl chloride followed by 1.02 g of ethyl N-((benzyloxy)carbonyl)-5-O-ethyl-L-glutam-1-yl-3-(1-naphthyl)-L-alaninate. The mixture was hydrogenated at 45 psi for 18 h. The bottle was purged with nitrogen and the catalyst was removed by filtration through celite. The filtrate was concentrated in vacuo to afford 0.81 g (97%) of ethyl 5-O-ethyl-L-glutam-1-yl-3-(1-naphthyl)-L-alaninate HCl as a light yellow foam, m.p. 85–90° C. (dec.).

EXAMPLE 11

Ethyl N-(N-(4-(((1,2-dihydro-3-methyl-1-oxobenzo (f)quinazolin-9-yl)methyl)amino)-2-fluorobenzoyl)-5-O-ethyl-L-glutam-1-yl)-3-(1-naphthyl)-L-alaninate A 100 mL 3-necked flask equipped with a nitrogen inlet and a magnetic stirrer was charged with 0.50 g of 4-(((1,2-dihydro-3-methyl-1-oxobenzo(f)quinazolin-9-yl)methyl) amino)-2-fluorobenzoic acid and 10 mL of DMPU (Aldrich). The mixture was alternately heated and sonicated to dissolve the solid and the resulting solution was stirred under nitrogen in the presence of 0.50 g of 3 Å molecular sieves for 18 h. The mixture was cooled to 0° C. in an ice bath and treated with 0.15 mL of N-methylmorpholine followed by 0.17 mL of isobutyl chloroformate. After stirring at 0° C. for 15 min the reaction mixture was treated with a solution of 0.69 g of ethyl 5-O-ethyl-L-glutam-1-yl-3-(1-naphthyl)-L-alaninate HCl and 0.17 mL of N-methylmorpholine in 4 mL of anhydrous DMF. The reaction was maintained at 0° C. for 1 h and was then allowed to warm to RT and stirred for an additional 4 h. The mixture was filtered to remove solids and the filtrate was mixed with 150 mL of water. The resulting crude solid was collected by filtration, dried in vacuo, and subjected to flash chromatography on 200 g of silica gel (1% MeOH/EtOAc→5% MeOH/EtOAc) to afford 0.40 g (40%) of ethyl N-(N-(4-(((1,2-dihydro-3-methyl-1-oxobenzo(f)quinazolin-9-yl)methyl)amino)-2-fluorobenzoyl)-5-O-ethyl-L-glutam-1-yl)-3-(1-naphthyl)-L-alaninate as a white powder, m.p. 225° C. (dec.).

$^1$H-NMR: (200 MHz, DMSO-$d_6$)δ 12.55 (s,1H, benzaquinoline NH), 9.87 (s, 1H, aromatic CH), 8.63 (d, 1H, J=7.5, amide NH), 8.24 (d, 1H, J=8.3, aromatic CH), 8.09 (d, 1H, J=7.7, aromatic CH), 8.03 (d, 1H, J=8.0, aromatic CH), 7.92 (d, 1H, J=7.1, aromatic CH), 7.79 (t, 1H, J=5.6, 4-aminobenzoyl NH), 7.68–7.30 (m, 9H, aromatic CH, amide NH), 6.56 (d, 1H, J=7.9, aromatic CH), 6.42 (d, 1H, J=14.4, aromatic CH), 4.68–4.43 (m, 4H, benzoquinazoline-9-$CH_2$, glu methine, naphthylala methine), 4.10–3.92 (m, 4H, ethyl $CH_2$), 3.63–3.30 (m, 2H, naphthyl-$CH_2$), 2.45 (benzoquinazoline $CH_3$), 2.29 (m, 2H, glu 4-$CH_2$), 2.07–1.74 (m, 2H, glu 3-$CH_2$), 1.14(t, 3H, J=7.1, ethyl $CH_3$), 1.03 (t, 3H, J=7.1, ethyl $CH_3$).

EXAMPLE 12

N-(N-(4-(((1,2-Dihydro-3-methyl-1-oxobenzo(f) quinazolin-9-yl)methyl)amino)-2-fluorobenzoyl)-L-glutam-1-yl)-3-(1-naphthyl)-L-alanine To a 50 mL 3-necked flask equipped with a magnetic stirrer and a nitrogen inlet were added 0.15 g of ethyl N-(N-(4-(((1,2-dihydro-3-methyl-1-oxobenzo(f)quinazolin-9-yl)methyl)amino)-2-fluorobenzoyl)-5-O-ethyl-L-glutam-1-yl)-3-(1-naphthyl)-L-alaninate, 8 mL of 1:1 THF:$H_2O$, and 20 mg of LiOH.$H_2O$. The mixture was stirred at RT under nitrogen. After 1 h analysis of the solution by tlc ($SiO_2$, 3% MeOH/$CH_2Cl_2$) showed no remaining starting material and a new component at $R_f$=0.0. The solution was acidified to pH 5 by addition of 1 N aqueous HCl and the resulting white suspension was concentrated in vacuo to dryness. Analysis of the residue by reverse phase HPLC (C18, 65:35:0.1 H₂O:MeCN:TFA) indicated a major component (95%) at k'=3.17 and a minor component (5%) at K'=4.90. The crude product was purified by semi-preparative reverse phase HPLC using gradient elution (C18, 70:30:0.1 æ65:35:0.1 H₂O:MeCN:TFA over 10 min). Pure fractions (as determined by analytical HPLC) were combined, concentrated to 20 mL in vacuo and lyophilized to afford 76 mg (50%) of N-(N-(4-(((1,2-dihydro-3-methyl-1-oxobenzo(f)-quinazolin-9-yl)methyl)amino)-2-fluorobenzoyl)-L-glutam-1-yl)-3-(1-naphthyl)-L-alanine as an off white powder, m.p. 180° C. (dec.).
HPLC: one peak on C18, K'=3.53, 65:35:0.1 H₂O:MeCN:TFA, flow rate=1 mL/min.
¹H-NMR: (300 MHz, DMSO-d₆)δ 13.30–12.20 (br m, COOH), 9.82 (s,1H, aromatic CH), 8.44 (d, 1H, J=8.1, amide NH), 8.26 (d,1H, J=8.9, aromatic CH), 8.11 (d, 1H, J=8.3, aromatic CH), 8.03 (d, 1H, J=8.3, aromatic CH), 7.84 (d, 1H, J=8.2, aromatic CH), 7.73 (d, 1H, J=7.8, aromatic CH) 7.67–7.27 (m, 9H, aromatic CH, amide NH), 6.53 (d, 1H, J=8.5, aromatic CH), 6.38 (d, 1H, J=14.7, aromatic CH), 4.63–4.38 (m, 4H, benzoquinazoline-9-CH₂, glu methine, naphthylala methine), 3.55 (m, 1H, naphthyl-CH₂), 3.27 (m, 1H, naphthyl-CH₂), 2.43 (s, 3H, benzoquinazoline CH₃), 2.18 (m, 2H, glu 4-CH₂), 2.00–1.70 (m, 2H, glu 3-CH₂).
Elemental Analysis: Calcd. for C₃₉H₃₄N₅O₇F.1.5H₂O.0.5TFA (MW 787.76): C, 60.99; H, 4.80; N, 8.89. Found: C, 60.96; H, 4.82; N, 8.98
Mass Spectrum: (FAB) 704(M+H)⁺, 613, 489, 371, 309.
UV Spectrum: (pH 7 Buffer) $\lambda_{max}(\epsilon)$ 223.4 (82600), 266.4 (53100), 348.6 (5500). $\lambda_{min}(\epsilon)$ 243.2 (23500), 340.2 (3430).

EXAMPLE 13

Ethyl N-(4-(((2,4-diamino-6-pteridinyl)methyl)
methylamino)benzoyl)-5-O-ethyl-L-glutam-1-yl-3-
(1-naphthyl)-L-alaninate To a solution of 0.24 mL of DECP (Aldrich) and 0.22 mL of Et₃N in 20 mL of anhydrous DMF in a 100 mL 3-necked flask were added 0.20 g of 4-(N-(2,4-diamino-6-pteridinylmethyl)-N-methylamino)benzoic acid hemihydrochloride dihydrate (Aldrich Chemical Co., Milwaukee Wis., 53233) and 0.04 mL of Et₃N dissolved in 3 mL of DMPU. The solution was stirred at RT under nitrogen for 3 h and treated with a solution of 0.23 g of ethyl 5-O-ethyl-L-glutam-1-yl-3-(1-naphthyl)-L-alaninate HCl and 0.15 mL of Et₃N in 2 mL of anhydrous DMF. After stirring for 70 h the reaction mixture was concentrated in vacuo to 3 mL and treated with 60 mL of ethyl ether to precipitate the crude product as a tacky orange solid. The ether was decanted and the product dissolved in 60 mL of CHCl₃. The solution was extracted with 1% aqueous NH₄OH, dried over anhydrous Na₂SO₄ and concentrated in vacuo to dryness. The yellow-orange residue was purified by flash chromatography on 150 g of silica gel (7:7:1 CH₂Cl₂: acetone:MeOH) to afford 0.26 g (70%) of ethyl N-(4-(((2,4-diamino-6-pteridinyl)methyl) methylamino)benzoyl)-5-O-ethyl-L-glutam-1-yl-3-(1-naphthyl)-L-alaninate as a yellow powder, m.p. 135° C. (dec).
¹H-NMR: (200 MHz, DMSO-d₆)δ 8.59 (s,1H, pteridinyl-7-CH), 8.45 (d, 1H, J=7.2, amide NH), 8.10 (d, 1H, J=8.0, aromatic CH), 8.04 (d, 1H, J=8.2, aromatic CH), 7.92 (d, 1H, J=6.8, aromatic CH), 7.83–7.45 (m, 6H, aromatic CH, NH₂), 7.41–7.23 (m, 2H, aromatic CH), 6.84 (d, 2H, J=8.8, aromatic CH), 6.65 (br s, 2H, NH₂), 4.81 (s, 2H, pteridinyl-CH₂), 4.63–4.39 (m, 2H, glu methine, naphthylala methine), 4.13–3.91 (m, 4H, ethyl CH₂), 3.63–3.32 (m, 2H, naphthyl-CH₂), 3.24 (s, 3H, N—CH₃), 2.34 (t, 2H, J=7.6, glu-4-CH₂), 2.10–1.80 (m, 2H, glu-3-CH₂), 1.17 (t, 3H, J=7.1, ethyl-CH₃), 1.03 (t, 3H, J=7.1, ethyl-CH₃).

EXAMPLE 14

N-(4-(((2,4-Diamino-6-pteridinyl)methyl)
methylamino)benzoyl)-L-glutam-1-yl-3-(1-
naphthyl)-L-alanine To a 50 mL 3-necked flask equipped with a magnetic stirrer and a nitrogen inlet were added 0.13 g of ethyl N-(4-(((2,4-diamino-6-pteridinyl)methyl)methylamino) benzoyl)-5-O-ethyl-L-glutam-1-yl-3-(1-naphthyl)-L-alaninate, 10 mL of EtOH and 15 mL of 0.2 N NaOH. The resulting solution was stirred at RT under N₂ for 2.5 h, acidified to pH 5 by addition of 1 N aqueous HCl, and concentrated in vacuo to dryness. Analysis of the yellow solid by reverse phase HPLC (C18, 70:30:0.1 H₂O:MeCN:TFA) indicated a major component (93%) at K'=4.3 and four minor components at K'=6.8, 3.5, 2.9 and 1.9. A 70 mg portion of the crude product was purified by semi-preparative reverse phase HPLC (C18, 70:30:0.1 H₂O:MeCN:TFA). Pure fractions (as determined by analytical HPLC) were combined, concentrated in vacuo to 20 mL and lyophilized to afford 36 mg (53%) of N-4-(((2,4-diamino-6-pteridinyl)methyl)methylamino)benzoyl)-L-glutam-1-yl-3-(1-naphthyl)-L-alanine as a yellow powder, m.p. 175° (dec).
HPLC: one peak on C18, K'=3.23, 70:30:0.1 H₂O:MeCN:TFA, flow rate=1 mL/min.
¹H-NMR: (300 MHz, DMSO-d₆)δ 13.00–11.95 (br m, 2H, COOH), 8.65 (s, 1H, pteridinyl-7-CH), 8.45 (br, 1H, NH₂), 8.36–8.18 (br, 1H, NH₂), 8.25 (d, 1H, J=7.5, amide NH), 8.10 (d, 1H, J=8.6, aromatic CH), 7.96 (d, 1H, J=7.8, aromatic CH), 7.90 (d, 1H, J=7.7, aromatic CH), 7.70 (m, 3H, aromatic CH), 7.60–7.45 (m, 3H, aromatic CH, NH₂), 7.39–7.15 (m, 3H, aromatic CH, amide NH, NH₂), 6.81 (d, 2H, J=8.6, aromatic CH, 4.84 (s, 2H, pteridinyl-CH₂), 4.51 (m, 1H, naphthylala methine), 4.42 (m, 1H, glu methine), 3.57 (m, 1H, naphthylala-CH₂), 3.28 (m, overlapping H₂O peak, naphthylala CH₂), 3.25 (s, 3H, N—CH₃), 2.23 (t, 2H, J=7.5, glu-4-CH₂), 2.02–1.72 (m, 2H, glu-3-CH₂).
Elemental Analysis: Calcd. for C₃₃H₃₃N₉O₆.1.5 H₂O.0.5 TFA (MW 735.72): C, 55.51; H, 5.00; N, 17.13. Found: C, 55.65; H, 5.09; N, 16.92.
Mass Spectrum: (FAB) 652 (M+H)⁺, 581, 461, 371, 309.
UV Spectrum: (pH 7 Buffer) $\lambda_{max}(\epsilon)$ 224.3 (74700), 260.3 (24900), 295.9 (24100), 372.5 (7150) $\lambda_{min}(\epsilon)$ 242.3 (15200), 271.0 (20500), 345.2 (5550).

EXAMPLE 15

N-((Benzyloxy)carbonyl)-5-O-methyl-L-glutamic
acid

To a 1 L 3-necked flask equipped with a thermometer and a magnetic stirrer were added 4.90 g of L-glutamic acid γ-methyl ester (Sigma) and 200 mL of water. The solution was heated to 60° C., treated with 6.40 g of NaHCO₃ followed by 5.20 mL of benzyl chloroformate (Aldrich) and allowed to cool to RT with vigorous stirring. After 4 h the reaction mixture was extracted with ethyl ether (4×100 mL) and the ether extracts were discarded. The aqueous solution was acidified to a congo red endpoint by addition of concentrated HCl. An oily emulsion resulted which was extracted with CH₂Cl₂ (4×60 mL). The combined organic extracts were washed with 0.05 N aqueous HCl (2×60 mL), dried over anhydrous Na₂SO₄ and concentrated in vacuo to afford 8.23 g (92%) of N-((benzyloxy)carbonyl)-5-O-methyl-L-glutamic acid as a white crystalline solid, m.p. 61–63° C.

EXAMPLE 16

Glycine Tert-butyl Ester-benzophenone Imine

A 500 mL 3-necked flask equipped with a magnetic stirrer and a nitrogen inlet was charged with 10.00 g of glycine-tert-butyl ester HCl (Sigma) and 200 mL of anhydrous $CH_2Cl_2$. The solution was treated with 10.80 g of benzophenone imine (Aldrich) and stirred at RT under nitrogen for 24 h. A fine white precipitate of $NH_4Cl$ formed during the reaction. The mixture was concentrated in vacuo to dryness to give a white solid which was suspended in 250 mL of ethyl ether and washed with water (3×200 mL) to remove $NH_4Cl$. The ether solution was dried over anhydrous $MgSO_4$ and concentrated in vacuo to afford a white solid. The material was dissolved in 30 mL of $CH_2Cl_2$ and triturated with addition of 150 mL of pertane. A white crystalline solid resulted which was collected by filtration, dried in vacuo, and identified as glycine tert-butyl ester-benzophenone imine by $^1$H-NMR yield=15.0 g (85%), m.p. 110–112° C.

EXAMPLE 17

2-Iodobenzyl Bromide

To a dry 100 mL 3-necked flask equipped with a nitrogen inlet and a magnetic stirrer were added 5.00 g of 2-iodobenzyl alcohol (Aldrich) and 20 mL of anhydrous $CH_2Cl_2$. The resulting suspension was cooled to 0° C. and treated with 0.71 mL of $PBr_3$ (Aldrich) by dropwise addition over a 2 minute period. The solid slowly dissolved giving a light yellow solution which was stirred under nitrogen at 0° C. for 2 h and then allowed to warm to RT with continued stirring for 18 h. The solution was concentrated in vacuo to dryness and the residue was dissolved in 60 mL of ethyl ether. The ether solution was washed with ice cold 5% aqueous $NaHCO_3$ (3×50 mL), dried over anhydrous $Na_2SO_4$, and concentrated in vacuo to afford 5.65 g (89%) of 2-iodobenzyl bromide as a white crystalline solid, m.p. 52–54° C.

EXAMPLE 18

2-Iodo-L-phenylalanine tert-butylester-benzophenone imine

A 500 mL 3-necked flask equipped with a nitrogen inlet and a magnetic stirrer was charged with 20.00 g of glycine tert-butyl ester-benzophenone imine, 24.13 g of 2-iodobenzyl bromide, 2.85 g of N-benzylcinchonidinium chloride (Fluka Chemical Corp., Ronkonkoma, N.Y., 11779), and 105 mL of $CH_2Cl_2$. The resulting solution was treated with 110 mL of 50% (W/W) aqueous NaOH and the mixture was stirred vigorously at RT under nitrogen. After 24 h, tlc (silica gel, 7:1 hexane:EtOAc) indicated a major new component at $R_f$=0.65, unreacted starting material at $R_f$32 0.85 and three minor components at $R_f$=0.20–0.45. The $CH_2Cl_2$ phase was separated, washed with water (3×70 mL), dried over anhydrous $Na_2SO_4$ and concentrated in vacuo to afford a thick pink oil. The crude product was subjected to flash chromatography on 550 g of silica gel eluting with 7:1 hexane:EtOAc (column was pretreated by passing through two column volumes of 0.5% $Et_3N$ in 7:1 hexane:EtOAc) to give 26.4 g (76%) of the desired enantiomer mixture as identified by $^1$H-NMR. The product was determine to by a mixture of two enantiomers by chiral HPLC (Pirkle phenylglycine, 99:1 hexane: isopropanol, flow rate=1 mL/min): K'=3.66 (76%), K'=3.28 (24%). The mixture was dissolved in 160 mL of hexane and allowed to crystallize at 4° C. for 2 days. The solid was separated by filtration and dried in vacuo to afford 10.72 g (31%) of racemic material. The filtrate was concentrated in vacuo to give 15.72 g (45%) of enantioenriched material (2-iodo-L-phenylalanine tert-butyl ester-benzophenone imine, ee=86%) as a transparent, viscous oil. The product was used in subsequent steps without further purification.

$^1$H-NMR: (200 MHz, $CDCl_3$) d 7.72 (d, 1H, J=7.8, aromatic CH), 7.60 (m, 2H, aromatic CH), 7.41–7.21 (m, 6H, aromatic CH), 7.19 (m, 2H, aromatic CH), 6.86 (m, 1H, aromatic CH), 6.55 (d, 2H, J=6.6, aromatic CH), 4.34 (dd; 1H; J=3.9, 9.6; methine), 3.48–3.21 (m, 2H, Ar—$CH_2$), 1.47 (s, 9H, t—Bu).

Mass Spectrum: (Cl, $CH_4$) 512 (M+H)$^+$, 484, 456, 410, 384, 217.

EXAMPLE 19

2Iodo-L-phenylalanine

A 500 mL round bottomed flask equipped with a reflux condenser and a magnetic stirrer was charged with 15.72 g of 2-iodo-L-phenylalanine tert-butyl ester-benzophenone imine (86% ee) and 165 mL of 6 N aqueous HCl. The mixture was heated at reflux with stirring for 4 h and cooled to RT to afford a mixture of white crystalline solid and an immicible organic phase (benzophenone). The mixture was partitioned between water (100 mL) and ethyl ether (70 mL). The aqueous phase was separated, washed with four additional 70 mL portions of ether and concentrated in vacuo to dryness to give 9.5 g (94%) of 2-iodo-L-phenylalanine HCl as a fluffy white solid, m.p. 240° C. (dec).

$^1$H-NMR: (300 MHz, DMSO-d$_6$) δ 8.90–8.23 (br s, 3H, —$NH_3^+$), 7.88 (d, 1H, J=8.1, aromatic CH), 7.39 (m, 2H, aromatic CH), 7.04 (m, 1H, aromatic CH), 4.06 (t, 1H, J=7.4, methine), 3.23 (m, 2H, Ar—$CH_2$).

EXAMPLE 20

Methyl 2-iodo-L-phenylalaninate

To a 500 mL 3-necked flask equipped with a magnetic stirrer and a reflux condenser were added 5.00 g of 2-iodo-L-phenylalanine HCl and 100 mL of anhydrous MeOH. The mixture was stirred and acidified by bubbling HCl gas through for 3 min. A clear solution resulted which was heated at reflux for 5 h. The solution was cooled to RT and concentrated in vacuo to dryness to give a white solid. The material was suspended in 120 mL of $CH_2Cl_2$ and washed with 5% aqueous $NaHCO_3$ (4×80 mL). The $CH_2Cl_2$ solution was concentrated to a volume of 20 mL, diluted to 60 mL with ethyl ether and treated with 16 mL ethereal HCl. A white solid precipitated which was collected by vacuum filtration and dried in vacuo to afford 4.90 g (94%) of methyl 2-iodo-L-phenylalaninate HCl, m.p. 194–196° C.

EXAMPLE 21

Methyl N-((benzyloxy)carbonyl)-5-O-methyl-L-glutam-1-yl-2-iodo-L-phenylalaninate A dry 500 mL 3-necked flask equipped with a nitrogen inlet and a magnetic stirrer was charged with 3.00 g of methyl 2-iodo-L-phenylalaninate HCl, 2.59 g of N-((benzyloxy)carbonyl)-5-O-methyl-L-glutamic acid and 80 mL of $CH_2Cl_2$. The mixture was cooled to 0° C. in an ice water bath and was treated with 0.97 mL of N-methylmorpholine followed by 1.77 g of EDC (Aldrich). The reaction mixture was stirred at 0° C. for 1 h and allowed to warm to RT with continued stirring for an additional 3 h. The solution was diluted with 100 mL of $CH_2Cl_2$, washed with 5% aqueous citric acid (3×70 mL), 5% aqueous $NaHCO_3$ (3×70 mL), and dried over anhydrous $Na_2SO_4$. Removal of the drying agent by filtration followed by in vacuo concentration of the filtrate afforded 4.30 g (84%) of an off-white crystalline solid, m.p. 100–112° C. Examination by $^1$H-NMR indicated methyl N-((benzyloxy)carbonyl)-5-O-methyl-L-glutam-1yl-2-iodo-L-phenylalaninate contaminated with approximately 4% of the (S,R)-diastereomer. The crude product was recrystallized twice from 1:1 EtOH—$H_2O$ to give 3.47 g (68%) of pure (S,S)-diastereomer as a white crystalline solid, m.p. 114–116° C.

EXAMPLE 22

Methyl N-((benzyloxy)carbonyl)-5-O-methyl-L-glutam-1-yl-2-(methoxycarbonyl)-L-phenylalaninate To a dry 100 mL 3-necked flask equipped with a thermometer, a magnetic stirrer, and a reflux condenser were added 1.50 g of methyl N-((benzyloxy)carbonyl)-5-O-methyl-L-glutam-1-yl-2-iodo-L-phenylalaninate, 0.149 g of $Pd(Ph_3P)_4$ (Aldrich), and 35 mL of 1:1 MeOH:THF under a nitrogen flush. The solution was deoxygenated by bubbling nitrogen through for 10 min and was then saturated with CO by bubbling CO through for 10 min. The solution changed color from yellow to bright orange during this period. The reaction vessel was put under CO balloon pressure by attaching a CO filled balloon to the condenser via a gas inlet adapter. The reaction mixture was heated to 60° C. with stirring. After 3 h, analysis by tlc ($SiO_2$, 1:1 hexane:EtOAc) indicated no remaining starting material, a new component at $R_f$=0.40, and two minor components at $R_f$=0.90–0.95. The solution was cooled to RT and concentrated in vacuo to give a yellow solid. This material was purified by flash chromatography on 85 g of silica gel (1:1 hexane:EtOAc) to afford 1.23 g (93%) of methyl N-((benzyloxy)carbonyl)-5-O-methyl-L-glutam-1-yl-2-(methoxycarbonyl)-L-phenylalaninate as a white crystalline solid, m.p. 128–130° C.

EXAMPLE 23

Methyl 5-O-methyl-L-glutam-1-yl-2-(methoxycarbonyl)-L-phenylalaninate

According to example 10, 1.10 g of methyl N-((benzyloxy)carbonyl)-5-O-methyl-L-glutam-1-yl-2-(methoxycarbonyl)-L-phenylalaninate was hydrogenolyzed in the presence of 0.214 g of 10% Pd(C) and 0.18 mL of acetyl chloride to afford 0.86 g (97%) of methyl-5-O-methyl-L-glutam-1-yl-2-(methoxycarbonyl)-L-phenylalaninate HCl as a light yellow foam, m.p. 77–80° C.

EXAMPLE 24

Methyl N-(N-(4-(((1,2-dihydro-3-methyl-1-oxo-benzo(f)quinazolin-9-yl)methyl)-amino)-2-fluorobenzoyl)-5-O-methyl-L-glutam-1-yl)-2-(methoxycarbonyl)-L-phenylalaninate According to example 11, 0.50 g of 4-(((1,2-dihydro-3-methyl-1-oxobenzo(f)quinazolin-9-yl)methyl)amino)-2-fluorobenzoic acid was coupled with 0.55 g of methyl 5-O-methyl-L-glutam-1-yl-2-(methoxycarbonyl)-L-phenylalaninate HCl using 0.17 mL of isobutyl chloroformate and 0.14 mL (2x) of N-methylmorpholine. The crude product was purified by flash chromatography on 250 g of silica gel (97:3→95.5 $CH_2Cl_2$:MeOH) to afford 0.29 g (30%) of methyl N-(N-(4-(((1,2-dihydro-3-methyl-1-oxo-benzo(f)quinazolin-9-yl)methyl)amino)-2-fluorobenzoyl)-5-O-methyl-L-glutam-1-yl)-2-(methoxycarbonyl)-L-phenylalaninate as a white powder, m.p. 180° C. (dec).

$^1$H-NMR: (300 MHz, DMSO-$d_6$) δ 12.52 (s,1H, benzaquinazoline NH), 9.86 (s, 1H, aromatic CH), 8.52 (d, 1H, J=7.6, amide NH), 8.23 (d, 1H, J=8.8, aromatic CH), 8.03 (d, 1H, J=8.4, aromatic CH), 7.80 (d, 1H, J=7.2, aromatic CH), 7.59 (m, 2H, aromatic CH, 4-amino-benzoyl NH), 7.50 (t, 1H, J=7.6, aromatic CH), 7.44–7.21 (m, 5H, aromatic CH, amide NH), 6.53 (d, 1H, J=8.0, aromatic CH), 6.40 (d, 1H, J=14.5, aromatic CH), 4.58 (m, 3H, benzoquinazoline 9-$CH_2$, methine), 4.45 (m, 1H, methine), 3.82(s, 3H, $ArCO_2CH_3$), 3.57 (s, 3H, $CO_2CH_3$), 3.55 (s, 3H, $CO_2CH_3$), 3.48 (m, 1H, phe Ar—$CH_2$), 3.10 (m, 1H, phe Ar—$CH_2$), 2.45 (s, 3H, $CH_3$), 2.27 (t, 2H, J=7.5, glu 4-$CH_2$), 2.01–1.72 (m, 2H, glu 3-$CH_2$).

EXAMPLE 25

N-(N-(4-(((1,2-Dihydro-3-methyl-1-oxobenzo(f)quinazolin-9-yl)methyl)amino)-2-fluorobenzoyl)-L-glutam-1-yl)-2-carboxy-L-phenylalanine A 50 mL 3-necked flask equipped with a nitrogen inlet and a magnetic stirrer was charged with 0.11 g of methyl N-(N-(4-(((1,2-dihydro-3-methyl-1-oxo-benzo(f)quinazolin-9-yl)methyl)amino)-2-fluorobenzoyl)-5-O-methyl-L-glutam-1-yl)-2-(methoxycarbonyl)-L-phenylalaninate and 15 mL of 1:1 THF:$H_2O$. The solution was treated with 62 mg of LiOH (Fisher Scientific Co., Fair Lawn, N.J.) and stirred at RT under nitrogen. After 18 h, analysis by HPLC (C18, 70:30:0.1 $H_2O$:MeCN:TFA) showed no remaining starting material (k'=4.89), a new component at K'=2.29 (92%), and three minor components between k'=0.72 and 1.13. The solution was concentrated in vacuo to 7 mL and subjected to semipreparative HPLC (C18, 80:20:0.1æ70:30:0.1 $H_2O$:MeCN:TFA over 25 min). Pure fractions (as determined by analytical HPLC) were combined and concentrated in vacuo to dryness. The residue was dissolved in 20 mL of 0.17 M aqueous LiOH, filtered, and acidified to pH=3.5 by addition of 1 N aqueous HCl. A white solid resulted which was separated by centrifugation and washed with four cycles of aqueous suspension-centrifugation-decantation. The product was suspended in 10 mL of water, frozen, and lyophilized to afford 60 mg (56%) of N-(N-(4-(((1,2-dihydro-3-methyl-1-oxobenzo(f)quinazolin-9-yl)methyl)amino)-2-fluorobenzoyl)-L-glutam-1-yl)-2-carboxy-L-phenylalanine as a fluffy white solid, m.p. 245° C. (dec).

HPLC: one peak on C18, K'=1.86, 70:30:0.1 $H_2O$:MeCN:TFA, flow rate=1 mL/min.

$^1$H-NMR: (300 MHz, DMSO-$d_6$) δ 13.00–11.70 (br s, COOH), 12.54 (s, 1H, benzoquinazopline NH), 9.84 (s, 1H, aromatic CH), 8.35 (d, 1H, J=7.9, amide NH), 8.22 (d, 1H, J=9.1, aromatic CH), 8.01 (d, 1H, J=8.2, aromatic CH), 7.78 (d, 1H, J=7.8, aromatic CH), 7.60 (m, 2H, aromatic CH, 4-aminobenzoyl NH), 7.50 (t, 1H, J=7.8, aromatic CH), 7.45–7.18 (m, 5H, aromatic CH, amide NH), 6.53 (d, 1H, J=8.5, aromatic CH), 6.39 (d, 1H, J=14.7, aromatic CH), 4.67–4.46 (m, 3H, benzoquinazoline 9-$CH_2$, methine), 4.41 (m, 1H, methine), 3.55 (dd; 1H; J=4.0, 12.3; phe Ar—$CH_2$), 3.06 (dd, 1H, J=10.2, 12.9; phe Ar—$CH_2$), 2.42 (s, 3H, $CH_3$), 2.16 (t, 2H, J=7.3, glu 4-$CH_2$), 1.98–1.64 (m, 2H, glu 3-$CH_2$).

Elemental Analysis: Calcd. for $C_{36}H_{32}N_5O_9F \cdot H_2O$ (MW 715.69): C, 60.42; H, 4.79; N, 9.79. Found C, 60.49; H, 4.83; N, 9.76.

Mass Spectrum: (Ion Spray) 698 (M+H)$^+$, 489, 361.

UV Spectrum: (pH7 Buffer) $\lambda_{max}$ ($\epsilon$) 265.3 (43700), 298.4 (25600), 347.9 (5320). $1_{min}(e)$ 241.5 (20300), 284.9 (24600), 340.0 (3140).

EXAMPLE 26

Methyl N-(4-(((2,4-diamino-6-pteridinyl)methyl) methylamino)benzoyl)-5-O-methyl-L-glutam-1-yl-2-(methoxycarbonyl)-L-phenylalaninate According to example 13, 0.29 g of 4-(N-(2,4-diamino-6-pteridinylmethyl)-N-methylamino)benzoic acid hemihydrochloride dihydrate (Aldrich) was reacted with 0.32 g of methyl 5-O-methyl-L-glutam-1-yl-2-(methoxycarbonyl)-L-phenylalaninate HCl using 0.35 mL of DECP (Aldrich) and 0.58 mL of Et$_3$N. The crude product was purified by flash chromatography on 100 g of silica gel (7:7:1 CH$_2$Cl$_2$:acetone:MeOH) to afford 0.27 (51%) of methyl N-(4-(((2,4-diamino-6-pteridinyl)methyl)methylamino) benzoyl)-5-O-methyl-L-glutam-1-yl-2-(methoxycarbonyl)-L-phenylalaninate as a yellow powder, m.p. 125–130° C.

EXAMPLE 27

N-(N-(4-(((2,4-Diamino-6-pteridinyl)methyl) methylamino)benzoyl)-L-glutam-1-yl)-2-carboxy-L-phenylalanine To a 50 mL 3-necked flask equipped with a magnetic stirrer and a nitrogen inlet were added 0.12 g of methyl N-(4-(((2,4-diamino-6-pteridinyl)methyl)methylamino) benzoyl)-5-O-methyl-L-glutam-1-yl)-2-(methoxycarbonyl)-L-phenylalaninate and 10 mL of 1:1 H$_2$O:THF. The mixture was treated with 29 mg of LiOH.H$_2$O (J. T. Baker Chemical Co., Phillipsburg, N.J.) and stirred at RT under nitrogen. After 48 h, analysis by HPLC (C18, 75:25:0.1 H$_2$O:MeCN:TFA) indicated a major new component at k'=1.70 (ca. 90%) and three minor components at K'=0.60, 1.03, and 2.58. The solution was neutralized by dropwise addition of 1 N aqueous HCl and concentrated in vacuo to dryness. The residue was dissolved in 10 mL of MeOH was removed by rotary evaporation and the remaining suspension was frozen and lyophilized to afford 65 mg (45%) of N-(4-(((2,4-diamino-6-pteridinyl)methyl)methylamino) benzoyl)-L-glutam-1-yl)-2-carboxy-L-phenylalanine as a yellow powder, m.p. 160° C. (dec).

HPLC: two peaks on C18, K'=2.49 (98%), k'=5.65 (2%); 78.22:0.1 H$_2$O:MeCN:TFA; flow rate=1 mL/min.

$^1$H-NMR: (300 MHz, DMSO-d$_6$) δ 13.10–11.90 (br5, COOH), 8.64 (s, 1H, pteridinyl 7-CH), 8.62 (br s, 1H, NH$_2$), 8.18 (d, 1H, J=8.0, amide NH), 7.92 (d, 1H, J=8.0, amide NH), 7.80–7.20 (br m, 2H, NH$_2$), 7.77 (d, 1H, J=7.3, aromatic CH), 7.70 (d, 2H, J=8.9, aromatic CH), 7.25 (m, 3H, aromatic CH), 6.81 (d, 2H, J=9.0, aromatic CH), 4.84 (s, 2H, pteridinyl-CH$_2$), 4.49 (m, 1H, methine), 4.39 (m, 1H, methine), 3.51 (m, 1H, phe Ar—CH$_2$), 3.24 (s, 3H, N—CH$_3$), 3.08 (m, 1H, phe AR—CH$_2$), 2.19 (t, 2H, J=7.6, glu 4-CH$_2$), 1.97–1.72 (m, 2H, glu 3-CH$_2$).

Elemental Analysis: Calcd. for $C_{30}H_{31}N_9O_8 \cdot 2.7H_2O \cdot 1.2TFA$ (MW 831.10): C, 46.82; H, 4.56; N, 15.17. Found C, 46.76; H, 4.48; N, 15.15.

Mass Spectrum: (Ion Spray) 646 (M+H)$^+$, 410, 369, 185.

UV Spectrum: (pH7 Buffer) $\lambda_{max}$ ($\epsilon$) 258.8 (23400), 307.0 (24200), 372.8 (7540). $1_{min}(e)$ 242.0 (16000), 273.2 (16200), 344.3 (5900).

EXAMPLE 28

Dimethyl N-((benzyloxy)carbonyl)-5-O-methyl-L-glutam-1-yl-L-aspartate

According to example 9, 2.01 g of L-aspartic acid dimethylester HCl (Sigma) was coupled with 3.00 g of N-((benzyloxy)carbonyl)-5-O-methyl-L-glutamic acid using 2.05 g of EDC (Aldrich) and 1.12 mL of N-methylmorpholine. This gave 3.03 g (88%) of dimethyl N-((benzyloxy)carbonyl)-5-O-methyl-L-glutam-1-yl-L-aspartate as a crystalline white solid, m.p. 86–88° C.

EXAMPLE 29

Dimethyl 5-O-methyl-L-glutam-1-yl-L-aspartate

According to example 10, 2.00 g of dimethyl N-((benzyloxy)carbonyl)-5-O-methyl-L-glutam-1-yl-L-aspartate was hydrogenolyzed in the presence of 0.45 g of 10% Pd(C) and 0.39 mL of acetyl chloride to afford 1.56 g (100%) of dimethyl 5-O-methyl-L-glutam-1-yl-L-aspartate HCl as a light yellow foam.

$^1$NMR: (200 MHz, DMSO-d$_6$) δ 9.14 (d, 1H, J=7.4, NH), 8.40 (br s, 3H, NH$_3^+$), 4.72 (m, 1H, glu methine), 3.89 (m, 1H, asp methine), 3.66 (s, 3H, CO$_2$CH$_3$), 3.65 (s, 3H, CO$_2$CH$_3$), 3.64 (s, 3H, CO$_2$CH$_3$), 2.85 (d, 2H, J=6.2, asp CH$_2$), 2.49 (m, 2H, glu 4-CH$_2$), 2.04 (m, 2H, glu 3-CH$_2$).

EXAMPLE 30

Dimethyl N-(N-(4-(((1,2-dihydro-3-methyl-1-oxo-benzo(f)quinazolin-9-yl)methyl)amino)-2-fluorobenzoyl)-5-O-methyl-L-glutam-1-yl)-L-aspartate According to example 11, 0.50 g of 4-(((1,2-dihydro-3-methyl-1-oxobenzo(f)quinazolin-9yl)methyl)amino)-2-fluorobenzoic acid was coupled with 0.45 g of dimethyl 5-O-methyl-L-glutam-1-yl-L-aspartate HCl using 0.17 mL of isobutyl chloroformate and 0.14 mL (2x) of N-methyl morpholine. The crude product was purified by flash chromatography on 250 g of silica gel (95:5 CH$_2$Cl$_2$:MeOH) to afford 0.33 g (38%) of dimethyl N-(N-(4-(((1,2-dihydro-3-methyl-1-oxo-benzo(f) quinazolin-9-yl)methyl)amino)-2-fluorobenzoyl)-5-O-methyl-L-glutam-1-yl)-L-aspartate as a white powder, m.p. 198–200° C.

$^1$H-NMR: (200 MHz, DMSO-d$_6$) δ 12.54 (s, 1H, benzoquinazoline NH), 9.85 (s, 1H, aromatic CH), 8.55 (d, 1H, J=7.7, amide NH), 8.23 (d, 1H, J=8.8, aromatic CH), 8.02 (d, 1H, J=8.4, aromatic CH), 7.70–7.45 (m, 4H, aromatic CH, amide NH), 7.33 (m, 1H, 4-amino-benzoyl NH), 6.55 (dd; 1H; J=8.8, 1.9; aromatic CH), 6.42 (dd; 1H; J=15.3, 1.7; aromatic CH), 4.72–4.41 (m, 4H, benzoquinazoline 9-CH$_2$, glu and asp methines), 3.62 (s, 3H, CO$_2$CH$_3$), 3.60 (s, 3H, CO$_2$CH$_3$), 3.55 (s, 3H, CO$_2$CH$_3$), 2.91–2.66 (m, 2H, asp CH$_2$), 2.42 (s, 3H, CH$_3$), 2.34 (t, 2H, J=7.7, glu 4-CH$_2$), 2.13–1.80 (m, 2H, glu 3-CH$_2$).

EXAMPLE 31

N-(N-(4-((1,2-Dihydro-3-methyl-1-oxobenzo(f) quinazolin-9-yl)methyl)amino)-2-fluorobenzoyl)-L-glutam-1-yl-L-aspartic acid According to example 12, 0.12 g of dimethyl N-(N-(4-(((1,2-dihydro-3-methyl-1-oxo-benzo(f)quinazolin-9-yl) methyl)amino)-2-fluorobenzoyl)-5-O-methyl-L-glutam-1-yl)-L-aspartic was saponified in 8 mL of 1:1 THF-H$_2$O using 45 mg of LiOH.H$_2$O (Baker). Analysis of the crude product by reverse phase HPLC (C18, 80:20:0.1 H$_2$O:MeCN:TFA) indicated a major component at K'=1.73 (90%) and a minor component at K'=1.28. The material was purified by semi-preparative HPLC using gradient elution (C18, 80:20:0.1→75:25:0.1 H$_2$O:MeCN:TFA over 20 min). Pure fractions (as determined by analytical HPLC) were combined and concentrated in vacuo. The residue was mixed with 20 mL of water and treated with enough LiOH.H$_2$O to dissolve the solid. The solution was filtered and acidified to pH=3.0 by addition of 1 N HCl. A white solid precipitated which was separated by centrifugation, washed with four cycles of aqueous suspension-centrifugation, washed with four cycles of aqueous suspension-centrifugation-decantation, and lyophilized to afford 57 mg (48%) of N-(N-(4-((1,2-dihydro-3-methyl-1-oxobenzo(f)quinazolin-9-yl)methyl)amino)-2-fluorobenzoyl)-L-glutam-1-yl-L-aspartic acid as an off-white solid, m.p. 185° C. (dec).
HPLC: one peak on C18, K'=1.42, 75:25:0.1 H$_2$O:MeCN:TFA, flow rate=1 mL/min.
$^1$H-NMR: (300 MHz, DMSO-d$_6$) δ 12.85–12.00 (br s, COOH), 12.53 (s, 1H, benzoquinazoline NH), 9.84 (s, 1H, aromatic CH), 8.36 (d, 1H, J=7.9, amide NH), 8.21 (d, 1H, J=8.8, aromatic CH), 8.01 (d, 1H, J=8.3, aromatic CH), 7.67–7.46 (m, 4H, aromatic CH, amide NH), 7.32 (m, 1H, 4-aminobenzoyl NH), 6.53 (d, 1H, J=8.5, aromatic CH), 6.40 (d, 1H, J=14.8, aromatic CH), 4.64–4.44 (m, 4H, benzoquinazoline 9-CH$_2$, glu methine, asp methine), 2.75–2.53 (m, 2H, asp CH$_2$), 2.42 (s, 3H, CH$_3$), 2.25 (t, 2H, J=7.3, glu 4-CH$_2$), 1.98 (m, 1H, glu 3-CH$_2$), 1.83 (m, 1H, glu 3-CH$_2$).
Elemental Analysis: Calcd. for C$_{30}$H$_{28}$N$_5$O$_9$F.1.8H$_2$O (MW 654.01): C, 55.10; H, 4.87; N, 10.71. Found: C, 55.04; H, 4.82; N, 10.61.
Mass Spectrum: (Ion Spray) 622 (M+H)$^+$, 316, 213, 156.
UV Spectrum: (pH7 Buffer) $\lambda_{max}$ (ε) 264.8 (46200), 298.4 (28500), 347.8 (6180).
$1_{min}$(ε) 237.9 (19500), 285.7 (27900), 340.0 (3820).

EXAMPLE 32

Dimethyl N-(4-(((2,4-diamino-6-pteridinyl)methyl)methylamino)benzoyl)-5-O-methyl-L-glutam-1-yl)-L-aspartate According to example 13, 0.200 g of 4-(2,4-diamino-6-pteridinylmethyl)-N-methylamino)benzoic acid hemihydrochloride dihydrate (Aldrich) was coupled with 0.18 g of dimethyl 5-O-methyl-L-glutam-1-yl-L-aspartate HCl using 0.24 mL of DECP (Aldrich) and 0.41 mL of Et$_3$N. The crude product was purified by flash chromatography on 100 g of silica gel (7:7:1 CH$_2$Cl$_2$:acetone:MeOH) to afford 0.17 g (53%) of dimethyl N-(4-(((2,4-diamino-6-pteridinyl)methyl)methylamino)benzoyl)-5-O-methyl-L-glutam-1-yl)-L-aspartate as a yellow powder, m.p. 130–135° C.

EXAMPLE 33

N-(4-(((2,4-Diamino-6-pteridinyl)methyl)methylamino)benzoyl)-L-glutam-1-yl-L-aspartic acid (Procedure A)

For Procedure B to prepare this compound, see Example 125.

A 50 mL 3-necked flask equipped with a magnetic stirrer and a nitrogen inlet was charged with 0.16 g of dimethyl N-(4-(((2,4-diamino-6-pteridinyl)methyl)methylamino) benzoyl)-5-O-methyl-L-glutam-1-yl)-L-aspartate and 10 mL of 1:1 THF:H$_2$O. The solution was treated with 44 mg of LiOH.H$_2$O (Baker) and stirred at RT under N$_2$. After 3 h, tlc (SiO$_2$, 7:7:1 CH$_2$Cl$_2$: acetone:MeOH) indicated no remaining starting material at R$_f$=0.30 and a single spot at R$_f$=0.0. Analysis by reverse phase HPLC (C18, 85:15:0.1 H$_2$O:MeCN:TFA) indicated a major component at k'=2.65 (90%) and a minor component at k'=1.94. The solution was neutralized by addition of 1 N HCl and concentrated in vacuo to dryness. The crude product was purified by semi-preparative HPLC (C18, 87:13:0.1 H$_2$O:MeCN:TFA). Pure fractions (as determined by analytical HPLC) were combined and concentrated in vacuo to dryness. The residue was dissolved in 20 mL of H$_2$O and lyophilized to afford 65 mg (32%) of N-(4-(((2,4-diamino-6-pteridinyl)methyl)methylamino)benzoyl)-L-glutam-1-yl-L-aspartic acid as a yellow-orange powder, m.p. 165–180° C. (dec).
HPLC: one peak on C18, k'=2.45, 85:15:0.1 H$_2$O:MeCN:TFA, flow rate=1 mL/min. $^1$H-NMR: (300 MHz, DMSO-d$_6$) δ 13.00–11.85 (br s, COOH), 9.17 (br, s, 1H, NH$_2$), 8.96 (br, s, 1H, NH$_2$), 8.71 (s, 1H, pteridinyl 7-CH), 8.60–8.30 (br, s, 1H, NH$_2$), 8.21 (d, 1H, J=8.0, amide NH), 8.06 (d, 1H, J=7.8, amide NH), 7.85–7.43 (br s, 1H, NH$_2$), 7.75 (d, 2H, J=8.7, aromatic CH), 6.82 (d, 2H, J=8.8, aromatic CH), 4.87 (s, 2H, pteridinyl-CH$_2$), 4.59–4.38 (m, 2H, 2 methines), 3.25 (s, 3H, N—CH$_3$), 2.75–2.53 (m, 2H, asp CH$_2$), 2.28 (t, 2H, J=7.5, glu 4-CH$_2$), 2.01 (m, 1H, glu 3-CH$_2$), 1.88 (m, 1H, glu 3-CH$_2$).
Elemental Analysis: Calcd. for C$_{24}$H$_{27}$N$_9$O$_8$.1.9H$_2$O.1.6TFA (MW 786.20): C, 41.55; H, 4.15; N, 16.03. Found: C, 41.53; H, 4.19; N, 16.00
Mass Spectrum: (Ion Spray) 570 (M+H)$^+$, 223.
UV Spectrum: (pH7 Buffer)$\lambda_{max}$ (ε) 258.7 (24400), 307.3 (26800), 372.9 (8080). $1_{min}$(ε) 240.0 (14800), 272.9 (17000), 345.0 (6420).

EXAMPLE 34

Diethyl N-((benzyloxy)carbonyl)-5-O-ethyl-L-glutam-1-yl-L-glutamate

According to example 9, 3.17 g of L-glutamic acid diethyl ester HCl (Sigma) was coupled with 4.09 g of N-((benzyloxy)carbonyl)-5-O-ethyl-L-glutamic acid using 2.66 g of EDC (Aldrich) and 1.45 mL of N-methylmorpholine. This gave 4.80 g (74%) of diethyl N-((benzyloxy)carbonyl)-5-O-ethyl-L-glutam-1-yl-L-glutamate as a white crystalline solid, m.p. 104° C.

EXAMPLE 35

Diethyl 5-O-ethyl-L-glutam-1-yl-L-glutamate

To a 500 mL Parr bottle were added 0.75 of diethyl N-((benzyloxy)carbonyl)-5-O-ethyl-L-glutam-1-yl-L-glutamate, 0.14 g of 10% Pd(C) and 60 mL of EtOH under a N$_2$ flush. The mixture was deoxygenated by bubbling N$_2$ through for 7 min, treated with 1.52 mL of 1 M ethereal HCl, and hydrogenated at 45 psi for 18 h. The bottle was purged with N$_2$, catalyst was removed by filtration through celite, and the filtrate was concentrated in vacuo to dryness to afford 0.60 (99%) of diethyl 5-O-ethyl-L-glutam-1-yl-L-glutamate HCl as a light yellow foam. $^1$H-NMR: (300 MHz, DMSO-d$_6$) δ9.11 (d, 1H, J=7.5, NH), 8.41 (br s, 3H, NH$_3$$^+$), 4.32 (m, 1H, methine), 4.06 (m, 6H, ethyl CH$_2$), 3.92 (m, 1H, methine), 2.47 (m, 4H, glu 4-CH$_2$), 2.12–1.79 (m, 4H, glu 3-CH$_2$), 1.19 (t, 9H, J=7.1, ethyl CH$_3$).

EXAMPLE 36

Diethyl N-(N-(4-(((1,2-dihydro-3-methyl-1-oxobenzo(f)quinazoling-9-yl)methyl)amino)-2-fluorobenzoyl)-5-O-ethyl-L-glutam-1-yl)-L-glutamate According to example 11, 0.57 g of 4-(((1,2-dihydro-3-methyl-1-oxobenzo(f)quinazoling-9yl)methyl)amino)-2- fluorobenzoic acid was coupled with 0.60 g of diethyl 5-O-ethyl-L-glutam-1-yl-L-glutamate HCl using 0.20 mL of isobutyl chloroformate and 0.17 mL (2×) of N-methylmorpholine. The crude product was purified by flash chromatography on 350 g of silica gel (EtOAc→98:2 EtOAc:MeOH) to afford 0.27 g (25%) of diethyl N-(N-(4-(((1,2-dihydro-3-methyl-1-oxobenzo(f)quinazoling-9-yl)methyl)amino)-2fluorobenzoyl)-5-O-ethyl-L-glutam-1yl)-L-glutamate as a white powder, m.p. 185–187° C.

EXAMPLE 37

N-(N-(4-(((1,2-Dihydro-3methyl-1-oxobenzo(f) quinazoline-9-yl)methyl)amino)-2fluorobenzoyl)-L-glutam-1-yl)-L-glutamic acid A 250 mL 3-necked flask equipped with a magnetic stirrer and a nitrogen inlet was charged with 0.217 g of diethyl N-(N-(4-(((1,2-dihydro-3methyl-1-oxobenzo(f)quinazoling-9-yl)methyl)amino)-2-fluorobenzoyl)-5-O-ethyl-L-glutam-1-yl)-L-glutamate, 40 mL of 0.2 N aqueous NaOH, and 15 mL of EtOH. The mixture was stirred at RT under $N_2$. The solid starting material slowly dissolved to give a clear solution. After 2 h, tlc ($SiO_2$, EtOAc) indicated no remaining starting material at $R_f$=0.15 and a new spot at $R_f$=0.0. The solution was acidified to pH=3.00 by addition of 1 N HCl. A white solid precipitated which was separated by centrifugation, washed with four cycles of aqueous suspension-centrifugation-decantation, and lyophilized to afford 0.17 g (84%) of N-(N-(4-(((1,2-dihydro-3-methyl-1-oxobenzo(f)quinazolin-9-yl)methyl)amino)-2-fluorobenzoyl)-L-glutam-1yl)-L-glutamic acid as a white powder, m.p. 180° C. (dec). The product was determined to be pure by HPLC. HPLC: one peak on C18, K'=1.66, 75:25:0.1 $H_2O$:MeCN:TFA, flow rate=1 mL/min. $^1$H-NMR: (300 MHz, DMSO-$d_6$) δ12.65-11.90 (br s, COOH), 12.53 (s, 1 H, benzoquinazoline NH), 9.84 (s, 1 H, aromatic CH), 8.29 (d, 1 H, J=7.5, amide NH), 8.22 (d, 1 H, J=8.9, aromatic CH), 8.01 (d, 1 H, J=8.0, aromatic CH), 7.60 (m, 3 H, aromatic CH, amide NH), 7.51 (t, 1 H, J=9.0, aromatic CH), 7.33 (m, 1 H, 4-aminobenzoyl NH), 6.54 (dd; 1 H; J=8.5, 1.9; aromatic CH), 6.41 (dd; 1 H; J=13.9, 1.4; aromatic CH), 4.57 (d, 2 H, J=5.2, benzoquinazoline 9$CH_2$), 4.49 (m, 1 H, methine), 4.22 (m, 1 H, methine), 2.43 (s, 3 H, $CH_3$), 2.28 (m, 4 H, glu 4-$CH_2$), 2.10-1.70 (m, 4 H, glu 3-$CH_2$). Elemental Analysis: Calcd. for $C_{31}H_{30}N_5O_9F.2H_2O$ (MW 671.64): C, 55.44; H, 5.10; N, 10.43. Found: C, 55.38; H, 5.12; N, 10.26.

Mass Spectrum: (FAB) 636 (M+H)$^+$, 613, 581, 549.

UV Spectrum: (pH7 Buffer) $\lambda_{max}$ (ε) 264.9 (45100), 296.1 (28000), 331.4 (7280), 348.1 (5990). $1_{min}^{(e)}$ 285.6 (27200), 329.3 (7040), 339.8 (3700). $^1sh^{(e)}$ 271.5 (41900).

EXAMPLE 38

Diethyl N-(4-(((2,4-diamino-6-pteridinyl)methyl) methylamino)benzoyl)-5-O-ethyl-L-glutam-1-yl-L-glutamate According to example 13, 0.142 g of 4-(N-(2,4-diamino-6-pteridinylmethyl)-N-methylamino)benzoic acid hemihydrochloride dihydrate (Aldrich) was coupled with 0.15 g of diethyl 5-O-ethyl-L-glutam-1-yl-L-glutamate-HCl using 0.18 mL of DECP (Aldrich) and 0.31 mL of $Et_3N$. The crude product was purified by flash chromatography on 120 g of silica gel (7:71 $CH_2Cl_2$:acetone:MeOH) to afford 0.14 g (56%) of diethyl N-(4-(((2,4-diamino-6-pteridinyl)methyl) methylamino)benzoyl)-5-O-ethyl-L-glutam-1-yl-L-glutamate as a yellow powder, m.p. 105–109° C.

EXAMPLE 39

N-(4-(((2,4-Diamino-6-pteridinyl)methyl) methylamino)benzoyl)-L-glutam-1-yl-L-glutamic acid (Procedure A)

For Procedure B to prepare this compound, see Example 129. According to example 33, 0.125 g of diethyl N-(4-(((2, 4-diamino-6-pteridinyl)methyl)methylamino)benzoyl)-5-O-ethyl-L-glutam-1yl-L-glutamate was saponified in 10 mL of 1:1 THF:$H_2O$ using 23 mg of LiOH (Fisher). After stirring at RT under $N_2$ for 18 h, the solution was acidified to pH=2.0 by addition of 1 N HCl and was then concentrated in vacuo to dryness. Analysis of the residue by HPLC (C18, 85:15:0.1 $H_2O$:MeCN:TFA) indicated a major component at K'=2.89 (90%) and two minor components at k'=2.46 and 1.17. The crude product was purified by semi-preparative HPLC (C18, 87:13:0.5 $H_2O$:MeCN:TFA) and lyophilized to afford 37 mg (24%) of N-(4-(((2,4-diamino-6-pteridinyl)methyl) methylamino)benzoyl)-L-glutam-1-yl-L-glutamic acid as a yellow powder, m.p. 178° C.

HPLC: one peak on C18, K'=2.90, 85:15:0.1 $H_2O$:MeCN:TFA, flow rate=1 mL/min.

$^1$H-NMR: (300 MHz, DMSO-$d_6$) δ 13.20-(br s, COOH), 9.30 (br s, 1 H, $NH_2$), 9.10 (br s, 1 H, $NH_2$), 8.74 (s, 1 H, pteridinyl 7-CH), 8.72-8.42 (br s, 1 H, $NH_2$), 8.20 (d, 1 H, J=7.5, amide NH), 8.07 (d, 1H, J=7.5, amide NH), 7.76 (d, 2 H, J=32 8.8, aromatic CH), 7.61-7.40 (br s, 1 H, $NH_2$), 6.83 (d, 2 H, J=8.8, aromatic CH), 4.90 (s, 2 H, pteridinyl-$CH_2$), 4.43 (m, 1 H, methine), 4.20 (m, 1 H, methine), 3.27 (s, 3 H, N-$CH_3$), 2.30 (m, 4 H, glu 4-$CH_2$), 2.08-1.77 (m, 4 H, glu 3-$CH_2$).

Elemental Analysis: Calcd. for $C_{25}H_{29}N_9O_8.2.3H_2O.1.7TFA$ (MW 818.84): C, 41.66; H, 4.35; N, 15.40. Found C, 41.61; H, 4.25; N, 15.44.

Mass Spectrum: (FAB) 584 (M+H)$^+$, 309, 275, 176, 55, 119.

UV Spectrum: (pH7 Buffer) $\lambda_{max}$ (ε) 220.9 (20500), 258.5 (21500), 306.7 (23200), 372.5 (7180). $1_{min}(e)$ 240.1 (13400), 272.5 (15100), 344.8 (5730).

EXAMPLE 40

3-Cyano-L-tyrosine

A solution of 5.70 g of 3-amino-L-tyrosine (Aldrich) in 35 mL of 2.15 N aqueous HCl was cooled to 0° C. and treated with a solution of 1.41 g of $NaNO_2$ (Aldrich) in 5 mL of water followed by 2.97 g of $Na_2CO_3$. After stirring at 0° C. for 7 min, the solution was slowly added (via an addition funnel) to a stirred mixture of 3.58 g of CuCN (Aldrich), 5.88 g of NaCN (Aldrich) and 5.72 g of $Na_2CO_3$ in 40 mL of water maintained at 75° C. in a 250 mL 3-necked flask equipped with a condenser. During the addition, vigorous evolution of nitrogen occurred and the reaction mixture changed color to dark red-orange. The reaction mixture was stirred at 75° C. for 2 h, heated to 95° C., and stirred for additional 1 h. After cooling to RT, the reaction mixture was acidified to pH=2.0 by addition of concentrated HCl via the addition funnel. The evolved gas was scrubbed through a 20% aqueous NaOH trap followed by a 5% NaOCl (Chlorox) trap . The mixture was filtered and the pH of the filtrate was adjusted to 6.0 with concentrated $NH_4OH$. The brown solution was mixed with 300 mL of water and stirred with 300 g of DOWEX 50WX-8 ion exchange resin (acid form). The resin was filtered, washed with 1 L of water, mixed with 500 mL of water, and the mixture was basified to pH 11 by addition of concentrated $NH_4OH$. The mixture was filtered and the filrate concentrated in vacuo to dryness. The dark brown residue was suspended in 20 mL of water and treated with enough 1 N aqueous NaOH to dissolve the solid. The pH was then adjusted to 6.0 by addition of 1 N aqueous HCl. A precipitate formed which was collected by filtration and dried in vacuo to afford 1.45 g (35%) of 3-cyano-L-tyrosine as a chocolate brown solid, m.p. >250° C. $^1$H-NMR: (200 MHz, DMSO-d$_6$) δ 9.60-7.20 (br s. NH$_2$), 7.39 (s, 1 H, aromatic CH), 7.30 (m, 1 H, aromatic CH), 6.98 (m, 1 H, aromatic CH), 3.52 (m, 1 H, methine), 2.92 (m, 2 H, ArCH$_2$).

EXAMPLE 41

Methyl 3-(methoxycarbonyl)-L-tyrosinate

A 250 mL 3-necked flask equipped with a reflux condenser and a magnetic stirrer was charged with 1.45 g of 3-cyano-L-tyrosine, 50 mL of concentrated HCl, and 50 mL of water. The solution was heated to reflux with stirring. After 2 days, analysis of the reaction mixture by HPLC (C18, 90:10:0.1 H$_2$O:MeCN:TFA) indicated a major component at k$^1$=2.23 (75%) and a minor component at k$^1$=1.59 (25%). After 4 days HPLC indicated only the k$^1$=2.23 material. The reaction mixture was cooled to RT, filtered, and the filtrate was concentrated in vacuo to dryness to give 1.2 g of 3-carboxy-L-tyrosine as a dark brown solid. IR analysis (nujol) indicated loss of the nitrile stretch of 3-cyano-L-tyrosine, at 2223 cm$^{-1}$. The crude solid was added to 60 mL of anhydrous MeOH in a 250 mL 3-necked flask equipped with a condenser and a magnetic stirrer. The mixture was acidified by bubbling HCl gas through for 5 min and heated to reflux with stirring. After 6 h, the reaction mixture was cooled to RT and neutralized with solid NaHCO$_3$. The mixture was concentrated in vacuo to dryness, mixed with 100 mL of water, and extracted with CH$_2$Cl$_2$ (4×50 mL). The combined extracts were washed with 5% aqueoous NaHCO$_3$ (2×50 mL), dried over anhydrous Na$_2$SO$_4$, and concentrated in vacuo to 10 mL. The solution was diluted with 35 mL of ether and treated with 5.5 mL of 1 M etheral HCl. A solid precipitated which was collected by filtration, washed with ether, and dried in vacuo to afford 0.90 (50%) of methyl 3-(methoxycarbonyl)-L-tyrosinate.HCl as an off-white powder, m.p. 211–213° C.

$^1$H-NMR: (300 MHz, DMSO-d$_6$) δ 10.45 (s, 1 H, OH), 8.59 (br, s, 3 H, NH$_3^+$), 7.66 (s, 1 H, aromatic CH), 7.38 (dd; 1 H: J=7.9, 1.1, aromatic CH), 6.97 (d, 1 H, J=7.9, aromatic CH), 4.26 (m, 1 H, methine), 3.89 (s, 3 H, CO$_2$CH$_3$), 3.68 (s, 3 H, CO$_2$CH$_3$), 3.09 (m, 2 H, ArCH$_2$).

EXAMPLE 42

Methyl N-((benzyloxy)carbonyl)-5-O-methyl-L-glutam-1-yl-3-(methoxycarbonyl)-L-tyrosinate According to example 9, 0.08 g of methyl 3-(methoxycarbonyl)-L-tyrosinate.HCl was coupled with 0.82 g of N-(benzyloxy)carbonyl)-5-O-methyl-L-glutamic acid using 0.56 g of EDC (Aldrich) and 0.30 mL of N-methylmorpholine. This gave 1.24 g (85%) of methyl N-((benzyloxy)carbonyl)-5-O-methyl-L-glutam-1-yl-3-(methoxycarbonyl)-L-tyrosinate as a white solid, m.p. 142–144° C.

EXAMPLE 43

Methyl 5-O-methyl-L-glutam-1-yl-3-(methoxycarbonyl)-L-tyrosinate

According to example 10, 0.99 g of methyl N-((benzyloxy)carbonyl)-5-O-methyl-L-glutam-1-yl-3-(methoxycarbonyl)-L-tyrosinate was hydrogenolyzed using 0.19 g of 10% Pd(C) and 0.15 mL of acetyl chloride in 90 mL of 2:1 EtOH:EtOAc to afford 0.75 g (95%) of methyl 5-O-methyl-L-glutam-1-yl-3-(methoxycarbonyl)-L-tyrosinate.HCl as a light yellow foam, m.p. 95–97° C. (dec).

EXAMPLE 44

Methyl N-(N-(4(((1,2-dihydro-3-methyl-1-oxobenzp (f)quinazolin-9-yl)methyl)amino)-2-fluorobenzoyl)-5-O-methyl-L-glutam-1-yl)-3-(methoxycarbonyl)-L-tyrosinate According to example 11, 0.65 g of 4-(((1,2-dihydro-3-methyl-1-oxobenzo(f)quinazoling-9-yl)methyl)amino)-2) fluorobenzoic acid was coupled with 0.75 g of methyl 5-O-methyl-L-glutam-1-yl-3-(methoxycarbonyl)-L-tyrosinate.HCl using 0.22 mL of isobutyl chloroformate and 0.19 mL (2×) of N-methylmorpholine. The crude product was purified by flash chromatography on 300 g of silica gel (99:1→94:6 EtOAc:MeOH) to afford 0.53 g (40%) of methyl N-(N-(4(((1,2-dihydro-3-methyl-1oxobenzo(f) quinazolin-9-methyl)amino)-2fluorobenzoyl)-5-O-methyl-L-glutam-1-yl)-3-(methoxycarbonyl)-L-tyrosinate as a white powder, m.p. 195–204° C. (dec).

$^1$H-NMR: (300 MHz, DMSO-d$_6$) δ 12.52 (benzoquinazoline NH), 10.38 (s, 1 H, OH), 9.83 (s, 1 H, aromatic CH), 8.45 (d, 1 H, J=7.5, amide NH), 8.21 (d, 1 H, J=8.9, aromatic CH), 8.00 (d, 1 H, J=8.3, aromatic CH), 7.60 (m, 3 H, aromatic CH, 4-aminobenzoyl NH), 7.48 (m, 2 H, aromatic CH), 7.36 (m, 2 H, aromatic CH, amide NH), 6.86 (d, 1 H, J=8.6, aromatic CH), 6.52 (dd; 1 H; J=8.5, 1.9; aromatic CH), 6.39 (dd; 1 H; J=13.9, 1.5; aromatic CH), 4.57 (d 2 H, J=5.6, benzoquinazoline 9-CH$_2$), 4.45 (m, 2 H, methines), 3.84 (s, 3 H, CO$_2$CH$_3$), 3.58 (s, 3 H, CO$_2$CH$_3$), 3.52 (s, 3 H, CO$_2$CH$_3$), 3.05-2.80 (m, 2 H, ArCH$_2$), 2.42 (s, 3 H, CH$_3$), 2.25 (t, 2 H, J=7.8, glu 4-CH$_2$), 2.00-1.77 (m, 2 H, glu 3-CH$_2$).

EXAMPLE 45

3-Carboxy-N-(N-(4-(((1,2-dihydro-3-methyl-1-oxobenzo(f)quinazolin-9-yl)methyl)amino)-2-fluorobenzoyl)-L-glutam-1-yl)-L-tyrosine A solution of 0.15 g of methyl N-(N-(4(((1,2-dihydro-3-methyl-1-oxobenzo(f)quinazolin-9-yl)methyl)amino)-2-fluorobenzoyl)-5-O-methyl-L-glutam-1-yl)-3-(methoxycarbonyl)-L-tyrosinate in 20 mL of 0.2 N aqueous NaOH was stirred at RT under N$_2$ for 18 h. Analysis of the solution by HPLC (C18, 70:30:0.1 H$_2$O:MeCN:TFA) indicated a major component at k'=1.9 (90%) and two minor components at k'=1.0 and 2.6. The solution was acidified to pH 2.5 by addition of 1 N HCl. A white precipitate resulted which was separated by centrifugation and purified by semi-preparative HPLC (C18, 75:25:0.1 H$_2$O:MeCN:TFA). Pure fractions (as determined by analytical HPLC) were combined and concentrated in vacuo to dryness. The residue was dissolved in 20 mL of 0.15 N aqueous NaOH and the solution by HPLC (C18, 70:30:0.1 H$_2$O:MeCN:TFA) indicated a major component at k'=1.9 (90%) and two minor component at k'=1.0 and 2.6. The solution was acidified to pH 2.5 by addition of 1 N HCl. A white precipitate resulted which was separated by centrifugation and purified by semi-preparative HPLC (C18, 75:25:0.1 H$_2$O:MeCN:TFA). Pure fractions (as determined by analytical HPLC) were combined and concentrated in vacuo to dryness. The residue was dissolved in 20 mL of 0.15 N aqueous NaOH and the solution was acidified to pH=3.0 by addition of 1 N HCl. The resulting white precipitate was separated by centrifugation, washed with four cycles of aqueous suspension-centrifugation-decantation, and lyophilized to afford 39 mg (26%) of 3-carboxy-N-(N-(4-(((1,2-dihydro-3-methyl-1-oxobenzo(f)quinazolin-9-yl)methyl)amino)-2-fluorobenzoyl)-L-glutam-1-yl)-L-tyrosine as a white powder, m.p. 198–205° C. (dec).

HPLC: one peak on C18, k'=1.86, 70:30:0.1 $H_2O$:MeCN:TFA, flow rate=1 mL/min. $^1$H-NMR: (200 MHz, DMSO-$d_6$) δ 13:00-11.00 (br m, COOH, benzoquinazoline NH), 9.86 (s, 1 H, aromatic CH), 8.28 (d, 1 H, J=7.5, amide NH), 8.24 (d, 1 H, J=8.9, aromatic CH), 8.03 (d, 1 H, J=8.4, aromatic CH), 7.70-7.42 (m, 5 H, aromatic CH, 4-aminobenzoyl NH), 7.40-7.24 (m, 2 H, aromatic CH, amide NH), 6.78 (d, 1 H, J=8.6, aromatic CH), 6.55 (dd; 1 H; J=8.5, 1.9: aromatic CH), 6.42 (dd; 1 H; J=13.9, 1.5; aromatic CH), 4.58 (d, 2 H, J=5.8, benzoquinazoline 9-$CH_2$), 4.55-4.31 (m, 2 H, methines), 3.06-2.75 (m, 2 H, Ar$CH_2$), 2.24 (s, 3 H, $CH_3$), 2.21 (t, 2 H, J=7.6, glu 4-$CH_2$), 2.08-1.70 (m, 2 H, glu 3-$CH_2$).

Elemental Analysis: Calcd. for $C_{36}H_{32}N_5O_{10}F.2.2$ $H_2O$ (MW 753.31): C, 57.40; H, 4.87; N, 9.30. Found: C, 57.37; H, 4.97; N, 9.28.

Mass Spectrum: (FAB) 714 (M+H)$^+$, 613, 549, 461, 360, 309.

UV Spectrum: (pH7 Buffer) $^1\lambda_{max}(e)$ 265.9 (44700), 300.2 (28200), 348.3 (5270). $^1\lambda_{min}(e)$ 246.3 (23400), 285.2 (25500), 340.8 (3630).

EXAMPLE 46 tert-Butyl 3-(tert-butoxycarbonyl)-L-tyrosinate

A 250 mL 3-necked flask equipped with a magnetic stirrer and a condenser was charged with 4.1 g of 3-cyano-L-tyrosine and 100 mL of 6 N aqueous HCl. The mixture was heated to reflux with stirring. After 36 h, HPLC (C18, 90:10:0.1 $H_2O$:MeCN:TFA) indicated no remaining starting material at k'=1.33 and a major new component at k'=1.69. The reaction mixture was cooled to RT, filtered to remove solids, and concentrated in vacuo to dryness. The residue was dissolved in 100 mL of 8:2 $H_2O$:MeOH and the solution was passed through two C18 plugs (3.5×4.5 cm, EM separations LiChroprep RP-18) washing with 8:2 $H_2O$:MeOH. The filtrate was concentrated in vacuo to dryness to afford 4.5 g of 3-carboxytyrosine as a brown solid. A portion of this material (1.30 g) was dissolved in 40 mL of 1,4-dioxane with 2 mL of concentrated $H_2SO_4$ and the solution was added to 30 mL of isobutylene (condensed at −78° C.) in a 300 mL pressure bottle equipped with a magnetic stirrer. The vessel was stoppered, warmed to RT and stirred. After 48 h, the bottle was cooled to 0° C. in an ice water bath, opened, and the mixture was treated with 20 g of $NaHCO_3$. After allowing the isobutylene to evaporate, the mixture was suspended in 300 mL of water and extracted with $CH_2Cl_2$ (4×100 mL). The combined $CH_2Cl_2$ extracts were washed with 5% aqueous $NaHCO_2$ (2×50 mL), dried over anhydrous $MgSO_4$, and concentrated in vacuo to give a yellow-brown oil. Analysis by tlc ($SiO_2$, 97:3 $CH_2Cl_2$:MeOH) indicated a major component at $R_f$=0.41 and three minor components at $R_f$=0.30, 0.25 and 0.0. The crude material was purified by flash chromatography on 75 g of silica gel (94:6 $CH_2Cl_2$:MeOH) to give 1.2 g of a light yellow oil. The oil was dissolved in 40 mL of ether and treated with 3.9 mL of 1 M ethereal HCl. A precipitate formed which was collected by filtration and dried in vacuo to afford 1.14 g (53%) of tert-butyl 3-(tert-butoxycarbonyl)-L-tyrosinate.HCl as a fluffy white solid. An analytical sample (26 mg) was prepared by recrystallization from MeOH-ether, m.p. 205° C. (dec). $^1$H-NHR: (300 MHz, DMSO-$d_6$) δ 10.69 (s, 1 H, OH), 8.39 (br s, 3 H, $NH_3^+$), 7.57 (d, 1H, J=2.2, aromatic CH), 7.43 (dd; 1 H; J=8.6, 2.2; aromatic CH), 6.96 (d, 1 H, J=8.4, aromatic CH), 4.12 (m, 1 H, methine), 3.11 (dd; 1 H ; J=14.3, 5.3; Ar$CH_2$), 2.97 (dd; 1 H, J=14.1, 8.1; Ar$CH_2$), 1.57 (s, 9 H, t-Bu), 1.36 (s, 9 H, t-Bu).

EXAMPLE 47 tert-butyl N-((benzyloxy)carbonyl)-5-O-tert-butyl-L-glutam-1-yl-3-(tert-butoxycarbonyl)-L-tyrosinate According to example 9, 0.323 g of tert-butyl 3-(tert-butoxycarbonyl)-L-tyrosinate.HCl was coupled with 0.292 g of N-benzyloxycarbonyl-L-glutamic acid γ-t-butyl ester (Sigma) using 0.174 g of EDC (Aldrich) and 0.095 mL of N-methylmorpholine. The crude product was purified by flash chromatography on 85 g of silica gel (75:25 hexane:EtOAc) to afford 0.49 g (89%) of tert-butyl N-((benzyloxy)carbonyl)-5-O-tert-butyl-L-glutam-1-yl-3-(tert-butoxycarbonyl)-L-tyrosinate as a tacky white foam.

$^1$H-NMR: (300 MHz, DMSO-$d_6$) δ 10.67 (s, 1 H, OH), 8.21 (d, 1 H, J=7.4, NH), 7.56 (s, 1 H, aromatic CH), 7.46-7.26 (m, 7 H, aromatic CH), 5.00 (m, 2 H, Ph$CH_2$O), 4.31 (m, 1 H, methine), 4.06 (m, 1 H, methine), 2.89 (d, 2 H, J=6.9, Ar$CH_2$), 2.21 (t, 2 H, J=7.7, glu 4-$CH_2$), 1.92-1.64 (m, 2 H, glu 3-$CH_2$), 1.57 (s, 9 H, t-Bu), 1.38 (s, 9 H, t-Bu), 1.33 (s, 9 H, t-Bu).

EXAMPLE 48 tert-Butyl 5-O-tert-butyl-L-glutam-1-yl-3-(tert-butoxycarbonyl)-L-tyrosinate

To a 300 mL Parr bottle were added 0.076 g of 10% Pd(C) and 20 mL of MeOH under a nitrogen flush. To this was added a solution of 0.49 g of tert-butyl N-((benzyloxy) carbonyl)-5-O-tert-butyl-L-glutam-1-yl-3-(tert-butoxycarbonyl)-L-tyrosinate in 50 mL of MeOH. The mixture was deoxygenated by bubbling nitrogen through for 7 min and was hydrogenated at 50 psi for 3 h. The vessel was purged with nitrogen, catalyst removed by filtration through celite, and the filtrate concentrated in vacuo to give a thick oil.

This material was purified by flash chromatography on 70 g of silica gel (98:2 $CH_2Cl_2$:MeOH) to afford 0.31 g (82%) of tert-butyl 5-O-tert-butyl-L-glutam-1-yl-3- (tert-butoxycarbonyl)-L-tyrosinate as a thick transparent oil. A small sample of the corresponding HCl salt for $^1$H-NMR analysis was prepared by treating 5 mg of the product with excess 1 N ethereal HCl and concentrating to dryness.

$^1$H-NMR: (200 MHz, DMSO-$d_6$) δ 10.68 (s, 1 H, OH), 8.99 (d, 1 H, J=7.1, NH), 8.33 (br s, 3 H, $NH_3^+$), 7.60 (d, 1 H; J=2.0, aromatic CH), 7.47 (dd: 1 H; J=8.6, 2.2; aromatic CH), 6.92 (d, 1 H, J=8.4, aromatic CH), 4.38 (m, 1 H, methine), 3.87 (m, 1 H, methine), 2.92 (d, 2 H, J=7.1, Ar$CH_2$), 2.34 (m, 2 H, glu 4-$CH_2$), 2.00 (m, 2 H, glu 3-$CH_2$), 1.59 (5, 9 H, t-Bu), 1.41 (s,9 H, t-Bu), 1.35 (s, 9 H, t-Bu).

EXAMPLE 49 tert-Butyl N-(4-(((2,4-diamino-6-pteridinyl)methyl) methylamino)benzoyl)-5-O-tert-butyl-L-glutam-1-yl-3-(tert-butoxycarbonyl)-L-tyrosinate A dry 100 mL 3-necked flask equipped with a nitrogen inlet and a magnetic stirrer was charged with 25 mL of anhydrous DMF, 0.26 mL of DECP (Aldrich) and 0.28 mL of Et$_3$N. To this solution was added 0.217 g of 4-(N-(2,4-diamino-6-pteridinylmethyl)-N-methylamino)benzoic) benzoic acid hemihydrochloride dihydrate (Aldrich). The solid starting material slowly dissolved to give a light yellow solution. After stirring for 3 h under N$_2$, the solution was treated with 0.29 g of tert-butyl 5-O-tert-butyl-L-glutam-1-yl-3-(tert-butoxycarbonyl)-L-tyrosinate in 5 mL of DMF. The solution was stirred for 18 h at RT and was then concentrated in vacuo to dryness. The residue was dissolved in 85 mL of CHCl$_3$. The resulting solution was washed with 1% aqueous NH$_4$OH (3×60 mL), dried over anhydrous MgSO$_4$, and concentrated to give a thick, yellow-orange oil. This material was purified by flash chromatography on 150 g of silica gel (7:7:1 CH$_2$Cl$_2$:acetone: MeOH) to afford 0.245 g (52%) of tert-butyl N-(4-(((2,4-diamino-6-pteridinyl)methyl)methylamino)benzoyl)-5-O-tert-butyl-L-glutam-1-yl-3-(tert-butoxycarbonly)-L-tyrosinate as a light yellow powder, m.p. 140–143° C.

$^1$H-NMR: (300 MHz, DMSO-d$_6$) δ 10.64 (s, 1 H, OH), 8.57 (s, 1 H, pteridinyl 7-CH), 8.15 (d, 1 H, J=7.4, amide NH), 7.99 (d, 1 H, J=7.9, amide NH), 7.71 (d, 2 H, J=8.8, aromatic CH), 7.67 (br s, 1 H, NH$_2$), 7.53 (d, 1 H, J=2.0, aromatic CH), 7.43 (br s, 1 H, NH$_2$), 7.37 (dd; 1 H; J=8.6, 2.1; aromatic CH), 6.81 (m, 3 H, aromatic CH), 6.59 (br s, 2 H, NH$_2$), 4.79 (s, 2 H, pteridinyl-CH$_2$), 4.43 (m, 1 H, methine), 4.32 (m, 1 H, methine), 3.21 (s, 3 H, N-CH$_3$), 2.90 (d, 2 H, J=7.1, ArCH$_2$), 2.24 (t, 2 H, J=32 7.9, glu 4-CH$_2$), 2.03-1.78 (m, 2 H, glu 3-CH$_2$), 1.54 (5, 9H, t-Bu), 1.36 (s, 9 H, t-Bu), 1.30 (s, 9 H, t-Bu).

EXAMPLE 50

N-(4-(((2,4-Diamino-6-pteridinyl)methyl) methylamino)benzoyl)-L-glutam-1-yl-3-carboxy-L-tyrosine A 100 mL 3-necked flask equipped with a magnetic stirrer and anitrogen inlet was charged with 0.20 g of tert-Butyl N-(4-(((2,4-diamino-6-pteridinyl)methyl)methylamino) benzoyl)-5-O-tert-butyl-L-glutam-1-yl-3-(tert-butoxycarbonyl)-L-tyrosinate and 20 mL of Ch$_3$NO$_2$. The yellow solution was stirred at RT and acidified by bubbling gaseous HCl through for 10 min. Upon HCl treatment, the color rapidly changed from yellow to orange to lighter yellow and a solid began to precipitate. The mixture was stirred at RT under N$_2$ for 1.5 h and was then concentrated in vacuo to dryness. The resulting yellow solid was suspended in 15 mL of water and treated with sufficient 1 N aqueous NaOH to give complete solution. The solution was filtered and neutralized by addition of 1 N aqueous HCl. A yellow precipitate resulted which was separated by centrifugation, washed with four cycles of aqueous suspension-centrifugation-decantation, and lyophilized to afford 140 mg (88%) of N-(4-(((2,4-Diamino-6-pteridinyl) methyl)methylamino)benzoyl)-L-glutam-1-yl-3-carboxy-L-tyrosine as a yellow-orange powder, m.p. 195° C. (dec).

HPLC: two peaks on C18; k'=3.16 (98%), k'=6.07 (2%); 80:20:0.1 H$_2$O:MeCN:TFA:flow rate =1 mL/min.

$^1$H-NMR: (300 MHz, DMSO-d$_6$) δ 13.15-11.80 (br s, COOH), 8.62 (s, 1 H, pteridinyl 7CH), 8.19 (br s, 1 H, NH$_2$) 8.00 (m, 3 H, amide NH (2), NH$_2$), 7.72 (d, 2 H, J=8.7, aromatic CH), 7.61 (d, 1 H, J=2.1, aromatic CH), 7.22 (m, 3 H, NH$_2$(2), aromatic CH), 6.81 (d, 2 H, J=8.7, aromatic CH), 6.66 (d, 1 H, J=7.8, aromatic CH), 4.81(s, 2 H, pteridinyl-CH$_2$), 3.39 (m, 2 H, methines), 3.21 (s, 3 H, N-CH$_3$), 2.94 (m, 1 H, ArCH$_2$), 2.86 (m, 1 H, ArCH$_2$), 2.27 (t, 2 H, J=7.9, glu 4-CH$_2$), 2.05-1.72 (m, 2 H, glu 3-CH$_2$).

Elemental Analysis: Calcd. for C$_{30}$H$_{31}$N$_9$O$_9$.1.8H$_2$O (MW 694.06): C, 51.92; H, 5.02; N, 18.16. Found: C, 51.84; H, 5.0Z; N, 18.19.

Mass Spectrum: (Ion Spray)662(M+H)$^+$, 385, 306, 235, 157.

UV Spectrum: (pH7 Buffer) $\lambda_{max}$ (ε) 258.6 (19900), 306.3 (23500), 372.6 (54900). $1_{min}$(ε) 245.4 (14800), 272.8 (12600), 347.0 (4040).

EXAMPLE 51

(2R, 3S, 5S)-Benzyl 3-(3-iodobenzyl)-2-oxo-2,3-diphenyl-4-morpholinecarboxylate A dry 500 mL 3-necked flask equipped with a magnetic stirrer and a nitrogen inlet was charged with 3.0 g of benzyl (2R, 3S)-6oxo-2,3-diphenyl-4-morpholinecarboxylate (Aldrich) and 180 mL of anhydrous THF. After gently warming the mixture to dissolve the solid starting material, the solution was cooled to −78° C. and was treated with 8.13 mL of 1 M sodium bis(trimethylsilyl)amide in THF (Aldrich) by slow addition via syringe through a rubber septum. The solution was stirred at −78° C. under N$_2$ for 40 min and was then treated with a solution of 2.41 g of 3-iodobenzyl bromide (Lancaster, Windham, NH 03087) in 5 mL of anhydrous THF. The reaction mixture was stirred at −78° C. for 2.5 h, mixed with 100 mL of water and the resulting mixture was concentrated in vacuo to dryness. The residue was dissolved in 100 mL of EtOAc, washed with water (3×100 mL), dried over anhydrous Na$_2$SO$_4$, and concentrated in vacuo to dryness to give a tan solid. Analysis by tlc (SiO$_2$, 8:2 hexane:EtOAc) indicated no remaining starting material at R$_f$=0.35, a major new component at R$_f$=0.50 and some unreacted 3-iodobenzyl bromide at R$_f$=0.80. The crude product was purified by flash chromatography on 150 g of silica gel (8:2 hexane:EtOAc) to afford 2.8 g (60%) of (2R, 3S, 5S)-benzyl 3-(3-iodobenzyl)-2-oxo-2,3-diphenyl-4-morpholinecarboxylate as a white crystalline solid, m.p. 167–168° C.

EXAMPLE 52

(2R, 3S, 5S)-Benzyl 3-(3-methoxycarbonyl)-2-oxo-2,3-diphenyl-4-morpholinecarboxylate A dry 100 mL 3-necked flask equipped with a magnetic stirrer, a reflux condenser, and a thermometer was charged with 2.56 g of (2R, 3S, 5S)-benzyl 3-(3-iodobenzyl)-2-oxo-5,6-diphenyl-4-morpholinecarboxylate and 50 mL of 1:1 THF:MeOH. The mixture was deoxygenated by bubbling N$_2$ through for 10 min and was treated with 1.0 mL of Et$_3$N followed by 0.24 g of Pd(Ph$_3$P)$_4$ (Aldrich). The mixture was saturated with CO and was heated to reflux (65° C.) with stirring. A slight positive pressure of CO was maintained by attaching a CO gas inlet adapter equipped with a mineral oil bubbler to the condenser. After 4 h at reflux, tlc (SiO$_2$, 8:2 hexane:EtOAc) indicated no remaining starting material at R$_f$=0.50 and a new component at R$_f$=0.30. The reaction mixture was cooled to RT at which point a voluminous white solid precipitated. The suspension was mixed with 100 mL of CH$_2$Cl$_2$ and the resulting solution was filtered through a silica gel plug (2.5×3 cm) and concentrated in vacuo to give a light yellow solid. This material was purified by flash chromatography on 150 g of silica gel (8:2 hexane:EtOAc) to afford 2.0 g (88%) of (2R, 3S, 5S)-benzyl 3-(3-methoxycarbonyl)-2-oxo-5,6-diphenyl-4-morpholinecarboxylate as an off-white crystalline solid, m.p. 180–182° C.

$^1$H-NMR: (200 MHz, DMSO-d$_6$) δ 8.05-7.80 (m, 2 H, aromatic CH), 7.72-6.97 (m, 14 H, aromatic CH), 6.73 (m, 1 H, aromatic CH), 6,58 (m, 2 H, aromatic CH), 6.25, 6.16 (d, J=2.2; d, J=2.6; 1 H total; 2 resonances for morpholine 2-H due to carbamate conformers), 5.36, 5.31 (d, J=2.6; J=2.6; 1 H total; 2 resonances for morpholine 3-H due to carbamate conformers), 5.16-4.88 (m, 3 H, morpholine 5-H, PhCH$_2$O), 3.88, 3.85 (5, 5, 3 H total, CO$_2$CH$_3$, conformers), 3.71-3.40 (m, 2 H, ArCH$_2$).

EXAMPLE 53

3-Methoxycarbonyl-L-phenylalanine

To a 500 mL Parr bottle were added 2.0 g of (2R, 3S, 5S)-benzyl 3-(3-methoxycarbonyl)-2-oxo-5,6-diphenyl-4-morpholinecarboxylate, 0.46 g of PdCl$_2$ (Aldrich) and 60 mL of 1:1 THF:MeOH. The mixture was deoxygenated by bubbling N$_2$ through for 10 min and was then hydrogenolyzed at 45 psi for 18 h. The bottle was purged with N$_2$ and the mixture filtered to remove catalyst. The filtrate was concentrated in vacuo to 5 mL and triturated with addition of 50 mL of ethr. A white solid precipitated which was collected by vacuum filtration, washed with 30 mL of ether, and dried in vacuo to afford 0.88 g (91%) of 3-methoxycarbonyl-L-phenylalanine.HCl, m.p. >200° C.

$^1$H-NMR: (200 MHz, DMSO-d$_6$) δ 8.50 (br s, 3 H, NH$_3^+$), 7.89 (m, 2 H, aromatic CH), 7.67-7.43 (m, 2 H, aromatic CH), 4.21 (m, 1 H, methine), 3.87 (s, 3 H, CO$_2$CH$_3$), 3.22 (d, 2 H, J=6.5, ArCH$_2$).

EXAMPLE 54 tert-Butyl 3-methoxycarbonyl-L-phenylalaninate

A solution of 0.88 g of 3-methoxycarbonyl-L-phenylalanine.HCl, and 1.5 mL of conc. H$_2$SO$_4$ in 20 mL of 1,4-dioxane was added to 25 mL of liquid isobutylene (condensed at −78° C. ) in a 300 mL pressure bottle equipped with a magnetic stirrer. The bottle was sealed and the mixture allowed to warm to RT with stirring. The initially heterogeneous mixture afforded a slightly cloudy solution after stirring for 18 h at RT. After 48 h the vessel was chilled in an ice water bath, opened, and the contents treated with 13 g of said NaHCO$_3$. The isobutylene was allowed to evaporate and the remaining mixture was concentrated in vacuo to dryness. The residue was suspended in 100 mL of water and extracted with EtOAc (4×40 mL). The combined EtOAc extracts were washed with 5% aqueous NaHCO$_3$ (3×50 mL), dried over anhydrous MgSO$_4$, and concentrated in vacuo to give an oil. This material was dissolved in 30 mL of ether and the solution was treated with 3.4 mL of 1 M ethereal HCl. A white solid precipitated which was collected by filtration and dried in vacuo to afford 0.79 g (74%) of tert-butyl 3-methoxycarbonyl-L-phenylalaninate.HCl, m.p. 165° C. (dec).

EXAMPLE 55 tert-Butyl N-((benzyloxy)carbonyl)-5-O-tert-L-glutam-1-yl-3-methoxycarbonyl-L-phenylalaninate According to example 9, 0.79 g of tert-butyl 3-methoxycarbonyl-L-phenylalaninate.HCl was coupled with 0.84 g of N-benzyloxycarbonyl-L-glutamic acid γ-tert-butyl ester (Sigma) using 0.50 g of EDC (Aldrich) and 0.27 mL of N-methylmorpholine. The crude product was purified by flash chromatography on 85 g of silica get (70:30 hexane:EtOAc) to afford 1.38 g (93%) of tert-butyl N-((benzyloxy)carbonyl)-5-O-tert-L-glutam-1-yl-3-methoxycarbonyl-L-phenylalaninate as a transparent glass.

$^1$H-NMR: (300 MHz, DMSO-d$_6$) δ 8.26 (d, 1 H, J=7.5, NH), 7.80 (m, 2 H, NH, aromatic CH), 7.43 (d, 1 H, J=7.7, aromatic CH), 7.44-7.23 (m, 7 H, aromaic CH), 4.99 (m, 2 H, PhCH$_2$O), 4.38 (m, 1 H, methine), 4.01 (m, 1 H, methine), 3.83 (s, 3 H, CO$_2$CH$_3$), 3.02 (m, 2 H, ArCH$_2$), 2.19 (t, 2 H, J=7.7, glu 4-CH$_2$), 1.90-1.61 (m, 2 H, glu 3-CH$_2$), 1.38 (s, 9 H, t-Bu), 1.32 (s, 9 H, t-Bu).

EXAMPLE 56 tert-Butyl 5-O-tert-L-glutam-1-yl-3-methoxycarbonyl-L-phenylalaninate

According to example 48, 1.38 g of tert-butyl N-((benzyloxy)carbonyl)-5-O-tert-L-glutam-1-yl-3-methoxycarbonyl-L-phenylalaninate was hydrogenolyzed using 0.23 g of 10% Pd(C) in 60 mL of MeOH. This afforded 1.0 g (94%) of tert-butyl 5-O-tert-L-glutam-1-yl-3-methoxycarbonyl-L-phenylalaninte as a thick, transparent oil. The product was carried on to the next step without purification. A sample of the corresponding HCl salt for $^1$H-NMR analysis was prepared by treating 7 mg of the product with excess 1 M ethereal HCl and concentrating to dryness.

$^1$H-NMR: (300 MHz, DMSO-d$_6$) δ 9.12 (d, 1 H, J=7.6, NH), 8.39 (br s, 3 H, NH$_3^+$), 7.82 (m, 2 H, aromatic CH), 7.60 (d,1 H, J=7.5, aromatic CH), 7.46 (t, 1 H, J=6.9, aromatic CH), 4.40 (m, 1 H, methine), 3.85 (m, 1 H, methine), 3.83 (s, 3 H, CO$_2$CH$_3$), 3.05 (d, 2 H, J=8.4, ArCH$_2$), 2.33 (t, 2 H, J=7.7, glu 4-CH$_2$), 1.97 (m, 2 H, glu 3-CH$_2$), 1.37 (s, 9 H, t-Bu), 1.31 (s, 9 H, t-Bu).

EXAMPLE 57 tert-Butyl N-(4-(((2,4-diamino-6-pteridinyl)methyl)methylamino)benzoyl)-5-O-tert-butyl-L-glutam-1-yl-3-(methoxycarbonyl)-L-phenylalaninate According to example 49, 0.200 g of 4-(N-(2,4-diamino-6-pteridinylmethyl)-N-methylamino)benzoic acid hemihydrochloride dihydrate (Aldrich) was coupled with 0.245 g of tert-butyl 5-O-tert-L-glutam-1-yl-3-methoxycarbonyl-L-phenylalaninate using 0.24 mL of DECP (Aldrich) and 0.26 mL of Et$_3$N in 20 mL of DMF. The crude product was purified by flash chromatography on 130 g of silica gel (12:12:1 CH$_2$Cl$_2$:acetone:MeOH) to afford 0.297 g (73%) of tert-butyl N-(4-(((2,4-diamino-6-pteridinyl)methyl)methylamino)benzoyl)-5-O-tert-butyl-L-glutam-1-yl-3-(methoxycarbonyl)-L-phenylalaninate as yellow powder, m.p. 130° C. (dec).

EXAMPLE 58

N-(4-(((2,4-Diamino-6-pteridinyl)methyl)methylamino)benzoyl)-L-glutam-1-yl-3-carboxy-L-phenylalanine According to example 50, 0.15 g of tert-butyl N-(4-(((2, 4-diamino-6-pteridinyl)methyl)methylamino)benzoyl)-5-O-tert-butyl-L-glutam-1-yl-3-(methoxycarbonyl)-L-phenylalaninate was treated with gaseous HCl in 20 mL of CH$_3$NO$_2$. After stirring the mixture at RT for 1 h, the mixture was concentrated in vacuo to dryness to give a yellow-orange solid. Analysis of this material by $^1$H-NMR indicated complete loss of the tert-butyl groups of the starting material. HPLC (C18, 75:25:0.1 H$_2$O:MeCN:TFA) indicated a single component at k'=3.50. The intermediate methyl ester was dissolved in 25 mL of 1:1 THF:H$_2$O, treated with 49 mg of LiOH.H$_2$O (Baker), and the solution was stirred at RT under N$_2$ for 18 h. Analysis by HPLC indicated n remaining k'=3.50 material and a single new component at k'=1.58. The solution was neutralized by addition of 1 N aqueous HCl. A yellow slurry resulted which was concentrated in vacuo to 2 mL and diluted with 20 mL of water. The precipitate was separated by centrifugation, washed with four cycles of aqueous suspension-centrifugation-decantation, and lyophilized to afford 0.109 g (84%) of N-(4-(((2,4-diamino-6-pteridinyl)methyl)methylamino)benzoyl)-L-glutam-1-yl-3-carboxy-L-phenylalanine as a yellow-orange powder, m.p. 195° C. (dec).

HPLC: one peak on C18, k'=1.93, 78:22:0.1 H$_2$O:MeCN:TFA, flow rate=1 mL/min.

$^1$H-NMR: (300 MHz, DMSO-d$_6$) δ 13.00-12.10 (br s, COOH), 8.58 (s, 1 H, pteridinyl 7-CH), 8.08 (d, 1 H, J=7.8, amide NH), 7.98 (d, 1 H, J=8.0, amide NH), 7.80 (s, 1 H, aromatic CH), 7.79-7.60 (m, 4 H, NH$_2$(1 ), aromatic CH), 7.49 (br s, 1 H, NH$_2$), 7.44 (d, 1 H, J=7.7, aromatic CH), 7.30 (t, 1 H, J=7.6, aromatic CH), 6.81 (d, 2 H, J=9.0, aromatic CH), 6.63 (br s, 2 H, NH$_2$), 4.79 (s, 2 H, pteridinyl-CH$_2$), 4.41 (m, 2 H, methines), 3.20 (s, 3 H, N-CH$_3$), 3.10 (m, 1 H, ArCHz), 2.97 (m, 1 H, ArCH$_2$), 2.23 (t, 2 H, J=7.8, glu 4-CH$_2$), 2.00-1.73 (m, 2 H, glu 3-CH$_2$).

Elemental Analysis: Calcd. for C$_{30}$H$_{31}$N$_9$O$_8$.1.5H$_2$O (MW 672.65) C, 53.57; H, 5.09; N, 18.74. Found: C, 53.58; H, 5.11; N, 18.72.

Mass Spectrum: (Ion Spray) 646 (M+H)$^+$, 437, 340, 308, 175.

UV Spectrum: (pH7 Buffer)λ$_{max}$ (ε) 258.7 (24300), 307.5 (25000), 372.7 (7880). λ$_{min}$ (ε) 244.0 (17900), 272.7 (16900), 346.2 (6440).

EXAMPLE 59 tert-Butyl N-(4-(((1,2-dihydro-3-methyl-1-oxobenzo (f)-quinazolin-9-yl)methyl)amino)-2-fluorobenzoyl)-5-O-tert-butyl-L-glutam-1-yl-3-(methoxycarbonyl)-L-phenylalaninante A 100 mL 3-necked flask equipped with a magnetic stirrer and a nitrogen inlet was charged with 0.150 g of 4-(((1,2-dihydro-3-methyl-1-oxobenzo(f)quinazolin-9-yl)methyl)amino)-2-fluorobenzoic acid, 0.221 g of tert-butyl 5-O-tert-L-glutam-1-yl-3-methoxycarbonyl-L-phenylalaninate, 65 mg of 3-hydroxy-1,2,3-benzotriazin-4(3 H)-one (Aldrich), and 24 mL of anhydrous DMF. The resulting light yellow solution was treated with 84 mg of EDC (Aldrich) and was stirred at RT under N$_2$ for 48 h. The DMF was removed in vacuo and the residue purified by flash chromatography on 150 g of silica gel (98:2→96:4 CH$_2$Cl$_2$:MeOH) to afford 0.255 g (78%) of tert-butyl N-4-(((1,2-dihydro-3-methyl-1-oxobenzo(f)-quinazolin-9-yl)methyl)amino)-2-fluorobenzoyl)-5-O-tert-butyl-L-glutam-1-yl-3-(methoxycarbonyl)-L-phenylalaninate as a white powder, m.p. 155–157° C.

EXAMPLE 60

N-(4-(((1,2-Dihydro-3-methyl-1-oxobenzo(f) quinazolin-9-yl)methyl)amino)-2-fluorobenzoyl)-L-glutam-1-yl-3-carboxy-L-phenylalanine According to example 50, 0.219 g of tert-butyl N-(4-(((1, 2-dihydro-3-methyl-1-oxobenzo(f)-quinazolin-9-yl)methyl) amino)-2-fluorobenzoyl)-5-O-tert-butyl-L-glutam-1-yl-3-(methoxycarbonyl)-L-phenylalaninate was treated with gaseous HCl in 20 mL of CH$_3$NO$_2$. After removal of the CH$_3$NO$_2$ in vacuo, the residue was saponified with 66 mg of LiOH.H$_2$O (Baker) in 20 mL of 1:1 THF:H$_2$O for 18 h. The solution was acidified to pH=2.5 by addition of 1 N HCl and the resulting precipitate was isolated and lyophilized in the usual manner to afford 0.162 g (84%) of N-(4-(((1,2-dihydro-3-methyl-1-oxobenzo(f)quinazolin-9-yl)methyl) amino)-2-fluorobenzoyl)-L-glutam-1-yl-3-carboxy-L-phenylalanine as a white powder, m.p. 187° C. (dec.)

HPLC: one peak on C18, k'=4.29, 75:25:0.1 H$_2$O:MeCN:TFA, flow rate=1 mL/min.

$^1$H-NMR: (300 MHz, DMSO-d$_6$) δ 13.00-12.25 (br m, COOH, benzoquinazoline NH), 9.83 (s, 1 H, aromatic CH), 8.32 (d, 1 H, J=7.4, amide NH), 8.22 (d, 1 H, J=9.0, aromatic CH), 8.00 (d, 1 H, J=8.5, aromatic CH), 7.81 (s, 1 H, aromatic CH), 7.75 (d, 1 H, J=8.0, aromatic CH), 7.60 (m, 2 H, aromatic CH), 7.49 (m, 3 H, aromatic CH, 4-aminobenzoyl NH), 7.35 (m, 2 H aromatic CH, amide NH), 6.52 (d, 1 H, J=8.8, aromatic CH), 6.39 (d, 1 H, J=15.2, aromatic CH), 4.57 (br s, 2 H, benzoquinazoline 9-CH$_2$), 4.45 (m, 2 H, methines), 3.12 (m, 1 H, ArCH$_2$), 2,96 (m, 1 H, ArCH$_2$), 2.42 (s, 3 H, CH$_3$), 2.19 (m, 2 H, glu-4-CH$_2$), 2.01-1.70 (m, 2 H, glu 3-CH$_2$).

Elemental Analysis: Calcd. for C$_{36}$H$_{32}$N$_5$O$_9$F.1.7H$_2$O (MW 728.30): C, 59.37; H, 4.90; N, 9.62. Found: C, 59.45; H, 4.93; N, 9.42.

Mass Spectrum: (Ion Spray) 698 (M+H)$^+$.

UV Spectrum: (pH7 Buffer) λ$_{max}$ (δ) 265.3 (45500), 296.5 (26100), 348.0 (5530). λ$_{min}$ (δ) 244.4 (22600), 287.0 (25500), 340.1 (3540).

EXAMPLE 61

2-Cyclopentylbenzyl alcohol

A 300 mL Parr bomb was charged with 10.0 g of 2-iodobenzyl alcohol (Aldrich), 80 mL of toluene, 30 mL of cyclopentene (Aldrich), 2.60 g of tri-ortho-tolylphosphine (Aldrich), and 6.6 mL of Et$_3$N. The mixture was deoxygenated by bubbling N$_2$ through for 10 min and was then treated with 0.96 g of Pd(OAc)$_2$ (Aldrich). The bomb was flushed with N$_2$, sealed, and heated to 100° C. for 18 h. The vessel was cooled to RT, purged with N$_2$ and opened. The dark red reaction mixture was concentrated in vacuo to give a red-brown syrup. This material was dissolved in 200 mL of CH$_2$Cl$_2$, washed with water (4×100 mL), dried over anhydrous MgSO$_4$, and concentrated in vacuo to afford a brown oil. Analysis by tlc (SiO$_2$, 8:2 hexane:EtOAc) indicated two new major components at R$_f$=0.45 and 0.50, tri-o-tolylphosphine at R$_f$=0.90, and 4 minor components at R$_f$=0.60, 0.70, 0.85 and 0.0. The crude product was purified by flash chromatography (twice) on 200 g of silica gel (9:1 hexane:EtOAc) to afford 6:1 g (82%) of a mixture of the R$_f$=0.45 and 0.50 materials. This material was determined to be a mixture of double bond isomers by $^1$H-NMR. The product (6.0g ) was then hydrogenated at 40 psi in 40 mL of MeOH in the presence of 0.60 g of 5% Pt(C) (Aldrich) for 4 h. The catalyst was removed by filteration through celite and the filtrate was concentrated in vacuo to afford 5.47 g (74% from 2-iodobenzyl alcohol) of 2-cyclopentylbenzyl alcohol as a light yellow-brown liquid.

$^1$H-NMR: (200 MHz, DMSO-d$_6$) δ 7.40-7.07 (m, 4 H, aromatic CH), 5.06 (t, 1 H, J=5.4, OH), 4.58 (d, 2 H, J=5.4, ArCH$_2$O), 3.24 (m, 1 H, cyclopentyl methine), 1.97 (m, 2 H, cyclopentyl CH$_2$), 1.89-1.42 (m, 6 H, cyclopentyl CH$_2$).

EXAMPLE 62

2-Cyclopentylbenzyl bromide

According to example 17, 5.47 g of 2-cyclopentylbenzyl alcohol was treated with 1.03 mL of PBr$_3$ in 25 mL of anhydrous $CH_2Cl_2$ to afford 6.9 g (93%) of 2-cyclopentylbenzyl bromide as a clear liquid.

$^1$H-NMR: (300 MHz, DMSO-$d_6$) δ 7.40-7.24 (m, 3 H, aromatic CH), 7.14 (m, 1 H, aromatic CH), 4.78 (s, 2 H, ArCH$_2$Br), 3.31 (m, 1 H, cyclopentyl methine), 2.05 (m, 2 H, cyclopentyl CH$_2$), 1.88-1.47 (m, 6 H, cyclopentyl CH$_2$).

EXAMPLE 63

(2R, 3S, 5S)-Benzyl 3-(3-cyclopentylbenzyl)-2-oxo-2,3-diphenyl-4-morpholinecarboxylate According to example 51, 1.47 g of benzyl (2R, 3S)-6-oxo-2,3-diphenyl-4-morpholinecarboxylate (Aldrich) was alkylated with 1.00 g of 2-cyclopentylbenzyl bromide using 3.99 mL of 1 M sodium bis(trimethylsilyl)amide in THF (Aldrich). The crude product was purified by flash chromatography on 125 g of silica gel (8:2 hexane:EtOAc) to afford 1.07 g (52%) of (2R, 3S, 5S)-benzyl 3-(3-cyclopentylbenzyl)-2-oxo-2,3-diphenyl-4-morpholinecarboxylate as a white solid, m.p. 161–163° C.

EXAMPLE 64

2-Cyclopentyl-L-phenylalanine

According to example 53, 1.0 g of (2R, 3S, 5S)-benzyl 3-(3-cyclopentylbenzyl)-2-oxo-5,6-diphenyl-4-morpholinecarboxylate was hydrogenolyzed in 40 mL of 1:1 THF:MeOH using 0.23 g of PdCL$_2$ to afford 0.373 g (76%) of 2-cyclopentyl-L-phenylalanine.HCl as an off-white powder, m.p. 175° C. (dec).

$^1$H-NMR: (200 MHz, DMSO-$d_6$) δ 8.49 (br s, 3 H, NH$_3^+$), 7.38-7.07 (m, 4 H, aromatic CH), 3.92 (m, 1 H, methine), 3.18 (m, 1 H, cyclopentyl methine), 1.98 (m, 2 H, cyclopentyl CH$_2$), 1.90-1.41 (m, 6 H, cyclopentyl CH$_2$).

EXAMPLE 65 tert-Butyl 2-cyclopentyl-L-phenylalaninate

According to example 53, 1.0 g of (2R, 3S, 5S)-benzyl 3-(3-cyclopentylbenzyl)-2-oxo-5,6-diphenyl-4-morpholinecarboxylate was hydrogenolyzed in 40 mL of 1:1 THF:MeOH using 0.23 g of PdCl$_2$ to afford 0.373 g (76%) of 2-cyclopentyl-L-phenylalanine.HCl as an off-white powder, m.p. 175° C. (dec.).

$^1$H-NMR: (200 MHz, DMSO-$d_6$) δ 8.49 (br s, 3 H, NH$_3^+$), 7.38-7.07 (m, 4 H, aromatic CH), 3.92 (m, 1 H, methine), 3.18 (m, 1 H, cyclopentyl methine), 1.98 (m, 2 H, cyclopentyl CH$_2$), 1.90-1.41 (m, 6 H, cyclopentyl CH$_2$).

EXAMPLE 66 tert-Butyl N-((benzyloxy)carbonyl)-5-O-tert-butyl-L-glutam-l-yl-2-cyclopentyl-L-phenylalaninate According to example 54, 0.23 g of 2-cyclopentyl-L-phenylalanine.HCl was treated with 25 mL of isobutylene in 20 mL of 1,4-dioxane in the presence of 0.13 mL of conc. H$_2$SO$_4$. Work-up afforded a clear oil which was dissolved in 20 mL of ether. The solution was treated with 1 mL of 1 M ethereal HCl and concentrated in vacuo to dryness to afford 0.28 g (100%) of tert-butyl 2-cyclopentyl-L-phenylalaninate.HCl as a light yellow glass.

$^1$H-NMR: (300 MHz, DMSO-$d_6$) δ 8.59 (br s, 3 H, NH$_3^+$), 7.28 (m, 2 H, aromatic CH), 7.10 (m, 2 H, aromatic CH), 3.91 (m, 1 H, methine), 3.30 (m, 1 H, ArCH$_2$), 3.18 (m, 1 H, cyclopentyl methine), 2.99 (dd; 1 H; J=10.1, 12.4; ArCH$_2$), 1.98 (m, 2 H, cyclopentyl CH$_2$), 1.89-1.46 (m, 6 H, cyclopentyl CH$_2$), 1.19 (s, 9 H, t-Btu).

EXAMPLE 66 tert-Butyl N-((benzyloxy)carbonyl)-5-O-tert-butyl-L-glutam-1-yl-2-cyclopentyl-L-phenylalaninate According to example 9, 0.25 g of tert-butyl 2-cyclopentyl-L-phenylalaninate.HCl was coupled with 0.26 g of N-benzyloxycarbonyl-L-glutamic acid γ-tert-butyl ester (Sigma) using 0.16 g of EDC (Aldrich) and 0.084 mL of N-methylmorpholine. The crude product was purified by flash chromatography on 85 g of silica gel (8:2 hexane:EtOAc) to afford 0.355 g (76%) of tert-butyl N-((benzyloxy)carbonyl)-5-O-tert-butyl-L-glutam-1-yl-2-cyclopentyl-L-phenylalaninate as a white solid, m.p. 95–96° C.

EXAMPLE 67 tert-Butyl 5-O-tert-butyl-L-glutam-1-yl-2-cyclopentyl-L-phenylalaninate

According to example 48, 0.355 g of tert-butyl N-((benzyloxy)carbonyl)-5-O-tert-butyl-L-glutam-1-yl-2-cyclopentyl-L-phenylalaninate was hydrogenolyzed using 60 mg of 10% Pd(C) in 45 mL of MeOH. This afforded 0.236 g (85%) of tert-butyl 5-O-tert-butyl-L-glutam-1-yl-2-cyclopentyl-L-phenylalaninate as a thick, transparent oil.

$^1$H-NMR: (200 MHz, DMSO-$d_6$) δ 8.23 (m, 1 H, NH), 7.34-7.00 (m, 4 H, aromatic CH), 4.37 (m, 1 H, methine), 3.36-2.85 (m, 5 H, ArCH$_2$, cyclopentyl methine, NH$_2$), 2.27-1.92 (m, 4 H, glu 4-CH$_2$, glu 3-CH$_2$), 1.90-1.46 (m, 8 H, cyclopentyl CH$_2$), 1.39 (s, 9 H, t-Btu), 1.32 (s, 9 H, t-Bu).

EXAMPLE 68 tert-Butyl N-(4(((2,4-diamino-6-pteridinyl)methyl) methylamino)benzoyl)-5-O-tert-butyl-L-glutam-1-yl-2-cyclopentyl-L-phenylalaninate According to example 49, 0.189 g of a 4-(N-(2,4-diamino-6-pteridinylmthyl)-N-methylamino)benzoic acid hemihydrochloride dihydrate (Aldrich) was coupled with 0.236 g of tert-butyl 5-O-tert-butyl-L-glutam-1-yl-2-cyclopentyl-L-phenylalaninate using 0.23 mL of DECP (Aldrich) and 0.24 mL of Et$_3$N in 20 mL of DMF. The crude product was purified by flash chromatography on 85 g of silica gel (12:12:1 CH$_2$Cl$_2$:acetone:MeOH) to afford 0.195 g (50%) of tert-butyl N-(4-(((2,4-diamino-6-pteridinyl) methyl)methylamino)benzoyl)-5-O-tert-butyl-L-glutam-1-yl-2-cyclopentyl-L-phenylalaninate as a yellow powder, m.p. 130-140° C.

EXAMPLE 69

N-(4-(((2,4-Diamino-6-pteridinyl)methyl) methylamino(benzoyl)-L-glutam-1-yl-2-cyclopentyl-L-phenylalanine According to example 50, 0.167 g of tert-butyl N-(4-(((2, 4-diamino-6-pteridinyl)methyl)methylamino)benzoyl)-5O-tert-butyl-L-glutam-1-yl-2-cyclopentyl-L-phenylalaninate was treated with gaseous HCl in 15 mL of CH$_3$NO$_2$ for 1 h. The reaction mixture was concentrated in vacuo to dryness to give a yellow solid. This material was suspended in ether, collected by vacuum filtration, and dried in vacuo to afford 1.15 g (91%) of N-(4-(((2,4-diamino-6-pteridinyl)methyl) methylamino)benzoyl)-L-glutam-1-yl-2-cyclopentyl-L-phenylalanine as a light yellow powder, m.p. 155° C. (dec).

HPLC: one peak on C18, k'=3.25, 65:35:0.1 H$_2$O:MeCN:TFA, flow rate=1 mL/min.

$^1$H-NMR: (300 MHz, DMSO-d$_6$) δ 13.25-12.95 (br s, COOH), 9.31 (s, 1 H, NH$_2$), 9.09 (s, 1 H, NH$_2$), 8.80-8.58 (br s, 1 N, NH$_2$), 8.72 (s, 1 H, pteridinyl 7-CH), 8.24 (d, 1 H, J=8.0, amide NH), 8.01 (d, 1 H, J=8.0, amide NH), 7.74 (m, 3 H, NH$_2$(1), aromatic CH), 7.22 (d, 1 H, J=8.1, aromatic CH), 7.12 (m, 2 H, aromatic CH), 6.93 (t, 1 H, J=7.4, aromatic CH), 6.82 (d, 2 H, J=9.0, aromatic CH), 4.88 (s, 2 H, pteridinyl-CH$_2$), 4.45 (m, 1 H, methine), 4.34 (m, 1 H, methine), 3.26-3.10 (m, 2 H, ArCH$_2$, cyclopentyl methine), 2.88 (m, 1 H, ArCH$_2$), 2.23 (t, 2 H, J=7.6, glu 4-CH$_2$), 2.06-1.40 (m, 10 H, glu 3-CH$_2$, cyclopentyl CH$_2$).

Elemental Analysis: Calcd. for C$_{34}$H$_{39}$N$_9$O$_6$·1.7 HCl·2.2 H$_2$O (MW 771.36): C, 52.94: H, 5.89; N, 16.34Cl, 7.81. Found: C, 52.57; H, 5.74; N, 16.13; Cl, 7.52.

Mass Spectrum: (Ion Spray) 670 (M+H)$^+$, 613, 459, 391, 309, 275.

UV Spectrum: (pH7 Buffer) λ$_{max}$ (ε) 259,.5 (24000), 308.5 (24000), 373.0 (7450). λ$_{min}$ (ε) 241.0 (14400), 274.2 (16200), 346.5 (5840).

EXAMPLE 70

3-Cyclopentylbenzyl alcohol

According to example 61, 10.0 g of 3-iodobenzyl alcohol (Aldrich) was treated with 30 mL of cyclopentene using 0.96 g of Pd(OAc)$_2$, 2.60 g of tri-ortho-tolylphosphine, and 6.6 mL of Et$_3$N. The resulting olefin mixture was hydrogenated for 2.5 h using 0.62 g of 5% Pt(C) in MeOH to afford 5.77 g (76%) of 3-cyclopentylbenzyl alcohol as a light yellow liquid.

$^1$H-NMR: (200 MHz, DMSO-d$_6$) δ 7.32-7.17 (m, 2 H, aromatic CHO, 5.14 (t, 1 H, J=5.5, OH), 4.48 (d, 2 H, J=5.6, ArCH$_2$O), 2.96 (m, 1 H, cyclopentyl methine), 2.01 (m, 2 H, cyclopentyl CH$_2$), 1.88-1.42 (m, 6 H, cyclopentyl CH$_2$).

EXAMPLE 71

3-Cyclopentylbenzyl bromide

According to example 17, 5.77 g of 3-cyclopentylbenzyl alcohol was treated with 1.09 mL of PBr$_3$ in 25 mL of anhydrous CH$_2$Cl$_2$ to afford 7.85 g (100%) of 3-cyclopentylbenzyl bromide as a light yellow liquid.

$^1$H-NMR: (300 MHz, DMSO-d$_6$) δ7.37-7.14 (m, 4 H, aromatic CH), 4.68 (s, 2 H, ArCH$_2$Br), 2.96 (m, 1 H, cyclopentyl methine), 2.00 (m, 2 H, cyclopentyl CH$_2$), 1.84-1.42 (m, 6 H, cyclopentyl CH$_2$).

EXAMPLE 72

(2R, 3S, 5S)-Benzyl 3-(3-cyclopentylbenzyl)-2-oxo-2,3-diphenyl-4-morpholinecarboxylate A dry 500 mL 3-necked flask equipped with a nitrogen inlet and a magnetic stirrer was charged with 1.47 g of benzyl (2R, 3S)-6-oxo-2,3-diphenyl-4-morpholinecarboxylate (Aldrich), 1.00 g of 3-cyclopentylbenzyl bromide, and 80 mL of anhydrous THF. The mixture was gently heated with stirring to dissolve the solid starting material and the resulting solution was cooled to −78° C. The solution was treated with 4.0 mL of 1 M sodium bis(trimethylsilyl)amide in THF (Aldrich) by slow addition via syringe through a rubber septum. After stirring at −78° C. for 4 h, the solution was mixed with 80 mL of water and worked-up according to example 51. The crude product was purified by flash chromatography on 85 g of silica gel (85:15 hexane:EtOAc) to afford 1.44 g (70%) of (2R, 3S, 5S)-Benzyl 3-(3-cyclopentylbenzyl)-2-oxo-2,3-diphenyl-4-morpholinecarboxylate as a white powder, m.p. 82–84° C.

EXAMPLE 73

3-Cyclopentyl-L-phenylalanine

According to example 53, 1.37 g of (2R, 3R, 5S)-benzyl 3-(3-cyclopentylbenzyl)-2-oxo-5,6-diphenyl-4-morpholinecarboxylate was hydrogenolyzed in 80 mL of 1:1 THF:MeOH using 0.31 g of PdCl$_2$ to afford 0.63 g (93%) of 3-cyclopentyl-L-phenylalanine·HCl as a white powder, m.p. >200° C.

$^1$H-NMR: (200 MHz, DMSO-d$_6$) δ 8.39 (br s, 3 H, NH$_3^+$), 7.31-7.12 (m, 3 H, aromatic CH), 7.08 (d, 1 H, J=7.3, aromatic CH), 4.17 (m, 1 H, methine), 3.11 (d, 2 H, J=6.1, ArCH$_2$), 2.96 (m, 1H, cyclopentyl methine), 1.99 (m, 2H, cyclopentyl CH$_2$), 1.88-1.45 (m, 6H, cyclopentyl CH$_2$).

EXAMPLE 74 tert-Butyl 3-cyclopentyl-L-phenylalaninate

According to example 54, 0.50 g of 3-cyclopentyl-L-phenylalanine•HCl was treated with 25 mL of isobutylene in 20 mL of 1,4-dioxane in the presence of 0.3 mL of conc. H$_2$SO$_4$. Work-up followed by acidification of the free amine with ethereal HCl afforded 0.49 g (82%) of tert-butyl 3-cyclopentyl-L-phenylalaninate•HCl as a white powder, m.p. 154–156° C.

EXAMPLE 75 tert-Butyl N-(benzyloxy)carbonyl)-5-O-tert-butyl-L-glutam-1-yl-3-cyclopentyl-L-phenylalaninate According to example 9, 0.49 g of tert-butyl 3-cyclopentyl-L-phenylalaninate•HCl was coupled with 0.51 g of N-Cbz-L-glutamic acid γ-tert-butyl ester (Sigma) using 0.30 g of EDC (Aldrich) and 0.16 mL of N-methylmorpholine. The crude product was purified by flash chromatography on 80 g of silica gel (8:2 hexane:EtOAc) to afford 0.75 g (82%) of tert-butyl N-((benzyloxy)carbonyl)-5-O-tert-butyl-L-glutam-1-yl-3-cyclopentyl-L-phenylalaninate as a thick transparent oil.

$^1$H-NMR: (300 MHz, DMSO-d$_6$) δ 8.22 (d, 1H, J=7.3, NH), 7.33 (m, 6H, aromatic CH), 7.20-6.97 (m, 3H, aromatic CH, NH), 5.01 (m, 2H, PhCH$_2$O), 4.33 (m, 1H, methine), 4.05 (m, 1H, methine), 2.91 (m, 3H, ArCH$_2$, cyclopentyl methine), 2.20 (t, 2H, J=7.7, glu 4-CH$_2$), 1.97 (m, 2H, glu 3-CH$_2$), 1.88-1.43 (m, 8H, cyclopentyl CH$_2$), 1.38 (s, 9H, t-Bu), 1.31 (s, 9H, t-Bu).

EXAMPLE 76 tert-Butyl 5-O-tert-butyl-L-glutam-1-yl-3-cyclopentyl-L-phenylalaninate

According to example 48, 0.75 g of tert-butyl N-((benzyloxy)carbonyl)-5-O-tert-butyl-L-glutam-1-yl-3-cyclopentyl-L-phenylalaninate was hydrogenolyzed using 0.12 g of 10% Pd(C) in 60 mL of MeOH. This afforded 0.58 g (99%) of tert-butyl-5-O-tert-butyl-L-glutam-1-yl-3-cyclopentyl-L-phenylalaninate as a transparent oil. A sample of the corresponding HCl salt for $^1$H-NMR analysis was prepared by treating 10 mg of the product with excess 1N ethereal HCl and concentrating to dryness.

¹H-NMR: (300 MHz, DMSO-d₆) δ 8.99 (d, 1H, J=7.0, NH). 8.32 (br s, 3H, NH₃⁺), 7.24-7.01 (m, 4H, aromatic CH), 4.38 (m, 1H, methine), 3.85 (m, 1H, methine), 2.93 (m, 3H, ArCH₂, cyclopentyl methine), 2.34 (t, 2H, J=7.7, glu 4-CH₂), 1.96 (m, 4H, glu 3-CH₂, cyclopentyl CH₂), 1.82-1.44 (m, 6H, cyclopentyl CH₂), 1.40 (s, 9H, t-Bu), 1.31 (s, 9H, t-Bu).

EXAMPLE 77 tert-Butyl 5-O-tert-butyl-N-(4-(((2,4-diamino-6-pteridinyl)methyl)methylamino)benzoyl)-L-glutam-1-yl-3-cyclopentyl-L-phenylalaninate According to example 49, 0.200 g of 4-(N-(2,4-diamino-6-pteridinylmethyl)-N-methylamino)benzoic acid hemihydrochloride dihydrate (Aldrich) was coupled with 0.25 g of tert-butyl 5-O-tert-butyl-L-glutam-1-yl-3-cyclopentyl-L-phenylalaninate using 0.24 mL of DECP (Aldrich) and 0.26 mL of Et₃N in 20 mL of DMF. The crude product was purified by flash chromatography on 150 g of silica gel (7:7:1 CH₂Cl₂:acetone:MeOH) to afford 0.195 g (47%) of tert-butyl 5-O-tert-butyl-N-(4-(((2,4-diamino-6-pteridinyl)methyl)methylamino)benzoyl)-L-glutam-1-yl-3-cyclopentyl-L-phenylalaninate as a yellow powder, m.p. 115–120° C.

EXAMPLE 78

N-(4-(((2,4-Diamino-6-pteridinyl)methyl) methylamino)benzoyl)-L-glutam-1-yl-3-cyclopentyl-L-phenylalanine According to example 50, 0.18 g of tert-butyl 5-O-tert-butyl-N-(4-(((2,4-diamino-6-pteridinyl)methyl) methylamino)benzoyl)-L-glutam-1-yl-3-cyclopentyl-L-phenylalaninate was treated with gaseous HCl in 20 mL of CH₃NO₂ for 1.25 h. Work-up and isolation in the usual manner afforded 0.135 g (84%) of N-(4-(((2,4-diamino-6-pteridinyl)methyl)methylamino)benzoyl)-L-glutam-1-yl-3-cyclopentyl-L-phenylalanine as a yellow-orange powder, m.p. 170° C. (dec).

HPLC: one peak on C18, k'-=2.86, 65:35:0.1 H₂O:MeCN:TFA, flow rate =1 mL/min. ¹H-NMR: (300 MHz, DMSO-d₆) δ 12.90-11.85 (br m, COOH), 8.58 (s, 1H, pteridinyl 7-CH), 8.04 (d, 1H, J=7.7, amide NH) 8.00 (d, 1H, J=8.1, amide NH, 7.72 (br s, 1H, NH₂), 7.71 (d, 2H, J=8.8, aromatic CH), 6.69 (br s, 2N, NH₂), 4.79 (s, 2H, pteridinyl-CH₂), 4.40 (m, 2H, methines), 3.22 (s, 3H, N-CH₃), 3.01 (m, 1H, ArCH₂), 2.94-2,.75 (m, 2H, ArCH₂, cyclopentyl methine), 2.24 (t, 2H, J=7.7, glu 4-CH₂), 2.03-1.76 (m, 4H, glu 3-CH₂, cyclopentyl CH₂), 1.73-1.35 (m, 6H, cyclopentyl CH₂).
Elemental Analysis: Calcd. for C₃₄H₃₉N₉O₆·1.6 H₂O (MW 698.56): C, 58.46; H, 6.09; N, 18.05. Found: C, 58.50; H, 6.08; N, 18.10.
Mass Spectrum: (FAB) 670 (M+H)⁺, 613, 437, 309, 275.
UV Spectrum: (pH7 Buffer) λ_max (ε) 259.7 (23300), 308.3 (23500), 371.7 (7030). λ_min (ε) 241.0 (13500), 274.8 (15300), 346.1 (5260).

EXAMPLE 79

2-Cyclohexylbenzyl alcohol

According to example 61, 10.0 g of 2-iodobenzyl alcohol was treated with 25 mL of cyclohexene (Aldrich) using 0.96 g of Pd(O Ac)₂, 2.60 g of tri-ortho-tolyphosphine, and 6.6 mL of Et₃N at 100° C. for 48 h. The resulting olefin mixture was hydrogenated for 6.5 h using 0.36 g of 5% Pt(C) in MeOH to afford 3.37 g (42%) of 2-cyclohexyl benzyl alcohol as a light yellow liquid.
¹H: (300 MHz, DMSO-d₆) δ 7.33 (d, 1H, J=7.4, aromatic CH), 7.27-7.08 (m, 3H, aromatic CH), 5.03 (t, 1H, J=5.4, OH), 4.34 (d, 2H, J=5.4, ArCH₂O), 2.76 (m, 1H, cyclohexyl methine), 1.85-1.61 (m, 5H, cyclohexyl CH₂), 1.48-1.22 (m, 5H, cyclohexyl CH₂).

EXAMPLE 80

2-Cyclohexylbenzyl bromide

According to example 17, 3.36 g of 2-cyclohexylbenzyl alcohol was treated with 0.59 mL of PBr₃ in 25 mL of anhydrous CH₂Cl₂ to afford 3.90 g of crude product (90% pure by ¹H-NMR). This material was vacuum distilled via short path (1.0 mmHg, 117–120° C.) to afford 3.54 g (79%) of 2-cyclohexylbenzyl bromide as a clear liquid.
¹H: (300 MHz, DMSO-d₆) δ 7.39 (d, 1H, J=5.7, aromatic CH), 7.29 (m, 2H, aromatic CH), 7.13 (m, 1H, aromatic CH), 4.76 (s, 2H, ArCH₂Br), 2.86 (m, 1H, cyclohexyl methine), 1.83-1.63 (m, 5H, cyclohexyl CH₂), 1.53-1.20 (m, 5H, cyclohexyl (CH₂).

EXAMPLE 81

(2R, 3S, 5S)-tert-Butyl 3-(2-cyclohexylbenzyl)-2-oxo-2,3-diphenyl-4-morpholinecarboxylate To a dry 250 mL 3-necked flask equipped with a magnetic stirrer and a nitrogen inlet was added a solution of 1.47 g of tert-butyl (2R, 3S)-(-)-6-oxo-2,3-diphenyl-4-morpholinecarboxylate (Aldrich) in 30 mL of THF and a solution of 1.00 g of 2-cyclohexylbenzyl bromide in 8 mL of THF. Both solutions had been dried over 3 Å molecular sieves for 24 h. Anhydrous THF was used for rinse (30 mL) to give a total solution volume of 68 mL. The resulting solution was cooled to −78° C. and was treated with 4.15 mL of 1M sodium bis-(trimethylsilyl) amide in THF (Aldrich) by slow addition via syringe through a rubber septum. After stirring at −78° C. for 3.5 h, the reaction mixture was mixed with 80 mL of water and subjected to rotary evaporation to remove THF. The resulting mixture was extracted with EtOAc (4×50 mL). The combined EtOAc extracts ere washed with saturated aqueous NaCl (2×70 mL), dried over anhydrous MgSO₄ and concentrated in vacuo to afford a white solid. Purification of this material by flash chromatography on 200 g of silica gel (8:2 hexane:EtOAc) afforded 1.2 g (58%) of (2R, 3S, 5S)-tert-butyl 3-(2-cyclohexylbenzyl)-2-oxo-2,3-diphenyl-4-morpholinecarboxylate as a white, crystalline solid, m.p. 195–198° C.

EXAMPLE 82

(2R, 3S, 5S)-6-Oxo-2,3-diphenyl-5-(2-cyclohexylbenzyl)morpholine

A dry 50 mL 3-necked flask equipped with a nitrogen inlet and a magnetic stirrer was charges with 2.10 g of (2R, 3S, 5S)-tert-butyl 3-(2-cyclohexylbenzyl)-2-oxo-5,6-diphenyl-4-morpholinecarboxylate and 33 mL of anhydrous CH₂Cl₂. The solution was stirred at RT and treated with 3.3 mL of RFA. After 3.5 h, tlc (SiO₂, 85:15 hexane:EtOAc) indicated no remaining starting material, a major new component at R_f=0.45, and two minor components at R_f=0.68 and 0.70. The solution was neutralized by addition of 9 mL of Et₃N and was concentrated in vacuo to give a thick oil. This material was dissolved in 80 mL of $CH_2Cl_2$, washed with water (3×60 mL) followed by 5% aqueous $NaHCO_3$ (3×60 mL and dried over anhydrous $MgSO_4$. Drying agent was removed by filtration and the filtrate concentrated in vacuo to afford a white solid. Purification of the crude product by flash chromatography on 150 g of silica gel (8:2 hexane:EtOAc) followed by recrystallization from EtOH-$H_2O$ afforded 1.27 g (75%) of (2R, 3S, 5S)-6-oxo-2,3-diphenyl-5-(2-cyclohexylbenzyl)morpholine as a white crystalline solid, m.p. 159–160° C.

EXAMPLE 83

2-Cyclohexyl-L-phenylalanine

According to example 53, 1.17 g of (2R, 3S, 5S)-6-oxo-2,3-diphenyl-5-(2-cyclohexylbenzyl)morpholine was hydrogenolyzed in 60 mL of 1:1 THF:EtOH using 0.34 g of $PdCl_2$ to afford 0.83 g of 2-cyclohexyl-L-phenylalanine•HCl as a fluffy white solid, m.p. 140° C. (dec).

EXAMPLE 84 tert-Butyl 2-cyclohexyl-L-phenylalaninate

According to example 54, 0.73 g of 2-cyclohexyl-L-phenylalanine•HCl was treated with 25 mL of isobutylene in 25 mL of 1,4-dioxane in the presence of 0.4 mL of conc. $H_2SO_4$. Work-up followed by acidification of the free amine with ethereal HCl afforded 0.70 g (80%) of tert-butyl 2-cyclohexyl-L-phenylalaninate•HCl as a yellow foam.
$^1$H-NMR: (300 MHz, DMSO-$d_6$) δ 8.53 (br s, 3H, $NH_3^+$), 7.27 (m, 2H, aromatic CH), 7.10 (m, 2H, aromatic CH), 3.86 (m, 1H, methine), 3.24 (m, 1H, $ArCH_2$), 2.97 (m, 1H, $ArCH_2$), 2.72 (m, 1H, cyclohexyl methineJ), 1.86-1.60 (m, 5H, cyclohexyl $CH_2$), 1.56-1.30 (m, 5H, cyclohexyl $CH_2$), 1.19 (s, 9H, t-Bu).

EXAMPLE 85 tert-Butyl N-((benzyloxy)carbonyl)-5-O-tert-butyl-L-glutam-1-yl-2-cyclohexyl-L-phenyalaninate According to example 9, 0.70 g of tert-butyl-2-cyclohexyl-L-phenylalaninate•HCl was coupled with 0.70 g of N-Cbz-L-glutamic acid-γ-tert-butyl ester (Sigma) using 0.42 g of EDC (Aldrich) and 0.23 mL of N-methylmorpholine. The crude product was purified by flash chromatography on 150 g of silica gel (8:2 hexane:EtOAc) to afford 0.97 g (76%) of tert-butyl N-((benzyloxy)carbonyl)-5-O-tert-butyl-L-glutam-1-yl-2-cyclohexyl-L-phenylalaninate as a white foam.
$^1$H-NMR: (300 MHz, DMSO-$d_6$) δ 8.32 (d, 1H, J=7.6, NH), 7.40-6.97 (m, 10H, aromatic CH, NH), 5.00 (m, 2H, $PhCH_2O$), 4.26 (m, 1H, methine), 4.04 (m, 1H, methine), 3.07 (m, 1H, $ArCH_2$), 2.93-2.70 (m, 2H, $ArCH_2$, cyclohexyl methine, 2.19 (t, 2H, J=7.7, glu 4-$CH_2$), 1.90-1.62 (m, 7H, glu 3-$CH_2$, cyclohexyl $CH_2$), 1.56-1.33 (m, 5H, cyclohexyl $CH_2$), 1.38 (s, 9H, t-Bu), 1.32 (s, 9H, t-Bu).
Mass Spectrum: (CI, $CH_4$) 623 (M+H)$^+$, 567, 539, 511, 489, 433, 193.

EXAMPLE 86 tert-Butyl 5-O-tert-butyl-L-glutam-1-yl-2-cyclohexyl-L-phenyalaninate

According to example 48, 0.97 g of tert-butyl N-((benzyloxy)carbonyl)-5-O-tert-butyl-L-glutam-1-yl-2-cyclohexyl-L-phenyalaninate was hydrogenolyzed using 0.16 g of 10% Pd(C) in 50 mL of MeOH. This afforded 0.76 g (100%) of tert-butyl 5-O-tert-butyl-L-glutam-1-yl-2-cyclohexyl-L-phenyalaninate as a thick transparent oil. A sample of the corresponding HCl salt for $^1$H-NMR analysis was prepared by treating 10 mg of the product with excess 1M ethereal HCl and concentrating to dryness.
$^1$H-NMR: (300 MHz, DMSO-$d_6$) δ 9.05 (d, 1H, J=7.5, NH), 8.24 (br s, 3H, $NH_3^+$), 7.20 (m, 3H, aromatic CH), 7.07 (t, 1H, J=7.1, aromatic CH), 4.28 (m, 1H, methine), 3.83 (m, 1H, methine), 3.08 (m, 1H, $ArCH_2$), 2.91 (m, 1H, $ArCH_2$), 1.78 (m, 1H, cyclohexyl methine), 2.34 (m, 2H, glu 4-$CH_2$), 2.00 (m, 2H, glu 3-$CH_2$), 1.89-1.60 (m, 5H, cyclohexyl $CH_2$), 1.57-1.20 (m, 5H, cyclohexyl $CH_2$), 1.40 (s, 9H, t-Bu), 1.33 (s, 9H, t-Bu).

EXAMPLE 87 tert-Butyl N-(4-(((2,4-diamino-6-pteridinyl)methyl)methylamino)benzoyl)-5-O-tert-butyl-L-glutam-1-yl-2-cyclohexyl-L-phenylalaninate According to example 49, 0.247 g of 4-(N-(2,4-diamino-6-pteridinylmethyl)-N-methylamino)benzoic acid hemihydrochloride dihydrate (Aldrich) was coupled with 0.35 g of tert-butyl 5-O-tert-butyl-L-glutam-1-yl-2-cyclohexyl-L-phenylalaninate using 0.30 mL of DECP (Aldrich) and 0.32 mL of $Et_3N$ in 25 mL of DMF. The crude product was subjected to flash chromatography twice (150 g $SiO_2$, 7:7:1. $CH_2Cl_2$:acetone:MeOH; 150 g $SiO_2$, 95:5 $CH_2Cl_2$:MeOH) to afford 0.297 g (57%) of tert-butyl N-(4-(((2,4-diamino-6-pteridinyl)methyl)methylamino)benzoyl)-5-O-tert-butyl-L-glutam-1-yl-2-cyclohexyl-L-phenylalaninate as a yellow powder, m.p. 135–140° C.

EXAMPLE 88

N-(4-(((2,4-Diamino-6-pteridinyl)methyl)methylamino)benzoyl)-L-glutam-1-yl-2-cyclohexyl-L-phenylalanine According to example 50, 0.271 g of tert-butyl N-(4-(((2,4-diamino-6-pteridinyl)methyl)methylamino)benzoyl)-5-O-tert-butyl-L-glutam-1-yl-2-cyclohexyl-L-phenylalaninate was treated with gaseous HCl in 20 mL of $CH_3NO_2$ for 1.5 h. Work-up and isolation in the usual manner afforded 0.191 g (79%) of N-(4-(((2,4-diamino-6-pteridinyl)methyl)methylamino)benzoyl)-L-glutam-1-yl-2-cyclohexyl-L-phenylalanine as a yellow-orange powder, m.p. 175° C. (dec).
HPLC: one peak on C 18, k'=4.05, 65:35:0.1 $H_2O$:MeCN:TFA, flow rate=1 mL/min.
$^1$H-NMR: (300 MHz, DMSO-$d_6$) δ 12.75-11.90 (br s, COOH), 8.58 (s, 1H pteridinyl 7-CH), 8.20 (d, 1H, J=7.9, amide NH), 7.98 (d, 1H, J=8.1, amide NH), 7.79 (br s, 1H, $NH_2$), 7.72 (d, 2H, J=8.9, aromatic CH), 7.59 (br s, 1H, $NH_2$), 7.19 (m, 1H, aromatic CH), 7.08 (m, 2H, aromatic CH), 6.92 (m, 1H, aromatic CH), 6.83 (d, 2H, J=8.9, aromatic CH), 6.75 (br s, 2H, $NH_2$), 4.80 (s, 2H, pteridinyl $CH_2$), 4.43 (m, 1H, methine), 4.31 (m, 1H, methine), 3.21 (s, 3H, N-$CH_3$), 3.12 (m, 1H, $ArCH_2$), 3.,92-3.70 (m, 2H, $ArCH_2$, cyclohexyl methine), 2.23 (t, 2H, J=7.7, glu 4-$CH_2$), 2.05-1.60 (m, 7H, glu 3-$CH_2$, cyclohexyl $CH_2$), 1.50-1.16 (m, 5H, cyclohexyl $CH_2$).
Elemental Analysis: Calcd. for $C_{35}H_{41}N_9O_6$•1.5 $H_2O$ (MW 710.79): C, 59.14; H, 6.24; N, 17.74. Found: C, 59.11; H, 6.20; N, 17.73.
Mass Spectrum: (FAB) 684 (M+H)$^+$, 613, 510, 385, 309.
UV Spectrum: (pH7 Buffer) $\lambda_{max}$ (ε) 259.7 (22300), 308.8 (22700), 374.0 (6850). $\lambda_{min}$ (ε) 241.7 (12800), 275.2 (14700), 346.3 (5170).

EXAMPLE 89

3-tert-Butylbenzyl bromide

A dry 100 mL 3-necked flask equipped with a nitrogen inlet, a condenser, a thermometer, and a magnetic stirrer was charged with 2.0 g of 3-tert-butyltoluene (Wiley Organics, Coshocton, Ohio 43812), 2.40 g of N-bromosuccinimide (Aldrich), and 30 mL of $CCl_4$. The mixture was treated with 0.16 g of benzoyl peroxide (Aldrich) and heated at 6-° C. under $N_2$. Careful temperature control is important to minimize by-product formation. After 1 h at 60° C. the reaction mixture was cooled to 0° C., filtered to remove succinimide, and the filtrate was concentrated in vacuo to afford a light yellow liquid. Analysis of this material by tlc ($SiO_2$, hexane) indicated a major new component at $R_f$=0.50, a minor component at $R_f$=0.55, and a trace of 3-tert-butyltoluene at $R_f$=0.75. The crude product was purified by flash chromatography on 100 g of silica gel (hexane) to afford 1.06 g (35%) of 3-tert-butylbenzyl bromide as a clear liquid.
$^1$H-NMR: (300 MHz, DMSO-$d_6$) δ 7.47 (s, 1H, aromatic CH), 7.39-7.21 (m, 3H, aromatic CH), 4.69 (s, 2H, $ArCH_2Br$), 1.27 (s, 9H, t-Bu).

EXAMPLE 90

(2R, 3S, 5S)-tert-Butyl 3-(3-tert-butylbenzyl)-2-oxo-2,3-diphenyl-4-morpholinecarboxylate According to example 81, 1.63 g of tert-butyl (2R, 3S)-(-)-6-oxo-2,3-diphenyl-4-morpholinecarboxylate (Aldrich) was alkylated with 1.0 g of 3-tert-butylbenzyl bromide in 70 mL of anhydrous THF using 4.62 mL of 1M sodium bis(trimethylsilyl)amide in THF (Aldrich). The crude product was purified by flash chromatography on 150 g of silica gel (9:1 hexane:EtOAc) to afford 1.84 g (80%) of (2R, 3S, 5S)-tert-butyl 3-(3-tert-butylbenzyl)-2-oxo-2,3-diphenyl-4-morpholinecarboxylate as a white foam, m.p. 65–90° C.

EXAMPLE 91

(2R, 3S, 5S)-6-Oxo-2,3-diphenyl-5-(3-tert-butylbenzyl)morpholine

According to example 82, 1.79 g of (2R, 3S, 5S)-tert-butyl 3-(3-tert-butylbenzyl)-2-oxo-5,6-diphenyl-4-morpholinecarboxylate was treated with 3 mL of TFA in 30 mL of $CH_2Cl_2$ for 3.4 h. Neutralization with 7.7 mL of $Et_3N$ and work-up in the usual manner gave a thick oil. Purification of the crude material by flash chromatography on 125 g of silica gel (75:25 hexane:EtOAc) afforded 0.90 g (63%) of (2R, 3S, 5S)-6-oxo-2,3-diphenyl-5-(3-tert-butylbenzyl) morpholine as a white crystalline solid, m.p. 136–137° C.

EXAMPLE 92

3-tert-Butyl-L-phenylalanine

According to example 53, 0.89 g of (2R, 3S, 5S)-6-oxo-2,3-diphenyl-5-(3-tert-butylbenzyl)morpholine was hydrogenolyzed in 40 mL of 1:1 THF:EtOH using 0.28 g of $PdCl_2$ to afford 0.57 g (99%) of 3-tert-butyl-L-phenylalanine•HCl as a white powder, m.p. ≧250° C.
$^1$H-NMR: (300 MHz, DMSO-$d_6$) δ 8.42 (br s, 3H, $NH_3^+$), 7.26 (m, 3H, aromatic CH), 7.08 (dd; 1H; J=7.0, 1.3; aromatic CH), 4.12 (m, 1H, methine), 3.12 (d, 2H, J=6.1, $ArCH_2$), 1.27 (s, 9H, t-Bu).

EXAMPLE 93 tert-Butyl 3-tert-butyl-L-phenylalaninate

According to example 54, 0.50 g of 3-tert-butyl-L-phenylalanine•HCl was treated with 30 mL of isobutylene in 25 mL of 1,4-dioxane in the presence of 0.4 mL of conc. $H_2SO_4$. Work-up in the usual manner followed by acidification of the free amine with ethereal HCl afforded 0.53 g (87%) of tert-butyl 3-tert-butyl-L-phenylalaninate•HCl as a light yellow foam.
$^1$H-NMR: (300 MHz, DMSO-$d_6$) δ 8.48 (br s, 3H, $NH_3^+$), 7.36-7.20 (m, 3H, aromatic CH), 7.08 (d, 1H, J=7.1, aromatic CH), 4.16 (m, 1H, methine), 3.19 (dd; 1H; J=13.9, 5.7; $ArCH_2$), 2.95 (dd; 1H; J=13.9, 8.6; $ArCH_2$), 1.28 (s, 9H, t-Bu), 1.27 (s, 9H, t-Bu).

EXAMPLE 94 tert-Butyl N-((benzyloxy)carbonyl)-5-O-tert-butyl-L-glutam-1-yl-3-tert-butyl-L-phenylalaninate According to example 9, 0.52 g of tert-butyl-3-tert-butyl-L-phenylalaninate•HCl was coupled with 0.56 g of N-Cbz-L-glutamic acid γ-tert-butyl ester (Sigma) using 0.33 g of EDC (Aldrich) and 0.18 mL of N-methylmorpholine. The crude product was purified by flash chromatography on 110 g of silica gel (75:25 hexane:EtOAc) to afford 0.77 g (78%) of tert-butyl N-((benzyloxy)carbonyl)-5-O-tert-butyl-L-glutam-1-yl-3-tert-butyl-L-phenylalaninate as a thick transparent oil.
$^1$H-NMR: (200 MHz, DMSO-$d_6$) δ 8.28 (d, 1H, J=7.3, NH), 7.42-7.13 (m, 9H, aromatic CH, NH), 7.04 (d, 1H, J=6.6, aromatic CH), 5.02 (s, 2H, $PhCH_2O$), 4.37 (m, 1H, methine), 4.07 (m, 1H, methine), 2.96 (d, 2H, J=7.6, $ArCH_2$), 2.21 (t, 2N, J=7.7. glu 4-$CH_2$), 1.97-1.60 (m, 2H, glu 3-$CH_2$), 1.39 (s, 9H, t-Bu), 1.31 (s, 9H, t-Bu), 1.27 (s, 9H, t-Bu).

EXAMPLE 95 tert-Butyl 5-O-tert-butyl-L-glutam-1-yl-3-tert-butyl-L-phenylalaninate

According to example 48, 0.76 g of tert-butyl N-((benzyloxy)carbonyl)-5-O-tert-butyl-L-glutam-1-yl-3-tert-butyl-L-phenylalaninate was hydrogenolyzed using 0.13 g of 10% Pd(C) in 60 mL of MeOH. This afforded 0.58 g (99%) of tert-butyl 5-O-tert-butyl-L-glutam-1-yl-3-tert-butyl-L-phenylalaninate as a thick transparent oil. A sample of the corresponding HCl salt for $^1$H-NMR analysis was prepared by treating 10 mg of the product with excess 1N ethereal HCl and concentrating to dryness.
$^1$H-NMR: (300 MHz, DMSO-$d_6$) δ 8.97 (d, 1H, J=7.0, NH), 8.27 (br s, 3H, $NH_3^+$), 7.31-7.15 (m, 3H, aromatic CH), 7.06 (d, 1H, J=6.8, aromatic CH), 4.38 (m, 1H, methine), 3.82 (m, 1H, methine), 2.96 (d, 2H, J=7.2, $ArCH_2$), 2.33 (m, 2H, glu 4-$CH_2$), 1.98 (m, 2H, glu 3-$CH_2$), 1.38 (s, 9H, t-Bu), 1.29 (s, 9H, t-Bu), 1.26 (s, 9H, t-Bu).

EXAMPLE 96 tert-Butyl N-(4-(((2,4-diamino-6-pteridinyl)methyl)methylamino)benzoyl)-5-O-tert-butyl-L-glutam-1-yl-3-tert-butyl-L-phenylalaninate According to example 49, 0.223 g of 4-(N-(2,4-diamino-6-pteridinylmethyl)-N-methylamino)benzoic acid hemihydrochloride dihydrate (Aldrich) was coupled with 0.30 g of tert-butyl-L-glutam-1-yl-3-tert-butyl-L-phenylalaninate using 0.27 mL of DECP (Aldrich) and 0.29 mL of $Et_3N$ in 25 mL of DMF. The crude product was subjected to flash chromatography twice (180 g of $SiO_2$, 7:7:1 $CH_2Cl_2$:acetone:MeOH; 185 g $SiO_2$, 95:5 $CH_2Cl_2$:MeOH) to afford 0.323 g (71%) of tert-butyl N-(4-(((2,4-diamino-6-pteridinyl)methyl)methylamino)benzoyl)-5-O-tert-butyl- L-glutam-1-yl-3-tert-butyl-L-phenylalaninate as a yellow powder, m.p, 128–135° C.

EXAMPLE 97

N-(4-(((2,4-Diamino-6-pteridinyl)methyl) methylamino)benzoyl)-L-glutam-1-yl-3-tert-butyl-L-phenylalanine (Procedure A)

For Procedure B to prepare this compound, see Example 130. According to example 50, 0.303 g of tert-butyl N-(4-(((2,4-diamino-6-pteridinyl)methyl)methylamino)benzoyl)-5-O-tert-butyl-L-glutam-1-yl-3-tert-butyl-L-phenylalaninate was treated with gaseous HCl in 40 mL of $CH_3NO_2$ for 1.5 h. Work-up and isolation in the usual manner afforded 0.215 g (79%) of N-(4-(((2,4-diamino-6-pteridinyl)methyl)methylamino)benzoyl)-L-glutam-1-yl-3-tert-butyl-L-phenylalanine as a yellow powder, m.p. 183° C. HPLC: one peak on C18, k'=2.54, 70:30:0.1 $H_2O$:MeCN:TFA, flow rate=1 mL/min.

$^1$H-NMR: (300 MHz, DMSO-$d_6$) δ 12.90-11.80 (br s, COOH), 8.59 (s, 1H, pteridinyl 7-CH), 8.08 (d, 1H, J=7.6, amide NH), 7.98 (d, 1H, J=8.0, amide NH), 7.89 (br s, 1H, $NH_2$), 7.70 (d, 2H, J=8.9, aromatic CH), 7.69 (br s, 1H, $NH_2$), 7.21 (s, 1H, aromatic CH), 7.16 (d, 1H, J=7.7, aromatic CH), 7.08 (t, 1H, J=7.6, aromatic CH), 6.99 (d, 1H, J=7.4, aromatic CH), 6.81 (m, 4H, aromatic CH, $NH_2$), 4.79 (s, 2H, pteridinyl $CH_2$), 4.43 (m, 2H, methines), 3.21 (s, 3H, N-$CH_3$), 3.03 (m, 1H, Ar$CH_2$), 2.91 (m, 1H, Ar$CH_2$), 2.24 (t, 2H, J=7.8 glu 4-$CH_2$), 2.04-1.74 (m, 2H, glu 3-$CH_2$), 1.20 (s, 9H, t-Bu).

Elemental Analysis: Calcd. for $C_{33}H_{39}N_9O_6$•1.8 $H_2O$ (MW 690.16): C, 57.43; H, 6.22; N, 18.27. Found: C, 57.34; H, 6.07; N, 18.26.

Mass Spectrum: (FAB) 658 (M+H)$^+$, 459, 307.

UV Spectrum: (pH7 Buffer) $\lambda_{max}$ (ε) 259.4 (22800), 308.1 (23000), 372.5 (7040). $\lambda_{min}$ (ε) 241.0 (13400), 274.6 (15200), 345.2 (5380).

EXAMPLE 98

N-((tert-Butoxy)carbonyl)-4-(bis(2-chloroethyl) amino)-L-phenylalanine

A dry 50 mL 3-necked flask equipped with a magnetic stirrer and a nitrogen inlet was charged with 0.10 g of 4'-(bis(2-chloroethyl)amino)-L-phenylalanine•$H_2O$ (Sigma), 14 mL of 1:1 DMF:$CH_3CN$, and 0.19 mL of $Et_3N$. The mixture was treated with 91 mg of 2-(tert-butoxycarbonyloxyimino)-2-phenylacetonitrile (BOC-ON, Fluka) and stirred at RT under $N_2$. After 18 h, the solid starting material had dissolved giving a light yellow solution which was concentrated in vacuo to dryness. Analysis of the residue by tlc (SiO$_2$, 9:1 CHCl$_3$:MeOH) indicated a major new component at $R_f$=0.65, BOC-ON derived components at $R_f$=1.0 and 0.71 and two trace components at $R_f$=0.60 and 0.35. The crude product was purified by flash chromatography on 60 g of silica gel (9:1 CHCl$_3$:MeOH) to afford 0.10 g (80%) of N-((tert-butoxy)carbonyl)-4-(bis(2-chloroethyl) amino)-L-phenylalanine as light yellow glass.

$^1$H-NMR: (300 MHz, DMSO-$d_6$) δ 7.04 (d, 2H, J=8.6, aromatic CH), 6.62 (d, 2H, J=8.5, aromatic CH), 6.46 (br s, 1H, NH), 3.87 (m, 1H, methine), 3.67 (s, 8H, N (CH$_2$CH$_2$Cl)$_2$), 2.90 (m, 1H, Ar$CH_2$), 1.33 (s, 9H, t-Bu).

EXAMPLE 99 tert-Butyl N-((tert-butoxy)carbonyl)-4-(bis(2-chloroethyl)amino)-L-phenylalanyl-(3-cyclopentyl)-L-phenylalaninate A 50 mL round bottomed flask equipped with a magnetic stirrer was charged with 96 mg of N-((tert-butoxy) carbonyl)-4-(bis(2-chloroethyl)amino)-L-phenylalanine 77 mg of tert-butyl 3-cyclopentyl-L-phenylalaninate•HCl, and 10 mL of CH$_2$Cl$_2$. The solution was cooled to 0° C. and treated with 48 mg of EDC (Aldrich) followed by 0.026 mL of N-methylmorpholine. The reaction mixture was stirred at 0° C. for 20 min, allowed to war to RT, and stirred for an additional 2 h. Analysis of the solution by tlc (SiO$_2$, 7:3 hexane:EtOAc) indicated a major new component at $R_f$=0.54 and four minor components at $R_f$=0.4, 0.37, 0.16 and 0.0. The solution was concentrated in vacuo to dryness and the residue was subjected to flash chromatography on 50 g of silica gel to afford 73 mg (46%) of tert-butyl-N-((tert-butoxy)carbonyl)-4-(bis(2-chloroethyl)amino)-L-phenylalanyl-(3-cyclopentyl)-L-phenylalaninate as a thick semi-solid.

$^1$H-NMR: (300 MHz, DMSO-$d_6$) δ 8.18 (d, 1H, J=7.8, NH), 7.19 (m, 1H, aromatic CH), 7.13-7.00 )m, 5H, aromatic CH, NH), 6.77 (d, 1H, J=8.8, aromatic CH), 6.63 (d, 2H, J=8.9, aromatic CH), 4.35 (m, 1H, methine), 4.05 (m, 1H, methine), 3.68 (s, 8H, N (CH$_2$CH$_2$Cl)$_2$), 2.93 (m, 3H, Ar$CH_2$, cyclopentyl methine), 2.79 (m, 1H, Ar$CH_2$), 2.58 (m, 1H, Ar$CH_2$), 1.80-1.43 (m, 8H, cyclopentyl $CH_2$), 1.29 (s, 18H, t-Bu).

EXAMPLE 100

4-(Bis(2-chloroethyl)amino)-L-phenylalanyl-3-cyclopentyl-L-phenylalanine

A 25 mL 3-necked flask equipped with a nitrogen inlet and a magnetic stirrer was charged with 65 mg of tert-butyl-N-((tert-butoxy)carbonyl)-4-(bis(2-chloroethyl)amino)-L-phenylalanyl-(3-cyclopentyl)-L-phenylalaninate and 8 mL of CH$_3$NO$_2$. The solution was acidified by bubbling HCl gas through for 10 min. After stirring at RT under $N_2$ for 30 min, the solution was concentrated in vacuo to dryness. Analysis of the resulting solid by HPLC (C18, 50:50:0.1 H$_2$O:MeCN:TFA) indicated a major component at k'=1.14 (96%) and a minor component at k'=1.60 (4%). The crude product was purified by semi-preparative HPLC (C18, 55:45:0.1→50:50:0.1 H$_2$O:MeCN:TFA over 20 min, flow rate=15 mL/min). Fractions containing pure product (k'=1.14 by analytical HPLC) were combined and concentrated in vacuo to 20 mL. The resulting suspension was frozen and lyophilized to afford 35 mg (55%) of 4-(bis(2-chlorethyl) amino)-L-phenylalanyl-3-cyclopentyl-L-phenylalanine as a white powder, m.p. 80–90° C.

HPLC: one peak on C 18, k'=1.05, 50:50:0.1 MeCN•H$_2$O:TFA, flow rate=1 mL/min.

$^1$H-NMR: (300 MHz, DMSO-$d_6$) δ 8.85 (d, 1H, J=7.8, NH), 8.00 br s, 3H, NH$_3^+$), 7.25-7.00 (m, 6H, aromatic CH), 6.70 (d, 2H, J=8.5, aromatic CH), 4.50 (m, 1H, methine), 3.89 (m, 1H, methine), 3.69 (5, 8H, N (CH$_2$CH$_2$Cl)$_2$), 3.12-2.83 (m, 4H, Ar$CH_2$, cyclopentyl methine), 2.77 (m, 1H, Ar$CH_2$), 1.97 (m, 2H, cyclopentyl CH$_2$), 1.84-1.43 (m, 6H, cyclopentyl CH$_2$).

$^{19}$F-NMR: (282 MHz, DMSO-$d_6$): d 1.26 (relative to TFA external standard).

Elemental Analysis: Calcd. for $C_{27}H_{35}N_3O_3Cl_2$•TFA•1.6 H$_2$O (MW 663.35): C, 52.51; H, 5.96; N, 6.33. Found: C, 52.16; H, 5.69; N, 6.69.

Mass Spectrum: (FAB) 520 (M+H)$^+$, 273.

UV Spectrum: (2.5×10$^{-3}$M NaOH) $\lambda_{max\ (\epsilon)}$ 261.5 (18700), 303.9 (2090), $\lambda_{min}$ (ε) 232.3 (5270), 288.2 (1760).

EXAMPLE 101

3-Iodo-O-(tert-butyldimethylsilyl)benzyl alcohol

A 100 mL 3-necked flask equipped with a magnetic stirrer and a nitrogen inlet was charged with 5.0 g of 3-iodobenzyl alcohol (Aldrich), 3.86 g of tert-butyldimethylsilyl chloride (Aldrich), 3.20 g of imidazole (Aldrich), and 30 mL of anhydrous DMF. The resulting solution was stirred under nitrogen for 4 h and concentrated in vacuo to give a clear viscous oil. This material was dissolved in 150 mL of EtOAc and the solution was washed with 5% aqueous NaHCO$_3$ (3×70 mL), dried over anhydrous MgSO$_4$ and concentrated in vacuo to give a clear liquid. The crude product was purified by flash chromatography on 200 g of silica gel (hexane) to afford 7.01 g (94%) of 3-iodo-O-(tert-butyldimethylsilyl)benzyl alcohol as a clear liquid.

$^1$H-NMR: (300 MHz, DMSO-d$_6$) δ 7.67 (s, 1H, aromatic CH), 7.56 (d, 1H, J=7.3, aromatic CH), 7.27 (d, 1H, J=9.2, aromatic CH), 7.06 (t, 1H, J=7.6, aromatic CH), 4.68 (s, 2H, ArCH$_2$O), 0.94 (s, 9H, t-Bu), 0.10 (s, 6H, SiMe$_2$).

EXAMPLE 102

3-(1-Hydroxycyclobutyl)-O-(tert-butyltrimethylsilyl) benzyl alcohol

T a dry 500 mL 3-necked flask equipped with a nitrogen inlet and a magnetic stirrer were added 7.0 g of 3-iodo-O-(tert-butyldimethylsilyl)benzyl alcohol and 100 mL of anhydrous THF. The solution was cooled to −78° C. in a dry ice-isopropanol bath and treated with 9.7 mL of 2.5M n-butyllithium/hexane (Aldrich) by dropwise addition via syringe through a rubber septum. After stirring at −78° C. for 20 min, the solution was treated with 1.80 mL of cyclobutanone (Aldrich) by dropwise addition. The reaction mixture was stirred at −78° C. for 20 min and then allowed to warm to RT. After 30 min at RT the solution was mixed with 100 mL of water an subjected to rotary evaporation to remove THF. The resulting emulsion was extracted with EtOAc (4×60 mL). The combined EtOAc extracts were washed with saturated brine, dried over anhydrous MgSO$_4$, and concentrated in vacuo to give a light yellow oil. This material was purified by flash chromatography on 160 g of silica gel (9:1 hexane:EtOAc) to afford 3.98 g (68%) of 3-(1-hydroxycyclobutyl)-O-(tert-butyltrimethylsilyl)benzyl alcohol as a clear liquid.

$^1$H-NMR: (300 MHz, DMSO-d$_6$) d 7.44 (s, 1H, aromatic CH), 7.38-7.23 (m, 2H, aromatic CH), 7.15 (d, 1H, J=7.4, aromatic CH), 5.45 (s, 1H, OH), 4.72 (s, 2H, ArCH$_2$O), 2.41-2.18 (m, 4H, cyclobutyl CH$_2$), 1.88 (m, 1H, cyclobutyl CH$_2$), 1.61 (m, 1H, cyclobutyl CH$_2$), 0.90 (s, 9H, t-Bu), 0.08 (s, 6H, SiMe$_2$).

EXAMPLE 103

3-Cyclobutylbenzyl alcohol

A dry 500 mL 3-necked flask equipped with a nitrogen inlet and magnetic stirrer was charged with 3.98 g of 3-(1-hydroxycyclobutyl)-O-(tert-butyltrimethylsilyl)benzyl alcohol and 85 mL of CH$_2$Cl$_2$. The solution was cooled to 0° C. under nitrogen and treated with 15.7 mL of TFA followed by 4.78 mL of triethylsilane. After stirring at 0° C. for 1 h, the solution was allowed to warm to RT. Analysis by tlc (SiO$_2$, 8:2 hexane:EtOAc) after 3.5 h at RT indicated unreacted starting material at R$_f$=0.15 and a new component at R$_f$=0.65. The solution was treated with an additional 3 mL of triethylsilane and stirred at RT for 18 h. The solution was cooled to 0° C. and neutralized by slow addition of 30 mL of Et$_3$N. The mixture was concentrated invacuo to give a light yellow liquid which was dissolved in 100 mL of EtOAc. The resulting solution was washed with saturated brine (3×80 mL), dried over anhydrous MgSO$_4$, and concentrated to give a clear liquid. This material was dissolved in 80 mL of anhydrous THF and treated with 60 mL of 1M (n-Bu)$_4$NF (Aldrich) in a 500 mL of 3-necked flask. After stirring at RT for 18 h, the solution was concentrated in vacuo and the residue dissolved in 100 mL of EtOAc. The solution was washed with saturated brine (4×80 mL), dried over anhydrous MgSO$_4$, and concentrated to give a clear oil. The crude product was purified by flash chromatography on 120 g of silica gel (8:2 hexane:EtOAc) to afford 1.29 g (59%) of 3-cyclobutylbenzyl alcohol as a clear liquid.

$^1$H-NMR: (300 MHz, DMSO-d$_6$) δ 7.29-7.05 (m, 4H, aromatic CH), 5.24 (t, J=5.7, OH), 4.48 (d, J=5.8, ArCH$_2$O), 3.51 (m, 1H, cyclobutyl methine), 2.30 (m, 2H, cyclobutyl CH$_2$), 2.17-1.88 (m, 3H, cyclobutyl CH$_2$), 1.82 (m, 1H, cyclobutyl CH$_2$).

EXAMPLE 104

3-Cyclobutylbenzyl bromide

According to example 17, 1.29 g of 3-cyclobutylbenzyl alcohol was treated with 0.26 mL of PBr$_3$ in 15 mL of anhydrous CH$_2$Cl$_2$ to afford 1.69 g of crude product (92% pure by 1H-NMR). This material was purified by flash chromatography on 65 g of silica gel (hexane) to afford 1.59 g (89%) of 3-cyclobutyl benzyl bromide as a clear liquid.

$^1$H-NMR: (300 MHz, DMSO-d$_6$) δ 7.35-7.13 (m, 4H, aromatic CH), 4.70 (s, 2H, ArCH$_2$Br), 3.53 (m, 1H, cyclobutyl methine), 2.39-1.75 (m, 6H, cyclobutyl CH$_2$).

EXAMPLE 105 tert-Butyl (2R, 3S, 5S)-6-oxo-2,3-diphenyl-5-(3-cyclobutylbenzyl)-4-morpholinecarboxylate According to example 81, 2.50 g of tert-butyl- (2R, 3S)-(-)-6-oxo-2,3-diphenyl-4-morpholinecarboxylate (Aldrich) was alkylated with 1.59 g of 3-cyclobutylbenzyl bromide in 80 mL of anhydrous THF using 7.41 mL of 1M sodium bis(trimethylsilyl)amide in THF (Aldrich). The crude product was subjected to flash chromatography on 120 g of silica gel (8:2 hexane:EtOAc) and then recrystallization from EtOH-water to afford 1.90 g (54%) of tert-butyl (2R, 3S, 5S)-6-oxo-2,3-diphenyl-5-(3-cyclobutylbenzyl)-4-morpholinecarboxylate as a white powder, m.p. 145–147° C.

EXAMPLE 106

(2R, 3S, 5S)-6-Oxo-2,3-diphenyl-5-(3-cyclobutylbenzyl)morpholine

According to example 82, 1.87 g of tert-butyl (2R, 3S, 5S)-6-oxo-2,3-diphenyl-5-(3-cyclobutylbenzyl)-4-morpholinecarboxylate was treated with 3.1 mL of TFA in 30 mL of CH$_2$Cl$_2$ for 4 h. Neutralization with 8 mL of Et$_3$N and work-up in the usual manner gave a light yellow residue. Purification of the crude material by flash chromatography on 85 g of silica gel (8:2 hexane:EtOAc) afforded 1.35 g (91%) of (2R, 3S, 5S)-6-oxo-2,3-diphenyl-5-(3-cyclobutylbenzyl)morpholine as a thick, transparent semi-solid.

$^1$H-NMR: (300 MHz, DMSO-d$_6$) δ 7.24-7.02 (m, 10H, aromatic CH), 6.92 (m, 4H, aromatic CH), 5.71 (s, 1H, morpholine 2-H), 4.64 (m, 1H, morpholine 3-H), 4.24 (m, 1H, morpholine 5-H), 3.42 (m, 1H, cyclobutyl methine), 3.26 (m, 1H, ArCH$_2$), 3.10 (m, 1H, ArCH$_2$), 2.76 (t, 1H, J=5.3, NH), 2.15 (m, 2H, cyclobutyl CH$_2$), 2.02-2.81 (m, 3H, cyclobutyl CH$_2$), 1.71 (m, 1H, cyclobutyl CH$_2$).

EXAMPLE 107

3-Cyclobutyl-L-phenylalanine

According to example 53, 1.35 g of (2R, 3S, 5S)-6-oxo-2,3-diphenyl-5-(3-cyclobutylbenzyl)morpholine was hydrogenolyzed in 60 mL of 1:1 THF:EtOH using 0.42 g of $PdCl_2$ to afford 0.79 g (91%) of 3-cyclobutyl-L-phenylalanine•HCl as a white powder, m.p. ≧200° C.

$^1$H-NMR: (300 MHz-DMSO-$d_6$) δ 8.40(br s, 3H, $NH_3^+$), 7.26 (m, 1H, aromatic CH), 7.13 (m, 2H, aromatic CH), 7.08 (d, 1H, J=7.4, aromatic CH), 4.13 (m, 1H, methine), 3.50 (m, 1H, cyclobutyl methine), 3.11 (d, 2H, J=7.4, $ArCH_2$), 2.29 (m, 2H, cyclobutyl $CH_2$), 2.18-1.88 (m, 3H, cyclobutyl $CH_2$), 1.83 (m, 1H, cyclobutyl $CH_2$).

EXAMPLE 108 tert-Butyl 3-cyclobutyl-L-phenylalaninate

According to example 54, 0.65 g of 3-cyclobutyl-L-phenylalanine•HCl was treated with 25 mL of isobutylene in 25 mL of 1,4-dioxane in the presence of 0.5 mL of conc. $H_2SO_4$. Work-up in the usual manner followed by acidification of the free amine with ethereal HCl afforded 0.64 g (81%) of tert-butyl 3-cyclobutyl-L-phenylalaninate•HCl as a white powder, m.p. 173–174° C.

EXAMPLE 109 tert-Butyl N-(benzyloxy)carbonyl)-5-O-tert-butyl-L-glutam-1-yl-3-cyclobutyl-L-phenylalaninate According to example 9, 0.64 g of tert-butyl 3-cyclobutyl-L-phenylalaninate•HCl was coupled with 0.69 g of N-Cbz-L-glutamic acid γ-tert-butyl ester (Sigma) using 0.41 g of EDC (Aldrich) and 0.23 mL of N-methylmorpholine. The crude product was purified by flash cromatography on 85 g of silica gel (7:3 hexane:EtOAc) to afford 0.98 g (80%) of tert-butyl N-((benzyloxy)carbonyl)-5-O-tert-butyl-L-glutam-1-yl-3-cyclobutyl-L-phenylalaninate as a thick transparent oil.

$^1$H-NMR: (300 MHz, DMSO-$d_6$) δ 8.21 (d, 1H, J=7.3, NH), 7.33 (m, 6H, aromatic CH, NH), 7.18 (m, 1H, aromatic CH), 7.02 (m, 3H, aromatic CH), 5.00 (m, 2H, $PhCH_2O$), 4.32 (m, 1H, methine, 4.05 (m, 1H, methine), 3.47 (m, 1H, cyclobutyl methine), 2.92 (d, 2H, J=7.6, $ArCH_2$), 2.31-2.12 (m, 4H, glu 4-$CH_2$, cyclobutyl $CH_2$), 2.11-1.62 (m, 6H, glu 3-$CH_2$, cyclobutyl $CH_2$), 1.37 (s, 9H, t-Bu), 1.29 (s, 9H, t-Bu).

EXAMPLE 110 tert-Butyl 5-O-tert-butyl-L-glutam-1-yl-3-cyclobutyl-L-phenylalaninate

According to example 48, 0.98 g of tert-butyl N-((benzyloxy)carbonyl)-5-O-tert-butyl-L-glutam-1-yl-3-cyclobutyl-L-phenylalaninate was hydrogenolyzed using 0.17 g of 10% Pd(C) in 55 mL of MeOH. This afforded 0.76 g (100%) of tert-butyl 5-O-tert-butyl-L-glutam-1-yl-3-cyclobutyl-L-phenylalaninate as a thick transparent oil. A sample of the corresponding HCl salt for $^1$H-NMR analysis was prepared by treating 10 mg of the product with excess 1N ethereal HCl and concentrating to dryness.

$^1$H-NMR: (300 MHz, DMSO-$d_6$) δ 8.92 (d, 1H, J=7.0, NH), 8.25 (br s, 3H, $NH_3^+$), 7.20 (m, 1H, aromatic CH), 7.08 (m, 3H, aromatic CH), 4.38 (m, 1H, methine), 3.83 (m, 1H, methine), 3.48 (m, 1H, cyclobutyl methine), 2.94 (d, 2H, J=7.8, $ArCH_2$), 2.16 (m, 4H, glu 4-$CH_2$, cyclobutyl $CH_2$), 2.15-1.86 (m, 5H, glu 3-$CH_2$, cyclobutyl $CH_2$), 1.79 (m, 1H, cyclobutyl $CH_2$), 1.38 (s, 9H, t-Bu), 1.31 (s, 9H, t-Bu).

EXAMPLE 111 tert-Butyl N-(4-(((2,4-diamino-6-pteridinyl)methyl)methylamino)benzoyl)-5-O-tert-butyl-L-glutam-1-yl-3-cyclobutyl-L-phenylalaninate According to example 49, 0.285 g of 4-(N-(2,4-diamino-6-pteridinylmethyl)-N-methylamino)benzoic acid hemihydrochloride dihydrate (Aldrich) was coupled with 0.38 g of tert-butyl 5-O-tert-butyl-L-glutam-1-yl-3-cyclobutyl-L-phenylalaninate using 0.34 mL of DECP (Aldrich) and 0.37 mL of $Et_3N$ in 25 mL of DMF. The crude product was subjected to flash chromatography on 100 g of silica gel (7:7:1 $CH_2Cl_2$:acetone:MeOH) to afford 0.45 g (78%) of tert-butyl N-(4-(((2,4-diamino-6-pteridinyl)methyl)methylamino)benzoyl)-5-O-tert-butyl-L-glutam-1-yl-3-cyclobutyl-L-phenylalaninate as a yellow powder, m.p. 120–125° C.

EXAMPLE 112

N-(4-(((2,4-Diamino-6-pteridinyl)methyl)methylamino)benzoyl)-L-glutam-1-yl-3-cyclobutyl-L-phenylalanine According to example 50, 0.40 g of tert-butyl N-(4-(((2,4-diamino-6-pteridinyl)methyl)methylamino)benzoyl)-5-O-tert-butyl-L-glutam-1-yl-3-cyclobutyl-L-phenylalaninate was treated with gaseous HCl in 60 mL of $CH_3NO_2$ for 1 h. Work-up and isolation in the usual manner afforded 0.281 g (79%) of N-(4-(((2,4-diamino-6-pteridinyl)methyl)methylamino)benzoyl)-L-glutam-1-yl-3-cyclobutyl-L-phenylalanine as a yellow powder, m.p. 175° C. (dec).

HPLC: one peak on C18, k'=2.50, 65:35:0.1 $H_2O$:MeCN:TFA, flow rate=1 mL/min.

$^1$H-NMR: (300 MHz, DMSO-$d_6$) δ 12.85-11.75 (br m, COOH), 8.58 (s, 1H, pteridinyl 7-CH), 8.04 (d, 1H, J=8.1, amide NH), 8.00 (d, 1H, J=8.7, amide NH), 7.75 (br s, 1H, $NH_2$), 7.71 (d, 2H, J=8.9, aromatic CH), 7.55 (br s, 1H, $NH_2$), 7.10-6.92 (m, 4H, aromatic CH), 6.82 (d, 2H, J=8.9, aromatic CH), 6.70 (br s, 2H, $NH_2$), 4.79 (s, 2H, pteridinyl-$CH_2$), 4.39 (m, 2H, methines), 3.40 (m, 1H, cyclobutyl methine), 3.21 (s, 3H, N-$CH_3$), 3.00 (m, 1H, $ArCH_2$), 2.88 (m, 1H, $ArCH_2$), 2.29-2.08 (m, 4H, glu 4-$CH_2$, cyclobutyl $CH_2$), 2.07-1.65 (m, 6H, glu 3-$CH_2$, cyclobutyl $CH_2$).

Elemental Analysis: Calcd. for $C_{33}H_{37}N_9O_6$•1.6 $H_2O$ (MW 684.54): C, 57.90; H, 5.92; N, 18.42. Found: C, 57.88; H, 5.90; N, 18.52.

Mass Spectrum: (Ion Spray) 656 $(M+H)^+$.

UV Spectrum: (pH 7 Buffer) $\lambda_{max}$ (ε) 259.5(22100), 308.0 (22300), 373.7 (6740). $\lambda_{min}$ (ε) 241.2 (12900), 274.5 (14600), 345.6 (5130).

EXAMPLE 113

6-Bromomethyl-3,4-dihydro-2-methyl-4-oxoquinazoline

According to example 4, 1.00 g of 3,4-dihydro-2,6-dimethyl-4-oxoquinazoline (Sen, A. B.; Gupta, J. K. *J. Indian Chem. Soc.*, 1962, 31, 369) was subjected to bromination using 1.05 g of N-bromosuccinimide (Aldrich) and 0.17 g of benzoyl peroxide in 50 mL of 1,2-dichloro-ethane for 30 min to afford 0.95 g (64%) of 6-bromomethyl-3,4-dihydro-2-methyl-4-oxoquinazoline as a tan solid.

$^1$H-NMR: (300 MHz, DMSO-$d_6$) δ 8.17 (s, 1H, aromatic CH), 7.85 (d, 1H, J=8.5, aromatic CH), 7.58 (d, 1H, J=8.5, aromatic CH), 4.88 (s, 2H, $ArCH_2Br$), 2.39 (s, 3H, $CH_3$).

EXAMPLE 114

Ethyl 5-N-methylamino-2-thiophenecarboxylate

A mixture of 2.0 g of ethyl 5-amino-2-thiophenecarboxylate (Mackay, D. *Can. J. Chem.*, 1966, 44, 2881–2891; Paul,H.; Migulla, H. *Arch. Pharm.*, 1978, 311, 679–691.), 2.05 g of methyl iodide (Aldrich), and 2.58 g of 2,6-lutidine (Aldrich) in 80 mL of DMF was stirred at 70° C. under nitrogen for 24 h. Analysis of the reaction mixture by tlc ($SiO_2$, 3:2 hexane:EtOAc) indicated starting material at $R_f$=0.51 and a new component at $R_f$=0.60. The mixture was treated with an additional 1.71 g of methyl iodide and was stirred at 70° C. for 8 h, RT for 72 h and 70° C. for an additional 8 h. The reaction mixture was mixed with 75 mL of water and extracted with EtOAc (3×150 mL). the combined EtOAc extracts were washed with saturated aqueous brine, dried over anhydrous $Na_2SO_4$ and concentrated in vacuo to dryness. The crude residue was subjected to flash chromatography on silica gel (75:25 hexane:EtOAc) to afford 0.67 g (38%) of ethyl 5-N-methylamino-2-thiophenecarboxylate as brown solid, m.p. 41–43° C.

EXAMPLE 115

Ethyl 5-(((3,4-dihydro-2-methyl-4-oxo-6-quinazolinyl)methyl)methylamino)-2-thiophene-carboxylate A 100 mL round bottomed flask equipped with a condenser and magnetic stirrer was charged with 0.66 g of 6-bromomethyl-3,4-dihydro-2-methyl-4-oxoquinazoline, 0.44 g of ethyl 5-N-methylamino-2-thiophenecarboxylate, 0.25 g of 2,6-lutidine, and 30 mL of anhydrous DMF. The mixture was stirred at 80° C. for 18 h. Analysis of the reaction mixture by tlc ($SiO_2$, 95:5$CH_2Cl_2$:MeOH) indicated starting materials and a new component at $R_f$32 0.41. The mixture was concentrated in vacuo to dryness and the residue was subjected to flash chromatography on 110 g of silica gel (95:5 $CH_2Cl_2$:MeOH). Fractions containing the $R_f$=0.41 component were combined and concentrated to afford 0.42 g (49%) of ethyl 5-(((3,4-dihydro-2-methyl-4-oxo-6 -quinazolinyl)methyl)methylamino)-2-thiophenecarboxylate as a light tan powder, m.p. ≧200° C.
$^1$H-NMR: (300 MHz, DMSO-$d_6$) δ 12.22 (br s, 1H, NH), 7.92 (s, 1H, aromatic CH), 7.65 (d, 1H, J=8.4, aromatic CH), 7.56 (d, 1H, J=8.5, aromatic CH), 7.48 (d, 1H, J=4.4, thienyl CH), 6.07 (d, 1H, J=4.3, thienyl CH), 4.70 (s, 2H, quinazolinyl-$CH_2$), 4.16 (q, 2H, J=7.2, ethyl $CH_2$), 3.09 (s, 3H, N-$CH_3$), 2.33 (s, 3H, quinazolinyl 2-$CH_3$), 1.22 (t, 3H, J=7.2, ethyl $CH_3$).

EXAMPLE 116

5-(((3,4-Dihydro-2-methyl-4-oxo-6-quinazolinyl) methyl)methylamino)-2-thiophene-carboxylic acid A 25 mL 3-necked flask equipped with a condenser, a thermometer, and a magnetic stirrer was charged with 0.20 g of ethyl 5-(((3,4-dihydro-2-methyl-4-oxo-6-quinazolinyl) methyl)methylamino)-2-thiophene-carboxylate, 6 mL of EtOH, and 6 mL of 1N aqueous NaOH. The resulting solution was stirred under nitrogen and RT for 25 min and then at 55° C. for 2 h. Analysis by tlc ($SiO_2$, 95:5 $CH_2Cl_2$) indicated no remaining starting material and a new component at $R_f$=0.06. The solution was cooled to RT and subjected to rotary evaporation to remove EtOH. The remaining solution was diluted with 10 mL of water and acidified to pH=3.5 by addition of 1N aqueous HCl. A tan precipitate formed which was collected by centrifugation, washed with four cycles of aqueous suspension-centrifugation-decantation, and lyophilized to afford 0.116 g (63%) of 5-(((3,4-dihydro-2-methyl-4-oxo-6-quinazolinyl)methyl) methylamino)-2-thiophene-carboxylic acid as a white powder, m.p. 195° C. (dec).
$^1$H-NMR: (200 MHz, DMSO-$d_6$) δ 12.40-11.90 (br m, COOH, NH), 7.95 (s, 1H, aromatic CH), 7.69 (m, 1H, aromatic CH), 7.58 (d, 1H, J=8.2, aromatic CH), 7.42 (d, 1H, J=4.2, thienyl CH), 6.04 (d, 1H, J=4.2, thienyl CH), 4.70 (s, 2H, quinazolinyl-$CH_2$), 3.09 (s, 3H, N-$CH_3$), 2.35 (s, 3H, quinazolinyl 2-$CH_3$).

EXAMPLE 117 tert-Butyl N-((5-(((3,4-dihydro-2-methyl-4-oxo-6-quinazolinyl)methyl)methylamino)-2-thienyl) carbonyl)-5-O-tert-butyl-L-glutam-1-yl-3-cyclopentyl-L-phenylalaninate A dry 50 mL 3-necked flask equipped with a nitrogen inlet and a magnetic stirrer was charged with 0.115 g of 5-(((3, 4-dihydro-2-methyl-4-oxo-6-quinazolinyl)methyl) methylamino)-2-thiophene-carboxylic acid, 0.165 g of tert-butyl 5-O-tert-butyl-L-glutam-1-yl-3-cyclopentyl-L-phenylalaninate 0.06 mL of $Et_3N$, and 7 mL of anhydrous DMF. The yellow solution was treated with 0.06 mL of DECP and was stirred at RT under nitrogen. After 2 h, tlc ($SiO_2$, 95:5 $CH_2Cl_2$:MeOH) indicated starting material at $R_f$=0.02, a major new component at $R_f$=0.37, and minor components at $R_f$=0.31 and 0.40. The reaction mixture was treated with an additional 0.03 mL of DECP and 0.03 mL of $Et_3N$ and was stirred for another 1 h at RT. TLC indicated little additional conversion. The solution was concentrated in vacuo to dryness and the residue dissolved in 60 mL of $CHCl_3$. The solution was washed with 5% aqueous $NaHCO_3$ (3×50 mL), dried over anhydrous $MgSO_4$, and concentrated to give a light yellow oil. The crude product was subjected to flash chromatography twice ($SiO_2$, 95:5 EtOAc:MeOH; $SiO_2$, 97:3 $CH_2Cl_2$:MeOH) to afford 0.119 g (46%) of tert-butyl N-((5-(((3,4-dihydro-2-methyl-4-oxo-6-quinazolinyl)methyl)methylamino)-2-thienyl)carbonyl)-5-O-tert-butyl-L-glutam-1-yl-3-cyclopentyl-L-phenylalaninate as a tan foam.
$^1$H-NMR: (400 MHz, DMSO-$d_6$) δ 12.19 (s, 1H, quinazoline NH), 8.18 (d, 1H, J=7.1, amide NH), 7.92 (m, 2H, amide NH, aromatic CH), 7.63 (dd; 1H; J=7.9, 1.8; aromatic CH), 7.57 (d, 1H, J=4.1, thienyl CH), 7.54 (d, 1H, J=8.0, aromatic CH), 7.12-6.94 (m, 4H, aromatic CH), 5.97 (d, 1H, J=4.1, thienyl CH), 4.63 (s, 2H, quinazolinyl-$CH_2$), 4.40-4.27 (m, 2H, methines), 3.02 (s, 3H, N-$CH_3$), 2.87 (m, 3H, Ar$CH_2$, cyclopentyl methine), 2.31 (s, 3H, quinazolinyl 2-$CH_3$), 2.20 (t, 2H, J=7.7, glu 4-$CH_2$), 1.91 (m, 3H, glu 3-$CH_2$, cyclopentyl $CH_2$), 1.83-1.40 (m, 7H, cyclopentyl $CH_2$), 1.35 (s, 9H, t-Bu), 1.27 (s, 9H, t-Bu).

EXAMPLE 118

N-((5-(((3,4-Dihydro-2-methyl-4-oxo-6-quinazolinyl)methyl)methylamino)-2-thienyl) carbonyl)-L-glutam-1-yl-3-cyclopentyl-L-phenylalanine According to example 50, 0.117 g of tert-butyl N-((5-(((3,4-dihydro-2-methyl-4-oxo-6-quinazolinyl)methyl) methylamino)-2-thienyl)carbonyl)-5-O-tert-butyl-L-glutam-1-yl-3-cyclopentyl-L-phenylalaninate was treated with gaseous HCl in 25 mL of $CH_3NO_2$ for 45 min. Removal of the $CH_3NO_2$ in vacuo gave a tan residue which was purified by semi-preparative reverse phase HPLC (C18, 70:30:01→60:40:01 $H_2O$:MeCN:TFA over 25 min). Fractions containing the major component (k'=1.61 on analytical HPLC, C18, 60:40:0.1 $H_2O$:MeCN:TFA) were combined, concentrated to 25 mL and lyophilized to afford 0.052 g (42%) of N-((5-(((3,4-dihydro-2-methyl-4-oxo-6-quinazolinyl)methyl)methylamino)-2-thienyl)carbonyl)-L-glutam-1-yl-3-cyclopentyl-L-phenylalanine as a yellow powder, m.p. 125° C. (dec).

HPLC: one peak on C18, k'=1.62, 60:40:0.1 H$_2$O:MeCN:TFA, flow rate =1 mL/min.

$^1$H-NMR: (300 MHz, DMSO-d$_6$)δ 8.09 (d, 1H, J=7.5, amide NH), 7.93 (m, 2H, amide NH, aromatic CH), 7.69 (d, 1H, J=8.0, aromatic CH), 7.56 (m, 2H, aromatic CH, thienyl CH), 7.10-6.92 (m, 4H, aromatic CH), 5.97 (d, 1H, J=4.3, thienyl CH), 4.66 (s, 2H, quinazolinyl-CH$_2$), 4.33 (m, 2H, methines), 3.06 (s, 3H, N-CH$_3$), 2.99 (m, 1H, ArCH$_2$), 2.85 (m, 1H, ArCH$_2$), 2.38 (s, 3H, quinazolinyl 2-CH$_3$), 2.22 (t, 2H, J=7.5, glu 4-CH$_2$), 2.02-1.37 (m, 10H, glu 3-CH$_2$, cyclopentyl CH$_2$).

$^{19}$F-NMR: (376 MHz, DMSO-d$_6$) δ 0.57 (relative to TFA external standard).

Elemental Analysis: Calcd. for C$_{35}$H$_{39}$N$_5$O$_7$S•1.2 TFA•1.3 H$_2$O (MW 834.03): C, 53.86; H, 5.17; N, 8.40; S, 3.84. Found: C, 53.85; H, 5.11; N, 8.36; S, 3.92.

Mass Spectrum: (Ion Spray) 691 (M+NH$_4^+$).

UV Spectrum: (pH 7 Buffer) λ$_{max}$ (ε) 225.2 (36600), 265.6 (10300), 353.1 (22200). λ$_{min}$ (ε) 214.3 (35200), 252.1 (9230), 288.4 (4120).

EXAMPLE 119 tert-Butyl 5-O-tert-butyl-N-(4-((3-(2,4-diamino-1,6-dihydro-6-oxo-5-pyrimidinyl)propyl)-trifluoroacetamido)benzoyl)-L-glutam-1-yl-3-cyclopentyl-L-phenylalaninate A 25 mL 3-necked flask equipped with a magnetic stirrer and a nitrogen inlet was charged with 0.258 g of 4-(N-(3-(2,4-diamino-1,6-dihydro-6-oxo-5-pyrimidinyl)propyl) trifluoroacetamido)benzoic acid (Styles, V. L., et al, *J. Heterocyclic Chem.*, 1990, 27, 1809), 0.250 g of tert-butyl 5-O-tert-butyl-L-glutam-1-yl-3-cyclopentyl-L-phenylalaninate, 0.077 g of 1-hydroxybenzotriazole hydrate (Aldrich), 5 mL of anhydrous DMF, and 0.07 mL of Et$_3$N. The solution was treated with 0.104 g of DCC (Fluka) and stirred at RT under nitrogen for 24 h. The mixture was filtered and the filtrate was concentrated in vacuo to dryness. The residue was dissolved in 70 mL of CH$_2$Cl$_2$, washed with 5% aqueous NaHCO$_3$ (3×50 mL), dried over anhydrous MgSO$_4$ and concentrated to give a tan oil. This material was purified by flash chromatography on silica gel (95:5 AE 90:10 CH$_2$Cl$_2$:MeOH) to afford 0.304 g (70%) of tert-butyl 5-O-tert-butyl-N-(4-((3-(2,4-diamino-1,6-dihydro-6-oxo-5-pyrimidinyl)propyl)trifluoroacetamido)-benzoyl)-L-glutam-1-yl-3-cyclopentyl-L-phenylalaninate as a tan glass, m.p. 124–130° C.

EXAMPLE 120 tert-Butyl-5-O-tert-butyl-N-(4-((3-(2,4-diamino-1,6-dihydro-6-oxo-5-pyrimidinyl)propyl)amino) benzoyl)-L-glutam-1-yl-3-cyclopentyl-L-phenylalaninate To a 100 mL round bottomed flask equipped with a nitrogen inlet and a magnetic stirrer were added 0.268 g of tert-butyl 5-O-tert-butyl-N-(4-((3-(2,4-diamino-1,6-dihydro-6 oxo-5-pyrimidinyl)propyl)trifluoroacetamido) benzoyl)-L-glutam-1-yl-3-cyclopentyl-L-phenylalaninate, and 7 mL of MeOH. The solution was treated with 0.18 mL of 40% (w/w) dimethylamine/water (Aldrich) followed by 0.45 mL of water and was stirred at RT under nitrogen for 24 h. The solution was concentrated in vacuo to dryness and the residue was subjected to flash chromatography on 60 g of silica gel (92:8 CH$_2$Cl$_2$:MeOH) to afford 0.185 g (78%) of tert-butyl 5-O-tert-butyl-N-(4-((3-(2,4-diamino-1,6-dihydro-6-oxo-5-pyrimidinyl)propyl)amino)benzoyl)-L-glutam-1-yl-3-cyclopentyl-L-phenylalaninate as a thick transparent semi-solid.

$^1$H-NMR: (200 MHz, DMSO-d$_6$)δ 9.80 (br s, 1H, pyrimidinyl NH), 8.20 (d, 1H, J=7.2, amide NH), 7.90 (d, 1H, J=8.0, amide NH), 7.67 (d, 2H, J=8.6, aromatic CH), 7.20-6.98 (m, 4H, aromatic CH), 6.55 (d, 2H, J=8.6, aromatic CH), 6.25 (m, 1H, NH), 5.94 (br s, 2H, NH$_2$), 5.77 (br s, 2H, NH$_2$), 4.54-4.29 (m, 2H, methines), 3.12-2.80 (m, 5H, cyclopentyl methine, ArCH$_2$, pyrimidinyl-CH$_2$CH$_2$CH$_2$N), 2.27 (m, 4H, glu 4-CH$_2$, pyrimidinyl-CH$_2$CH$_2$CH$_2$N), 2.10-1.82 (4H, glu 3-CH$_2$, cyclopentyl CH$_2$), 1.80-1.45 (m, 8H, cyclopentyl CH$_2$, pyrimidinyl-CH$_2$CH$_2$CH$_2$N), 1.39 (s, 9H, t-Bu), 1.32 (s, 9H, t-Bu).

EXAMPLE 121

N-(4-((3-(2,4-Diamino-1,6-dihydro-6-oxo-5-pyrimidinyl)propyl)amino)benzoyl)-L-glutam-1-yl-3-cyclopentyl-L-phenylalanine A 100 mL round bottomed flask equipped with a magnetic stirrer was charged with 0.180 g of tert-butyl 5-O-tert-butyl-N-(4-((3-(2,4-diamino-1,6-dihydro-6-oxo-5-pyrimidinyl) propyl)amino)benzoyl)-L-glutam-1-yl-3-cyclopentyl-L-phenylalaninate and 25 mL of CH$_3$NO$_2$. The mixture was acidified by bubbling HCl gas through for 5 min, however, the solid starting material did not dissolve. Analysis of the reaction mixture by tlc (SiO$_2$, 92.8 CH$_2$Cl$_2$:MeOH) indicated minimal conversion of the starting material. The mixture was concentrated in vacuo to dryness. A yellow residue resulted which was suspended in 20 mL of CH$_2$Cl$_2$ and treated with 1 mL of anisole followed by 15 mL of TFA. The solid quickly dissolved giving a yellow solution which was stirred at RT under nitrogen. After 1 h, tlc indicated no remaining starting material and a new spot of R$_f$=0.0. The solution was concentrated to dryness and the residue was purified by semi-preparative reverse phase HPLC (C18, 70:30:0.1 H$_2$O: MeCN:TFA). Fractions containing pure material were combined, concentrated to 30 mL and lyophilized to afford 0.098 g (47%) of N-(4-((3-(2,4-diamino-1,6-dihydro-6-oxo-5-pyrimidinyl)propyl)amino)benzoyl)-L-glutam-1-yl-3-cyclopentyl-L-phenylalanine as a fluffy white solid, m.p. 125° C. (dec).

HPLC: one peak on C18, k'=1.64, 70:30:0.1 H$_2$O:MeCN:TFA, flow rate=1 mL/min. $^1$H-NMR: (300 MHz, DMSO-d$_6$)δ 12.91-11.10 (br s, COOH, pyrimidinyl NH), 8.07 (d, 1H, J=7.6, amide NH), 7.88 (d, 1H, J=7.9, amide NH), 7.70 (br s, 1H, NH$_2$), 7.62 (m, 3H, NH$_2$, aromatic CH), 7.13-6.70 (m, 6H, NH$_2$, aromatic CH), 6.53 (d, 2H, J=8.6, aromatic CH), 4.40 (m, 2H, methines), 3.01 (m, 3H, cyclopentyl methine, pyrimidinyl-CH$_2$CH$_2$CH$_2$N), 2.86 (m, 2H, ArCH$_2$), 2.25 (m, 4H, glu 4-CH$_2$, pyrimidinyl-CH$_2$CH$_2$CH$_2$N), 2.01-1.78 (m, 4H, glu 3-CH$_2$, cyclopentyl CH$_2$), 1.76-1.37 (m, 8H, cyclopentyl CH$_2$, pyrimidinyl-CH$_2$CH$_2$CH$_2$N).

$^{19}$F-NMR: (282 MHz, DMSO-d$_6$)δ 3.92 (relative to TFA external standard).

Elemental Analysis: Calcd. for C$_{33}$H$_{41}$N$_7$O$_7$ 1.8 TFA 1.6 H$_2$O (MW 881.80): C, 49.85; H, 5.26; N, 11.12. Found: C, 49.81; H, 5.24; N, 11.11.

Mass Spectrum: (Ion Spray) 648 (M+H)$^+$.

UV Spectrum: (pH 7 Buffer) λ$_{max}$ (ε) 280.1 (29700). λ$_{min}$ (ε) 247.4 (7590). sh (ε) 302.9 (20400).

EXAMPLE 122

Di-tert-butyl N-(benzyloxy)carbonyl)-5-O-tert-butyl-L-glutam-1-yl-L-asparate

According to example 9, 1.00 g of L-aspartic acid di-t-butyl ester hydrochloride (Sigma) was coupled with 1.20 g of N-Cbz-L-glutamic acid λ-t-butyl ester (Sigma) using 0.72 g of EDC (Aldrich) and 0.39 mL of N-methylmorpholine. The crude product was purified by flash chromatography on 80 g of silica gel (75:25 hexane:EtOAc) to afford 1.10 g (55%) of tert-butyl N-((benzyloxy)carbonyl)-5-O-tert-butyl-L-glutam-1-yl-4-O-tert-butyl-L-aspartate as a white solid, m.p. 119–120° C.

EXAMPLE 123

Di-tert-butyl 5-O-tert-butyl-L-glutam-1-yl-L-asparate

According to example 48, 0.389 g of tert-butyl N-((benzyloxy)carbonyl)-5-O-tert-butyl-L-glutam-1-yl-4-O-tert-butyl-L-aspartate was hydrogenolyzed using 0.07 g of 10% Pd(C) in 40 mL of MeOH. This afforded 0.29 g (98%) of di-tert-butyl 5-O-tert-butyl-L-glutam-1-yl-L-asparate as a thick transparent oil. A sample of the corresponding HCl salt for $^1$H-NMR analysis was prepared by treating 10 mg of the product with excess 1N ethereal HCl and concentrating to dryness.

$^1$H-NMR: (300 MHz, DMSO-$d_6$)δ 8.91 (d, 1H, J=7.8, NH), 8.31 (br s, 3H, $NH_3^+$), 4.52 (m, 1H, methine), 3.83 (m, 1H, methine), 2.63 (d, 2H, J=6.1, asp $CH_2$), 2.36 (m, 2H, glu 4-$CH_2$), 1.94 (m, 2H, glu 3-$CH_2$), 1.38 (s, 27H, t-Bu).

EXAMPLE 124

Di-tert-butyl 5-O-tert-butyl-N-(4-(((2,4-diamino-6-pteridinyl)methyl)methylamino)benzoyl)-L-glutam-1-yl-L-aspartate According to example 49, 0.30 g of 4-(N-(2,4-diamino-6-pteridinylmethyl)-N-methylamino)benzoic acid hemihydrochloride dihydrate (Aldrich) was coupled with 0.34 g of di-tert-butyl 5-O-tert-butyl-L-glutam-1-yl-L-asparate using 0.36 mL of DECP (Aldrich) and 0.39 mL of $Et_3N$ in 25 mL of DMF. The crude product was subjected to flash chromatography twice ($SiO_2$, 7:7:1 $CH_2Cl_2$:acetone:MeOH; $SiO_2$, 96:4→95:5 $CH_2Cl_2$:MeOH) to afford 0.213 g (37%) of di-tert-butyl 5-O-tert-butyl-N-(4-(((2,4-diamino-6-pteridinyl)methyl)methylamino)benzoyl)-L-glutam-1-yl-L-asparate as a yellow powder, m.p. 130–135° C.

EXAMPLE 125

N-(4-(((2,4-Diamino-6-pteridinyl)methyl)methylamino)benzoyl)-L-glutam-1-yl-L-aspartic acid (Procedure B)

For Procedure A to prepare this compound, see Example 33.

According to example 50, 0.307 g of di-tert-butyl 5-O-tert-butyl-N-(4-(((2,4-diamino-6-pteridinyl)methyl)methylamino)benzoyl)-L-glutam-1-yl-L-asparate was treated with gaseous HCl in 40 mL of $CH_3NO_2$ for 1.5 h. The reaction mixture was concentrated to 5 ml and mixed with 50 mL of ether. The resulting solid was collected by filtration and dried in vacuo. The product was dissolved in 25 mL of water, filtered and lyophilized to afford 0.246 g (89%) of N-(4-(((2,4-diamino-6-pteridinyl)methyl)methylamino)benzoyl)-L-glutam-1yl-L-aspartic acid as a yellow-orange powder, m.p. 160° C. (dec).

HPLC: one peak on C18, k'=0.70, 85:15:0.1 $H_2O$:MeCN:TFA, flow rate=1 mL/min. $^1$H-NMR: (300 MHz, DMSO-$d_6$)δ 13.12 (br s, COOH), 9.31 (s, 1H, $NH_2$), 9.08 (s, 1H, $NH_2$), 8.72 (s, 1H, pteridinyl 7-CH), 8.68 (br s, 1H, $NH_2$), 8.22 (d, 1H, J=8.0, amide NH), 8.09 (d, 1H, J=7.9, amide NH), 7.79 (br s, 1H, $NH_2$), 7.75 (d, 2H, J=8.9, aromatic CH), 6.82 (d, 2H, J=8.9, aromatic CH), 4.87 (s, 2H, pteridinyl-$CH_2$), 4.59-4.40 (m, 2H, methines), 3.24 (s, 3H, N—$CH_3$), 2.75-2.52 (m, 2H, asp $CH_2$), 2.27 (t, 2H, J=7.8, glu 4-$CH_2$), 2.10-1.78 (m, 2H, glu 3$CH_2$).

Elemental Analysis: Calcd. for $C_{24}H_{27}N_9O_8$·2HCl1.3 $H_2O$ (MW 665.87): C, 43.29; H, 4.78; N, 18.93; Cl, 10.65. Found: C, 43.42; H, 4.90; N, 18.83; Cl, 10.46.

Mass Spectrum: (FAB) 570 $(M+H)^+$.

UV Spectrum: (pH 7 buffer) $\lambda_{max}$ (ε) 258.7 (21900), 306.4 (23800), 372.2 (7250). $\lambda_{min}$ (ε) 240.1 (13400), 272.4 (15200), 345.0 (5740).

EXAMPLE 126

Di-tert-butyl N-((benzyloxy)carboxyl)-5-O-tert-butyl-L-glutam-1-yl-L-glutamate

According to example 9, 0.88 g of L-glutamic acid di-t-butyl ester hydrochloride (Sigma) was coupled with 1.00 g of N-Cbz-L-glutamic acid γ-t-butyl ester (Sigma) using 0.60 g of EDC (Aldrich) and 0.33 mL of N-methylmorpholine. The crude product was purified by flash chromatography on silica gel (75:25 hexane:EtOAc) to afford 1.49 g (87%) of tert-butyl N-((benzyloxy)carbonyl)-5-O-tert-butyl-L-glutam-1-yl-5-O-tert-butyl-L-glutamate as a thick transparent oil.

$^1$H-NMR: (300 MHz, DMSO-$d_6$)δ 8.21 (d, 1H, J=7.6, NH), 7.42 (d, 1H, J=8.2, NH), 7.33 (m, 5H, aromatic CH), 5.01 (m, 2H, Ph$CH_2$O), 4.17-3.96 (m, 2H, methines), 2.24 (m, 4H, glu 4-$CH_2$), 1.96-1.64 (m, 4H, glu 3-$CH_2$), 1.37 (s, 27H, t-Bu).

EXAMPLE 127

Di-tert-butyl 5-O-tert-butyl-L-glutam-1-yl-L-glutamate

According to example 48, 0.60 g of tert-butyl N-((benzyloxy)carboxyl)-5-O-tert-butyl-L-glutam-1-yl-5-O-tert-butyl-L-glutamate was hydrogenolyzed using 0.10 g of 10% Pd(C) in 45 mL of MeOH. This afforded 0.45 g (98%) of di-tert-butyl 5-O-tert-butyl-L-glutam-1-yl-L-glutamate as a thick transparent oil. A sample of the corresponding HCl salt for $^1$H-NMR analysis was prepared by treating 10 mg of the product with excess 1N ethereal HCl and concentrating to dryness.

$^1$H-NMR: (200 MHz, DMSO-$d_6$) δ 8.86 (d, 1H, J=7.3, NH), 8.31 (br s, 3H, $NH_3^+$), 4.21 (m, 1H, methine), 3.87 (m, 1H, methine), 2.35 (m, 4H, glu 4-$CH_2$), 2.07-1.66 (m, 4H, glu 3-$CH_2$), 1.39 (s, 27H, t-Bu).

EXAMPLE 128

Di-tert-butyl- 5-O-tert-butyl-N-(4-(((2,4-diamino-6-pteridinyl)methyl)methylamino)benzoyl)-L-glutam-1-yl-L-glutamate According to example 49, 0.30 g of 4-(N-(2,4-diamino-6-pteridinylmethyl)-N-methylamino)benzoic acid hemihydrochloride dihydrate (Aldrich was coupled with 0.386 g of di-tert-butyl 5-O-tert-butyl-L-glutam-1-yl-L-glutamate using 0.36 mL of DECP (Aldrich) and 0.39 mL of $Et_3N$ in 25 mL of DMF. The crude product was subjected to flash chromatography on 150 g of silica gel (7:7:1 $CH_2Cl_2$:acetone:MeOH) to afford 0.432 g (73%) of di-tert-butyl 5-O-tert-butyl-N-(4-(((2,4-diamino-6-pteridinyl)methyl)methylamino)benzoyl)-L-glutam-1-yl-L-glutamate as a yellow powder, m.p. 130–145° C.

EXAMPLE 129

N-(4-(((2,4-Diamino-6-pteridinyl)methyl) methylamino)benzoyl)-L-glutam-1-yl-L-glutamic acid (Procedure B)

For Procedure A to prepare this compound, see Example 39.

According to example 50, 0.382 g of di-tert-butyl 5-O-tert-butyl-N-(4-(((2,4-diamino-6-pteridinyl)methyl) methylamino)benzoyl)-L-glutam-1-yl-L-glutamate was treated with gaseous HCl in 50 mL of $CH_3NO_2$ for 1 h. The reaction mixture was concentrated to 10 mL and mixed with 50 mL of ether. The resulting solid was collected by filtration and dried in vacuo. The product was dissolved in 25 mL of water, filtered and lyophilized to afford 0.265 g (76%) of N-(4-(((2,4-diamino-6-pteridinyl)methyl)methylamino) benzoyl)-L-glutam-1-yl-L-glutamic acid as a yellow-orange powder, m.p. 155° C. (dec).

HPLC: one peak on C18, k'=0.88, 85:15:0.1 $H_2O$:MeCN:TFA, flow rate=1 mL/min. $^1$H-NMR: (300 MHz, DMSO-$d_6$), δ 13.18 (br s, COOH), 9.29 (s, 1H, $NH_2$), 9.07 (s, 1H, $NH_2$), 8.72 (s, 1H, pteridinyl 7-CH), 8.69 (br s, 1H, $NH_2$), 8.19 (d, 1H, J=7.7, amide NH), 8.09 (d, 1H, J=7.9, amide NH), 7.87 (br s, 1H, $NH_2$), 7.74 (d, 2H, J=8.9, aromatic CH), 6.81 (d, 2H, J=8.9, aromatic CH), 4.87 (s, 2H, pteridinyl-$CH_2$), 4.42 (m, 1H, methine), 4.19 (m, 1H, methine), 3.24 (s, 3H, N—$CH_3$), 2.28 (m, 4H, glu 4-$CH_2$), 2.07-1.71 (m, 4H, glu 3-$CH_2$).

Elemental Analysis: Calcd. for $C_{25}H_{29}N_9O_8$ .1.9 HCl 2 $H_2O$ (MW 688.87): C, 43.59, H, 5.11; N, 18.30; Cl, 9.78 . Found: C, 43.72; H, 5.07; N, 18.16; Cl, 9.97.

Mass Spectrum: (FAB) 584 $(M+H)^+$.

UV Spectrum: (pH 7 Buffer) $\lambda_{max}$ (ε) 258.8(23700), 306.2 (25600), 371.9 (7830). $\lambda_{min}$ (ε) 240.4 (14300), 272.9 (16600), 344.6 (6150).

EXAMPLE 130

N-(4-(((2,4-Diamino-6-pteridinyl)methyl) methylamino)benzoyl)-L-glutam-1-yl-3-tert-butyl-L-phenylalanine (Procedure B)

For Procedure A to prepare this compound, see Example 97.

According to example 50, 3.51 g of tert-butyl N-(4-(((2,4-diamino-6-pteridinyl)methyl)methylamino)benzoyl)-5-O-tert-butyl-L-glutam-1-yl-3-tert-butyl-L-phenylalaninate was treated with gaseous HCl in 150 mL of $CH_3NO_2$ for 1 h. The reaction mixture was concentrated in vacuo to a slurry and mixed with 100 mL of ether. The solid was collected by vaccum filtration and dissolved in 150 mL of 6:4 MeCN:$H_2O$. The solution was subjected to rotary evaporation to remove MeCN and the resulting suspension was frozen and lyophilized to afford 3.167 g (93%) of N-(4-(((2,4-diamino-6-pteridinyl)methyl)methylamino)benzoyl)-L-glutam-1-yl-3-tert-butyl-L-phenylalanine as a yellow-orange powder, m.p. 165° C. (dec).

HPLC: one peak on C18, k'=2.30, 70:30:0.1 $H_2O$:MeCN:TFA, flow rate=1 ml/min. $^1$H-NMR: (300 MHz, DMSO-$d_6$)δ 13.35-12.95 (br s, COOH), 9.30 (s, 1H, $NH_2$), 9.07 (s, 1H, $NH_2$), 8.71 (s, 1H, pteridinyl 7-CH), 8.68 (br s, 1H, $NH_2$), 8.14 (d, 1H, J=7.6, amide NH), 8.02 (d, 1H, J=7.8, amide NH), 7.89 (br s, 1H, $NH_2$), 7.71 (d, 2H, J=8.9, aromatic CH), 7.21 (s, 1H, aromatic CH), 7.18-7.05 (m, 2H, aromatic CH), 6.98 (d, 1H, J=7.4, aromatic CH), 6.79 (d, 2H, J=8.9, aromatic CH), 4.85 (s, 2H, pteridinyl-$CH_2$), 4.39 (m, 2H, methines), 3.23 (s, 3H, N—$CH_3$), 3.03 (m, 1H, Ar$CH_2$), 2.90 (m, 1H, Ar$CH_2$), 2.20 (t, 2H, J=7.6, glu 4-$CH_2$), 2.01-1.76 (m, 2H, glu 3-$CH_2$), 1.19 (s, 9H, t-Bu).

Elemental Analysis: Calcd. for $C_{33}H_{39}N_9O_6$ 1.5HCl 1.8 $H_2O$ (MW 744.85): C, 53.21; H, 5.97; Cl, 7.14. Found: C, 53.20; H, 5.97; N, 16.96; Cl, 7.20.

Mass Spectrum: (Ion Spray) 658 $(M+H)^+$.

UV Spectrum: (pH 7 Buffer) $\lambda_{max}$ (ε) 259.5(24400), 308.0 (24400), 371.5 (7410). $\lambda_{min}$ (ε) 241.4 (14600), 274.2 (16200), 345.1 (5680).

EXAMPLE 131 tert-Butyl 5-O-tert-butyl-N-(4-(((1,2-dihydro-3-methyl-1-oxobenzo(f)quinazolin-9-yl)methyl) amino)-2-fluorobenzoyl)-L-glutam-1-yl-3-cyclopentyl-L-phenylalaninate A dry 50 mL 3-necked flask equipped with a magnetic stirrer and a nitrogen inlet was charged with 0.150 g of 4-(((1,2-dihydro-3-methyl-1-oxobenzo(f)quinazolin-9-yl) methyl)amino)-2-fluorbenzoic acid, 0.198 g of tert-butyl 5-O-tert-butyl-L-glutam-1-yl-3-cyclopentyl-L-phenylalaninate, and 7 mL of anhydrous DMF. The mixture was cooled to 0° C. and treated with 0.058 mL of $Et_3N$ followed by 0.063 mL of DECP. The solid starting material rapidly dissolved to give a clear solution. The solution was allowed to warm to RT and was stirred at RT under nitrogen. After 3 h, tlc ($SiO_2$, 95:5 $CH_2Cl_2$:MeOH) indicated a major new component at $R_F$=0.41 and minor components at $R_f$=0.38 and 0.06. The solution was concentrated in vacuo to dryness and the residue was dissolved in 70 mL of $CHCl_3$. The $CHCl_3$ solution was washed with 5% aqueous $NaHCO_3$ (3×60 mL), dried over anhydrous $Na_2SO_4$ and concentrated to give a yellow glass. The crude product was purified by flash chromatography on silica gel (95:5→93:7 $CH_2Cl_2$:MeOH) to afford 0.258 g (80%) of tert-butyl 5-O-tert-butyl-N-(4-(((1,2-dihydro-3-methyl-1-oxobenzo(f) quinazolin-9-yl)methyl)amino)-2-fluorobenzoyl)-L-glutam-1-yl-3-cyclopentyl-L-phenylalaninate as a transparent glass.

$^1$H-NMR: (300 MHz, DMSO-$d_6$)δ 12.54 (s, 1H, benzoquinazoline NH), 9.86 (s, 1H, aromatic CH), 8.39 (d, 1H, J=7.6, amide NH), 8.23 (d, 1H, J=9.0, aromatic CH), 8.02 (d, 1H, J=8.4, aromatic CH), 7.68-7.41 (m, 4H, aromatic CH, amide NH), 7.35 (m, 1H, 4-aminobenzoyl NH), 7.21-6.97 (m, 4H, aromatic CH), 6.56 (d, 1H, J=8.8, aromatic CH), 6.41 (d, 1H, J=15.0, aromatic CH), 4.67-4.30 (m, 4H, benzoquinazoline 9-$CH_2$, methines), 3.06-2.77 (m, 3H, Ar$Ch_2$, cyclopentyl methine), 2.43 (s, 3H, $CH_3$), 2.19 (m, 2H, glu 4-$CH_2$), 2.00-1.38 (m, 10H, glu 3-$CH_2$, cyclopentyl $CH_2$), 1.35 (s, 9H, t-Bu), 1.32 (s, 9H, t-Bu).

EXAMPLE 132

N-(4-(((1,2-Dihydro-3-methyl-1-oxobenzo(f) quinazolin-9-yl)methyl)amino)-2-fluorobenzoyl)-L-glutam-1-yl-3-cyclopentyl-L-phenylalanine According to example 50, 0.25 g of tert-butyl 5-O-tert-butyl-N-(4-(((1,2-dihydro-3-methyl-1-oxobenzo(f) quinazolin-9-yl)methyl)amino)-2-fluorobenzoyl)-L-glutam-1-yl-3cyclopentyl-L-phenylalaninate was treated with gaseous HCl in 40 mL of $CH_3NO_2$ for 1 h. The reaction mixture was concentrated in vacuo to give a yellow residue. Analysis of this material by HPLC (C18, 65:35:0.1 $H_2O$:MeCN:TFA) indicated a major component at k'=2.82 and minor components at k'=3.33, 1.53, and 0.83. The crude product ws subjected to semi-preparative reverse phase HPLC (C18, 65:35:0.1 H$_2$O:MeCN:TFA). Fractions containing pure product (as determined by analytical HPLC) were combined and concentrated to dryness. The residue was mixed with 20 ml of water and treated with sufficient 1N aqueous NaOH to give complete solution. The solution was filtered and acidified to pH 3.0 by addition of 1N aqueous HCl. A white precipitate resulted which was separated by centrifugation, washed with 4 cycles of aqueous suspension-centrifugation-decantation, and lyophilized to afford 0.141 g (62%) of N-(4-(((1,2-dihydro-3-methyl-1-oxobenzo(f) quinazolin-9-yl)methyl)amino-2-fluorobenzoyl)-L-glutam-1yl-3-cyclopentyl-L-phenylalanine as a fluffy white powder, m.p>200° C.

HPLC: one peak on C18, k'=2.77, 65:55:0.1 H$_2$O:MeCN:TFA, flow rate=1 mL/min. $^1$H-NMR: (300 MHz, DMSO-d$_6$)δ 12.90-11.80 (br, m COOH, benzoquinazoline NH), 9.82 (s, 1H, aromatic CH), 8.27 (d, 1H, J=7.9, amide NH), 8.19 (d, 1H, J=8.7, aromatic CH), 7.99 (d, 1H, J=8.4, aromatic CH), 7.58 (m, 2H, aromatic CH), 7.45 (m, 2H, aromatic CH, amide NH), 7.31 (m, 1H, 4-aminobenzoyl NH), 7.05 (m, 2H, aromatic CH), 6.97 (d, 2H, J=7.9, aromatic CH), 6.51 (d, 1H, J=8.7, aromatic CH), 6.37 (d, 1H, J=15.2, aromatic CH), 4.55 (d, 2H, J=5.2, benzoquinazoline 9-CH$_2$), 4.43 (m, 2H, methines, 3.02 (m, 1H, ArCH$_2$), 2.82 (m, 2H, ArCH$_2$, cyclopentyl methine), 2.41 (s, 3H, CH$_3$), 2.16 (t, 2H, J=7.7, glu 4-CH$_2$), 1.98-1.71 (m, 4H, glu 3-CH$_2$, cyclopentyl CH$_2$), 1.69-1.31 (m, 6H, cyclopentyl CH$_2$).

Elemental Analysis: Calcd. for C$_{40}$H$_{40}$N$_5$O$_7$F 0.5H$_2$O (MW 730.79): C, 65.74; H, 5.65; N, 9.58. Found: C, 65.76; H, 5.68; N, 9.57.

Mass Spectrum: (FAB) 722 (M+H)$^+$.

UV Spectrum: (pH 7 Buffer) λ$_{max}$ (ε) 265.9 (47900), 299.6 (27300), 348.4 (5710). λ$_{min}$ (ε) 240.6 (19900), 284.5 (24900), 340.0 (3450). sh (ε) 332.3 (6780).

EXAMPLE 133 tert-Butyl N-(4-(((2-amino-3,4-dihydro-4—oxo-6-quinazolinyl)methyl)(2-propynyl)amino)benzoyl)-5-O-tert-butyl-L-glutam-1-yl-3-cyclopentyl-L-phenylalaninate A 50 mL 3-necked flask equipped with a magnetic stirrer and a nitrogen inlet was charged with 0.097 g of 4-(((2-amino-3,4-dihydro-4-oxo-6-quinazolinyl)methyl)(2-propynyl)amino)benzoic acid (Jones, T. R., et al, *J. Med. Chem.*, 1986, 29, 1114; Nair, M. G., et al, *J. Med. Chem.*, 1986, 29, 1754; Ghazala, M., et al, *J. Med. Chem.*, 1986, 29, 1263; Acharya, S. P., et al, *J. Heterocyclic Chem.*, 1975, 12, 1283), 0.142 g of tert-butyl 5-O-tert-butyl-L-glutam-1-yl-3-cyclopentyl-L-phenylalaninate, 0.044 g of 3-hydroxy-1,2,3-benzotriazin-4(3H)-one (Aldrich, and 7 mL of anhydrous DMF. The mixture was treated with 0.057 g of EDC and was stirred at RT under nitrogen. The solid starting material slowly dissolved to give a clear solution. After 3 days the solution was concentrated in vacuo to dryness and the residue was subjected to flash chromatography on silica gel (98.2→95:5 CH$_2$Cl$_2$:MeOH) to afford 0.142 g (65%) of tert-butyl N-(4-(((2-amino-3,4-dihydro-4-oxo-6-quinazolinyl)methyl)(2-propynyl)amino)benzoyl)-5-O-tert-butyl-L-glutam-1-yl-3-cyclopentyl-L-phenylalaninate as a white solid, m.p. 115° C. (dec).

EXAMPLE 134

N-(4(((2-Amino-3,4-dihydro-4-oxo-6-quinazolinyl) methyl)(2-propynyl)amino)benzoyl)-L-glutam-1-yl-3-cyclopentyl-L-phenylalanine According to example 50, 0.114 g of tert-butyl N-(4-(((2-amino-3,4-dihydro-4-oxo-6-quinazolinyl)methyl)(2-propynyl)amino)benzoyl)-5-O-tert-butyl-L-glutam-1-yl-3-cyclopentyl-L-phenylalaninate was treated with gaseous HCl in CH$_3$NO$_2$ for 2 h. The reaction mixture was concentrated to dryness and the residue was suspended in 50 mL of ether. The resulting solid was collected by filtration and dried in vacuo. The crude product was purified by semi-preparative reverse phase HPLC (C18, 68:32:0.1→60:40:0.1 H$_2$O:MeCN:TFA). Fractions containing pure product (as determined by analytical HPLC) were combined and concentrated to dryness. The residue was suspended in water and lyophilized to afford 0.053 g (45%) of N-(4-(((2-amino-3,4-dihydro-4-oxo-6-quinazolinyl) methyl)(2-propynyl)amino)benzoyl)-L-glutam-1-yl-3-cyclopentyl-L-phenylalanine as a fluffy white solid, m.p. 158° C. (dec).

HPLC: two peaks on C18;k'=1.27 (98.8%), k'=0.50 (1.2%); 62:38:0.1 H$_2$O:MeCN:TFA; flow rate=1 mL/min.

$^1$H-NMR: (300 MHz, DMSO-d$_6$)δ 12.90-11.80 (br m, COOH), 8.07 (d, 1H, J=7.9, amide NH), 8.03 (d, 1H, J=7.9, amide NH), 7.87 (s, 1H, aromatic CH), 7.71 (d, 2H, J=8.7, aromatic CH), 7.62 (d, 1H, J=8.6, aromatic CH), 7.57-7.24 (br s, 2H, NH$_2$), 7.31 (d, 1H, J=8.6, aromatic CH), 7.13-6.95 (m, 4H, aromatic CH), 6.82 (d, 2H, J=8.8, aromatic CH), 4.71 (s, 2H, quinazolinyl-CH$_2$), 4.41 (m, 2H, methines), 4.30 (s, 2H, propargyl CH$_2$), 3.19 (s, 1H, propargyl CH), 3.10-2.77 (m, 3H, ArCH$_2$, cyclopentyl methine), 2.23 (t, 2H, J=7.6, glu 4-CH$_2$), 2.02-1.76 (m, 4H, glu 3-CH$_2$, cyclopentyl CH$_2$, 1.75-1.38 (m, 6H, cyclopentyl CH$_2$).

$^{19}$F-NMR: (282 MHz, DMSO-d$_6$)δ 1.53 (relative to TFA external standard).

Elemental Analysis: Calcd. for C$_{38}$H$_{40}$N$_6$O$_7$TFA 2.2H$_2$O (MW 846.43): C, 56.76; H, 5.41; N, 9.93. Found: C, 56.79; H, 5.42; N, 9.95.

Mass Spectrum: (FAB) 693 (M+H)$^+$.

UV Spectrum: (pH 7 Buffer) λ$_{max}$ (ε) 227.2 (48400), 306.4 (24500). λ$_{min}$ (ε) 213.5 (40200), 252.2 (11500).

EXAMPLE 135

Ethyl N-((benzyloxy)carbonyl)-5-O-ethyl-L-glutam-1-yl-L-phenylalaninate

A 500 mL round bottom flask equipped with a magnetic stirrer and a nitrogen inlet was charged with 10.0 g of N-benzyloxycarbonyl-L-glutamic acid γ-ethyl ester, 7.43 g of L-phenylalanine ethyl ester hydrochloride (Aldrich), 100 mL of CH$_2$Cl$_2$, and 4.51 mL of Et$_3$N. The solution was cooled to 0° C. and treated with a solution of 6.67 g of DCC (Fluka) in 25 ml of CH$_2$Cl$_2$. The solution was stirred at 0° C. for 1 h and then allowed to warm to RT. After an additional 3 h, the mixture was filtered to remove dicyclohexylurea. The filtrate was washed with 10% aqueous citric acid (3×50 mL), saturated aqueous NaHCO$_3$ (3×50 mL), followed by one 60 mL portion of water. The solution was dried over anhydrous Na$_2$SO$_4$, concentrated to 30 mL, and triturated with addition of 50 mL of ether followed by 150 mL of pentane. The resulting precipitate was collected by filtration and dried in vacuo to afford 12.9 g (82%) of ethyl N-((benzyloxy)carbonyl)-5-O-ethyl-L-glutam-1-yl-L-phenylalaninate as a white crystalline solid, m.p. 85–87° C.

EXAMPLE 136

Ethyl 5-O-ethyl-L-glutam-1-yl-L-phenylalaninate

According to example 10, 13.08 g of ethyl N-((benzyloxy)carbonyl)-5-O-ethyl-L-glutam-1-yl-L- phenylalaninate was hydrogenolyzed in 300 mL of EtOH using 2.43 g of 10% Pd(C) and 2 mL of acetyl chloride to afford 9.84 g (94%) of ethyl 5-O-ethyl-L-glutam-1-yl-L-phenylalaninate HCl as a white foam.

$^1$H-NMR: (200 MHz, DMSO-d$_6$)δ 9.08 (d, 1H, J=7.0, NH), 7.90-7.40 (br s, 3H, NH3$^+$), 7.29 (m, 5H, aromatic CH), 4.50 (m, 1H, methine), 4.07 (m, 4H, ethyl CH$_2$), 3.80 (m, 1H, methine), 3.04 (m, 2H, ArCH$_2$), 2.46 (m, 2H, glu 4-CH$_2$), 1.99 (m, 2H, glu 3-CH$_2$), 1.20 (t, 3H, J=7.1, ethyl CH$_3$), 1.13 (t, 3H, J=7.1, ethyl CH$_3$).

EXAMPLE 137

Ethyl N-((S)-4-(ethoxycarbonyl)-2-(4-nitrophthalimido)butanoyl)-L-phenylalaninate A 1 L round bottom flask equipped with a magnetic stirrer, a condenser, a nitrogen inlet, and a Dean Stark trap was charged with 7.28 g of ethyl 5-O-ethyl-L-glutam-1-yl-L-phenylalaninate HCl, 3.68 g of 4-nitrophthalic anhydride (American Tokyo Kasei, Portland, Oreg. 97203), 300 mL of toluene, and 2.43 g of diisopropylethylamine (Aldrich). The reaction mixture was heated at reflux for 2 h, allowed to cool to RT, and stirred at RT overnight under nitrogen. The toluene was removed by rotary evaporation and the residue was dissolved in 400 mL of CH$_2$Cl$_2$. The solution was washed with water (2×200 mL), 5% aqueous NaHCO$_3$ (2×250 mL), and dried over anhydrous MgSO$_4$. The drying agent was removed by filtration and the filtrate was concentrated to 100 mL. The concentrate was mixed with excess ether to induce precipitation. The precipitate was collected by filtration and dried in vacuo to afford 6.72 g (67%) of ethyl N-((S)-4-(ethoxycarbonyl)-2-(4-nitrophthalimido)butanoyl)-L-phenylalaninate as a white solid. $^1$H-NMR: (300 MHz, DMSO-d$_6$)δ 8.65 (m, 2H, aromatic CH, NH), 8.49 (s,1H, aromatic CH), 8.13 (d, 1H, J=8.6, aromatic CH), 7.27-7.06 (m, 5H, aromatic CH), 4.70 (m, 1H, methine), 4.39 (m, 1H, methine), 4.04 (q, 2H, J=7.1, ethyl CH$_2$), 3.93 (q, 2H, J=7.1, ethyl CH$_2$), 2.94 (dd; 1H: J=13.7, 5.8; ArCH$_2$) ,2.82 (dd; 1H; J=13.6, 9.4, ArCH$_2$), 2.34 (m, 3H, glu 4-CH$_2$, glu 3-CH$_2$), 2.18 (m, 1H, glu 3-CH$_2$), 1.11 (t, 6H, J=7.1, ethyl CH$_3$).

EXAMPLE 138

Ethyl N-((S)-2-(4-aminophthalimido)-4-(ethoxycarbonyl)butanoyl)-L-phenylalaninate To a 300 mL Parr bottle were added 1.17 g of 10% Pd(C) and 20 mL of EtOAc under a nitrogen flush. To this mixture was added a solution of 6.72 g of ethyl N-((S)-4-(ethoxycarbonyl)-2-(4-nitrophthalimido)butanoyl)-L-phenylalaninate in 200 mL of EtOAc. The mixture was deoxygenated by bubbling nitrogen through and then hydrogenated at 45 psi for 1 h. The bottle was purged with nitrogen and the catalyst was removed by filtration through celite. The filtrate was concentrated in vacuo to give a residue which was purified by flash chromatography or silica gel (1:1→3:7 hexane:EtOAc). This afforded 5.66 g (88%) of ethyl N-((S)-2-(4-aminophthalimido)-4-(ethoxycarbonyl) butanoyl)-L-phenylalaninate as a bright yellow solid.

$^1$H-NMR: (300 MHz, DMSO-d$_6$)δ 8.50 (d, 1H, J=7.4, NH), 7.48 (d, 1H, J=8.2, aromatic CH), 7.26-7.08 (m, 5H, aromatic CH), 6.92 (s, 1H, aromatic CH), 6.82 (dd; 1H; J=8.3, 1.6; aromatic CH), 6.47 (s, 2H, NH$_2$), 4.54 (m, 1H, methine), 4.35 (q, 1H, J=7.4, methine), 4.07-3.86 (m, 4H, ethyl CH$_2$), 2.92 (m, 2H, ArCH$_2$), 2.40-2.13 (m, 4H, glu 4-CH$_2$, glu 3-CH$_2$), 1.09 (m, 6H, ethyl CH$_3$).

EXAMPLE 139

Ethyl N-((S)-2-(5-amino-1-oxo-2-isoindolinyl)-4-(ethoxycarbonyl)butanoyl)-L-phenylalaninate A zinc-mercury amalgam was prepared by stirring 19.8 g of zinc dust (Mallinckrodt, Inc., Paris, Ky., 40361) in 500 mL of 10% aqueous HCl for 10 min. The HCl solution was decanted and the zinc was washed with water until neutral pH was achieved. A warm solution of 0.10 g of HgCl$_2$ in water was added to the zinc and the mxture was stirred for 10 min. The amalgam was collected by filtration, washed consecutively with with water, EtOH, and ether and air dried. The dry amalgam was added to a solution of 3.0 g of ethyl N-((S)-2-(4-aminophthalimido)-4-(ethoxycarbonyl) butanoyl)-L-phenylalaninate and 60 mL of 1N ethereal HCl in 250 mL of EtOH which was maintained at 0° C. in an ice bath. After stirring at 0° C. for 25 min, tlc (SiO$_2$, 3:7 hexane:EtOAc) indicated only a trace of starting material at Rf=0.58 and two new components at Rf=0.52 and 0.63. The reaction mixture was filtered to remove the amalgam and the filtrate was concentrated in vacuo to 200 mL. The solution was hydrogenated at 50 psi in the presence of 0.54 g of 10% Pd(C) for 18 h. The catalyst was removed by filtration through celite and the filtrate was neutralized by addition of excess NaHCO$_3$ and then concentrated to dryness. The residue was partitioned between water and CH$_2$Cl$_2$ and the layers were separated. The CH$_2$Cl$_2$ solution was washed with water (2×200 mL) and the water layer was extracted with EtOAc (200 mL). The CH$_2$Cl$_2$and EtOAc solutions were combined, dried over anhydrous Na$_2$SO$_4$, and concentrated to give 2.77 g of a pale yellow foam. Analysis of this material by tlc (SiO$_2$, 9:1 CH$_2$Cl$_2$:acetone) indicated four major components at R$_f$=0.50, 0.41 0.29, and 0.20. These materials were separated by flash chromatography on silica gel (9:1 CH$_2$Cl$_2$:acetone). Comparative $^1$H-NMR analysis indicated the R$_f$=0.29 material to be ethyl N-((S)-2-(5-amino-1-oxo-2-isoindolinyl)-4-(ethoxycarbonyl)butanoyl)-L-phenylalaninate. The product was obtained as a pale yellow foam, 0.646 g (22%). $^1$H-NMR: (300 MHz, DMMSO-d$_6$),δ 8.48 (d, 1H, J=7.7, NH), 7.32 (d, 1H, J=8.2, aromatic CH), 7.14 (s, 5H, aromatic CH), 6.59 (m, 2H, aromatic CH), 5.78 (s, 2H, NH$_2$), 4.73 (m, 1H, methine), 4.43 (m, 1H, methine), 4.13-3.90 (m, 6H, ethyl CH$_2$, isoindolinyl methylene), 3.07-2.85 (m, 2H, ArCH$_2$), 2.26-2.01 (m, 3H, glu 4-CH$_2$, glu 3-CH$_2$), 1.88 (m, 1H, glu 3-CH$_2$), 1.12 (m, 6H, ethyl CH$_3$).

EXAMPLE 140

Ethyl N-((S)-2-(5-(((1,2-dihydro-3-methyl-1-oxobenzo(f)quinazolin-9-yl)methyl)amino)-1-oxo-2-isoindolinyl)-4-(ethoxycarbonyl)butanoyl)-L-phenylalaninate According to example 5, 1.04 g of 9-bromomethyl-3-methylbenzo(f)quinazolin-1-(2H)-one was reacted with 1.65 g of ethyl N-((S)-2-(5-amino-1-oxo-2-isoindolinyl)-4-(ethoxycarbonyl)butanoyl)-L-phenylalaninate using 0.84 g of NaHCO$_3$. The reaction mixture was stirred at 100° C. for 5 h, cooled to RT, and stirred at RT for 18 h. Analysis by tlc (SiO$_2$, 4:1 CH$_2$Cl$_2$:acetone) indicated incomplete reaction. An additional 0.3 g of 9-bromomethyl-3-methylbenzo(f) quinazolin-1(2H)-one was added and the reaction mixture was stirred at 100° C. for 4 h. The mixture was cooled to RT and filtered to remove solids. The crude product was absorbed onto 25 g of silica gel by adding silica gel to the filtrate, concentrating to dryness, and storing in vacuo. The product/silica gel mixture was loaded onto a column (1000 g SiO$_2$) and subjected to flash chromatography (CH$_2$Cl$_2$→95:5 CH$_2$Cl$_2$:MeOH) to give 0.30 g of pure product. Impure chromatography fractions were combined, concentrated, and subjected to flash chromatography a second time (98:2→95:5 CH$_2$Cl$_2$:MeOH) to give 0.26 g of pure product. This afforded a total yield of 0.56 g (23%) of ethyl N-((S)-2-(5-(((1,2-dihydro-3-methyl-1-oxobenzo(f)quinazolin-9-yl)methyl)amino)-1-oxo-2-isoindolinyl)-4-(ethoxycarbonyl)butanoyl)-L-phenylalaninate as a white solid, m.p. 140° C. (dec).

EXAMPLE 141

N-((S)-4-Carboxy-2-(5-(((1,2-dihydro-3-methyl-1-oxobenzo(f)quinazolin-9-yl)methyl)amino)-1-oxo-2-isoindolinyl)butanoyl)-L-phenylalanine To a 100 mL 3-necked flask equipped with a magnetic stirrer and a nitrogen inlet were added 0.90 g of ethyl N-((S)-2-(5-(((1,2-dihydro-3-methyl-1-oxobenzo(f)quinazolin-9-yl)methyl)amino)-1-oxo-2-isoindolinyl)-4-(ethoxycarbonyl)butanoyl)-L-phenylalaninate, 3 mL of EtOH and 10 mL of 0.2N aqueous NaOH. The solution was stirred at RT under nitrogen for 2 h and was acidified to pH 3.0 by addition of 1N HCl. A white precipitate resulted which was separated by centrifugation. Analysis of this material by analytical HPLC (C18, 70:30:0.10 H$_2$O:MeCN:TFA) indicated a major component at K'=1.93 (90%) and a minor component at k'=2.41. The crude product was purified by semi-preparative reverse phase HPLC (C18, 75:25:0.1 H$_2$O:MeCN:TFA). Fractions containing pure product (k'=1.93 by analytical HPLC using above conditions) were combined and concentrated in vacuo to dryness. The residue was dissolved in 15 mL of 0.1N aqueous NaOH and the solution was adjusted to pH 3.0 by addition of 1N HCl. The resulting precipitate was collected by centrifugation, washed with four cycles of aqueous suspension-centrifugation-decantation, and lyophilized to afford 0.035 g (40%) of N-((S)-4-carboxy-2-(5-(((1,2-dihydro-3-methyl-1-oxobenzo(f)quinazolin-9-yl)methyl)amino)-1-oxo-2-isoindolinyl)butanoyl)-L-phenylalanine as a white powder, m.p. 180° C.

HPLC: one peak on C18, k'=2.3, 70:30:0.10 H$_2$O:MeCN:TFA, flow rate=1 mL/min. $^1$H-NMR: (300 MHz, DMSO-d$_6$)δ 12.83-12.56 (br s, 1H, COOH), 12.73 (s, 1H, benzoquinazoline NH), 12.20-11.90 (br s, 1H, COOH), 9.88 (s, 1H, aromatic CH), 8.19 (m 2H, amide NH, aromatic CH), 8.00 (d, 1H, J=8.4, aromatic CH), 7.66 (d, 1H, J=7.4, aromatic CH), 7.57 (d, 1H, J=8.7, aromatic CH), 7.33 (d, 1H, J=8.6, aromatic CH), 7.17 (m, 1H, isoindolinyl 5-NH), 7.03 (d, 2H, J=7.2, aromatic CH), 6.90 (m, 3H, aromatic CH), 6.72 (d 1H, J=7.8, aromatic CH), 6.59 (s, 1H, aromatic CH), 4.67 (m, 1H, methine), 4.57 (d, 2H, J=5.9, benzoquinazoline 9-CH$_2$), 4.38 (m, 1H, methine), 4.02 (d, 1H, J=16.8, isoindolinyl methylene), 3.76 (d, 1H, J=16.9, isoindolinyl methylene), 3.00 (m, 1H, ArCH$_2$), 2.80 (m, 1H, ArCH$_2$), 2.41 (s, 3H, CH$_3$), 2.02 (m, 3H, glu 4-CH$_2$, glu 3-CH$_2$), 1.76 (m, 1H, glu 3-CH$_2$).

Elemental Analysis: Calcd. for C$_{36}$H$_{33}$N$_5$O$_7$ 2.3H$_2$O (MW 689.12): C, 62.75; H, 5.50; N, 10.16. Found: C, 62.82; H, 5.50; N, 10.18.

Mass Spectrum: (FAB) 648 (M+H) $^+$.

UV Spectrum: (pH 7 Buffer) λ$_{max}$ (ε) 265.6 (38900), 301.7 (21100), 348.4 (4870). λ$_{min}$ (ε) 245.1 (19700), 284.1 (18300), 341.8 (3420). sh (e) 331.7 (7570).

EXAMPLE 142 tert-Butyl (2R, 3S, 5S)-6-oxo-2,3-diphenyl-5-(3-(trimethylsilyl)benzyl)-4-morpholinecarboxylate A dry 250 mL 3-necked flask equipped with a magnetic stirrer and a nitrogen inlet was charged with 2.08 g of t-butyl (2R, 3S)-(-)-6-oxo-2,3-diphenyl-4-morpholinecarboxylate (Aldrich), 1.43 g of 3-(trimethylsilyl)benzyl bromide (Yamakawa, T., et al, *J. Med. Chem.*, 1990, 33, 1430), and 45 mL of anhydrous THF. The solution was cooled to −78° C. and was treated with 6.17 mL of 1 M sodium bis (trimethylsilyl)amide/THF (Aldrich) via syringe through a rubber septum. The solution was stirred at −78° C. for 3.5 h and was then poured into 150 mL of water. The resulting mixture was extracted with EtOAc (4×50 mL). The combined EtOAc extracts were washed with saturated brine (3×100 mL), dried over anhydrous Na$_2$SO$_4$, and concentrated in vacuo to give a light yellow oil. The crude material was purified by flash chromatography on silica gel (9:1 hexane:EtOAc) to afford 2.6 g (88%) of tert-butyl (2R, 3S, 5S)-6-oxo-2,3-diphenyl-5-(3-(trimethylsilyl)benzyl)-4-morpholinecarboxylate as a white powder, m.p. 88–90° C.

EXAMPLE 143

(2R, 3S, 5S)-6-Oxo-2,3-diphenyl-5-(3-(trimethylsilyl)benzyl)morpholine

According to example 82, 2.47 g of tert-butyl (2R, 3S, 5S)-6-oxo-2,3-diphenyl-5-(3-(trimethylsilyl)benzyl)-4-morpholinecarboxylate was treated with 4.1 mL of TFA in 40 mL of CH$_2$Cl$_2$ for 3 h. Neutralization with 8 mL of Et$_3$N and work-up in the usual manner gave a thick oil. Purification of the crude material by flash chromatography on 80 g of silica gel (85:15 hexane:EtOAc) afforded 1.70 g (83%) of (2R, 3S, 5S)-6-oxo-2,3-diphenyl-5-(3-(trimethylsilyl)benzyl)benzyl)morpholine as a white crystalline solid, m.p. 94–95° C.

EXAMPLE 144 tert-Butyl 3-(trimethylsilyl)-L-phenylalaninate

According to example 53, 158 g of 2R, 3S 5S)-6-oxo-2,3-diphenyl-5-(3-(trimethylsilyl)benzyl)morpholine was hydrogenolyzed in 70 mL of 1:1 THF:EtOH using 0.70 g of PdCl$_2$. Analysis of the product $^1$H-NMR indicated partial desilylation of the phenyl ring. The mixture was subjected to esterification according to example 54 using 25 mL of isobutylene and 0.5 mL of conc. H$_2$SO$_4$ in 25 mL of 1,4-dioxane. Work-up in the usual manner afforded a light yellow oil which by tlc (SiO$_2$, EtOAc) consisted of two components at R$_f$=0.53 and 0.47. The R$_f$=0.53 material was isolated by flash chromatography twice on silica gel (EtOAc then 1:1 hexane:EtOAc). This gave 0.161 g (15%) of tert-butyl 3-(trimethylsilyl)-L-phenylalaninate as a clear oil. A sample of the corresponding HCl salt was prepared for $^1$H-NMR by treating 5 mg of product with excess 1N ethereal HCl and concentrating to dryness.

$^1$H-NMR: (200 MHz, DMSO-d$_6$)δ 8.53 (br s, 3H, NH$_3^+$), 7.50-7.20 (m, 4H, aromatic CH), 4.14 (m, 1H, methine), 3.21 (m, 1H, ArCH$_2$), 2.98 (m, 1H, ArCH$_2$), 1.26 (s, 9H, t-Bu), 0.23 (s, 9H, trimethylsilyl).

EXAMPLE 145 tert-Burtyl N-(benzyloxy)carbonyl)-5-O-tert-L-glutam-1-yl-3-(trimethylsilyl)-L-phenylalaninate To a 50 mL 3-necked flask equipped with a magnetic stirrer and a nitrogen inlet were added 0.161 g of tert-butyl 3-(trimethlsilyl)-L-phenylalaninate, 0.194 g of N-Cbz-L-glutamic acid γ-tert-butyl ester (Sigma), and 10 mL of CH$_2$Cl$_2$. The solution was cooled in to 0° C. and was treated with 0.110 g of EDC. The reation mixture was stirred of 0°

C. for 1.5 h and was then allowed to warm to RT. After an additional 16 h of stirring at RT, the solution was concentrated in vacuo to dryness in the presence of 5 g of silica gel. The resulting mixture was applied to a column and the product isolated by flash chromatography ($SiO_2$, 75:25 hexane:EtOAc) to afford 0.320 g (95%) of tert-butyl N-((benzyloxy)carbonyl)-5-O-tert-butyl-L-glutam-1yl-3-(trimethylsilyl)-L-phenylalaninate as a thick, transparent glass.

$^1$H-NMR: (200 MHz, DMSO-$d_6$)δ 8.29 (d, 1H, J=7.0, NH), 7.50-7.18 (m, 10H, aromatic CH, NH), 5.02 (s, 2H, $PhCH_2O$), 4.38 (m, 1H, methine), 4.07 (m, 1H, methine), 2.97 (d, 2H, J=7.3, $ArCH_2$), 2.23 (t, 2H, J=7.6, glu 4-$CH_2$), 1.96-1.60 (m, 2H, glu 3-$CH_2$), 1.40 (s, 9H, t-Bu), 1.31 (s, 9H, t-Bu), 0.24 (s, 9H, trimethylsilyl).

EXAMPLE 146 tert-Butyl 5-O-tert-butyl-L-glutam-1-yl-3-(trimethylsilyl)-L-phenylalaninate

According to example 48, 0.315 g of tert-butyl N-((benzyloxy)carbonyl)-5-O-tert-butyl-L-glutam-1-yl-3-(trimethylsilyl)-L-phenylalaninate was hydrogenolyzed using 0.051 g of 10% Pd(C) in 35 mL of MeOH. This afforded 0.24 g (98%) of tert-butyl 5-O-tert-butyl-L-glutam-1-yl-3-(trimethylsilyl)-L-phenylalaninate as a thick transparent oil. A sample of the corresponding HCl salt for $^1$H-NMR analysis was prepared by treating 5 mg of the product with excess 1N ethereal HCl and concentrating to dryness. $^1$H-NMR: (200 MHz, DMSO-$d_6$)δ 8.99 (d, 1H, J=7.2, NH), 8.28 (br s, 3H, $NH_3^+$), 7.47-7.24 (m, 4H, aromatic CH), 4.42 (m, 1H, methine), 3.86 (m, 1H, methine), 3.01 (d, 2H, J=7.2, $ArCH_2$), 2.37 (m, 2H, glu 4-$CH_2$), 2.01 (m, 2H, glu 3-$CH_2$), 1.42 (s, 9H, t-Bu), 1.32 (s, 9H, t-Bu), 0.26 (s, 9H, trimethylsilyl).

EXAMPLE 147 tert-Butyl N-(4-(((2,4-diamino-6-pyeridinyl)methyl)methylamino)benzoyl)-5-O-tert-butyl-L-glutam-1-yl-3-(trimethylsilyl)-L-phenylalaninate According to example 49, 0.095 g of 4-(N-(2,4-diamino-6-pteridinylmethyl)-N-methylamino)benzoic acid hemihydrochloride dihydrate (Aldrich) was coupled with 0.12 g of tert-butyl 5-O-tert-butyl-L-glutam-1-yl-3-(trimethylsilyl)-L-phenylalaninate using 0.11 mL of DECP (Aldrich) and 0.12 mL of $Et_3N$ in 11 mL of DMF. The crude product was subjected to flash chromatography on silica gel (7:7:1 $CH_2Cl_2$:acetone:MeOH) to afford 0.141 g (72%) of tert-butyl N-(4-(((2,4-diamino-6-pteridinyl)methyl)methylamino)benzoyl)-5-O-tert-butyl-L-glutam-1-yl-3-(trimethylsilyl)-L-phenylalaninate as a yellow powder, m.p. 188–125° C.

$^1$H-NHR: (200 MHz, DMSO-$d_6$)δ 8.58 (s, 1H, pteridinyl 7-CH), 8.23 (d, 1H, J=7.5, amide NH), 8.00 (d, 1H, J=7.8, amide NH), 7.74 (d, 2H, J=8.7, aromatic CH), 7.70 (br s, 1H, $NH_2$), 7.48 (br s, 1H, $NH_2$), 7.33 (m, 2H, aromatic CH), 7.22 (m, 2H, aromatic CH), 6.83 (d, 2H, J=8.8, aromatic CH), 6.63 (br s, 2H, $NH_2$), 4.79 (s, 2H, pteridinyl-$CH_2$), 4.53-4.29 ((m, 2H, methines), 3.23 (s, 3H, N-$CH_3$), 2.96 (d, 2H, J=7.0, $ArCH_2$), 2.23 (m, 2H, glu 4-$CH_2$), 2.04-1.77 (m, 2H, glu 3-$CH_2$), 1.38 (s, 9H, t-Bu), 1.28 (s, 9H, t-Bu), 0.21 (s, 9, trimethylsilyl).

EXAMPLE 148

N-(4-(((2,4-Diamino-6-pyeridinyl)methyl)methylamino)benzoyl)-L-glutam-1-yl-3-(trimethylsilyl)-L-phenylalanine A 100 mL 3-necked flask equipped with a magnetic stirrer and a nitrogen inlet was charged with 0.111 g of tert-butyl N-(4-(((2,4-diamino-6-pyeridinyl)methyl)methylamino)benzoyl)-5-O-tert-butyl-L-glutam-1-yl-3-(trimethylsilyl)-L-phenylalaninate and 25 mL of $CH_3NO_2$. The resulting solution was treated with 5 mL of TFA and stirred at RT. After 1 h, the solution was concentrated in vacuo to dryness. The residue was dissolved in 3 mL of $CH_3NO_2$ and the solution was treated with 20 mL of ethyl ether. A yellow solid precipitated which was collected by filtration and dried in vacuo. The product was dissolved in 3 mL of 1:1 $H_2O:CH_3CN$ and the solution mixed with 50 mL of water. A suspension resulted which was frozen and lyophilized to afford 0.90 g (82%) of N-(4-(((2,4-diamino-6-pteridinyl)methyl)methylamino)benzoyl)-L-glutam-1-yl-3-(trimethylsilyl)-L-phenylalanine as a yellow powder, m.p. 155° C. (dec).

HPLC: one peak of C18, k'=1.55, 65:35:0.1 $H_2O$:MeCN:TFA, flow rate=1 mL/min. $^1$H-NMR: (300 MHz, DMSO-$d_6$)δ 13.00-11.75 (br s, COOH), 8.64 (s, 1H, pteridinyl 7-CH), 8.60 (br s, 1H, $NH_2$), 8.39 (br s, 1H, $NH_2$), 8.11 (d, 1H, J=7.7, amide NH), 7.97 (d, 1H, J=8.1, amide NH), 7.75-7.10 (br m, 2H, $NH_2$), 7.69 (d, 2H, J=8.9, aromatic CH), 7.28 (m, 2H, aromatic CH), 7.14 (m, 2H, aromatic CH), 6.79 (d, 2H, J=8,9, aromatic CH), 4.82 (s, 2H, pteridinyl-$CH_2$), 4.39 (m, 2H, methines), 3.21 (s, 3H, N-$CH_3$), 3.02 (m, 1H, $ArCH_2$), 2.88 (m, 1H, $ArCH_2$), 2.20 (t, 2H, J=7.8, glu 4-$CH_2$), 2.00-1.72 (m, 2H, glu 3-$CH_2$), 0.17 (s, 9H, trimethylsilyl).

Elemental Analysis: Calcd. for $C_{32}H_{39}N_9O_6Si.0.8$ TFA.1.2 $H_2O$ (MW 786.64): C, 51.30; H, 5.41; N, 16.03. Found: C, 51.24; H, 5.39; N, 16.07.

Mass Spectrum: (FAB) 674 $(M+H)^+$.

UV Spectrum: (pH 7 Buffer) $\lambda_{max}$ (ε) 259.5 (23500), 308.0 (24300), 373.2 (7210). $\lambda_{min}$ (ε) 240.7 (12700), 273.9 (15500), 345.0 (5210).

EXAMPLE 149 tert-Butyl 3-iodo-L-tyrosinate

A mixture of 5.0 g of 3-iodo-L-tyrosine (Aldrich) and 2.5 mL of conc. $H_2SO_4$ in 85 mL of 1,4-dioxane was added to 30 mL of liquid isobutylene (condensed at −78° C.) in a 300 mL pressure bottle. The vessel was stoppered and the contents stirred at RT. After 3 days the bottle was cooled in an ice water bath, opened and the solution poured into a mixture of 10 g of $NaHCO_3$ in 150 mL of water. The resulting mixture was subjected to rotary evaporation to remove isobutylene and dioxane. A white solid resulted which was collected by filtration and dried in vacuo. Analysis by tlc ($SiO_2$, $CH_2Cl_2$:MeOH) indicated major and minor components at $R_f$ 0.52 and 0.60 respectively. The crude product was purified by flash chromatography on silica gel (95:5 $CH_2Cl_2$:MeOH) to afford 3.4 g (58%) of tert-butyl 3-iodo-L-tyrosinate as a white crystalline solid, m.p. 158–159° C.

EXAMPLE 150 tert-Butyl N-((benzyloxy)carbonyl)-4-O-((benzyloxy)carbonyl)-3-iodo-L-tyrosinate A 500 mL round bottomed flask equipped with a magnetic stirrer and a nitrogen inlet was charged with 5.15 g of tert-butyl 3-iodo-L-trosinate, 250 mL of 1,4-bioxane, and 4.55 mL of $Et_3N$. The resulting solution was treated with 4.66 mL of benzyl chloroformate by slow addition. After 30 min, tlc ($SiO_2$, 8:2 hexane:EtOAc) indicated no remaining starting material and a single new component at $R_f$=0.50.

The solution was concentrated in vacuo and the residue mixed with 200 mL of water. The mixture was extracted with EtOAc (4×50 mL). The combined EtOAc extracts were washed with 5% aqueous NaHCO$_3$, dried over anhydrous MgSO$_4$, and concentrated in vacuo. The crude product was subjected to flash chromatography on silica gel (8:2 hexane:EtOAc) to afford 7.49 g (84%) of tert-butyl-N-((benzyloxy)carbonyl)-4-O-((benzyloxy)carbonyl)-3-iodo-L-tyrsinate as a transparent foam.

$^1$H-NMR: (200 MHz, DMSO-d$_6$)δ 7.77 (m, 2H, NH, aromatic CH), 7.53-7.21 (m, 12H, aromatic CH), 5.32 (s, 2H, PhCH$_2$O), 5.20 (s, 2H, PhCH$_2$O), 4.12 (m, 1H, methine), 2.92 (m, 2H, ArCH$_2$), 1.35 (s, 9H, t-Bu).

EXAMPLE 151 tert-Butyl 3-cyclopentyl-L-tyrosinate

A 300 mL Parr bomb was charged with 5.13 g of tert-butyl N-((benzyloxy)carbonyl)-4-O-((benzyloxy)carbonyl)-3-iodo-L-tyrosinate, 120 mL of toluene, 30 mL of cyclopentene and 0.49 g of tri-ortho-tolylphosphine. The solution was deoxygenated by bubbling nitrogen through for 10 min and was treated with 0.182 g of Pd(OAc)$_2$ and 1.24 mL of Et3N. The bomb was flushed with nitrogen, sealed, and heated to 110° C. for 48 h. The vessel was cooled to RT, purged with nitrogen and opened. The reaction mixture was filtered to remove solids and the filtrate was concentrated in vacuo to dryness. The residue was dissolved in 200 mL of EtOAc and the solution was washed with water(4×100 mL), dried over anhydrous NaSO$_4$ and concentrated to give a thick brown oil. Analysis by tlc (SiO$_2$, 8:2 hexane:EtOAc) indicated two major components at $R_f$=0.50 and 0.40. The crude mixture was subjected to flash chromatography on silica gel (8:2 hexane:EtOAc). This afforded 2.0 g (43%) of the $R_f$=0.50 material identified as the bis(benzyloxycarbonyl) olefin mixture by $^1$H-NMR. In addition, 0.90 g (25%) of the $R_f$=0.40 material was obtained and was identified as the N-benzyloxycarbonyl olefin mixture resulting from loss of the O-benzyloxycarbonly group. The bis (benzyloxycarbonyl) olefin mixture (2.00 g) ws subjected to catalytic hydrogenation (45 psi) in the presence of 0.35 g of 10% Pd(C) in 70 mL of MeOH for 18 h. The crude product was purified by flash chromatography (SiO$_2$, EtOAc) to give 0.99 g (93%) of tert-butyl 3-cyclopentyl-L-tyrosinate as a transparent glass. The N-Benzyloxycarbonyl olefin mixture (0.90 g) was similarly hydrogenated and purified to afford 0.52 g (83%) of tert-butyl 3-cyclopentyl-L-tyrosinate.

$^1$H-NMR: (200 MHz, DMSO-d$_6$)δ 9.05 (s, 1H, OH), 6.92 (d, 1H, J=1.9, aromatic CH), 6.80 (dd; 1H; J=8.0, 2.0; aromatic CH), 6.66 (d, 1H, J=8.0, aromatic CH), 3.16 (m, 1H, cyclopentyl methine), 2.67 (d, 2H, J=6.66, ArCH$_2$), 2.00-1.40 (m, 10H, cyclopentyl CH$_2$, NH$_2$), 1.33 (s, 9H, t-Bu).

EXAMPLE 152 tert-Butyl N-(benzyloxy)carbonyl)-5-O-tert-butyl-L-glutam-1-yl-3-cyclopentyl-L-tyrosinate According to example 145, 0.99 g of tert-butyl 3-cyclopentyl-L-tyrosinate was coupled with 1.09 g of N-Cbz-L-glutamic acid γ-tert-butyl ester (Sigma) using 0.65 g of EDC in 20 mL of CH$_2$Cl$_2$ for 4 h. The crude product was purified by flash chromatography on silica gel (7:3 hexane:EtOAc) to afford 1.8 g (89%) of tert-butyl N-((benzyloxy)carboxyl)-5-O-tert-butyl-L-glutam-1-yl-3-cyclopentyl-L-tyosinate as a colorless foam.

$^1$H-NMR: (200 MHz, DMSO-d$_6$)δ 9.08 (s, 1H, OH), 8.17 (d, 1H, J=7.5, NH), 7.36 (m, 6H, aromatic CH, NH), 6.96 (s, 1H, aromatic CH), 6.81 (d, 1H, J=8.1, aromatic CH), 6.67 (d, 1H, J=8.1, aromatic CH), 5.01 (m, 2H, PhCH$_2$O), 4.28 (m, 1H, methine), 4.08 (m, 1H, methine), 3.17 (m, 1H, cyclopentyl methine), 2.82 (d, 2H, J=6.9, ArCH$_2$), 2.21 (t, 2H, J=7.7, glu 4-CH$_2$), 1.99-1.46 (m, 10H, glu 3-CH$_2$, cyclopentyl CH$_2$), 1.40 (s, 9H, t-Bu), 1.33 (s, 9H, t-Bu).

EXAMPLE 153 tert-Butyl 5-O-tert-butyl-L-glutam-1-yl-3-cyclopentyl-L-tyrosinate

According to example 48, 1.75 g of tert-butyl N-((benzyloxy)carbonyl)-5-O-tert-butyl-L-glutam-1-yl-3-cyclopentyl-L-tyrosinate was hydrogenolyzed using 0.28 g of 10% Pd(C) in 70 mL of MeOH for 3 h. The crude product was subjected to flash chromatography on silica gel (95:5 CH$_2$Cl$_2$:MeOH) to afford 1.26 g (92%) of tert-butyl 5-O-tert-butyl-L-glutam-1-yl-3-cyclopentyl-L-tyrosinate as a white crysatalline solid, m.p. 108–110 C.

EXAMPLE 154 tert-Butyl N-(4(((2,4-diamino-6-pteridinyl)methyl) methylamino)benzoyl)-5-O-tert-butyl-L-glutam-1-yl-3-cyclopentyl-L-tyrosinate to a dry 100 mL 3-necked flask equipped with a magnetic stirrer and a nitrogen inlet were added 35 mL of anhydrous DMF, 1.14 mL of Et$_3$N, and 0.99 mL of DECP. To the resulting solution were added 1.24 g of 4-(N-(2,4-diamino-6-pteridinylmethyl)-N-methylamino)benzoic acid hemihydrochloride dihydrate (Aldrich). The solid starting material slowly dissolved to give a yellow solution. After 45 min, a solution of 1.60 g of tert-butyl 5-O-tert-butyl-L-glutam-1-yl-3-cyclopentyl-L-tyrosinate in 8 mL of DMF was added. The solution was stirred at RT for 24 h and was then concentrated in vacuo to dryness. The residue was dissolved in 150 mL of CHCl$_3$. The solution was washed with 5% aqueous NH$_4$OH (3×70 mL), dried over anhydrous MgSO$_4$, and concentrated in vacuo. The crude product was subjected to flash chromatography on silica gel twice (7:7:1 CH$_2$Cl$_2$:acetone:MeOH, 93:7 CH$_2$Cl$_2$:MeOH) to afford 2.08 g (80%) of tert-butyl N-(4-(((2,4-diamino-6-pteridinyl) methyl)methylamino)benzoyl)-5-O-tert-butyl-L-glutam-1-yl-3-cyclopentyl-L-tyrosinate as a yellow powder, m.p. 145–148° C.

EXAMPLE 155

N-(4-(((2,4-Diamino-6-pteridinyl)methyl) methylamino)benzoyl)-L-glutam-1-yl-3-cyclopentyl-L-tyrosine According to example 50, 2.04 g of tert-butyl N-(4-(((2, 4-diamino-6-pteridinyl)methyl)methylamino)benzoyl)-5-O-tert-butyl-L-glutam-1-yl-3-cyclopentyl-L-tyrosinate was treated with gaseous HCl in 65 mL of CH$_3$NO$_2$ for 1 h. The yellow suspension was concentrated to a slurry and mixed with 80 mL of ethyl ether. The resulting precipitate was collected by filtration and dried in vacuo. The product was dissolved in 40 mL of 8:2 H$_2$O:MeCN and the solution was filtered and concentrated to 30 mL. A yellow suspension was obtained which was diluted with 150 mL if water, frozen, and lyophilized to give 1.71 g (86%) of N-(4-(((2,4-diamino-6-pteridinyl)methyl)methylamino)benzoyl)-L-glutam-1-yl-3-cyclopentyl-L-tyrosine as a yellow-orange powder, m.p. 175° C. (dec).

HPLC: one peak on C18, k'=2.98, 75:25:0.1 H$_2$O:MeCN:TFA, flow rate=1 mL/min.

$^1$H-NMR: (300 MHz, DMSO-d$_6$) δ 13.12 (br m, COOH), 9.30 (s, 1H, NH$_2$), 9.09 (s, 1H, NH$_2$), 8.71 (s, 1H, pteridinyl 7-CH), 8.67 (br s, 1H, NH$_2$), 8.02 (m, 2H, amide NH's), 7.78 (br s, 1H, NH$_2$), 7.71 (d, 2H, J=8.7, aromatic CH), 6.91 (s, 1H, aromatic CH), 6.79 (m, 3H, aromatic CH), 6.61 (d, 1H, J=8.1, aromatic CH), 4.86 (s, 2H, pteridinyl-CH$_2$), 4.42 (m, 1H, methine), 4.29 (m, 1H, methine), 3.24 (s, 3H, N—CH$_3$), 3.09 (m, 1H, cyclopentyl methine), 2.93–2.71 (m, 2H, ArCH$_2$), 2.23 (t, 2H, J=7.8, glu 4-CH$_2$), 2.03–1.74 (m, 4H, glu 3-CH$_2$, cyclopentyl CH$_2$), 1.73–1.37 (m, 6H, cyclopentyl CH$_2$).

Elemental Analysis: Calcd. for C$_{34}$H$_{39}$N$_9$O$_7$·1.6HCl·1.7H$_2$O (MW 774.70): C, 52.71; H, 5.72; N, 16.27; Cl, 7.32. Found: C, 52.79; H, 5.71; N, 16.16; Cl, 7.35.

Mass Spectrum: (Ion Spray) 686 (M+H)$^+$.

UV Spectrum: (pH 7 Buffer λ$_{max}$ (ε) 259.3 (24700), 307.8 (24800), 372.5 (7780). λ$_{min}$ (ε) 242.3 (15500), 272.9 (17800), 344.6 (6080). sh(ε) 221.3 (28900), 286.4 (21100).

EXAMPLE 156

3-(3-hydroxy-3-pentyl)-O-(tert-butyltrimethylsilyl) benzyl alcohol

To a dry 250 mL 3-necked flask equipped with a magnetic stirrer and a nitrogen inlet were added 5.0 g of 3-iodo-O-(tert-butyldimethylsilyl)benzyl alcohol and 40 mL of anhydrous ethyl ether. The solution was cooled to –78° C. under nitrogen and was treated with 23.2 mL of 1.3 M sec-butyllithium/cyclohexane (Aldrich) via syringe. After 20 min, the solution was treated with 3.1 mL of 3-pentanone (Aldrich). The reaction mixture was stirred at –78° C. for 1.5 h and was then allowed to warm to RT. After 3 h at RT the solution was quenched by addition of 5 mL of water, stirred for several minutes and then mixed with 80 mL of water. The two phases were separated and the aqueous solution was extracted with an additional 50 mL portion of ether. The ether extract was combined with the original ether solution. This solution was washed with saturated aqueous brine (3×50 mL), dried over anhydrous MgSO$_4$, and concentrated to afford a clear liquid. Analysis by tlc (SiO$_2$, 9:1 hexane:EtOAc) indicated a major new component at R$_f$=0.47. The crude product was purified by flash chromatography on silica gel (9:1 hexane:EtOAc) to afford 3.9 g (88%) of 3-(3-hydroxy-3-pentyl)-O-(tert-butyltrimethylsilyl)benzyl alcohol as a clear liquid.

$^1$H-NMR: (200 MHz, DMSO-d$_6$) δ 7.33 (s, 1H, aromatic CH), 7.26 (m, 2H, aromatic CH), 7.12 (m, 1H, aromatic CH), 4.72 (s, 2H, ArCH$_2$O), 4.48 (s, 1H, OH), 1.72 (m, 4H, pentyl CH$_2$), 0.90 (s, 9H, t-Bu), 0.64 (t, 6H, J=7.5, pentyl CH$_3$), 0.06 (s, 6H, SiMe$_2$).

EXAMPLE 157

3-(3-Pentyl)benzyl alcohol

A 250 mL round bottomed flask equipped with a nitrogen inlet and a magnetic stirrer was charged with 3.9 g of 3-(3-hydroxy-3-pentyl)-O-(tert-butyltrimethylsilyl)benzyl alcohol and 25 mL of CH$_2$Cl$_2$. The solution was cooled to 0° C. in an ice bath and was treated with 15 mL of TFA followed by 5 mL of Et$_3$SiH (Aldrich). After 30 min at 0° C. the ice bath was removed and the solution was stirred at RT for 18 h. The solution was concentrated to a viscous liquid. This material was dissolved in ether (60 mL), washed with 5% aqueous NaHCO$_3$ (3×50 mL), dried over anhydrous MgSO$_4$, and concentrated in vacuo. The resulting liquid was dissolved in 10 mL of THF and treated with 63 mL of 1M Bu$_4$NF/THF (Aldrich). After stirring at RT for 18 h, the solution was concentrated and the resulting syrup mixed with 80 mL of water. The mixture was extracted with ether (4×30 mL). The combined extracts were washed with 5% aqueous NaHCO$_3$ (3×50 mL), dried over anhydrous MgSO$_4$, and concentrated to afford a light yellow liquid. Analysis by tlc (SiO$_2$, 9:1 hexane:EtOAc) indicated a major new component at R$_f$=0.30. The crude product was purified by flash chromatography on silica gel (85:15 hexane:EtOAc) to give 1.84 g (82%) of 3-(3-pentyl)benzyl alcohol as a clear liquid.

$^1$H-NMR: (300 MHz, DMSO-d$_6$) δ 7.21 (t, 1H, J=7.5, aromatic CH), 7.10 (m, 2H, aromatic CH), 6.99 (d, 1H, J=7.4, aromatic CH), 5.12 (t, 1H, J=5.8, OH), 4.46 (d, 2H, J=5.8, ArCH$_2$O), 2.26 (m, 1H, pentyl methine), 1.62 (m, 2H, pentyl CH$_2$), 1.49 (m, 2H, pentyl CH$_2$), 0.69 (t, 6H, J=7.4, pentyl CH$_3$).

EXAMPLE 158

3-(3-Pentyl)benzyl bromide

According to example 17, 1.84 g of 3-(3-pentyl)benzyl alcohol was treated with 0.34 mL of PBr$_3$ in 25 mL of anhydrous CH$_2$Cl$_2$ to afford 2.23 g (90%) of 3-(3-Pentyl) benzyl bromide as a clear liquid.

$^1$H-NMR: (200 MHz, DMSO-d$_6$) δ 7.26 (m, 3H, aromatic CH), 7.12 (m, 1H, aromatic CH), 4.70 (s, 2H, ArCH$_2$), 2.33 (m, 1H, pentyl methine), 1.78–1.40 (m, 4H, pentyl CH$_2$), 0.73 (t, 6H, J=7.3, pentyl CH$_3$).

EXAMPLE 159 tert-Butyl (2R, 3S, 5S)-6-oxo-2,3-diphenyl-5-(3-(3-pentyl)benzyl)-4-morpholinecarboxylate According to example 142, 3.27 g of tert-butyl (2R, 3S)-(–)-6-oxo-2,3-diphenyl-4-morpholinecarboxylate was alkylated with 2.23 g of 3-(3-pentyl)benzyl bromide in 70 mL of anhydrous THF using 9.71 mL of 1 M sodium bis(trimethylsilyl)amide in THF. The crude product was subjected to flash chromatography on silica gel (9:1 hexane:EtOAc) and then recrystallization from EtOH-water to afford 2.26 g (48%) of tert-butyl (2R, 3S, 5S)-6-oxo-2,3-diphenyl-5-(3-(3-pentyl)benzyl-4-morpholinecarboxylate as a white crystalline solid, m.p. 143–144° C.

EXAMPLE 160

(2R, 3S, 5S)-6-Oxo-2,3-diphenyl-5-(3-(3-pentyl) benzyl)morpholine

To a 250 mL round bottomed flask equipped with a magnetic stirrer and a nitrogen inlet were added 2.19 g of tert-butyl (2R, 3S, 5S)-6-oxo-2,3-diphenyl-5-(3-(3-pentyl) benzyl)-4-morpholinecarboxylate and 45 mL of anhydrous CH$_2$Cl$_2$. The solution was cooled to 0° C. and was treated with 3.5 mL of TFA. The solution was allowed to warm to RT and was stirred under nitrogen. After 5 h, tlc (SiO$_2$, 9:1 hexane:EtOAc) indicated a trace of starting material and a major new component at R$_f$=0.42. The reaction mixture was poured into 150 mL of 6% aqueous NaHCO$_3$ and stirred for several minutes. The phases were separated and the aqueous portion was extracted with 3 additional 40 mL portions of CH$_2$Cl$_2$. The extracts were combined with the original CH$_2$Cl$_2$ solution and washed with 5% aqueous NaHCO$_3$ (3×60 mL. The solution was dried over anhydrous MgSO$_4$ and concentrated to give a light tan solid. This material was purified by flash chromatography on silica gel (85:15 hexane:EtOAc) to afford 1.47 g (84%) of (2R, 3S, 5S)-6-oxo-2,3-diphenyl-5-(3-(3-pentyl)benzyl)morpholine as a white crystalline solid. An analytical sample was prepared by recrystallization from EtOH—H$_2$O. Melting point, 96–97° C.

EXAMPLE 161

3-(3-Pentyl)-L-phenylalanine

To a 300 mL Parr bottle were added 0.41 g of PdCl$_2$, 1.36 g of (2R, 3S, 5S)-6-oxo-2,3-diphenyl-5-(3-(3-pentyl)benzyl) morpholine, 50 mL of EtOH, and 30 mL of THF. The mixture was deoxygenated by bubbling nitrogen through for 10 min and was hydrogenated at 45 psi for 18 h. The vessel was purged with nitrogen, catalyst removed by filtration through celite, and the filtrate concentrated in vacuo to a volume of 15 mL. The solution was chilled in an ice bath and triturated with additional of 50 mL of hexane. A fine precipitate slowly formed. After storing at 5° C. overnight, the solid was collected by filtration and dried in vacuo to afford 0.65 g (72%) of 3-(3-pentyl)-L-phenylalanine.HCl as a white powder, m.p. 170° C. (dec).

EXAMPLE 162 tert-Butyl 3-(3-pentyl)-L-phenylalaninate

According to example 54, 0.60 g of 3-(3-pentyl)-L-phenylalanine.HCl was treated with 30 mL of isobutylene in 35 mL of 1,4-dioxane in the presence of 0.5 mL of conc. H$_2$SO$_4$. Work-up in the usual manner followed by acidification with 2 mL of 1N ethereal HCl afforded 0.53 g (74%) of tert-butyl 3-(3-pentyl)-L-phenylalaninate.HCl as a light yellow glass.

$^1$H-NMR: (200 MHz, DMSO-d$_6$) δ 8.63 (br s, 3H, NH$_3^+$), 7.28 (t, 1H, J=7.45, aromatic CH), 7.10 (m, 3H, aromatic CH), 4.12 (m, 1H, methine), 3.23 (dd; 1H; J=13.9, 5.1; ArCH$_2$), 2.96 (dd; 1H; J=13.9, 9.1; ArCH$_2$), 2.32 (m, 1H, pentyl methine), 1.78–1.40 (m, 4H, pentyl CH$_2$), 1.28 (s, 9H, t-Bu), 0.74 (t, 6H, J=7.3, pentyl CH$_3$).

EXAMPLE 163 tert-Butyl N-((benzyloxy)carbonyl)-5-O-tert-butyl-L-glutam-1-yl-3-(3-pentyl)-L-phenylalaninate According to example 145, 0.53 g of tert-butyl 3-(3-pentyl)-L-phenylalaninate.HCl was coupled with 0.55 g of N-Cbz-L-glutamic acid γ-tert-butyl ester using 0.33 g of EDC and 0.18 mL of N-methylmorpholine in 15 mL of anhydrous CH$_2$Cl$_2$. The crude product was purified by flash chromatography on silica gel (8:2 hexane:EtOAc) to afford 0.80 g (81%) of tert-butyl N-((benzyloxy)carbonyl)-5-O-tert-butyl-L-glutam-1-yl-3-(3-pentyl)-L-phenylalaninate as a white crystalline solid, m.p. 50–53° C.

EXAMPLE 164 tert-Butyl 5-O-tert-butyl-L-glutam-1-yl-3-(3-pentyl)-L-phenylalaninate

According to example 48, 0.72 g of tert-butyl N-((benzyloxy)carbonyl)-5-O-tert-butyl-L-glutam-1-yl-3-(3-pentyl)-L-phenylalaninate was hydrogenolyzed using 0.12 g of 10% Pd(C) in 70 mL of MeOH. This afforded 0.51 g (91%) of tert-butyl 5-O-tert-butyl-L-glutam-1-yl-3-(3-pentyl)-L-phenylalaninate as a thick transparent oil. A sample of the corresponding HCl salt for $^1$H-NMR analysis was prepared by treating 5 mg of the product with excess 1N ethereal HCl and concentrating to dryness.

$^1$H-NMR: (200 MHz, DMSO-d$_6$) δ 9.03 (d, 1H, J=6.9, NH), 8.38 (br s, 3H, NH$_3^+$), 7.23 (t, 1H, J=7.2, aromatic CH), 7.06 (m, 3H, aromatic CH), 4.39 (m, 1H, methine), 3.87 (m, 1H, methine), 3.01 (d, 2H, J=7.4, ArCH$_2$), 2.35 (m, 3H, pentyl methine glu 4-CH$_2$), 2.01 (m, 2H, glu 3-CH$_2$), 1.74–1.48 (m, 4H, pentyl CH$_2$), 1.41 (s, 9H, t-Bu), 1.32 (s, 9H, t-Bu), 0.73 (t, 6H, J=7.3, pentyl CH$_3$).

EXAMPLE 165 tert-Butyl N-(4-(((2,4-diamino-6-pteridinyl)methyl) methylamino)benzoyl)-5-O-tert-butyl-L-glutam-1-yl-3-(3-pentyl)-L-phenylalaninate According to example 49, 0.199 g of 4-(N-(2,4-diamino-6-pteridinylmethyl)-N-methylamino)benzoic acid hemihydrochloride dihydrate was coupled with 0.25 g of tert-butyl 5-O-tert-butyl-L-glutam-1-yl-3-(3-pentyl)-L-phenylalaninate using 0.24 mL of DECP and 0.26 mL of Et$_3$N in 25 mL of DMF. The crude product was subjected to flash chromatography twice on silica gel (7:7:1 CH$_2$Cl$_2$:acetone:MeOH; 95:5CH$_2$Cl$_2$:MeOH) to afford 0.215 g (52%) of tert-butyl N-(4-(((2,4-diamino-6-pteridinyl)methyl)methylamino)benzoyl)-5-O-tert-butyl-L-glutam-1-yl-3-(3-pentyl)-L-phenylalaninate as a yellow powder, m.p. 175° C. (dec).

EXAMPLE 166

N-(4-(((2,4-Diamino-6-pteridinyl)methyl) methylamino)benzoyl)-L-glutam-1-yl-3-(3-pentyl)-L-phenylalanine According to example 50, 0.184 g of tert-butyl N-(4-(((2, 4-diamino-6-pteridinyl)methyl)methylamino)benzoyl)-5-O-tert-butyl-L-glutam-1-yl-3-(3-pentyl)-L-phenylalaninate was treated with gaseous HCl in 25 mL of CH$_3$NO$_2$ for 45 min. The yellow suspension was concentrated in vacuo to dryness. Analysis of the product by HPLC (C18, 65:35:0.1 H$_2$O:MeCN:TFA) indicated a major component at k'=1.61 and a minor component at k'=0.25. The crude product was purified by semi-preparative HPLC (C18, 65:35:0.1 H$_2$O:MeCN:TFA). Fractions containing pure product (analytical HPLC) were combined and subjected to rotary evaporation to remove CH$_3$CN. A yellow suspension resulted which was frozen and lyophilized to afford 0.12 g (58%) of N-(4-(((2,4-diamino-6-pteridinyl)methyl) methylamino)benzoyl)-L-glutam-1-yl-3-(3-pentyl)-L-phenylalanine as a yellow powder, m.p. 120° C. (dec).

HPLC: one peak on C18, k'=1.61, 65:35:0.1 H$_2$O:MeCN:TFA, flow rate=1 mL/min.

$^1$H-NMR: (300 MHz, DMSO-d$_6$) δ 12.87–11.90 (br m, 2H, COOH), 9.20 (br s, 1H, NH$_2$), 9.00 (br s, 1H, NH$_2$), 8.70 (s, 1H, pteridinyl 7-CH), 8.60–8.23 (br m, 2H, NH$_2$), 8.11 (d, 1H, J=7.6, amide NH), 7.96 (d, 1H, J=7.8, amide NH), 7.70 (d, 2H, J=8.7, aromatic CH), 7.07 (m, 1H, aromatic CH), 6.98 (d, 2H, J=7.9, aromatic CH), 6.90 (d, 1H, J=7.6, aromatic CH), 6.80 (d, 2H, J=8.6, aromatic CH), 4.86 (s, 2H, pteridinyl-CH$_2$), 4.41 (m, 2H, methines), 3.23 (s, 3H, N—CH$_3$), 2.92 (m, 2H, ArCH$_2$), 2.21 (m, 3H, pentyl methine, glu 4-CH$_2$), 2.03–1.77 (m, 2H, glu 3-CH$_2$), 1.68–1.37 (m, 4H, pentyl CH$_2$), 0.62 (m, 6H, pentyl CH$_3$).

Elemental Analysis: Calcd. for C$_{34}$H$_{41}$N$_9$O$_6$.1.5TFA.1.8H$_2$O (MW 875.22): C, 50.78; H, 5.31; N, 14.40. Found: C, 50.76; H, 5.40; N, 14.34.

Mass Spectrum: (Ion Spray) 672 (M+H)+.

UV Spectrum: (pH 7 Buffer) $\lambda_{max}$ ($\epsilon$) 259.8 (20000), 308.7 (19800), 373.7 (5890). $\lambda_{min}$($\epsilon$) 241.5 (11600), 275.0 (13200), 345.8 (4420).

EXAMPLE 167

2-Iodo-4-nitro-L-phenylalanine

A 250 mL round bottomed flask equipped with a magnetic stirrer was charged with 60 mL of fuming sulfuric acid (Aldrich) and 12.1 g of iodine (Aldrich). To the resulting dark red solution was added 10.0 g of 4-nitro-L-phenylalanine by slow addition. The flask was fitted with a $CaCl_2$ drying tube and the reaction mixture was stirred at RT for 18 h. The mixture was then poured onto 300 g of crushed ice. A yellow-brown emulsion resulted which was treated with 7.4 g of sodium thiosulfate and stirred. The resulting light brown suspension was basified to pH=9 by addition of solid $NaCO_3$. This was followed by acidification to pH=5.5 by addition of conc. $H_2SO_4$. A brown solid precipitated which was collected by filtration and dried in vacuo. This afforded 6.54 g (41%) of 2-iodo-4-nitro-L-phenylalanine as a brown powder, m.p.>200° C.

$^1$H-NMR: (200 MHz, DMSO-$d_6$/TFA) d 8.62 (s, 1H, aromatic CH), 8.46 (br s, 3H, $NH_3^+$), 8.26 (d, 1H, J=8.5, aromatic CH), 7.65 (d, 1H, J=8.5, aromatic CH), 4.22 (m, 1H, methine), 3.34 (m, 2H, $ArCH_2$).

EXAMPLE 168

Ethyl 2-iodo-4-nitro-L-phenylalaninate

According to example 8, 1.40 g of 2-iodo-4-nitro-L-phenylalanine was esterified by refluxing in 50 mL of ethanolic HCl for 18 h. Work-up in the usual manner followed by flash chromatography on silica gel (95:5 $CH_2Cl_2$:MeOH) afforded 1.19 g (78%) of ethyl 2-iodo-4-nitro-L-phenylalaninate as a yellow crystalline solid, m.p. 33–34° C.

EXAMPLE 169

Ethyl N-((benzyloxy)carbonyl)-2-iodo-4-nitro-L-phenylalaninate

To a 250 mL round bottomed flask equipped with a magnetic stirrer and a nitrogen inlet were added 4.7 g of ethyl 2-iodo-4-nitro-L-phenylalaninate, 125 mL of 1,4-dioxane, and 2.2 mL of $Et_3N$. The solution was cooled in an ice water bath and treated with 2.2 mL of benzyl chloroformate by slow addition. The ice bath was removed and the reaction mixture was stirred at RT for 18 h. The mixture was filtered and the filtrate was concentrated to dryness. The brown residue was dissolved in EtOAc, washed with 5% aqueous $NaHCO_3$ (4×75 mL), dried over anhydrous $MgSO_4$ and concentrated in vacuo. Analysis of the crude product by tlc ($SiO_2$, 75:25 hexane:EtOAc) indicated a major new component at $R_f$=0.35 and minor components at $R_f$=0.40 and 0.25. The $R_f$=0.35 product was isolated by flash chromatography on silica gel (75:25 hexane:EtOAc). This afforded 2.08 g (32%) of ethyl N-((benzyloxy)carbonyl)-2-iodo-4-nitro-L-phenylalaninate as a white powder, m.p. 85–87° C.

EXAMPLE 170

Ethyl 4-amino-2-cyclopentyl-L-phenylalaninate

According to example 151, 1.65 g of ethyl N-((benzyloxy)carbonyl)-2-iodo-4-nitro-L-phenylalaninate was subjected to Heck coupling with 20 mL of cyclopentene using 60 mL of toluene, 0.074 g of $Pd(OAc)_2$, 0.20 g of tri-ortho-tolylphosphine, and 0.51 mL of $Et_3N$. The reaction was carried out at 110° C. for 24 h. Analysis of the crude product by tlc ($SiO_2$, 8:2 hexane:EtOAc) indicated a major product at $R_f$=0.40 and minor components at $R_f$=0.38, 0.60, and 0.95. The $R_f$=0.40 material was isolated by flash chromatography on silica gel (8:2 hexane:EtOAc). This afforded 1.03 g (71%) of the desired olefin mixture as a clear liquid. This material was subjected to catalytic hydrogenation at 45 psi for 18 h using 55 mL of MeOH and 0.25 g of 10% Pd(C). The crude product was purified by flash chromatography ($SiO_2$, 99:1 EtOAc:MeOH) to give 0.56 g (61% for both steps) of ethyl 4-amino-2-cyclopentyl-L-phenylalaninate as a thick transparent oil.

$^1$H-NMR: (200 MHz, DMSO-$d_6$) $\delta$ 6.72 (d, 1H, J=8.2, aromatic CH), 6.50 (d, 1H, J=2.3, aromatic CH), 6.29 (dd; 1H; J=8.1, 2.3; aromatic CH), 4.80 (br s, 2H, aromatic $NH_2$), 4.00 (q, 2H, J=7.1, ethyl $CH_2$), 3.12 (m, 1H, cyclopentyl methine), 2.72 (m, 2H, $ArCH_2$), 2.03–1.37 (m, 10H, cyclopentyl $CH_2$, $NH_2$), 1.11 (t, 3H, J=7.1, ethyl $CH_3$).

EXAMPLE 171

Ethyl 2-cyclopentyl-L-tyrosinate

To a 500 mL 3-necked flask equipped with a nitrogen inlet and a magnetic stirrer were added a solution of 0.56 g of ethyl 4-amino-2-cyclopentyl-L-phenylalaninate in 60 mL of 0.1 M aqueous $H_2SO_4$. After cooling to 3° C., the solution was treated with a solution of 0.148 g of sodium nitrite (Aldrich) in 10 mL of water. The solution was stirred at 3° C. for 10 min and was then treated with 95 mL of 1.5 M aqueous $CuSO_4$ followed by 0.25 g of $Cu_2O$ (Aldrich). The mixture was heated to 45° C. for 35 min with stirring. Gas evolution was evident during this period. The mixture was cooled to RT and filtered. The blue filtrate was treated with 1N aqueous NaOH to pH=5.5. The resulting blue-green suspension was transfered to a separatory funnel and extracted with $CHCl_3$ (5×100 mL). The combined $CHCl_3$ extracts were dried over $MgSO_4$ and concentrated to give 0.12 g of a green oil. The blue-green suspension was then treated with solid $NaHCO_3$ until gas evolution ceased and was extracted with $CHCl_3$ a second time (4×50 mL). The combined extracts were washed with water, dried ($MgSO_4$), and concentrated to give 0.076 g of an oil. This material was combined with the original 0.12 g of product and purified by flash chromatography ($SiO_2$, 95:5 $CH_2Cl_2$:MeOH) to afford 0.168 g (30%) of ethyl 2-cyclopentyl-L-tyrosinate as a thick, transparent oil.

$^1$H-NMR: (200 MHz, DMSO-$d_6$) $\delta$ 9.07 (s, 1H, OH), 6.87 (d, 1H, J=8.2, aromatic CH), 6.66 (d, 1H, J=2.4, aromatic CH), 6.48 (dd; 1H; J=8.1, 2.4; aromatic CH), 4.00 (q, 2H, J=7.1, ethyl $CH_2$), 3.16 (m, 1H, cyclopentyl methine), 2.78 (m, 2H, $ArCH_2$), 2.05–1.32 (m, 10H, cyclopentyl $CH_2$, $NH_2$), 1.10 (t, 3H, J=7.1, ethyl $CH_3$).

EXAMPLE 172

Ethyl N-((benzyloxy)carbonyl)-5-O-ethyl-L-glutam-1-yl-2-cyclopentyl-L-tyrosinate According to example 145, 0.153 g of ethyl 2-cyclopentyl-L-tyrosinate was coupled with 0.171 g of N-Cbz-L-glutamic acid γ-ethyl ester using 0.111 g of EDC in 8 mL of $CH_2Cl_2$ for 4.5 h. The crude product was purified by flash chromatography twice on silica gel (1:1 hexane:EtOAc; 95:5 $CH_2Cl_2$:MeOH) to afford 0.245 g (78%) of ethyl N-((benzyloxy)carbonyl)-5-O-ethyl-L-glutam-1-yl-2-cyclopentyl-L-tyrosinate as a colorless foam.

$^1$H-NMR: (300 MHz, DMSO-$d_6$) δ 9.09 (s, 1H, OH), 8.37 (d, 1H, J=7.3 NH), 7.33 (m, 6H, aromatic CH, NH), 6.88 (d, 1H, J=8.4, aromatic CH), 6.63 (s, 1H, aromatic CH), 6.43 (d, 1H, J=8.3, aromatic CH), 4.99 (m, 2H, PhCH$_2$O), 4.28 (m, 1H, methine), 4.00 (m, 5H, ethyl CH$_2$, methine), 3.09 (m, 1H, cyclopentyl methine), 2.96 (m, 1H, ArCH$_2$), 2.83 (m, 1H, ArCH$_2$), 2.29 (t, 2H, J=7.9, glu 4-CH$_2$), 2.02–1.53 (m, 8H, glu 3-CH$_2$, cyclopentyl CH$_2$), 1.46 (m, 2H, cyclopentyl CH$_2$), 1.15 (t, 3H, J=7.1, ethyl CH$_3$), 1.04 (t, 3H, J=7.1, ethyl CH$_3$).

EXAMPLE 173

Ethyl 5-O-ethyl-L-glutam-1-yl-2-cyclopentyl-L-tyrosinate

According to example 48, 0.24 g of ethyl N-((benzyloxy)carbonyl)-5-O-ethyl-L-glutam-1-yl-2-cyclopentyl-L-tyrosinate was hydrogenolyzed using 0.042 g of 10% Pd(C) in 85 mL of MeOH. The crude product was purified by flash chromatography (SiO$_2$, 95:5 CH$_2$Cl$_2$:MeOH) to afford 0.154 g (84%) of ethyl 5-O-ethyl-L-glutam-1-yl-2-cyclopentyl-L-tyrosinate as a thick transparent oil.

$^1$H-NMR: (300 MHz, DMSO-$d_6$) δ 9.08 (s, 1H, OH), 8.23 (d, 1H, J=7.9, NH), 6.87 (d, 1H, J=8.1, aromatic CH), 6.63 (d, 1H, J=2.1, aromatic CH), 6.44 (dd; 1H; J=8.1, 2.1; aromatic CH), 4.31 (m, 1H, methine), 4.00 (m, 4H, ethyl CH$_2$), 3.12 (m, 2H, glu methine cyclopentyl methine), 2.98 (m, 1H, ArCH$_2$), 2.82 (m, 1H, ArCH$_2$), 2.27 (t, 2H, J=7.9, glu 4-CH$_2$), 2.00–1.35 (m, 12H, glu 3-CH$_2$, NH$_2$, cyclopentyl CH$_2$), 1.07 (t, 3H, J=7.1, ethyl CH$_3$), 1.16 (t, 3H, J=7.1, ethyl CH$_3$).

EXAMPLE 174

Ethyl N-(4-(((2,4-diamino-6-pteridinyl)methyl)methylamino)benzoyl)-5-O-ethyl-L-glutam-1-yl-2-cyclopentyl-L-tyrosinate According to example 49, 0.131 g of 4-(N-(2,4-diamino-6-pteridinylmethyl)-N-methylamino)benzoic acid hemihydrochloride dihydrate was coupled with 0.15 g of ethyl 5-O-ethyl-L-glutam-1-yl-2-cyclopentyl-L-tyrosinate using 0.08 mL of DECP and 0.10 mL of Et$_3$N in 12 mL of DMF. The crude product was subjected to flash chromatography twice on silica gel (93:7 CH$_2$Cl$_2$:MeOH; 92:8 CH$_2$Cl$_2$:MeOH) to afford 0.134 g (52%) of ethyl N-(4-(((2,4-diamino-6-pteridinyl)methyl)methylamino)benzoyl)-5-O-ethyl-L-glutam-1-yl-2-cyclopentyl-L-tyrosinate as a yellow powder, m.p. 135–150° C.

$^1$H-NMR: (300 MHz, DMSO-$d_6$) δ 9.06 (s, 1H, OH), 8.54 (s, 1H, pteridinyl 7-CH), 8.34 (d, 1H, J=7.4, amide NH), 7.96 (d, 1H, J=8.2, amide NH), 7.70 (d, 2H, J=8.6, aromatic CH), 7.63 (br s, 1H, NH$_2$), 7.43 (br s, 1H, NH$_2$), 6.86 (d, 1H, J=8.4, aromatic CH), 6.80 (d, 2H, J=8.9, aromatic CH), 6.60 (m, 3H, aromatic CH, NH$_2$), 6.40 (dd; 1H; J=8.2, 1.9; aromatic CH), 4.77 (s, 2H, pteridinyl-CH$_2$), 4.42 (m, 1H, methine), 4.25 (m, 1H, methine), 4.07–3.89 (m, 4H, ethyl CH$_2$), 3.19 (s, 3H, N—CH$_3$), 3.08 (m, 1H, cyclopentyl methine), 2.94 (m, 1H, ArCH$_2$), 2.82 (m, 1H, ArCH$_2$), 2.31 (t, 2H, J=7.9, glu 4-CH$_2$), 2.04–1.32 (m, 10H, glu 3-CH$_2$, cyclopentyl CH$_2$), 1.13 (t, 3H, J=7.1, ethyl CH$_3$), 1.02 (t, 3H, J=7.1, ethyl CH$_3$).

EXAMPLE 175

N-(4-(((2,4-Diamino-6-pteridinyl)methyl)methylamino)benzoyl)-L-glutam-1-yl-2-cyclopentyl-L-tyrosine A solution of 0.130 g of ethyl N-(4-(((2,4-diamino-6-pteridinyl)methyl)methylamino)benzoyl)-5-O-ethyl-L-glutam-1-yl-2-cyclopentyl-L-tyrosinate in 10 mL of 1:1 THF:H$_2$O was treated with 17 mg of LiOH and the solution was stirred at RT under nitrogen. The hydrolysis was monitored by HPLC (C18, 70:30:0.1 H$_2$O:MeCN:TFA, flow rate=1 mL/min). An additional 10 mg portion of LiOH was added after 3 h. Analysis by HPLC (above conditions) 2 h after the second LiOH addition indicated a single component at k'=0.62. The solution was neutralized by addition of 1N HCl. A yellow precipitate resulted which was collected by centrifugation, washed with four cycles of aqueous suspension-centrifugation-decantation, frozen, and lyophilized to afford 0.106 g (83%) of N-(4-(((2,4-diamino-6-pteridinyl)methyl)methylamino)benzoyl)-L-glutam-1-yl-2-cyclopentyl-L-tyrosine as a yellow powder, m.p. 185° C. (dec).

HPLC: one peak on C18, k'=2.10, 75:25:0.1 H$_2$O:MeCN:TFA, flow rate=1 mL/min.

$^1$H-NMR: (300 MHz, DMSO-$d_6$) δ 12.75–11.85 (br m, COOH), 9.03 (br s, 1H, OH), 8.56 (s, 1H, pteridinyl 7-CH), 8.13 (d, 1H, J=7.9, amide NH), 7.96 (d, 1H, J=7.8, amide NH), 7.72 (br s, 1H, NH$_2$), 7.70 (d, 2H, J=8.7, aromatic CH), 7.53 (br s, 1H, NH$_2$), 6.89 (d, 1H, J=8.4, aromatic CH), 6.80 (m, 3H, aromatic CH, NH$_2$), 6.69 (br s, 1H, NH$_2$), 6.60 (s, 1H, aromatic CH), 6.38 (dd; 1H; J=8.3, 2.2; aromatic CH), 4.78 (s, 2H, pteridinyl-CH$_2$), 4.41 (m, 1H, methine), 4.22 (m, 1H, methine), 3.21 (s, 3H, N—CH$_3$), 3.12 (m, 1H, cyclopentyl methine), 3.00 (dd; 1H; J=14.3, 5.3; ArCH$_2$), 2.76 (dd; 1H; J=14.3, 8.8; ArCH$_2$), 2.23 (t, 2H, J=7.9, glu 4-CH$_2$), 2.05–1.30 (m, 10H, glu 3-CH$_2$, cyclopentyl CH$_2$).

Elemental Analysis: Calcd. for C$_{34}$H$_{39}$N$_9$O$_7$.2.5H$_2$O (MW 730.78): C, 55.88; H, 6.07; N, 17.25. Found: C, 55.91; H, 5.94; N, 17.10.

Mass Spectrum: (Ion Spray) 686 (M+H)$^+$.

UV Spectrum: (pH 7 Buffer) $\lambda_{max}$ (ε) 259.0 (25000), 308.2 (25500), 371.5 (7960). $\lambda_{min}$(ε) 242.3 (16000), 273.0 (17700), 346.8 (6350). sh (e) 220.9 (30100), 288.1 (21000).

EXAMPLE 176 tert-Butyl 3,5-diiodo-L-tyrosinate

A solution of 5.0 g of 3,5-diiodo-L-tyrosine and 0.95 mL of 70% aqueous HClO$_4$ in 155 mL of tert-butyl acetate was stirred at RT under nitrogen for 4 days. The solution was neutralized by addition of 150 mL of 5% aqueous NaHCO$_3$ and the mixture was subjected to rotary evaporation to remove tert-butyl acetate. An off-white precipitate resulted which was collected by filtration and dried in vacuo. The crude product was subjected to flash chromatography on silica gel (97:3 CH$_2$Cl$_2$:MeOH) to afford 4.2 g (75%) of tert-butyl 3,5-diiodo-L-tyrosinate as a white powder, m.p. 165–168° C.

EXAMPLE 177 tert-Butyl N-(9-fluorenylmethyloxycarbonyl)-5-O-tert-butyl-L-glutam-1-yl-3,5-diiodo-L-tyrosinate According to example 145, 1.50 g of tert-butyl 3,5-diiodo-L-tyrosinate was coupled with 1.31 g of N-FMOC-L-glutamic acid γ-tert-butyl ester using 0.62 g of EDC in 45 mL of CH$_2$Cl$_2$ for 3 h. The crude product was purified by flash chromatography on silica gel (7:3 hexane:EtOAc) to afford 1.78 g (65%) of tert-butyl N-(9-fluorenylmethyloxycarbonyl)-5-O-tert-butyl-L-glutam-1-yl-3,5-diiodo-L-tyrosinate as a light brown foam.

$^1$H-NMR: (200 MHz, DMSO-$d_6$) δ 9.41 (s, 1H, OH), 8.27 (d, 1H, J=7.0, NH), 7.91 (d, 2H, J=7.2, aromatic CH), 7.75

(m, 2H, aromatic CH), 7.61 (s, 2H, aromatic CH), 7.57–7.28 (m, 5H, aromatic CH, NH), 4.26 (m, 4H, fluorenyl-CH$_2$O, fluorenyl methine, α-methine), 4.08 (m, 1H, α-methine), 2.83 (d, 2H, J=7.4, ArCH$_2$), 2.25 (t, 2H, J=7.9, glu 4-CH$_2$), 1.83 (br m, 2H, glu 3-CH$_2$), 1.41 (s, 9H, t-Bu), 1.33 (s, 9H, t-Bu).

EXAMPLE 178 tert-Butyl 5-O-tert-butyl-L-glutam-1-yl-3,5-diiodo-L-tyrosinate

To a solution of 1.66 g of tert-butyl N-(9-fluorenylmethyloxycarbonyl)-5-O-tert-butyl-L-glutam-1-yl-3,5-diiodo-L-tyrosinate in 7 mL of anhydrous DMF were added 1.71 mL of piperidine (Sigma). After stirring at RT under nitrogen for 1 h, the solution was mixed with 75 mL of water and was extracted with CH$_2$Cl$_2$. The combined CH$_2$Cl$_2$ solutions were washed with aqueous NaCl (4×30 mL), dried over MgSO$_4$, and concentrated in vacuo to give a white solid. Analysis of the crude product by tlc (SiO$_2$, 95:5 CH$_2$Cl$_2$:MeOH) indicated major new components at R$_f$=0.4 and 0.5. The R$_f$=0.4 material was isolated by flash chromatography on silica gel (95:5 CH$_2$Cl$_2$:MeOH) to afford 1.1 g (87%) of tert-butyl 5-O-tert-butyl-L-glutam-1-yl-3,5-diiodo-L-tyrosinate as a white foam, m.p. 45–57° C. A sample of the corresponding HCl salt was prepared for NMR by treating 10 mg of product with 1N ethereal HCl and concentrating to dryness.

$^1$H-NMR: (200 MHz, DMSO-d$_6$) δ 9.42 (br s, 1H, OH), 8.98 (d, 1H, J=7.0, NH), 8.33 (br s, 3H, NH$_3^+$), 7.67 (s, 2H, aromatic CH), 4.36 (m,1H, methine), 3.88 (m, 1H, methine), 2.86 (d, 2H, J=7.0, ArCH$_2$), 2.38 (m, 2H, glu 4-CH$_2$), 2.01 (m, 2H, glu 3-CH$_2$), 1.41 (s, 9H, t-Bu), 1.35 (s, 9H, t-Bu).

EXAMPLE 179 tert-Butyl N-(4-(((2,4-diamino-6-pteridinyl)methyl)methylamino)benzoyl)-5-O-tert-butyl-L-glutam-1-yl-3,5-diiodo-L-tyrosinate According to example 154, 0.25 g of tert-butyl 5-O-tert-butyl-L-glutam-1-yl-3,5-diiodo-L-tyrosinate was coupled with 0.132 g of 4-(N-(2,4-diamino-6-pteridinylmethyl)-N-methylamino)benzoic acid hemihydrochloride dihydrate using 0.06 mL of DECP, 0.07 mL of Et$_3$N, and 10 mL of DMF. The crude product was purified by flash chromatography on silica gel (95:5 CH$_2$Cl$_2$:MeOH) to afford 0.18 g (50%) of tert-butyl N-(4-(((2,4-diamino-6-pteridinyl)methyl)methylamino)benzoyl)-5-O-tert-butyl-L-glutam-1-yl-3,5-diiodo-L-tyrosinate as a yellow powder, m.p. 172° C. (dec).

EXAMPLE 180

N-(4-(((2,4-Diamino-6-pteridinyl)methyl)methylamino)benzoyl)-L-glutam-1-yl-3,5-diiodo-L-tyrosine According to example 50, 0.119 g of tert-butyl N-(4-(((2,4-diamino-6-pteridinyl)methyl)methylamino)benzoyl)-5-O-tert-butyl-L-glutam-1-yl-3,5-diiodo-L-tyrosinate was treated with gaseous HCl in 15 mL of CH$_3$NO$_2$ for 30 min. The yellow suspension was concentrated in vacuo to dryness. Analysis of the product by $^1$H-NMR and reverse phase HPLC indicated the desired product contaminated with minor impurities. The mixture was purified by semi-preparative HPLC (C18, 77:23:0.1 H$_2$O:MeCN:TFA). Fractions containing pure product were combined and subjected to rotary evaporation to remove MeCN. The resulting suspension was frozen and lyophilized to afford 0.024 g (18%) of N-(4-(((2,4-diamino-6-pteridinyl)methyl)methylamino)benzoyl)-L-glutam-1-yl-3,5-diiodo-L-tyrosine as a yellow powder, m.p. 205° C. (dec).

HPLC: one peak on C18, k'=2.74, 77:23:0.1 H$_2$O:MeCN:TFA, flow rate=1 mL/min.

$^1$H-NMR: (300 MHz, DMSO-d$_6$) δ 13.20–11.90 (br m, COOH), 9.35 (s, 1H, OH), 9.21 (br s, 1H, NH$_2$), 9.02 (br s, 1H, NH$_2$), 8.70 (s, 1H, pteridinyl 7-CH), 8.52 (br s, 1H, NH$_2$), 8.13 (d, 1H, J=7.6, amide NH), 7.98 (d, 1H, J=7.9, amide NH), 7.72 (d, 2H, J=9.0, aromatic CH), 7.57 (s, 2H, aromatic CH), 7.51 (br s, 1H, NH$_2$), 6.80 (d, 2H, J=8.9, aromatic CH), 4.86 (s, 2H, pteridinyl-CH$_2$), 4.41 (m, 1H, methine), 4.30 (m, 1H, methine), 3.23 (s, 3H, N—CH$_3$), 2.81 (m, 2H, ArCH$_2$), 2.25 (t, 2H, J=7.6, glu 4-CH$_2$), 1.90 (m, 2H, glu 3-CH$_2$).

Elemental Analysis: Calcd. for C$_{29}$H$_{29}$N$_9$O$_7$I$_2$·1.7 TFA·2.3 H$_2$O (MW 1104.69): C, 35.23; H, 3.22; N, 11.41. Found: C, 35.25; H, 3.24; N, 11.44.

Mass Spectrum: (Ion Spray) 870 (M+H)$^+$.

UV Spectrum: (pH 7 Buffer) λ$_{max}$ (ε) 219.7 (48900), 258.0 (26500), 306.0 (26200), 373.3 (7780). λ$_{min}$ (ε) 214.9 (48300), 246.0 (23700), 273.7 (18400), 347.6 (6200).

EXAMPLE 181

Methyl 4-hydroxy-3-iodobenzoate

To a 500 mL 3-necked flask equipped with a magnetic stirrer, a thermometer, and a condenser were added 10.0 g of methyl 4-hydroxybenzoate (Aldrich) and 30 mL of glacial acetic acid. To this suspension was added a solution of 11.74 g of iodine monochloride in 30 mL of glacial acetic acid via addition funnel. The solution was heated at 80° C. for 1 h, 45° C. for 18 h, and 90° C. for an additional 4 h. Cooling to RT afforded a thick red-orange suspension which was transferred to a 1 L separatory funnel and dissolved in 500 mL of CHCl$_3$ by shaking vigorously. The dark purple solution was washed with water (2×100 mL), saturated aqueous sodium thiosulfate (2×100 mL), and 5% aqueous NaHCO$_3$ (2×100 mL). A light yellow solution resulted which was dried over MgSO$_4$, and concentrated in vacuo to give a white solid. This material was recystallized from water-MeOH to afford 14.92 g (82%) of methyl 4-hydroxy-3-iodobenzoate as a white crystalline solid, m.p. 145–146° C.

EXAMPLE 182

Methyl 4-hydroxy-3-cyclopentylbenzoate

According to example 151, 5.0 g of methyl 4-hydroxy-3-iodobenzoate was subjected to Heck coupling with 25 mL of cyclopentene using 80 mL of toluene, 0.40 g of Pd(OAc)$_2$, 1.10 g of tri-ortho-tolylphosphine, and 2.76 mL of Et$_3$N. The reaction was carried out at 110° C. for 24 h. Analysis of the crude product by tlc (SiO$_2$, 75:25 hexane: EtOAc) indicated a major new component at R$_f$=0.50. This material was isolated by flash chromatography on silica gel (75:25 hexane:EtOAc). This gave 2.97 g (76%) of the desired olefin mixture ($^1$H-NMR) as a brown solid. This material was subjected to catalytic hydrogenation at 45 psi for 18 h using 80 mL of MeOH and 1.0 g of 10% Pd(C). This afforded 2.59 g (65% for both steps) of methyl 4-hydroxy-3-cyclopentylbenzoate as a white solid, m.p. 114–116° C.

EXAMPLE 183

Methyl 4-((tert-butyldimethylsilyl)oxy)-3-cyclopentylbenzoate

A 100 mL 3-necked flask equipped with a magnetic stirrer and a nitrogen inlet was charged with 1.79 g of methyl 4-hydroxy-3-cyclopentylbenzoate, 1.22 g of imidazole (Aldrich), 30 mL of anhydrous DMF, and 1.47 g of tert-butyldimethylsilyl chloride (Aldrich). The solution was stirred at RT under nitrogen for 24 h and then concentrated in vacuo to give a thick oil. This material was subjected to flash chromatography on silica gel (95:5 hexane:EtOAc) to afford 2.43 g (89%) of methyl 4-((tert-butyldimethylsilyl)oxy)-3-cyclopentylbenzoate as a clear liquid.

$^1$H-NMR: (200 MHz, DMSO-d$_6$) δ 7.81 (d, 1H, J=2.0, aromatic CH), 7.72 (dd; 1H; J=8.4, 2.0; aromatic CH), 6.93 (d, 1H, J=8.4, aromatic CH), 3.80 (s, 3H, CH$_3$), 3.30 (m, 1H, cyclopentyl methine), 2.06–1.37 (m, 8H, cyclopentyl CH$_2$), 0.98 (s, 9H, t-Bu), 0.27 (s, 6H, SiMe$_2$).

EXAMPLE 184

4-((tert-Butyldimethylsilyl)oxy)-3-cyclopentylbenzyl alcohol

To a 100 mL 3-necked flask equipped with a magnetic stirrer and a nitrogen inlet were added 2.58 g of methyl 4-((tert-butyldimethylsilyl)oxy)-3-cyclopentylbenzoate and 15 mL of anhydrous toluene. The solution was cooled in an ice water bath and was treated with 19.3 mL of 1M diisobutylaluminum hydride in toluene (Aldrich). The solution was stirred at 0° C. for 30 min and was allowed to warm to RT. After 2 h at RT the solution was poured into 130 mL of saturated aqueous potassium sodium tartrate and the resulting mixture was stirred for 20 min. The mixture was then extracted with ethyl ether (3×70 mL). The combined ether extracts were washed with water (3×70 mL), dried over anhydrous MgSO$_4$, and concentrated to give a cloudy oil. The crude product was purified by flash chromatography on silica gel (8:2 hexane:EtOAc) to afford 1.94 g (82%) of 4-((tert-butyldimethylsilyl)oxy)-3-cyclopentylbenzyl alcohol as a clear liquid.

$^1$H-NMR: (200 MHz, DMSO-d$_6$) δ 7.18 (d, 1H, J=2.0, aromatic CH), 7.02 (dd; 1H; J=8.2, 2.2; aromatic CH), 6.76 (d, 1H, J=8.0, aromatic CH), 5.02 (t, 1H, J=5.8, OH), 4.40 (d, 2H, J=5.6, ArCH$_2$O), 3.29 (m, 1H, cyclopentyl methine), 2.04–1.38 (m, 8H, cyclopentyl CH$_2$), 1.03 (s, 9H, t-Bu), 0.22 (s, 6H, SiMe$_2$).

EXAMPLE 185

4-((tert-Butyldimethylsilyl)oxy)-3-cyclopentylbenzaldehyde

A solution of 1.94 g of 4-((tert-butyldimethylsilyl)oxy)-3-cyclopentylbenzyl alcohol in 70 mL of anhydrous CH$_2$Cl$_2$ was treated with 2.05 g of pyridinium chlorochromate (Aldrich) and was stirred at RT under nitrogen. After 30 min, tlc (SiO$_2$, 85:15 hexane:EtOAc) indicated no remaining starting material and a major new component at R$_f$=0.80. The mixture was filtered to remove solids and the filtrate was washed with 5% aqueous citric acid (4×50 mL) followed by 5% aqueous NaHCO$_3$ (4×50 mL). The CH$_2$Cl$_2$ solution was dried over anhydrous MgSO$_4$ and concentrated in vacuo to give a brown oil. This material was purified by flash chromatography on silica gel (9:1 hexane:EtOAc) to afford 1.52 g (79%) of 4-((tert-butyldimethylsilyl)oxy)-3-cyclopentylbenzaldehyde as a clear oil.

$^1$H-NMR: (200 MHz, DMSO-d$_6$) δ 9.88 (s, 1H, aldehyde CH), 7.80 (d, 1H, J=2.0, aromatic CH), 7.69 (dd; 1H; J=8.2, 2.0; aromatic CH), 7.03 (d, 1H, J=8.3, aromatic CH), 3.29 (m, 1H, cyclopentyl methine), 2.08–1.43 (m, 8H, cyclopentyl CH$_2$), 1.01 (s, 9H, t-Bu), 0.30 (s, 6H, SiMe$_2$).

EXAMPLE 186 tert-Butyl trans-4-((tert-butyldimethylsilyl)oxy)-3-cyclopentylcinnamate

To a 100 mL 3-necked flask equipped with a magnetic stirrer, a nitrogen inlet and a reflux condenser were added 1.57 g of tert-butyl diethylphosphonoacetate (Aldrich) and 20 mL of anhydrous ethyl ether. This was followed by addition of 0.40 g of 60% NaH mineral oil dispersion. The resulting cloudy solution was heated at reflux for 25 min, cooled to 0° C. and treated with a solution of 1.52 g of 4-((tert-butyldimethylsilyl)oxy-3-cyclopentylbenzaldehyde in 10 mL of ether. A thick yellow gel resulted which was broken up with a spatula. The mixture was allowed to warm to RT and stirring was continued for an additional 1 h. Analysis by tlc (SiO$_2$, 95:5 hexane:EtOAc) indicated a major new component at R$_f$=0.48 and minor components at R$_f$=0.06, 0.41 and 0.98. The mixture was diluted with 70 mL of ether, washed with saturated brine, and dried over anhydrous MgSO$_4$. The drying agent was removed by filtration and the filtrate concentrated to give a yellow oil. This material was purified by flash chromatography on silica gel (97:3 hexane:EtOAc) to afford 1.53 g (77%) of tert-butyl trans-4-((tert-butyldimethylsilyl)oxy-3-cyclopentylcinnamate as a clear oil.

$^1$H-NMR: (200 MHz, DMSO-d$_6$) δ 7.59–7.36 (m, 3H, aromatic CH, olefinic CH), 6.83 (d, 1H, J=8.4, aromatic CH), 6.38 (d, 1H, J=15.8, olefinic CH), 3.27 (m, 1H, cyclopentyl methine), 2.02–1.52 (m, 8H, cyclopentyl CH$_2$), 1.49 (s, 9H, t-Bu), 1.00 (s, 9H, Si-t-Bu), 0.25 (s, 6H, SiMe$_2$).

EXAMPLE 187

(2R, 3S)-tert-Butyl 3-(4-((tert-butyldimethylsilyl)oxy-3-cyclopentylphenyl)-2,3-dihydroxypropionate To a 250 mL 3-necked flask equipped with a magnetic stirrer and a nitrogen inlet were added 20 mL of tert-butyl alcohol, 20 mL of water, 5.32 g of AD-mix-α (Sharpless, K. B.; et al. *J. Org. Chem.*, 1992, 57, 2768–2771; reagent purchased from Aldrich) and 0.36 g of methanesulfonamide (Aldrich). This was followed by addition of 1.53 g of tert-butyl trans-4-((tert-butyldimethylsilyl)oxy)-3-cyclopentylcinnamate. The reaction mixture was stirred at RT under nitrogen. After 18 h, 5.7 g of sodium sulfite were added and the mixture was stirred for 30 min. The mixture was concentrated in vacuo to 15 mL, diluted with 100 mL of water and extracted with EtOAc (4×50 mL). The combined EtOAc extracts were washed with water (3×50 mL), dried over anhydrous MgSO$_4$ and concentrated to give a cloudy oil. This material was purified by flash chromatography on silica gel (75:25 hexane:EtOAc) to afford 1.44 g (87%) of tert-butyl (2R, 3S)-3-(4-((tert-butyldimethylsilyl)oxy)-3-cyclopentylphenyl)-2,3-dihydroxypropionate as a thick clear oil.

$^1$H-NMR: (200 MHz, DMSO-d$_6$) δ 7.16 (s, 1H, aromatic CH), 7.01 (d, 1H, J=8.2, aromatic CH), 6.73 (d, 1H, J=8.2, aromatic CH), 5.28 (d, 1H, J=5.4, OH), 5.25 (d, 1H, J=7.1, OH), 4.55 (t, 1H, J=5.6, propionate 2-methine), 3.93 (t, 1H, J=6.8, propionate 3-methine), 3.27 (m, 1H, cyclopentyl methine), 2.04–1.37 (m, 8H, cyclopentyl CH$_2$), 1.24 (s, 9H, t-Bu), 0.99 (s, 9H, Si-t-Bu), 0.21 (s, 6H, SiMe$_2$).

EXAMPLE 188

(R)-tert-Butyl 3-(4-((tert-butyldimethylsilyl)oxy)-3-cyclopentylphenyl)-2-hydroxypropionate To a 300 mL Parr bottle were added 0.35 g of 10% Pd(C) and 20 mL of tert-butyl alcohol under a nitrogen flush. To this was added a solution of 1.42 g of tert-butyl (2R, 3S)-3-(4-((tert-butyldimethylsilyl)oxy-3-cyclopentylphenyl)-2,3-dihydroxypropionate in 40 mL of tert-butyl alcohol. The mixture was deoxygenated by bubbling nitrogen through for 5 min while gently warming the bottle to avoid freezing of tert-butyl alcohol. The mixture was treated with 4 drops of concentrated $HClO_4$ and hydrogenated at 45 psi and 40° C. for 72 h. The vessel was purged with nitrogen, catalyst removed by filtration through celite, and the filtrate concentrated in vacuo to 20 mL. The solution was mixed with 60 mL of 5% aqueous $NaHCO_3$ and the mixture extracted with EtOAc (4×40 mL). The combined EtOAc extracts were washed with 5% aqueous $NaHCO_3$ (3×50 mL), dried over anhydrous $MgSO_4$ and concentrated to give a cloudy oil. This material was purified by flash chromatography on silica gel (9:1 hexane:EtOAc) to afford 1.17 g (86%) of tert-butyl (R)-3-(4-((tert-butyldimethylsilyl)oxy)-3-cyclopentylphenyl)-2-hydroxypropionate as a thick transparent oil.

$^1$H-NMR: (200 MHz, DMSO-$d_6$) δ 7.05 (d, 1H, J=2.1, aromatic CH), 6.92 (dd; 1H; J=8.4, 2.1; aromatic CH), 6.69 (d, 1H, J=8.2, aromatic CH), 5.33 (d, 1H, J=5.7, OH), 4.08 (m, 1H, methine), 3.23 (m, 1H, cyclopentyl methine), 2.78 (d, 2H, J=6.1, Ar$CH_2$), 2.00–1.38 (m, 8H, cyclopentyl $CH_2$), 1.32 (s, 9H, t-Bu), 0.99 (s, 9H, Si-t-Bu), 0.20 (s, 6H, Si$Me_2$).

EXAMPLE 189

(S)-tert-Butyl 2-((N-((benzyloxy)carbonyl)-5-O-tert-butyl-L-glutam-1-yl)oxy)-3-(4-((tert-butyldimethylsilyl)oxy)-3-cyclopentylphenyl) propionate To a 100 mL 3-necked flask equipped with a magnetic stirrer and a nitrogen inlet were added 1.14 g of tert-butyl (R)-3-(4-((tert-butyldimethylsilyl)oxy)-3-cyclopentylphenyl)-2-hydroxypropionate, 20 mL of anhydrous THF, 1.01 g of N-Cbz-L-glutamic acid γ-tert-butyl ester (Sigma), and 0.78 g of triphenylphosphine (Aldrich). The solution was cooled to 0° C. and was treated with 0.47 mL of diethyl azodicarboxylate (Aldrich) by dropwise addition. The solution was allowed to warm to RT and stirring under nitrogen was continued. After 3.5 h, tlc ($SiO_2$, 85:15 hexane:EtOAc) indicated a major new component at $R_f$=0.46 and some remaining alcohol starting material at $R_f$=0.51. The solution was again cooled to 0° C. and treated with an additional 0.18 g of N-Cbz-L-glutamic acid γ-tert-butyl ester, 0.14 g of triphenylphosphine, and 0.085 mL of diethyl azodicarboxylate. After warming to RT and stirring for 18 h tlc indicated only a trace of starting material. The solution was concentrated in vacuo to dryness and the crude product purified by flash chromatography ($SiO_2$, 85:15 hexane:EtOAc). This afforded 1.86 g (84%) of (S)-tert-butyl 2-((N-((benzyloxy)carbonyl)-5-O-tert-butyl-L-glutam-1-yl)oxy)-3-(4-((tert-butyldimethylsilyl)oxy)-3-cyclopentylphenyl)propionate as a thick transparent oil.

$^1$H-NMR: (200 MHz, DMSO-$d_6$) δ 7.76 (d, 1H, J=8.0, NH), 7.34 (m, 5H, aromatic CH), 7.11 (s, 1H, aromatic CH), 6.96 (d, 1H, J=8.1, aromatic CH), 6.68 (d, 1H, J=8.1, aromatic CH), 5.01 (m, 3H, PhCH$_2$O, propionate methine), 4.19 (m, 1H, glu methine), 3.21 (m, 1H, cyclopentyl methine), 3.01 (d, 2H, J=5.1, Ar$CH_2$), 2.32 (t, 2H, J=7.8, glu 4-$CH_2$), 2.12–1.43 (m, 10H, glu 3-$CH_2$, cyclopentyl $CH_2$), 1.39 (s, 9H, t-Bu), 1.26 (s, 9H, t-Bu), 0.98 (s, 9H, Si-t-Bu), 0.19 (s, 9H, Si$Me_2$).

EXAMPLE 190

(S)-tert-Butyl 2-((N-(benzyloxy)carbonyl)-5-O-tert-butyl-L-glutam-1-yl)oxy)-3-(3-cyclopentyl-4-hydroxyphenyl)propionate A solution of 1.85 g of (S)-tert-butyl 2-((N-(benzyloxy)carbonyl)-5-O-tert-butyl-L-glutam-1-yl)oxy)-3-(4-((tert-butyldimethylsilyl)oxy-3-cyclopentylphenyl)propionate in 20 mL of anhydrous THF was treated with 2.63 mL of 1M tetrabutylammonium fluoride/THF (Aldrich) and was stirred at 0° C. under nitrogen. After 15 min, tlc ($SiO_2$, 75:25 hexane:EtOAc) indicated no remaining starting material and a single new component at $R_f$=0.41. The solution was mixed with 80 mL of water and was extracted with EtOAc (4×40 mL). The combined EtOAc extracts were washed with saturated brine (3×60 mL), dried over anhydrous $MgSO_4$ and concentrated in vacuo to give a clear oil. This material was subjected to flash chromatography on silica gel (75:25 hexane:EtOAc) to afford 1.5 g (96%) of (S)-tert-butyl 2-((N-((benzyloxy)carbonyl)-5-O-tert-butyl-L-glutam-1-yl)oxy)-3-(3-cyclopentyl-4-hydroxyphenyl)propionate as a white foam.

$^1$H-NMR: (200 MHz, DMSO-$d_6$) δ 9.11 (s, 1H, OH), 7.77 (d, 1H, J=8.2, NH), 7.33 (m, 5H, aromatic CH), 7.01 (d, 1H, J=1.6, aromatic CH), 8.85 (dd; 1H; J=8.2, 1.7; aromatic CH), 6.68 (d, 1H, J=8.2, aromatic CH), 5.04 (s, 2H, Ph$CH_2$O), 4.97 (m, 1H, propionate methine), 4.18 (m, 1H, glu methine), 3.17 (m, 1H, cyclopentyl methine), 2.96 (d, 2H, J=6.0, Ar$CH_2$), 2.34 (t, 2H, J=7.4, glu 4-$CH_2$), 2.13–1.43 (m, 10H, glu 3-$CH_2$, cyclopentyl $CH_2$), 1.40 (s, 9H, t-Bu), 1.29 (s, 9H, t-Bu).

EXAMPLE 191

(S)-tert-Butyl 2-((5-O-tert-butyl-L-glutam-1-yl)oxy)-3-(3-cyclopentyl-4-hydroxyphenyl)propionate According to example 48, 1.49 g of (S)-tert-butyl 2-((N-((benzyloxy)carbonyl)-5-O-tert-butyl-L-glutam-1-yl)oxy)-3-(3-cyclopentyl-4-hydroxyphenyl)propionate was hydrogenolyzed using 0.24 g of 10% Pd(C) in 70 mL of MeOH. Analysis of the crude product by tlc ($SiO_2$, 4:6 hexane:EtOAc) indicated a major component at $R_f$=0.47 and minor components at $R_f$=0.60 and 0.15. The crude product was purified by flash chromatography on silica gel (4:6 hexane:EtOAc) to afford 0.76 g (65%) of (S)-tert-butyl 2-((5-O-tert-butyl-L-glutam-1-yl)oxy)-3-(3-cyclopentyl-4-hydroxyphenyl)propionate as a white foam.

$^1$H-NMR: (200 MHz, DMSO-$d_6$) δ 9.12 (s, 1H, OH), 7.00 (s, 1H, aromatic CH), 6.86 (d, 1H, J=8.2, aromatic CH), 6.68 (d, 1H, J=8.2, aromatic CH), 4.92 (t, 1H, J=6.2, propionate methine), 4.04 (q, 1H, J=7.0, glu methine), 3.19 (m, 1H, cyclopentyl methine), 2.95 (d, 2H, J=6.4, Ar$CH_2$), 2.33 (t, 2H, J=7.4, glu 4-$CH_2$), 2.00–1.48 (m, 12H, glu 3-$CH_2$, $NH_2$, cyclopentyl $CH_2$), 1.39 (s, 9H, t-Bu), 1.31 (s, 9H, t-Bu).

EXAMPLE 192

(S)-tert-Butyl 3-(3-cyclopentyl-4-hydroxyphenyl)-2-((5-O-tert-butyl-(4-(((2,4-diamino-6-pteridinyl) methyl)methylamino)benzoyl)-L-glutam-1-yl)oxy) propionate According to example 154, 0.414 g of (S)-tert-butyl 2-((5-O-tert-butyl-L-glutam-1-yl)oxy)-3-(3-cyclopentyl-4-hydroxyphenyl)propionate was coupled with 0.32 g of 4-(N-(2,4-diamino-6-pteridinylmethyl)-N-methylamino)benzoic acid hemihydrochloride dihydrate using 0.19 mL of DECP, 0.23 mL of $Et_3$N, and 25 mL of DMF. The crude product was subjected to flash chromatography twice on silica gel (14:14:1 $CH_2Cl_2$:acetone:MeOH; 95:5 Æ91:9 $CH_2Cl_2$:MeOH) to afford 0.46 g (69%) of (S)-tert-butyl 3-(3-cyclopentyl-4-hydroxyphenyl)-2-((5-O-tert-butyl-(4-(((2,4-diamino-6-pteridinyl)methyl)methylamino)benzoyl)-L-glutam-1-yl)oxy)propionate as a yellow powder, m.p. 135–137° C.

¹H-NMR: (300 MHz, DMSO-d₆) δ 9.07 (s, 1H, OH), 8.55 (s, 1H, pteridinyl 7-CH), 8.30 (d, 1H, J=7.6, amide NH), 7.71 (d, 2H, J=8.6, aromatic CH), 7.64 (br s, 1H, NH₂), 7.42 (br s, 1H, NH₂), 6.97 (d, 1H, J=1.6, aromatic CH), 6.80 (m, 3H, aromatic CH), 6.59 (m, 3H, aromatic CH, NH₂), 4.92 (t, 1H, J=6.1, propionate methine), 4.77 (s, 2H, pteridinyl-CH₂), 4.49 (m, 1H, glu methine), 3.19 (s, 3H, N—CH₃), 3.12 (m, 1H, cyclopentyl methine), 2.93 (m, 2H, ArCH₂), 2.33 (t, 2H, J=7.2, glu 4-CH₂), 2.08 (m, 1H, glu 3-CH₂), 1.87 (m, 3H, glu 3-CH₂, cyclopentyl CH₂), 1.77–1.40 (m, 6H, cyclopentyl CH₂),1.36 (s, 9H, t-Bu), 1.25 (s, 9H, t-Bu).

EXAMPLE 193

(S)-3-(3-Cyclopentyl-4-hydroxyphenyl)-2-((N-(4-(((2,4-diamino-6-pteridinyl)methyl)methylamino)benzoyl)-L-glutam-1-yl)oxy)propionic acid According to example 50, 0.43 g of (S)-tert-butyl 3-(3-cyclopentyl-4-hydroxyphenyl)-2-((5-O-tert-butyl-(4-(((2,4-diamino-6-pteridinyl)methyl)methylamino)benzoyl)-L-glutam-1-yl)oxy)propionate was treated with gaseous HCl in 50 mL of CH₃NO₂ for 45 min. The yellow suspension was concentrated in vacuo to dryness. The product was suspended in 25 mL of water and was treated with sufficient 1N aqueous NaOH to give complete solution. The solution was filtered and the pH adjusted to 5.5 by addition of 1N HCl. A yellow precipitate resulted which was separated by centrifugation, washed with four cycles of aqueous suspension-centrifugation-decantation, frozen and lyophilized to afford 0.345 g (88%) of (S)-3-(3-cyclopentyl-4-hydroxyphenyl)-2-((N-(4-(((2,4-diamino-6-pteridinyl)methyl)methylamino)benzoyl)-L-glutam-1-yl)oxy)propionic acid as a yellow-orange powder, m.p. 165° C. (dec).

HPLC: one major peak on C18, k'=2.02; 3.6% of methotrexate was detected at k'=0.09; 70:30:0.1 H₂O:MeCN:TFA, flow rate=1 mL/min.

¹H-NMR: (300 MHz, DMSO-d₆) δ 12.40–11.90 (br s, COOH), 9.03 (br s, 1H, OH), 8.57 (s, 1H, pteridinyl 7-CH), 8.27 (d, 1H, J=7.6, amide NH), 7.86 (br s, 1H, NH₂), 7.70 (d, 2H, J=8.9, aromatic CH), 7.65 (br s, 1H, NH₂), 6.97 (d, 1H, J=1.6, aromatic CH), 6.80 (m, 5H, NH₂, aromatic CH), 6.61 (d, 1H, J=8.2, aromatic CH), 4.96 (t, 1H, J=5.9, methine), 4.78 (s, 2H, pteridinyl-CH₂), 4.49 (m, 1H, methine), 3.19 (s, 3H, N—CH₃), 3.16 (m, 1H, cyclopentyl methine), 2.94 (d, 2H, J=5.8, ArCH₂), 2.34 (t, 2H, J=7.5, glu 4-CH₂), 2.10 (m, 1H, glu 3-CH₂), 1.87 (m, 3H, glu 3-CH₂, cyclopentyl CH₂), 1.78–1.40 (m, 6H, cyclopentyl CH₂).

Elemental Analysis: Calcd. for C₃₄H₃₈N₈O₈.2.1 H₂O (MW 724.56): C, 56.36; H, 5.87; N, 15.47. Found: C, 56.13; H, 5.59; N, 15.46.

Mass Spectrum: (Ion Spray) 687 (M+H)⁺.

UV Spectrum: (pH 7 Buffer) λ$_{max}$ (ε) 259.2 (23100), 307.3 (23300), 372.4 (7190). λ$_{min}$ (ε) 242.0 (14300), 272.9 (16900), 343.6 (5460). sh (e) 219.8 (26400), 280.7 (19900).

EXAMPLE 194

Methyl 3-tert-butyl-4-hydroxybenzoate

To a 500 mL 3-necked flask equipped with a magnetic stirrer, a nitrogen inlet, and a condenser were added 10.0 g of 3-tert-butyl-4-hydroxybenzoic acid (ICN Biomedicals. Inc., Aurora, Ohio 44202), and 200 mL of MeOH. The solution was acidified by bubbling HCl gas through for 5 min. and was then heated at reflux for 5 h. The solution was cooled to RT and concentrated in vacuo to dryness. The resulting solid was dissolved in EtOAc. The solution was washed three times with 5% aqueous NaHCO₃, dried over anhydrous MgSO₄ and concentrated to dryness to afford 9.65 g (90%) of methyl-3-tert-butyl-4-hydroxybenzoate as a white crystalline solid, m.p. 144–145° C.

EXAMPLE 195

Methyl 3-tert-butyl-4-((tert-butyldimethylsilyl)oxy)benzoate

According to example 183, 5.00 g of methyl-3-tert-butyl-4-hydroxybenzoate was silylated using 4.34 g of tert-butyldimethylsilyl chloride, 3.59 g of imidazole, and 70 mL of anhydrous DMF. The crude product was purified by flash chromatography on silica gel (9:1 hexane:EtOAc) to afford 6.1 g (79%) of methyl 3-tert-butyl-4-((tert-butyldimethylsilyl)oxy)benzoate as a clear liquid.

¹H-NMR: (200 MHz, DMSO-d₆) δ 7.89 (d, 1H, J=2.3, aromatic CH, 7.76 (dd; 1H; J=8.5, 2.3; aromatic CH), 6.98 (d, 1H, J=8.4, aromatic CH), 3.82 (s, 3H, CO₂CH₃), 1.37 (s, 9H, t-Bu), 1.03 (s, 9H, Si-t-Bu), 0.37 (s, 6H, SiMe₂).

EXAMPLE 196

3-tert-Butyl-4-((tert-butyldimethylsilyl)oxy)benzyl alcohol

According to example 184, 5.00 g of methyl 3-tert-butyl-4-((tert-butyldimethylsilyl)oxy)benzoate was reduced using 31.8 mL of 1M diisobutylaluminum hydride/toluene and 50 mL of anhydrous toluene. Analysis of the reaction mixture by tlc after 30 min indicated some remaining starting material. To ensure complete reduction, an additional 5 mL of 1M diisobutylaluminum hydride/toluene was added and the reaction was allowed to proceed for an additional 5 min. Work-up in the usual manner afforded 4.11 g (90%) of 3-tert-butyl-4-((tert-butyldimethylsilyl)oxy)benzyl alcohol as a cloudy oil. The product was used without further purification.

¹H-NMR: (200 MHz, DMSO-d₆) δ 7.20 (d, 1H, J=2.0, aromatic CH), 7.04 (dd; 1H; J=8.2, 2.1; aromatic CH), 6.80 (d, 1H, J=8.0, aromatic CH), 5.01 (t, 1H, J=5.7, OH), 4.39 (d, 2H, ArCH₂O), 1.36 (s, 9H, t-Bu), 1.02 (s, 9H, Si-t-Bu), 0.32 (s, 6H, SiMe₂).

EXAMPLE 197

3-tert-Butyl-4-((tert-butyldimethylsilyl)oxy)benzyl bromide

A 500 mL round-bottomed flask equipped with a magnetic stirrer was charged with 3.6 g of 3-tert-butyl-4-((tert-butyldimethylsilyl)oxy)benzyl alcohol and 25 mL of anhydrous CH₂Cl₂. The solution was cooled in an ice water bath and was treated with 5.68 g of dibromotriphenylphosphorane (Aldrich). The reaction mixture was warmed to RT, stirred for 2.5 h and then diluted with 100 mL of CH₂Cl₂. The resulting solution was washed with 5% aqueous NaHCO₃ (4×60 mL), dried over anhydrous MgSO₄ and concentrated to give a white solid. The crude product was purified by flash chromatography on silica gel (95:5 hexane:EtOAc) to afford 3.86 g (88%) of 3-tert-butyl-4-((tert-butyldimethylsilyl)oxy)benzyl bromide as a white crystalline solid, m.p. 54–55° C.

EXAMPLE 198 tert-Butyl (2R, 3S, 5S)-6-oxo-2,3-diphenyl-5-(3-tert-butyl-4-((tert-butyldimethylsilyl)oxy)benzyl)-4-morpholinecarboxylate According to example 142, 3.82 g of tert-butyl (2R, 3S)-(−)-6-oxo-2,3-diphenyl-4-morpholinecarboxylate was alkylated with 3.86 g of 3-tert-butyl-4-((tert-butyldimethylsilyl)oxy)benzyl bromide in 80 mL of anhydrous THF using 11.34 mL of 1 M sodium bis(trimethylsilyl)amide in THF. The crude product was subjected to flash chromatography on silica gel (85:15 hexane:EtOAc) to afford 4.85 g (71%) of tert-butyl (2R, 3S, 5S)-6-oxo-2,3-diphenyl-5-(3-tert-butyl-4-((tert-butyldimethylsilyl)oxy)benzyl)-4-morpholinecarboxylate as a white foam, m.p. 75–83° C.

EXAMPLE 199

(2R, 3S, 5S)-6-Oxo-2,3-diphenyl-5-(3-tert-butyl-4-hydroxybenzyl)morpholine

To a 250 mL 3-necked flask equipped with a nitrogen inlet and a magnetic stirrer were added 4.51 g of tert-butyl (2R, 3S, 5S)-6-oxo-2,3-diphenyl-5-(3-tert-butyl-4-((tert-butyldimethylsilyl)oxy)benzyl)-4-morpholinecarboxylate and 50 mL of anhydrous THF. The solution was cooled in an ice water bath, treated with 7.51 mL of 1M nBu$_4$NF/THF (Aldrich), and then allowed to warm to RT with stirring under nitrogen. After 1.5 h, tlc (SiO$_2$, 85:15 hexane:EtOAc) indicated no remaining starting material and a single new component at R$_f$=0.52. The solution was diluted with 125 mL of EtOAc, washed with water (4×100 mL), dried over MgSO$_4$, and concentrated to give a thick, clear oil. Mass spectral analysis (APCI) indicated the desired intermediate with m/e=538 (M+H+Na)$^+$. The oil was dissolved in 50 mL of CH$_2$Cl$_2$ and the solution treated with 15 mL of TFA. After stirring for 40 min, tlc (SiO$_2$, 65:35 hexane:EtOAc) indicated a single new component at R$_f$=0.36. The solution was neutralized by addition of saturated aqueous NaHCO$_3$. The mixture was transferred to a separatory funnel and the layers separated. The CH$_2$Cl$_2$ solution was washed with additional saturated NaHCO$_3$ (3×50 mL), dried over MgSO$_4$ and concentrated in vacuo to give a clear foam. The crude product was purified by flash chromatography (SiO$_2$, 7:3 hexane:EtOAc) to afford 2.66 g (89%) of (2R, 3S, 5S)-6-oxo-2,3-diphenyl-5-(3-tert-butyl-4-hydroxybenzyl)morpholine as a white foam, m.p. 76–80° C.

EXAMPLE 200

3-tert-Butyl-L-tyrosine

To a 300 mL Parr bottle were added 0.73 g of PdCl$_2$ and 20 mL of 1:1 THF:EtOH. To this was added a solution of 2.43 g of (2R, 3S, 5S)-6-oxo-2,3-diphenyl-5-(3-tert-butyl-4-hydroxybenzyl)morpholine in 80 mL of 1:1 THF:EtOH. The mixture was deoxygenated by bubbling nitrogen through for 10 min and was hydrogenated at 45 psi for 18 h. The vessel was purged with nitrogen, catalyst removed by filtration, and the filtrate concentrated in vacuo. The residue was partitioned between water and hexane. The aqueous solution was washed with four additional 50 mL portions of hexane, subjected to brief rotary evaporation to remove residual hexane, frozen and lyophilized to afford 1.47 g (92%) of 3-tert-butyl-L-tyrosine.HCl as a tan hygroscopic solid.

$^1$H-NMR: (200 MHz, DMSO-d$_6$) δ 9.40 (br s, 1H, OH), 8.36 (br s, 3H, NH$_3$$^+$), 7.04 (s, 1H, aromatic CH), 6.91 (d, 1H, J=8.2, aromatic CH), 6.78 (d, 1H, J=8.2, aromatic CH), 4.05 (m, 1H, methine), 3.02 (d, 2H, J=5.6, ArCH$_2$), 1.34 (s, 9H, t-Bu).

EXAMPLE 201 tert-Butyl 3-tert-butyl-L-tyrosinate

To a 250 mL round bottomed flask equipped with a magnetic stirrer were added 30 mL of isobutylene (condensed at −78° C.), 1.30 g of 3-tert-butyl-L-tyrosine.HCl, 60 mL of 1,4-dioxane, and 0.5 mL of concentrated H$_2$SO$_2$. The flask was sealed with a rubber septum and wired shut. After stirring at RT for 18 h, the flask was vented and the contents poured into a solution of 10 g of NaHCO$_3$ in 150 mL of water. The mixture was subjected to rotary evaporation to remove isobutylene. An emulsion resulted which was extracted with EtOAc (4×40 mL). The combined extracts were washed with 5% aqueous NaHCO$_3$ (3×50 mL), dried over anhydrous MgSO$_4$, and concentrated to give a light yellow foam. Analysis of the product by tlc (SiO$_2$, 95:5 CH$_2$Cl$_2$:MeOH) indicated major and minor components at R$_f$=0.45 and 0.49 respectively. The R$_f$=0.45 product was isolated by flash chromatography on silica gel (95:5 CH$_2$Cl$_2$:MeOH) to afford 0.61 g (44%) of tert-butyl-3-tert-butyl-L-tyrosinate as a white foam, m.p. 43–52° C.

EXAMPLE 202 tert-Butyl N-((benzyloxy)carbonyl)-5-O-tert-butyl-L-glutam-1-yl-3-tert-butyl-L-tyrosinate According to example 145, 0.57 g of tert-butyl 3-tert-butyl-L-tyrosinate was coupled with 0.66 g of N-Cbz-L-glutamic acid γ-tert-butyl ester (Sigma) using 0.39 g of EDC in 20 mL of CH$_2$Cl$_2$ for 4 h. The crude product was purified by flash chromatography on silica gel (65:35 hexane:EtOAc) to afford 0.99 g (83%) of tert-butyl N-((benzyloxy)carbonyl)-5-O-tert-butyl-L-glutam-1-yl-3-tert-butyl-L-tyrosinate as a white foam, m.p. 62–66° C.

EXAMPLE 203 tert-Butyl 5-O-tert-butyl-L-glutam-1-yl-3-tert-butyl-L-tyrosinate

According to example 48, 0.93 g of tert-butyl N-((benzyloxy)carbonyl)-5-O-tert-butyl-L-glutam-1-yl-3-tert-butyl-L-tyrosinate was hydrogenolyzed using 0.15 g of 10% Pd(C) in 70 mL of MeOH for 3.5 h. The crude product was subjected to flash chromatography on silica gel (EtOAc) to afford 0.63 g (87%) of tert-butyl 5-O-tert-butyl-L-glutam-1-yl-3-tert-butyl-L-tyrosinate as a thick transparent oil.

$^1$H-NMR: (200 MHz, DMSO-d$_6$) δ 9.17 (s, 1H, OH), 8.11 (d, 1H, J=7.8, NH), 6.96 (d, 1H, J=1.7, aromatic CH), 6.84 (dd; 1H; J=8.1, 1.9; aromatic CH), 6.68 (d, 1H, J=8.0, aromatic CH), 4.33 (m,1H, methine), 3.14 (m, 1H, methine), 2.84 (d, 2H, J=7.0, ArCH$_2$), 2.23 (t, 2H, J=7.9, glu 4-CH$_2$), 1.88–1.46 (m, 4H, glu 3-CH$_2$, NH$_2$), 1.40 (s, 9H, t-Bu), 1.33 (s, 18H, t-Bu's).

EXAMPLE 204 tert-Butyl N-(4-(((2,4-diamino-6-pteridinyl)methyl)methylamino)benzoyl)-5-O-tert-butyl-L-glutam-1-yl-3-tert-butyl-L-tyrosinate According to example 154, 0.320 g of tert-butyl 5-O-tert-butyl-L-glutam-1-yl-3-tert-butyl-L-tyrosinate was coupled with 0.254 g of 4-(N-(2,4-diamino-6-pteridinylmethyl-N-methylamino)benzoic acid hemihydrochloride dihydrate using 0.15 mL of DECP, 0.19 mL of Et$_3$N, and 20 mL of DMF. The crude product was purified by flash chromatography on silica gel (7:7:1 CH$_2$Cl$_2$:acetone:MeOH) to afford 0.32 g (61%) of tert-butyl N-(4-(((2,4-diamino-6-pteridinyl)methyl)methylamino)benzoyl)-5-O-tert-butyl-L-glutam-1-yl-3-tert-butyl-L-tyrosinate as a yellow powder, m.p. 125° C. (dec).

EXAMPLE 205

N-(4-(((2,4-Diamino-6-pteridinyl)methyl)methylamino)benzoyl)-L-glutam-1-yl-3-tert-butyl-L-tyrosine According to example 50, 0.287 g of tert-butyl N-(4-(((2,4-diamino-6-pteridinyl)methyl)methylamino)benzoyl)-5-O- tert-butyl-L-glutam-1-yl-3-tert-butyl-L-tyrosinate was treated with gaseous HCl in 55 mL of $CH_3NO_2$ for 1 h. The suspension was concentrated in vacuo to give a yellow powder. This material was suspended in 30 mL of water and treated with sufficient 1N aqueous NaOH to give complete solution. The yellow solution was filtered and acidified to pH=5.5 by addition of 1N aqueous HCl. The resulting yellow precipitate was separated by centrifugation, washed with four cycles of aqueous suspension-centrifugation-decantation, frozen and lyophilized to afford 0.178 g (68%) of N-(4-(((2,4-diamino-6-pteridinyl)methyl)methylamino) benzoyl)-L-glutam-1-yl-3-tert-butyl-L-tyrosine as a yellow powder, m.p. 185° C. (dec).

HPLC: one peak on C18, K'=3.14, 75:25:0.1 $H_2O$:MeCN:TFA, flow rate=1 mL/min.

$^1$H-NMR: (300 MHz, DMSO-$d_6$)δ 12.80–11.80 (br m), 9.09 (s, 1H, OH), 8.55 (s, 1H, pteridinyl 7-CH), 8.01 (d, 1H, J=7.9, amide NH), 7.97 (d, 1H, J=8.1, amide NH), 7.78 (br s, 1H, $NH_2$), 7.68 (d, 2H, J=8.9, aromatic CH), 7.57 (br s, 1H, $NH_2$), 6.93 (d, 1H, J=1.6, aromatic CH), 6.85–6.64 (m, 5H, aromatic CH, $NH_2$), 6.60 (d, 1H, J=8.2, aromatic CH), 4.77 (s, 2H, pteridinyl-$CH_2$), 4.42 (m, 1H, methine), 4.29 (m, 1H, methine), 3.19 (s, 3H, N-$CH_3$), 2.83 (m, 2H, Ar$CH_2$), 2.23 (t, 2H, J=7.8, glu 4-$CH_2$), 1.90 (m, 2H, glu 3-$CH_2$), 1.25 (s, 9H, t-Bu).

Elemental Analysis: Calcd. for $C_{33}H_{39}N_9O_7$·2.3 $H_2O$ (MW 715.16): C, 55.42; H, 6.14; N, 17.63. Found: C, 55.58; H, 5.97; N, 17.47.

Mass Spectrum: (Ion Spray) 674 $(M+H)^+$.

UV Spectrum: (pH 7 Buffer) $\lambda_{max}$ (ε) 259.4 (23700), 307.4 (23500), 372.5 (7330). $\lambda_{min}$ (ε) 242.8 (14900), 273.0 (17000), 344.7 (5660). sh (e) 222.1 (26400), 287.2 (19600).

EXAMPLE 206

Sequencing of Human Carboxypeptidase A1 cDNA

A Hind III - Sal I cDNA fragment encoding the rat preprocarboxypeptidase A1 (CPA1) (Gardell et al., Nature, 317:551–555, 1985) was isolated from pMP36 provided by Dr. M. Phillips (UCSF). The 1.2 kb Hind III - Sal I rat CPA1 cDNA was radiolabeled with [$^{32}$P]dCTP and Prime-it kit (Stratagene) and then used to screen a lambda gt11 human pancreas cDNA library (Clontech) according to the method of Grunstein and Hogness (Proc. Nat. Acad. Sci 72: 5016–5020, 1975). Purified isolated plaques that hybridized to the rate CPA1 cDNA probe were obtained after three rounds of screening.

Lambda DNA from purified plaques was prepared from overnight growth liquid cultures using Qiagen columns and according to the manufacturer's protocol (Qiagen). Human CPA1 cDNA inserts were liberated from lambda DNA by digestion with EcoRI and purification of the cDNA inserts by low-melting agarose gel electrophoresis. The EcoRI cDNA inserts were cloned into the EcoRI site of pGEM 7z(+) (Promega) and denoted as pHCPA plasmids. Following overnight growth in liquid culture, plasmid pHCPA DNA was prepared using Qiagen columns.

DNA sequencing of isolated HCPA1 lambda plaques and of plasmids containing HCPA1 cDNA was performed with [$^{35}$S]dATP and the fmol sequencing system (Promega). Oligonucleotide primers that flanked the cloning site of lambda gt11 or the multiple cloning sites in pGEM 7(+) and the TA vector (Invitrogen) were used initially to determined cDNA sequence. Oligonucleotide primers that corresponded to regions of the determined sequence were synthesized which permitted the entire cDNA sequence of both strands of HCPA1 to be determined. (Seq ID NO: 1)

EXAMPLE 207

Cloning of Human Carboxypeptidase A2

Human carboxypeptidase A2 (CPA2) was cloned from a human pancrease cDNA library constructed in lambda gt11 (Clontech). The probe used as an 1198 base fragment of rat CPA2, This probe was amplified from QUICK-Clone rat pancreas cDNA (Clontech) using PCR. The upstream primer corresponded to the sequence between positions 12–33 in the rate cDNA coding sequence (5'-CCTGTTATTGGCTGCCCTACTT-3')(SEQ ID NO: 5), while the downstream primer was the complement to the sequence between positions 1888–1209 (5'-AAGCCAGGTCTCTTCTGCTGTC-3') (SEQ ID NO: 6) (Gardell, S. J. J. Biol. Chem. 263 17828 (1988)). The standard PCR conditions were a 94° C. preincubation followed by 30 cycles of one minute at 94° C., two mins at 56° C., and three mins at 72° C. The 1198 bp PCR product was extracted with 100 ul chloroform and the upper aqueous phase containing the DNA was passed through a CHROMA SPIN-100 column (Clontech) to remove the primers. The sequence of the rate CPA2 PCR product was confirmed with DNA sequencing using the PCR primers as sequencing primers. Sequencing of the DNA was done with [$^{32}$P] dATP using the fmol sequencing kit (Promega).

The rat CPA2 DNA was radiolabelled with [$^{32}$P] dCTP and the Prime-it II Random Primer Labelling kit (Stratagene) and then used to screen the human pancreas cDNA library. The library was plated using E. coli strain Y1090 on 150 mm plates (approximately 10,000 plaques/plate) and duplicate nitrocellulose lifts made. The filters were blocked in hybridization solution (50% formamide, 5X SSPE, 50X Denhardt's solution, 0.1% SDS, and 100 ug/ml sonicated salmon sperm DNA) for 3 hours at 42° C. Labelled rate CPA2 PCR product was added and hybridized to the filters overnight at 45° C. The filters were washed for 1 hour at 60° C. in 0.1X SSC, 0.1% SDS and exposed to autoradiography film while moist. One duplicate plaque from each plate was picked and subjected to another round of screening as described above. Positive plaques after the second round of screening were picked and the size of the lambda gt11 insert DNA was determined using PCR. Lambda gt11 forward and reverse sequencing primers (Clontech) that flanked the EcoRI cloning site of lambda gt11 were used as the upstream and downstream PCR primers, respectively. Well-isolated plaques were picked, with a portion suspended in 10 ul water, and heated at 95° C. for 5 min, and the remainder being used to make a phage stock for future screening. The 10 ul containing the plaque DNA was used directly as the template in PCR using the conditions described above.

Amplified insert DNA was visualized on agarose gels and the two plaques giving the largest insert DNA were screened a third time. Lambda DNA from the two plaques was isolated and sequenced in both directions using the fmol kit (Promega) and the lambda gt11 forward and reverse primers (Clontech). One clone contained regions highly homologous to the 5' and 3' regions of rat CPA2 and was chosen for further study.

The insert cDNA was liberated from the lambda DNA by digestion with EcoRI, gel purified, and cloned in the EcoRI site of the pGEM-7Zf(+) vector (Promega). Sequencing was carried out using [$^{33P}$] dATP and the fmol kit (Promega) as described above. Oligonucleotide primers that corresponded to regions of the determined sequence were synthesized which permitted the entire cDNA sequence of hCPA2 to be determined. The cDNA was found to contain an open reading frame coding for a protein of 417 amino acids. This protein shares 87% identity with rate CPA2 at the amino acid level and 85% identity at the cDNA level. This protein shares 63% identity with human CPA1 at both the amino acid and nucleotide levels. Thus the protein was classified as human carboxypeptidase CPA1 and CPA2. The amino acid numbering scheme used throughout this document is that of CPA1. All mutations described for CPA 1 and CPA2 refer to this numbering scheme.

EXAMPLE 208

Expression of HCPA1 in Yeast

The size of cDNA inserts within isolated HCPA1 lambda plaques was determined using oligonucleotide primers that flanked the EcoR1 cloning site of lambda gt11 and polymerase chain reaction (PCR). Single isolated, plaques were picked, suspended in 200 μl water and heated at 95° C. for 5 minutes. Ten μl of each suspension was used for PCR amplification according to manufacturer's instructions (Perkin Elmer/Cetus). The standard PCR reaction conditions consisted of 1 minute at 95° C., 0.5 minute at 50° C., and 3 minutes at 72° C. The reaction products were visualized following agarose gel electrophoresis.
CPA-11 5'-gCT gAA gCT TCg gAg gAC TTT-3' (SEQ ID NO: 15)
CPA-12 5'-TCT TgA CCg CCT ggA TgC Tg-3' (SEQ ID NO: 16)

The express of HCPA1 in S. cerevisae was based on the strategy employed by Gardell et al (Nature, 317; 551–555, 1985). Two oligonucleotide primers, CPA 11 and 12, were used to amplify a 200 bp fragment from pHCPA by PCR as described above. The amplified fragment contained a new 5' Hind III site created by CPA 11 that would allow ligation in frame with the alpha factor leader of pMP36 as described by Phillips et al (J. Biol. Chem. 265; 20692–20698, 1990). The PCR fragment was ligated into the TA vector (Invitrogen) and the entire DNA sequence of the fragment determined as described earlier. A colony that contained the desired 5' alteration was selected for further use, TAHCPAexp.

Plasmid pHCPA was restricted with Aat II and EcoR1 to liberate a 1.1 kb HCPA1 fragment. This fragment was purified following low melting point agarose gel electrophoresis and ligated into TAHCPAexp that had been restricted with AatII amd EcoR1 to yield the plasmid TAH-CPA. The TAHCPA was digested with EcoR1, treated with T4 DNA polymerase, and Sal I linkers were added and ligated to the 3' end of HCPA1 as described by Maniatis (Molecular Cloning: A Laboratory Manual, Cold Spring Harbor Press, 1989). TAHCPA that now contained 5' Hind III and 3' Sal I site was restricted with Hind III and Sal I to liberate a 1.2 kb HCPA1 cDNA fragment. This fragment was ligated together with the large Hind III fragment and the small Hind III-SalI fragment of pMP36 to produce pMP36 HCPA1.

Yeast expression of the cloned human enzyme is based on the method of Phillips, M. et al. J. Biol. Chem. 265, 20692 (1990). Plasmid pMP36 containing HCPA1 was restricted sequentially with BAMH1, SAL1 and SSP1 with intervening purification by either phenol extractions or use of Promega Magic Mini Columns with manufacturer supplied procedures. Alternatively, the One-Phor-All buffer system (Pharmacia) can be used in a concurrent restriction by all three enzymes.

Following SSP1 restriction, the mixture was separated on a 1% low melting gel giving 5 distinct bands. The band of interest at about 2.8 kb (the second from top) was excised from the gel and purified using a Schleicher and Schuell Elutip-D column with the supplied procedures.

The BAM/SAL/SSP fragment was then ligated into pBS24.1 shuttle vector (produced from pBS24.1-AGC3 kindly provided by Dr M Phillips, UCSF with BAMH1/SAL1 restriction) overnight at 16° C. using the T4 ligase system (Gibco BRL). The ligated vector was precipitated with ammonium acetate and ethanol at −80° C. for 4 hrs and resuspended in 10 μl TE.

4 μl of the vector was electroporated into 40 μl of DH5alpha E. coli using a Bio RAd Gene Pulser at 2000 volts with a time constant around 4. One ml of Miller Hinton broth was added and the sample incubated at 37° C. for one hour. Three 100 μl samples of each was plated out onto ampicillin containing LB plates.

The resultant colonies were replated on fresh plates. 100 ml volumes of Müeller-Hinton/ampicillin broth were innoculated with colonies and incubated overnight at 37° C. The plasmid was extracted using the Qiagen Maxi extraction procedure.

Approximately 500 to 2000 ng of the PBS24.1 plasmid DNA extracted above was electroporated into 40 μl of competent DLM101 alpha yeast cells. One ml of sorbitol was added immediately after electroporation to rescue the cells. 100 μl samples were plated out on dishes of YNB (yeast nitrogen broth) lacking uracil which were incubated at 30° C. Positive clones were picked. Transformants were grown in minimal synthetic medium (Wickersham, L. J., U.S. Dept. of Agric. Tech. Bull. No. 1029 (1951), lacking leucine, for 48 hrs. This culture was then used to seed a 350 liter fermenter.

EXAMPLE 209

Purification of HCPA1 or its Mutants From Yeast

A 350 l culture of proCPA-producing S. cerevisiae (T268G/p2619) was grown in a 500 l New Brunswick fermentor for 65 h at 30° C. with 175 lpm air flow, 5 psig head pressure and 150 rpm agitation. The medium contained 1% yeast extract (Difco), 2% tryptone (Difco), 1% glucose, 20 mM $KPO_4$, pH 7.5, 50 μg/ml ampicillin and 0.007% (v/v) Mazu DF 60P antifoaming agent (Mazei Chemicals, Inc.). The final $OD_{600}$ was 14. After cooling to 15–20° C. the cells were removed from the medium by cross-flowfiltration on a Sartorius Sartocon II system equipped with 7 0.6 $m^2$ polyolefin filter units. The protein in the medium was concentrated with 10K MWCO cross-flow filters and the fluid exchanged by diafiltration with 20 mM Tris-Cl. pH 8, 0.1 mM Zn-acetate (buffer A). All subsequent buffers contained 0.1 mM Zn-acetate. Ammonium sulfate (AS) was added to 0.5M to the 10K concentrate and it was loaded onto a 250 ml radial flow Phenyl-sepharose column equilibrated in buffer A with 0.5 M AS. The proCPA was eluted with a 1.5 l 0.5–0 M AS gradient followed by a buffer A wash. The Phenyl-Sepharose procedure was repeated with the breakthrough material to recover unbound proCPA from the first run. Fractions containing proCPA were pooled and concentrated and dialyzed on a Sartorius 10K Easy Flow filter (0.2 $m^2$) into buffer A. This was loaded onto a Hi Load 26/10 Q-Sepharose High Performance (Pharmacia) column (53 ml) and eluted with a 1 liter 0–0.5M NaCl gradient in buffer A. The proCPA eluted between 120–220 mM NaCl with the peak tube at ~150 mM. Fractions containing proCPA were pooled and the proCPA was cleaved to mature CPA with trypsin (2 μg/ml) at 37° C. for 1 h. PMSF was added (0.5 mM) and the pool was dialyzed in buffer A. The Q-Sepharose HP step was repeated and the activated CPA eluted between 80–140 mM with the peak tube at 120 mM. Previous IEF experiments have shown the proCPA has a pI=4.75 while the mature CPA has a pI=6.2. The CPA fractions were pooled and concentrated with 10K Centripreps (Amicon) to 15 ml and this was passed through a HiLoad 26/60 Superdex 75 (Pharmacia) column in 3 runs (5 ml each). The elution buffer was buffer A with 150 mM NaCl. The CPA fractions were pooled, concentrated with 10K Centripreps and exchanged with Sigma PBS containing 0.1 mM Zn-acetate. The final volume (15 ml) was passed through a 0.2 $\mu$ syringe filter and stored at 4° C. The protein was 24.5 mg/ml by the Lowry assay using BSA standards. The specific activity for a typical preparation of the mutant with Gly at 268 was 163 u/mg. Total protein=368 mg.

EXAMPLE 210

Expression of HCPA2 in Yeast

The expression of HCPA2 in *S. cerevisiae* was employed the same strategy described for HCPA1 (Example 208) with the following exceptions: 1) the PCR primers used to introduce the new 5' Hind III site were:

YEAST 1: 5'-gCA gAA gCT TCA gAA ACg TTT gTg ggA gAT CAA gTTCTT gAg ATT gTA CC-3' (SEQ ID NO: 19)

YEAST 2: 5'-CTC TTT gTC CAA CAg gAC CTg-3' (SEQ ID NO: 20)

2) a Hinc II site rather than Aat II was used to subclone the mutagenic PCR fragment to the 5' end of the HCPA2 cDNA, and 3) the cloned PCR product was cut from the TA vector and subcloned into the pGEM-7Zf(+) vector containing the HCPA2 cDNA. PCR was carried out with the YEAST 1 and 2 primers as described for HCPA1. The mutagenic PCR product was cloned into the TA vector and the sequence confirmed. This fragment was cut from the TA vector using Hind III and Hinc II and cloned into the corresponding sites of pHCPA2 and the resulting construct designated pHCPA2-Y. The unique 3' Eco RI site of pHCPA2-Y was changed to a Sal I site using linkers as described above with the resulting construct designated pHCPA2-YSal I. The 1.2 kb Hind III/Sal I HCPA2 fragment derived from pHCPA2-Sal I was excised from the vector and ligated together with the large Hind III/Sal I fragment of pMP36 (Phillips, M. et al, J. Biol. Chem., 265, 20692–20698 (1990)) to produce pMP36HCPA2.

Yeast expression of clone HCPA2 was as described above for HCPA1 (Example 208). Human CPA2 has two internal Bam HI sites not present in human CPA1 so partial digestion was needed for the final subcloning step. pMP36HCPA2 was digested to completion with Sal I and partially digested with Bam HI (as described above) to yield the 2.7 kb fragment containing the alcohol dehydrogenase/GADPH promoter and regulatory region (A/G promoter) attached to human CPA2 fused in frame to the yeast α factor leader. This fragment was ligated into the Sal I/Hind III site of pBS24.1 forming pBSHCPA2. The construct was amplified in DH5α and used to electroporate yeast as described above (Example 208).

EXAMPLE 211

Purification of HCPA2 or it Mutants From Yeast

An overnight culture (grown in Leu⁻ medium) of *S. cerevisiae* expressing proCPA2 as used to start 2 l of culture in 1% yeast extract (Difco), 2% tryptone (Difco), 1% glucose, 20 mM KPO$_4$, pH 7.5, and 50 $\mu$g/ml ampicillin. The culture was grown for 48 hrs at 30° C. and the supernatant cleared by centrifugation at 6000 X g for 10 min at 4° C. The protein in the supernatant was concentrated on an Amicon PM-10 Ultrafiltration membrane to 114 ml. The concentrated supernatant was made to 20 mM Tris-HCl (pH 8.0), 0.1 mM Zn-acetate and 0.5 M ammonium sulfate and loaded onto a 1.8×20 cm Phenyl-Sepharose column (Pharmacia) equilibrated in buffer A with 0.5 M ammonium sulfate. The protein was eluted with a 120 ml linear gradient (1 ml/min) from buffer B (20 mM Tris-HCl pH 7.5, 0.1 mM Zn-acetate) with 0.5 M ammonium sulfate to buffer B with 20% (v/v) ethanol. Fractions containing carboxypeptidase activity were pooled and dialyzed against buffer B. The dialyzed pool was loaded onto an HR 5/5 (1 ml) Mono Q column (Pharmacia) and eluted with a 30 ml linear gradient (1 ml/min) from 0–0.5 M NaCl in buffer B. Fractions containing carboxypeptidase activity were pooled and dialyzed against buffer B. The pooled proCPA2 was activated with trypsin (10 $\mu$g/ml) at 37° C. for 1 hr and the trypsin inactivated with PMSF added to 0.5 mM. The mature CPA 2 was dialyzed against buffer B and again loaded onto the 1 ml Mono Q column (Pharmacia) and eluted as above. Fractions containing carboxypeptidase activity were pooled, dialyzed against buffer B, and concentrated 10 fold in an Amicon Ultrafiltration cell using a PM-10 membrane. The concentrated mature CPA2 was loaded onto an HR 10/30 Superose 12 column (25 ml) and eluted isocratically (0.4 ml/min.) in phosphate buffered saline (10 mM Na$_2$HPO$_4$, 0.15 M NaCl, pH 7.2). For wild type HCPA2 the protein was 0.65 mg/ml (4.13 mg total) and for the 268 Gly mutation the concentration was 0.3 mg/ml (4.47 mg total) as determined with the Micro BCA Assay (Pierce Chemical Co.) using BSA standards.

EXAMPLE 212

Expression of Mutant HCPA2

The A250G and T268G mutations of HCPA2 were constructed as described above (Example 216) for mutant forms of HCPA1 using the T7-Gen In Vitro Mutagenesis Kit (United States Biochemical, No. 74500). The mutagenic oligonucleotide primers (Oligos Etc.) to mutate the A250 (gCC) and T268 (ACC) to Gly (ggC) are shown below:

A250G 5'-TCC TCC ACT gCC TTg gTA gAT-3' Gly=ggC (SEQ ID NO: 21)

T268G 5'-CAg TTC AAA gCC AAA TgA gTA-3' Gly= ggC (SEQ ID NO: 22)

Mutagenic codons are underlined.

Using these oligonucleotide primers the following mutant forms of HCPA2 were produced:

1. A250G
2. T268G

Each of the above mutagenized HCPA2 cassettes was sequenced to verify that only the desired DNA mutations were produced. The mutagenized cassettes were subcloned into pMP36HCPA2 that could further be processed for expression in *S. cerevisiae* using methods described in Example 210.

EXAMPLE 213

Synthesis of a Chemical Conjugate Between Campath-1-H or ING-1 and Human Carboxypeptidase A Mutants 2 mg of mutant carboxypeptidase A was combined with 0.15 mg of Sulfo-SMCC (Pierce Chemical Co) in 475 $\mu$l of Dulbecco's Phosphate Buffered Saline (PBS). The resulting solution was stirred for 45 minutes at 25° C. The modified enzyme was purified through a 1×13 cm G-25 medium column equilibrated with PBS. Purified product can be stored at 4° C. for 24 hrs.

Maleimide content was determined by combining 0.5 ml of 6.3 µM modified enzyme with 6 µl of 1 mM mercaptoethanolamine. After 30 minutes, 20 µl of 4 mg/ml Ellman's reagent was added, and after another 20 minutes absorbance at 412 nm was determined. Based upon a molar absorptivity of 13.6 mM$^{-1}$, the purified product was found to contain 1 maleimide per enzyme molecule. The modification had no effect upon enzyme activity.

The antibody was modified with 2-iminothiolane (Pierce Chemical Co). 0.35 mg of antibody solution was combined with 0.055 mg of 2-iminothiolane in 0.1 M triethanolamine-HCl, 2 mM EDTA, pH 8.0 under anaerobic conditions, reacted with stirring for 1 hr and 45 mins. The modified antibody was purified through a 1×13 cm G-25 medium column equilibrated with 0.02 M sodium acetate, 0.1 M NaCl, pH 5.8, bubbled with and maintained under a He atmosphere. The purified modified antibody solution was collected directly into the solution of modified carboxypeptidase A. The resulting solution was adjusted to pH 7.4 with NaOH, made anaerobic, and allowed to react, with stirring, at 4° C. for 18 hours. (Optionally free maleimide groups may be removed by reacting the solution with 0.3 mM mercaptoethanolamine at room temperature for one hour). The solution concentrated to 1 ml. The resulting concentrated conjugate was purified from aggregates, unreacted enzyme and small molecules by chromatography on Superose 12 HR 10/30. The enzyme specific activity of the conjugate was found to be appropriate for a one to one conjugate with antibody. Antibody (Campath-IH® or ING-1) % immunoreactivity and antigen binding affinity of the conjugate were both found to be high.

EXAMPLE 214

The enzyme was modified by the protocol described for Example 213 above, while the antibody was modified with dithiothreitol. 0.7 mg of antibody solution was combined with 0.035 µmol of dithiothreitol in 350 µl of 0.1 M triethanolamine-HCl, 2 mM EDTA, pH 8.0 under anaerobic conditions and reacted with stirring for 1 hr. The modified antibody was purified through a 1×13 cm G-25 medium column equilibrated with 0.02 M sodium acetate, 0.1 M NaCl, pH 5.8, bubbled with and maintained under a He atmosphere. The purified antibody solution was collected directly into the solution of NaOH, made anaerobic, and allowed to react, with stirring, at 24° C. for 30 min and at 4° C. for 18 hrs. Then the solution was concentrated to 1 ml. The resulting concentrated conjugate was purified from aggregates, unreacted enzyme and small molecules by chromatography on Superose 12 HR 10/30. The enzyme specific activity of the conjugate was found to be appropriate for a one to one conjugate with antibody. Antibody % immunoreactivity and antigen binding affinity were both found to be high.

EXAMPLE 215

The enzyme was modified by the protocol described for Example 4 above, while the antibody was modified with SATA (Pierce Chemical Co). 0.225 mg of antibody solution was combined with 0.003 mg of SATA in a total volume of 150 µl of Dulbecco's Phosphate Buffered Saline (PBS) and allowed to react with stirring for 45 mins. the modified antibody was purified through a 1×13 cm G-25 medium column equilibrated with PBS. The purified modified antibody solution was mixed with the modified enzyme and made anaerobic, 300 µl of anaerobic 0.5 M NH$_2$OH was added and the solution allowed to react, with stirring, at 25° C. for 2 hrs followed by 4° C. for 18 hrs. Free maleimide groups were removed by reacting the solution with 0.3 mM mercaptoethanolamine at room temperature for one hour, and the solution was then concentrated to 1 ml. The resulting concentrated conjugate was purified from aggregates, unreacted enzyme and small molecules by chromatography on Superose 12 IIR 10/30. The enzyme specific activity of the conjugate was found to be appropriate for a one to one conjugate with antibody. Antibody antigen binding affinity was found to be high.

EXAMPLE 216

Figure 3:
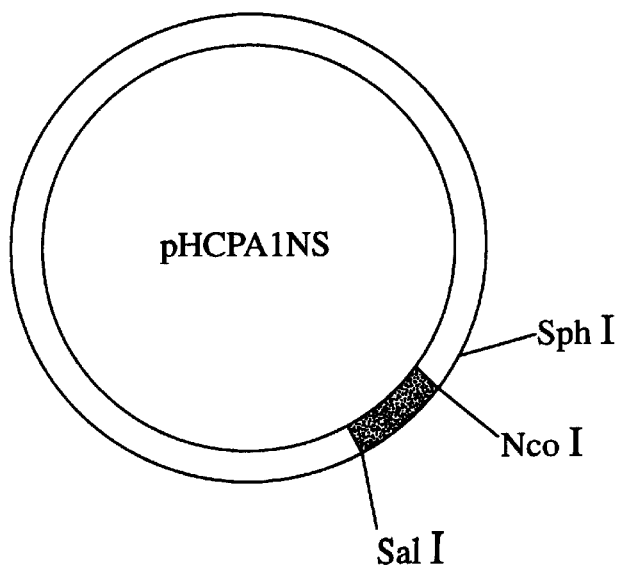
FIG. 3 depicts the vector pHCPAINS, produced by ligating the HCPA1 NcoI-SalI fragment into the Nco I and Sal I cloning sites of pGEM5zf(−). The HCPA1 Nco I-Sal I fragment encodes amino acids 186–309 of mature HCPA1.
Figure 4:
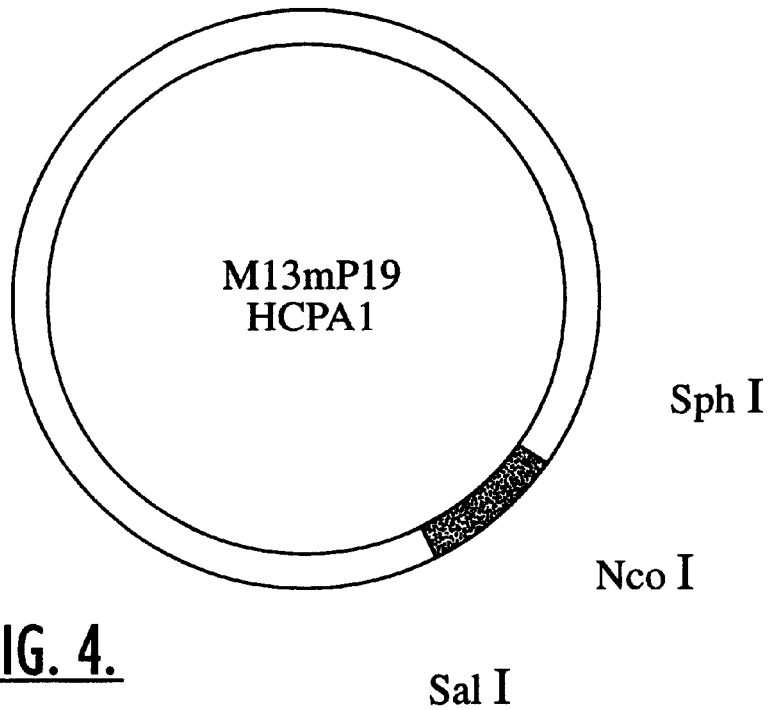
FIG. 4 depicts the vector M13mp19HCPA1, produced by restricting pHCPAINS with Sph I and Sal I to obtain the HCPA1 Nco I-Sal I fragment and an additional 9 base pair pGEM5zf(−) sequence; the Sph I-Sal I fragment was then cloned into M13mp19 using Sph I Sal I cloning sites.
Figure 7:
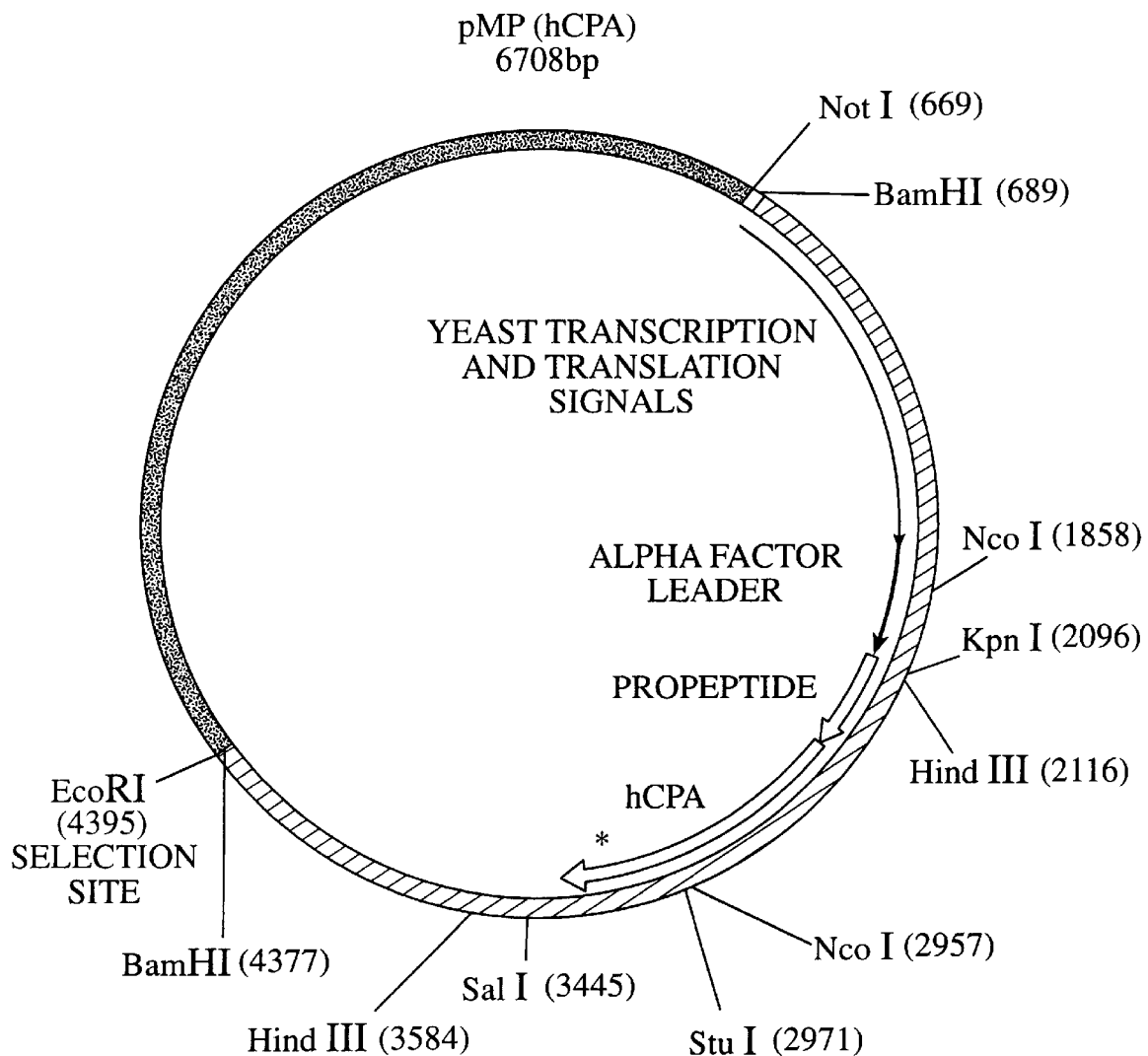
FIG. 7 diagrams pMP vector containing proHCPA cDNA as a fusion with yeast alpha-factor leader, used in expression of HCPA.

Expression of Mutant HCPA1 pMP36 containing wild type (WT) proHCPA1 cDNA (as a fusion with yeast alpha-factor leader described above, see FIG. 7) was restricted with Nco I and Sal I to liberate a 481 bp cDNA fragment. This fragment begins a nucleotide 893, proceeds to the very 3' end of HCPA1 cDNA and encodes amino acids 186–309 of mature HCPA1. The HCPA1 Nco I-Sal I fragment was ligated into the Nco I and Sal I cloning sites of pGEM5zf(-) (Promega) to generate pHCPAINS (FIG. 3). pHCPAINS was then restricted with Sph I and Sal I to liberate the HCPA1 Nco I-Sal I fragment and additional (9 bp) pGEM5zf(-) sequence. This Sph I-Sal I fragment was cloned into M13mp19 (BRL) using its Sph I and Sal I cloning sites to generate M13mp19HCPA1 (FIG. 4).

Single stranded M13mp19HCPA1 DNA was used as template for olignucleotide-directed mutagenesis using the T7-GEN In Vitro Mutagenesis Kit (United States Biochemical, No. 74500). Mutagenic oligonucleotide primers (Oligos Etc) listed below were used to mutate residues I255 (ATT) and T268 (ACC) either separately or in tandem.

1. I255A 5'-ggT CCA gTC AgC AgT gCT TCC-3' Ala= gCT (SEQ ID NO: 7)
2. T268A 5'-gAg CTC gAA ggC gAA ggA gTA-3' Ala= gCC (SEQ ID NO: 8)
3. T268G 5'-gAg CTC gAA gCC gAA ggA gTA-3' Gly=ggC (SEQ ID NO: 9)

Mutagenic codons are underlined.

Using these oligonucleotide primers the following mutant forms of HCPA1 were produced.

1. I255A
2. T268A
3. T268G
4. I255A/T268A

Figure 5:
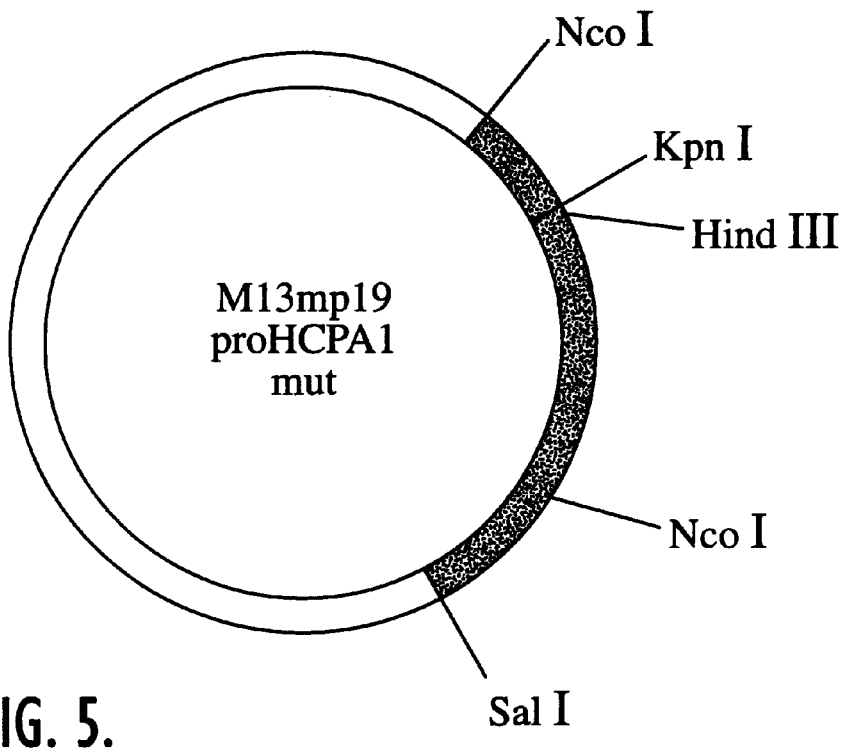
FIG. 5 depicts M13mp19 proHCPA1 mutants containing a 1.2kb fragment of pMP36 HCPA1 (wildtype). Single stranded M13mp19HCPA1 DNA was used for oligonucleotide-directed mutagenesis, to produce mutant forms of HCPA1. A 1.2 kb fragment of pMP36HCPA1 (wildtype) was then cloned into the Nco I site of M13mp19CPA1 mutants.
Figure 6:
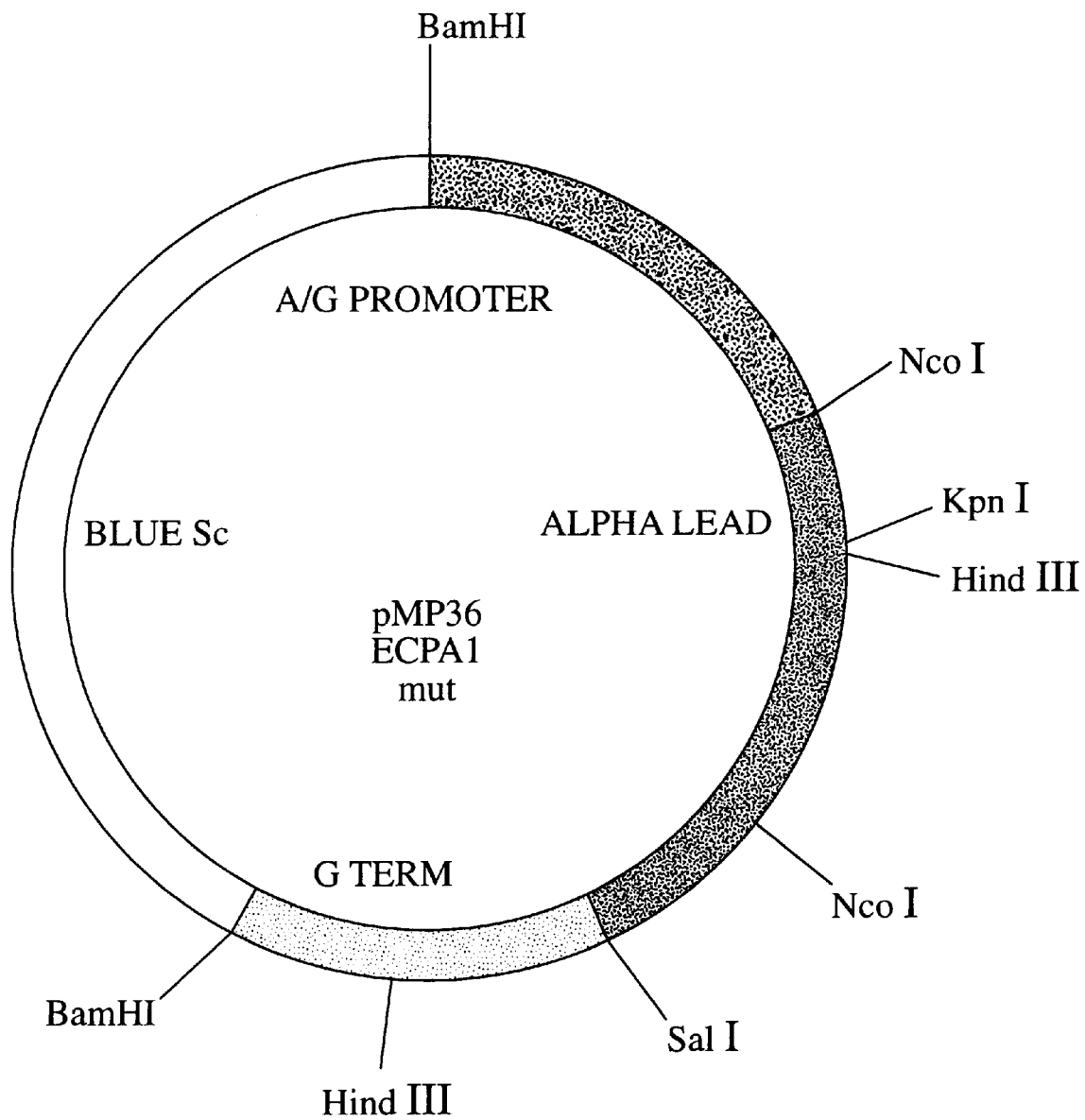
FIG. 6 depicts pMP36ECPA1 mutant, produced by restricting M13mp19 proHCPA1 mutants with Hind III and Sal I, to obtain a 1.2 kb cDNA fragment encoding the entire proHCPA1 mutant enzyme; this fragment was ligated into the Hind III and Sal I sites of pMP36 to provide pMPHCPA1 mutants that could be further processed for expression in S. cerevisae.

Each of the above mutagenized HCPA1 cassettes was sequenced to verify that only the desired DNA mutations were produced.

pMP36 HCPA1 w.t. was restricted with NcoI to liberate a 1.2 kb fragment that was cloned into the Nco I site of M13mp19HCPA1 mutants. After the correct orientation of the Nco I fragment within M13mp19 proHCPA1 mutants (FIG. 5) was verified the DNAs were restricted with Hind III and Sal I which liberated a 1.2 kb cDNA fragment encoding the entire proHCPA1mutant enzyme. This fragment was then ligated into the Hind III and Sal I sites of pMP36 yielding pMPHCPA1 mutants (FIG. 6) that could then be further processed for expression in *S. cerevisae* using the methods described in Examples 208 and 209.

EXAMPLE 217

Expression of Mutant HCPA1

Alternatively, the mutations have been conveniently generated in hCPA in the pMP36 plasmid (pMP36 HCPA1) by the unique site elimination (USE) procedure of Clontech Laboratories, Inc. using the manufacturers' reagents and protocols.

In the protocol, elimination of a unique EcoRI in the pMP36 HCPA1 plasmid was used for selection with the oligonucleotide XS5 (TCC CCC GGG CTG CAG GAT ATC GAT (SEQ ID NO: 10) AGC TGG GCT GTG T). The oligonucleotides used to generate three specific mutations in hCPA by this protocol follow:

T 268 H (ACC codon to CAC) with oligonucleotide XT2 (ATC AAG TAC TCC TCC CAG CTC CGG GAC) (SEQ ID NO: 11)

S 253 G (AGC codon to GGT) with oligonucleotide XT3 (TTT ATC AAG CCA GTG GAG GTA TTG ACT GGA CC) (SEQ ID NO: 12)

A 250 G (GCC codon to GGC) with oligonucleotide XT4 (AAG GCA ATT TAT CAA GGC AGT GGA AGC ACT ATT) (SEQ ID NO: 13)

The mutations were isolated using the oligonucleotides listed above and XS5 (TCC CCC GGG CTG CAG GAT ATC GAT AGC TGG GCT GTG T) (SEQ ID NO: 14) which eliminates a unique EcoRI site. Plasmids containing the desired mutations were selected by digesting the wild type pMP36(hCPA) with EcoRI (uncut plasmids transform 10 to 100× more efficiently than linearized plasmid). In addition, the XS5 selection oligonucleotide introduces an EcoRV site which can then be used to screen for mutant plasmids. In the mutant plasmids the EcoRV is unique and can therefore be used as a selection site to construct double mutants with an oligonucleotide than converts the EcoRV site back to an EcoRI site.

The mutant pMP36 HCPA so generated could then be further processed for expression in *S. cerevisae* using the methods described in Examples 208 and 209.

EXAMPLE 218

Stability and Biodistribution of Prodrugs In Vivo

Mice were dosed i.p. or i.v. bolus with 50 mg/kg of prodrug by administration of a 5 mg/ml solution in PBS, pH 6–8. Animals were sacrificed after 30 min and 2 h and the plasma, and tissues were collected. Plasma was frozen at −70° C. and tissues were snap frozen in liquid nitrogen and stored at −70° C. Duplicate animals were sacrificed for each time point. Plasma was prepared for extraction by 4-fold dilution with ice cold 0.1 N HCl. Tissues were prepared for extraction by homogenization in 5 volumes of ice cold 0.1 N HCl with a Polytron equipped with a PTA 7 generator (Brinkman Instruments, Westbury, N.Y.). Drugs were subsequently extracted by adding 500 μl of −20° C. acetonitrile to 200 μl of the 0.1N HCl homogenate. After a 5 min incubation on ice, samples were centrifuged at 12,400 x g for 15 min. Supernatants were collected and diluted 3.57 fold with PBS to reduce the final acetonitrile concentration to 20%. Diluted supernatants were then analyzed by HPLC as described below. Drug recovery was estimated by spiking control tissue homogenates with either drug or prodrug prior to the acetonitrile extraction step. After correction for recovery of these standards, the levels of drug and prodrug in tissues and the stability of the prodrug in these tissues were calculated using HPLC.

Samples were analyzed on a 4 μm C18 Nova-Pak 3.9×300 mm steel HPLC column equipped with a C18 guard column with UV detection at a flow rate of 1 ml/min.

Samples were injected onto the HPLC column equilibrated with 2% acetic acid, pH 3.0, containing either 5% or 20% acetonitrile depending upon the compound being analyzed. Upon sample injection a 25 or 35 min linear gradient was initiated raising the acetonitrile concentration to 50% acetonitrile. Three compounds (ASP-MTX, o-cyclopentyl-PHE-MTX and m-cyclopentyl-PHE-MTX) were analyzed on a 10 μm C18 uBondapak column (3.9×300 mm) equilibrated with 16% acetonitrile in 5 mM tetrabutylammonium hydrogen sulfate, 10 mM $NH_4H_2PO_4$. The column was then eluted with a 30 min linear gradient of up to 50% acetonitrile.

Results indicated in Table 1. The results show that a compound that is a good substrate for wild type CPA, such as compound #10, is not stable in vivo. This type of compound is not useful for ADEPT. However, compounds which are good substrates for a mutant enzyme but not for the wild type enzyme, such as compounds 8, 9, 11, 12, 13 and 14 and others, are stable in vivo and are as such useful in ADEPT.

The data shown in Table 1 indicate the concentration of prodrug detected over time in minutes as either μM in the case of plasma or nmol/g in the case of tissues. The figures in brackets indicate the stability of the prodrug expressed as the percentage of material (sum of drug and prodrug) observed as intact prodrug.

Except as indicated all experiments were carried out in CD-1 nude mice.

TABLE 1

| Prodrug | Time | PLASMA | | LIVER | | KIDNEY | | SPLEEN | |
|---|---|---|---|---|---|---|---|---|---|
| 1 | 30 | 41.5 | (99) | 770.3 | (98) | 175.8 | (98) | 23.4 | (100) |
| 259W91 | 120 | 4.2 | (100) | 579.8 | (97) | 70.3 | (97) | 1.8 | (100) |
| 2 | 30 | 33.0 | (100) | 42.0 | (98) | 9.0 | (98) | ND | |
| 519W91 | 90 | 5.5 | (96) | 9.1 | (100) | 1.3 | (98) | ND | |
|  | 180 | 3.5 | (97) | 0.8 | (100) | 0.2 | (100) | ND | |
| 2 | 30 | 22.1 | (100) | | | | | | |
| 519W91 | 120 | 0.3 | (93) | | | | | | |
| 3 | 30 | 96.3 | (93) | 128.8 | (79) | 41.7 | (82) | 76.6 | (95) |
| 552W92 | 120 | 5.1 | (87) | 267.9 | (74) | 9.2 | (74) | 12.1 | (89) |
| 3 | 30 | 32.4 | (93) | 135.3 | (87) | 29.2 | (89) | 30.9 | (100) |
| 552W92 | 120 | 2.8 | (48) | 371.2 | (90) | 4.0 | (74) | 1.5 | (100) |

TABLE 1-continued

| Prodrug | Time | | | | | | | | |
|---|---|---|---|---|---|---|---|---|---|
| 4 | 30 | 71.4 | (100) | 343.4 | (99) | 94.5 | (100) | 30.9 | (99) |
| 2484W92 | 120 | 1.4 | (99) | 33.3 | (98) | 14.5 | (99) | ND | |
| 5 | 30 | 114.6 | (98) | 118.2 | (81) | 42.5 | (93) | 34.3 | (85) |
| 2749W92 | 120 | 9.4 | (95) | 7.5 | (41) | 3.0 | (96) | 32 | (81) |
| 6 | 30 | 46.7 | (100) | 287.8 | (97) | 93.4 | (98) | 3.4 | (70) |
| 3347W92 | 120 | 2.0 | (100) | 161.6 | (93) | 12.6 | (98) | 0.0 | (0) |
| 7 | 30 | 51.4 | (100) | 171.9 | (100) | 55.4 | (100) | 12.4 | (100) |
| 3855W92 | 120 | 0.2 | (100) | 7.5 | (89) | 3.8 | (100) | 1.0 | (100) |
| 8 | 30 | 28.5 | (95) | 113.5 | (90) | 5.6 | (84) | 1.4 | (98) |
| 250W93 | 120 | 1.1 | (90) | 43.9 | (76) | 3.2 | (81) | 1.1 | (100) |
| 9 | 30 | 1.1 | (100) | 54.3 | (83) | 6.8 | (100) | 8.4 | (100) |
| 637W93 | 120 | ND | | 126.2 | (94) | 1.3 | (100) | ND | |
| (BALB/C) | 30 | 4.9 | (100) | | | | | | |
| 10 | 30 | 17.8 | (30.2) | 335.1 | (94.425) | 26.9 | (100) | 19.9 | (80.4) |
| 1311W92 | 120 | 1.1 | (2.1) | 0.6 | (7.55) | 0.0 | | ND | |
| 11 | 30 | 222 | (97.075) | 53.8 | (81.35) | 7.3 | (83.475) | 2.7 | (95.45) |
| 3352W93 | 120 | ND | | 47.8 | (73.325) | 3.0 | (82.3) | ND | |
| 12 | 30 | 2.6 | (100) | 58.6 | (91.325) | 2.2 | (53.433) | ND | |
| 1834W93 | 120 | 0.7 | (100) | 39.5 | (89.25) | 0.2 | (21.55) | ND | |
| 13 | 30 | 3.3 | (100) | 47.7 | (100) | 3.7 | (100) | 0.6 | (100) |
| 5755U93 | 120 | 0.6 | (100) | 129.0 | (100) | 0.5 | (100) | 0.2 | (100) |
| 14 | 30 | 1.1 | (100) | 22.5 | (100) | 4.6 | (100) | 2.4 | (100) |
| 4204W93 | 120 | ND | | 42.1 | (100) | ND | | ND | |

| Prodrug | Time | LARGE INTESTINE | | CECUM | | SMALL INTESTINE | | FECES | | TUMOR | |
|---|---|---|---|---|---|---|---|---|---|---|---|
| 1 | 30 | 12.2 | (93) | 6.0 | (96) | 48.2 | (83) | | | 6.0 | (96) |
| 259W91 | 120 | 1.0 | (100) | 1.2 | (76) | 55.6 | (68) | | | 1.2 | (76) |
| 2 | 30 | 5.9 | (93) | 2.7 | (98) | | | | | 2.7 | (98) |
| 519W91 | 90 | 0.7 | (60) | ND | | | | | | ND | |
| | 180 | 1.3 | (52) | ND | | | | | | ND | |
| 2 | 30 | | | | | 170.2 | (91) | | | | |
| 519W91 | 120 | | | | | 17.6 | (47) | | | | |
| 3 | 30 | 23.4 | (87) | | | | | | | | |
| 552W92 | 120 | 1.7 | (89) | | | | | | | | |
| 3 | 30 | 14.9 | (94) | | | 27.7 | (10) | | | | |
| 552W92 | 120 | 1.1 | (87) | | | 1.8 | (1) | | | | |
| 4 | 30 | 25.3 | (100) | 6.7 | (100) | 188.1 | (99) | | | 6.7 | (100) |
| 2484W92 | 120 | 45.4 | (100) | 1.3 | (100) | 69.1 | (98) | | | 1.3 | (100) |
| 5 | 30 | 28.4 | (93) | 4.7 | (95) | 32.1 | (40) | | | 4.7 | (95) |
| 2749W92 | 120 | 1.6 | (8) | 2.9 | (88) | 1.6 | (2) | | | 2.9 | (88) |
| 6 | 30 | 5.7 | (100) | 7.5 | (82) | 21.3 | (86) | 42 | (21) | 7.5 | (82) |
| 3347W92 | 120 | 19.4 | (65) | 0.8 | (59) | 14.2 | (54) | 207 | (52) | 0.8 | (59) |
| 7 | 30 | 12.1 | (100) | 6.9 | (100) | 127.4 | (100) | | | 6.9 | (100) |
| 3855W92 | 120 | 91.8 | (100) | 1.5 | (100) | 24.1 | (97) | | | 1.5 | (100) |
| 8 | 30 | 5.2 | (93) | 6.8 | (75) | 364.5 | (77) | 150.2 | (71) | | |
| 250W93 | 120 | 27.3 | (57) | 235.1 | (56) | 31.7 | (35) | 646.2 | (55) | | |
| 9 | 30 | 2.6 | (100) | 4.1 | (100) | 377.9 | (97) | 1104.1 | (97) | | |
| 637W93 | 120 | 6.2 | (100) | 108.3 | (99) | 211.0 | (93) | 1505.7 | (94) | | |
| (BALB/C) | 30 | | | | | 420.3 | (98) | 1604.27 | (98) | | |
| 10 | 30 | 19.3 | (65.35) | 3.0 | (65) | 17.3 | (16) | | | 3.0 | (65) |
| 1311W92 | 120 | 1.1 | (21.6) | ND | | ND | (0) | | | ND | |
| 11 | 30 | 2.7 | (74.45) | 4.5 | (100) | 301.3 | (86.725) | 426.8 | (92.275) | 4.8 | (100) |
| 3352W93 | 120 | 4.4 | (84.95) | 0.8 | (100) | 140.0 | (67.7) | 389.8 | (67.925) | 2.4 | (88.1) |
| 12 | 30 | ND | | 16.3 | (100) | 550.8 | (91) | 1205 | (93) | 1.6 | (92.8) |
| 1834W93 | 120 | 14.7 | (66.925) | 402.3 | (80.7) | 44.9 | (67) | 1941 | (82) | ND | |
| 13 | 30 | 7.9 | (100) | 14.4 | (100) | 373.7 | (100) | 665.8 | (100) | | |
| 5755U93 | 120 | 12.5 | (100) | 4.8 | (100) | 322.1 | (100) | 738.4 | (100) | | |
| 14 | 30 | 9.4 | (100) | 4.1 | (100) | 218.3 | (100) | 535.0 | (90.675) | | |
| 4204W93 | 120 | 34.6 | (76.775) | 65.3 | (48.75) | 127.8 | (100) | 932.8 | (88.05) | | |

Prodrugs 1 to 14 shown in TABLE 1 are as follows:
1. N-(N-(4(((1,2-dihydro-3-methyl-1-oxobenzo(F)quinazolin-9-yl)methyl)amino)-2-fluorobenzoyl)-L-glutam-1-yl)-L-glutamic acid
2. N-((S)-4-carboxy-2-(5-(((1,2-dihydro-3-methyl-1-oxobenzo(F)quinazolin-9-yl)methyl)amino)-1-oxo-2-isoindolinyl)butanoyl)-L-phenylalanine
3. N-(N-(2-fluoro-4-(((1,2-dihydro-3-methyl-1-oxobenzo(F)quinazolin-9-yl)methyl)amino)benzoyl)-L-glutam-1-yl)-3-(1-naphthyl)-L-alanine
4. N-(N-(4(((1,2-dihydro-3-methyl-1-oxobenzo(F)quinazolin-9-yl)methyl)amino)-2-fluorobenzoyl)-L-glutam-1-yl)-2-carboxy-L-phenylalanine
5. N-(N-(4-(((1,2-dihydro-3-methyl-1-oxobenzo(F)quinazolin-9-yl)methyl)amino)-2-fluorobenzoyl)-L-glutam-1-yl-2-iodo-L-phenylalanine
6. N-(4-((2,4-diamino-6-pteridinyl)methyl)methylamino)benzoyl)-L-glutam-1-yl-L-aspartic acid
7. N-(4-((2,4-diamino-6-pteridinyl)methyl)methylamino)benzoyl)-L-glutam-1-yl-2-carboxy-L-phenylalanine
8. N-(4-((2,4-diamino-6-pteridinyl)methyl)methylamino)benzoyl)-L-glutam-1-yl-2-cyclopentyl-L-phenylalanine
9. N-(4-(((2,4-diamino-6-pteridinyl)methyl)methylamino)benzoyl)-L-glutam-1-yl-3-cyclopentyl-L-phenylalanine
10. N-(4-(((2,4-diamino-6-pteridinyl)methyl)methylamino)benzoyl)-L-glutam-1-yl-L-phenylalanine.

TABLE 1-continued

11. N-(4-(((2,4-diamino-6-pteridinyl)methyl)methylamino)benzoyl)-L-glutam-1-yl-3-cyclobutyl-L-phenylalanine.
12. N-(4-(((2,4-diamino-6-pteridinyl)methyl)methylamino)benzoyl)-L-glutam-1-yl-3-tert-butyl-L-phenylalanine.
13. N-(4-(((2,4-diamino-6-pteridinyl)methyl)methylamino)benzoyl)-L-glutam-1-yl-3-cyclopentyl-L-tyrosine.
14. N-(4-(((3-(2,4-diamino-1,6-dihydro-6-oxo-5-pyrimidinyl)propyl)amino)benzoyl)-L-glutam-1-yl-3-cyclopentyl-L-phenylalanine

EXAMPLE 219

Molecular Modelling of Human CPA1

The Brookhaven Protein Database (Bernstein F. C. et al., J. Mol. Biol. 112, 535–542 [1977]) was searched and bovine CPA selected as that likely to have the greatest structural similarity to human CPA (HCPA) based on the base sequence homology. The COMPOSER algorithm which was used to develop the HCPA model is part of the commercially available SYBYL molecular modelling package sold by TRIPOS Associates (SYBYL Molecular Modeling Software, Version 5.3, November 1989, TRIPOS Associates Inc., St. Louis, Mo. 63144). The COMPOSER algorithm was used to fit the amino acid residues of the human CPA sequence into the 3D coordinates of the crystal structure of bovine CPA to determine a best fit and consequently a projected 3D structure for HCPA.

EXAMPLE 220

Cell Culture Targetting and Therapy

Wein-133 B-cell lymphoma cells were incubated with a conjugate of wild-type HCPA1 and Campath for 20 min. Cells were then washed to remove unbound conjugate and returned to cell culture at 500,000 cells ml$^{-1}$. Cells were cultured in the presence of varying concentrations of the prodrug MTX-Phe and levels of inhibition of growth analysed after 3 days. Results are illustrated in FIG. 1. Similar results were obtained when a conjugate of mutant 268 Gly with Campath was substituted for the wild type conjugate.

EXAMPLE 221

Prodrug Toxicity

The stable prodrug of the present invention should in addition to being stable in vivo also be less toxic in the host than the parent drug in order to permit larger dosing levels of prodrug and in turn generation of local high concentrations of active agent. We have found that the maximum tolerated dose for methotrexate in the mouse (female, strain CD-1 nu/nu) is 4 mg/kg IV once daily for 5 days. Doses of N-(4-(((2,4-diamino-6-pteridinyl)methyl)methylamino) benzoyl)-L-glutam-1-yl-2-cyclopentyl-L-phenylalanine up to 20 mg/kg IV once daily for 5 days were tolerated, and doses of up to 40 mg/kg of N-(4-(((2,4-diamino-6-pteridinyl)methyl)methylamino)benzoyl)-L-glutam-1-yl-3-cyclopentyl-L-phenylalanine or N-(4-(((2,4-diamino-6-pteridinyl)methyl)methylamino)benzoyl)-L-glutam-1-yl-3-tert-butyl-L-phenylalanine IV once daily for 5 days produced no toxicity; therefore the maximally tolerated doses of the latter two compounds are greater than 40 mg/kg. In Swiss nu/nu mice, the maximum tolerated dose of methotrexate is 2.5 mg/kg IV daily for 5 days. In these mice, N-(4-(((2,4-diamino-6-pteridinyl)methyl)methylamino) benzoyl)-L-glutam-1-yl-3-cyclopentyl-L-tyrosine was tolerated at doses to 50 mg/kg IV daily for 5 days while N-(4-(((2,4-diamino-6-pteridinyl)methyl)methylamino) benzoyl)-L-glutam-1-yl-3-cyclobutyl-L-phenylalanine showed some toxicity at does of 30 mg/kg IV daily for 5 days. Thus, in Swiss nu/nu mice, with this daily ×5 schedule, the MTD for N-(4-(((2,4-diamino-6-pteridinyl)methyl) methylamino)benzoyl)-L-glutam-1-yl-3-cyclopentyl-L-tyrosine and N-(4-(((2,4-diamino-6-pteridinyl)methyl) methylamino)benzoyl)-L-glutam-1-yl-3-cyclobutyl-L-phenylalanine would be >50 mg/kg and <30 mg/kg, respectively. Thus the prodrugs of the present invention are indeed much better tolerated than the corresponding active agent.

EXAMPLE 222

Activity of a Mutant Human Carboxypeptidase A1 with a Stable Prodrug

As indicated herein, the in vivo stable prodrug of the present invention should be a better substrate for a mutant enzyme than the corresponding wild type enzyme in order for the stable prodrug to be activated selectively at the tumour. Table 2 shows the enzyme kinetics for several prodrugs of methotrexate with wild type human carboxypeptidase A1 and mutants with thr 268 mutated to either Ala or Gly. The most relevant kinetic constant in the table is the kcat/Km, which provides an estimate of the second order rate constant for the enzyme catalyzed conversion of prodrug to methotrexate. Thus, the larger the kcat/Km, the more efficient the enzyme with particular substrate. It can be seen that the kcat/Km for human CPA1 with one of the best substrates for this wild type enzyme N-(4-(((2,4-diamino-6-pteridinyl)methyl)methylamino)benzoyl)-L-glutam-1-yl-L-phenylalanine the prodrug of MTX, is 0.44 /uM/sec. The kcat/Km values for N-(4-(((2,4-diamino-6-pteridinyl) methyl)methylamino)benzoyl)-L-glutam-1-yl-2-cyclopentyl-L-phenylalanine, N-(4-(((2,4-diamino-6-pteridinyl)methyl)methylamino)benzoyl)-L-glutam-1-yl-3-cyclopentyl-L-phenylalanine, N-(4-(((2,4-diamino-6-pteridinyl)methyl)methylamino)benzoyl)-L-glutam-1-yl-3-tertbutyl-L-phenylalanine, N-(4-(((2,4 -diamino-6-pteridinyl)methyl)methylamino)benzoyl)-L-glutam-1-yl-3-cyclobutyl-L-phenylalanine, and N-(4-(((2,4-diamino-6-pteridinyl)methyl)methylamino)benzoyl-L-glutam-1-yl-3-cyclopentyl-L-tyrosine for the human CPA1 are much lower; indeed the human CPA catalyzed reactions with the latter four prodrugs were not measureable. However, the kcat/Km for these five stable prodrugs with 268 Gly are 0.157, 0.092, 0.38, 1.8 and 0.18/uM/sec, respectively. Thus, the single mutations at 268 from thr to gly converted very poor substrates in the wild type enzyme to excellent substrates in the mutant enzyme. Indeed in the case of N-(4-(((2,4-diamino-6-pteridinyl)methyl)methylamino)benzoyl)-L-glutam-1-yl-3-tertbutyl-L-phenylalanine the activity of 268 Gly with the prodrug is not different than the human CPA1 with N-(4-(((2,4-diamino-6-pteridinyl)methyl) methylamino)benzoyl)-L-glutam-1-yl-L-phenylalanine, one of its best substrates. Further, in the case of N-(4-(((2,4-diamino-6-pteridinyl)methyl)methylamino)benzoyl)-L-glutam-1-yl-3-cyclobutyl-L-phenylalanine the activity of 268 Gly is 4 times better than CPA1 with N-(4-(((2,4-diamino-6-pteridinyl)methyl)methylamino)benzoyl)-L-glutam-1-yl-L-phenylaline. Thus, the compounds are much better substrates for the mutant enzyme than the wild type enzyme which permits very specific tumor targeted activation of the nontoxic, stable prodrug to the active agent.

TABLE 2

| Prodrug | kinetic constant | Human CPA1 | 268ala | 268gly |
|---|---|---|---|---|
| N-(4-(((2,4-diamino-6-pteridinyl)methyl)methylamino)benzoyl)-L-glutam-1-yl-L-phenylalanine | $K_m$ (uM) | 4.3 | 0.9 | 0.3 |
| | $k_{cat}$ (1/sec) | 1.9 | 2.0 | 2.2 |
| | $k_{cat}/K_m$ | 0.44 | 2.25 | 7.35 |
| N-(4-(((2,4-diamino-6-pteridinyl)methyl)methylamino)benzoyl)-L-glutam-1-yl-2-cyclopentyl-L-phenylalanine | $K_m$ (uM) | 61 | 56 | 15 |
| | $k_{cat}$ (1/sec) | 0.012 | 0.088 | 2.35 |
| | $k_{cat}/K_m$ | 0.0002 | 0.0016 | 0.157 |
| N-(4-(((2,4-diamino-6-pteridinyl)methyl)methylamino)benzoyl)-L-glutam-1-yl-3-cyclopentyl-L-phenylalanine | $K_m$ (uM) | ND | 31 | 15 |
| | $k_{cat}$ (1/sec) | ND | 0.001 | 1.4 |
| | $k_{cat}/K_m$ | ND | 0.00003 | 0.092 |
| N-(4-(((2,4-diamino-6-pteridinyl)methyl)methylamino)benzoyl)-L-glutam-1-yl-3-tertbutyl-L-phenylalanine | $K_m$ (uM) | ND | ND | 2.1 |
| | $k_{cat}$ (1/sec) | ND | ND | 0.81 |
| | $k_{cat}/K_m$ | ND | ND | 0.38 |
| N-(4-(((2,4-diamino-6-pteridinyl)methyl)methylamino)benzoyl)-L-glutam-1-yl-3-cyclobutyl-L-phenylalanine | $K_m$ (uM) | ND | 160 | 1.8 |
| | $k_{cat}$ (1/sec) | ND | 0.12 | 3.0 |
| | $k_{cat}/K_m$ | ND | 0.00075 | 1.8 |
| N-(4-(((2,4-diamino-6-pteridinyl)methyl)methylamino)benzoyl)-L-glutam-1-yl-3 cyclopentyl-L-tyrosine | $K_m$ (uM) | ND | 50 | 18 |
| | $k_{cat}$ (1/sec) | ND | 0.0006 | 3.0 |
| | $k_{cat}/K_m$ | ND | 0.00001 | 0.18 |

ND = not determined; rate to slow to assay. $k_{cat} \leq 0.0005$/sec.

Kinetics were determined by a modification of the coupled assay of Kuefner, et al (1989) *Biochemistry* 28 2288–2297 in which the product MTX is converted by excess carboxypeptidase G to the pteroate of MTX. In this assay the reaction is followed spectrophotometrically at 315 nm; at this wavelength the change in molar absorbtivity for the coupled reaction was determined to be 9.57 $mM^{-1}$ $cm^{-1}$. Assays were performed at 25° C. in 25 mM tris-HCl, 100 mM NaCl, pH 7.4. Prodrugs were preincubated at 25° C. with buffer and 17 milliunits of Sigma #C-9658 carboxypeptidase G in 1 ml total volume. Assay was initiated with carboxypeptidase A or the appropriate mutant. Initial velocities were obtained, and standard Michaelis-Menten calculations were used to determine kinetic constants (in *Biochemistry*, Lehninger, A. L. 1970, Worth Publishers, Inc, NY).

TABLE 3

Antibodies and Antigens

| Antigen | Antibody | Current uses |
|---|---|---|
| Tumor associated Antigens | | |
| Pan Adenocarcinoma | ING-1 (Wellcome) | Imaging and therapy of various carcinomas. |
| Cytokeratins | c174 (Biomira) | Imaging and therapy of Squamous cell carcinomas. |
| Cytokeratins | 16.88 (Organon Teknika) | Imaging and therapy of Squamous cell carcinomas. |
| Carcinoembryonic Antigen | NR-CO-02 (NeoRex) | Imaging and therapy of colon/gastrointestinal tumors |
| Carcinoembryonic Antigen | PR.1A3 (ICRF) | Imaging and therapy of colon/gastrointestinal tumors |
| Carcinoembryonic Antigen | Immu-14 (Immunomedics) | Imaging and therapy of colon/gastrointestinal tumors |
| Carcinoembryonic Antigen | Col-1 (Dow) | Imaging and therapy of colon/gastrointestinal tumors |
| Carcinoembryonic Antigen | C110 (Abbott) | Imaging and therapy of colon/gastrointestinal tumors |
| Carcinoembryonic Antigen | A5B7 (Brit. J. Cancer, 1986, 54, 75) | Imaging and therapy of colon/gastrointestinal tumors |
| Carcinoembryonic Antigen | BW431/26 (Br J. Cancer 1992, 65, 234) (Cancer Immunol Immunother 1992, 34, 343) | Imaging and therapy of colon/gastrointestinal tumors |
| Carcinoembryonic Antigen | C46.3 (Cytogen) | Imaging and therapy of colon/gastrointestinal tumors |

TABLE 3-continued

Antibodies and Antigens

| Antigen | Antibody | Current uses |
|---|---|---|
| Pan Adenocarcinoma | MAb 12.8 (Biochem Pharmacol 1991, 42, 2062) | Imaging and therapy of various carcinomas. |
| Pan Adenocarcinoma (TAG-72) | CC49 and B72.3 (Dow) | Imaging and therapy of various carcinomas. |
| Histones | TNT-1 and TNT-2 (Techniclone) | All tumors with necrosis |
| Folate binding Protein | MOV18 (Centocor) | Ovarian Carcinoma |
| Folate binding Protein | MOV19 (Int. J. Cancer 39, 297, 1987) | Ovarian Carcinoma |
| Pan Adenocarcinoma | 323/A3 (Centocor) | Imaging and therapy of various carcinomas. |
| Pan Adenocarcinoma | 17.1A (Centocor) | Imaging and therapy of various carcinomas. |
| Renal cell | G250 (Centocor) | Imaging and therapy of Renal Cell carcinomas. |
| 200 Kd squamous cell surface antigen | U36 (Centocor) | Imaging and therapy of Squamous cell carcinomas. |
| 22 Kd squamous cell surface antigen | E48 (Centocor) | Imaging and therapy of Squamous cell carcinomas. |
| 125 Kd colon adenocarcinoma cell surface glycoprotein | SF-25 (Centocor) | Imaging and therapy of various carcinomas. |
| High molecular weight mucins | Various mucin targeting antibodies (Trends Biochemical Science, 1992, 17, 359) | Imaging and therapy of various carcinomas. |
| High molecular weight Mucin | HMFG1 (Cancer Research, 1992, 52, 904) | Imaging and therapy of various carcinomas. |
| High molecular weight Mucin | BrE-3 (Hybridoma, 1993, 12, 15) | Imaging and therapy of various carcinomas. |
| Lung squamous cell carcinoma antigen | RS7-3G11 (Antibody, Immunoconjugates and Radiopharmaceuticals, 1991 4 703) | Imaging and therapy of lung squamous cell carcinomas. |
| LE$^Y$ related tumor antigen | BR64 and BR96 (Bristol-Meyers Squibb) | Imaging and therapy of various carcinomas. |
| HER2 protooncogene product | P185HER2 (NeoRx) | Imaging and therapy of various carcinomas, especially breast, |
| human carcinoma antigen | 15A82a (Cytogen) | Imaging and therapy of various carcinomas. |
| human Chorionic gonadotropin | W14A and SB10 (Int J. Cancer, 1984, 33, 429 Br. J. Cancer, 1990, 61, 659) | Imaging and therapy of various carcinomas. |

TABLE 4

Amino acid coding sequences for human CPA1 and CPA2.*

```
              -110        -100         -90         -80         -70
HCPA1   MRGLLVLSVLLGAVFGKEDFVGHQVLRISVADEAQVQKVKELEDLEHLQL
HCPA2   ::LI:FFGA:F:HIYCL:T:::D:::E:VPSN:E:IKNLLQ::AQ:::::

-60         -50         -40         -30         -°
HCPA1   DFWRGPAHPGSPIDVRMPFPSIQAVKIFLESHGISYETMIEDVQSLLDEE
HCPA2   :::KS:TTS:ETAH::V::VNV::::V::::Q::A:SI::::::V:::K:

-10           1          11          21          31
HCPA1   QEQMFAFRSRARSTDTFNYATYHTLEEIYDFLDLLVAENPHLVSKIQIGN
HCPA2   N:E:LFN:R:E:-SGN::FGA:::::::SQEM:N::::H:G::::VN::S 41          51          61          71          81
HCPA1   TYEGRPIYVLKFSTGGSKRPAIWIDTGIHSREWVTQASGVWFAKKITQDY
HCPA2   SF:N::MN:::::::::-DK::::L:A:::A::::::::TAL:T:N::VS::

91         101         111         121         131
```

TABLE 4-continued

Amino acid coding sequences for human CPA1 and CPA2.*

```
HCPA1            GQDAAFTAILDTLDIFLEIVTNPDGFAFTHSTNRMWRKTRSHTAGSLCIG
HCPA2            :K:PSI:S:::A:::::LP::::::YV:SQTK::::::::::KVS:::V:

141       151       161       171       181
HCPA1            VDPNRNWDAGFGLSGASSNPCSETYHGKFANSEVEVKSIVDFVKDHGNIK
HCPA2            :::::::::::GP:A::::::DS:::PS::::::::::::I:S::KV:

191       201       211       221       231
HCPA1            AFISIHSYSQLLMYPYGYKTEPVPDQDELDQLSKAAVTALASLYGTKFNY
HCPA2            :::TL:::::::::F:::::CTKLD:F:::SEVAQK:AQS:R::H:::YKV 241       251       261       271       281
HCPA1            GSIIKAIYQASGSTIDWTYSQGIKYSFTFELRDTGRYGFLLPASQIIPTA
HCPA2            :P:CSV::::::GS:::S:DY::::::A::::::::::::::R::L:::

291       301
HCPA1(SEQ ID NO:2) KETWLALLTIMEHTLNHRY
HCPA2(SEQ ID NO:4) E::::F:KA::::VRD:::
```

*Numbering scheme for CPA1 is used. Dashes at positions 3 and 57 indicate a gap in the A2 sequence required for optimal alignment with A1.
Colons indicate identity between A1 and A2.
Prepro-CPA begins at amino acid -110 and runs to +309.
Pro-CPA begins at amino acid -94 and runs to +309.
mature CPA begins at amino acid +1 and runs to +309.

TABLE 5

Amino acid sequences for the 268Gly mutations of human CPA1 and CPA2.*

```
(mut.)           -110      -100      -90       -80       -70
HCPA1            MRGLLVLSVLLGAVFGKEDFVGHQVLRISVADEAQVQKVKELEDLEHLQL
HCPA2            ::LI:FFGA:F:HIYCL:T:::D:::E:VPSN:E:IKNLLQ::AQ:::::

(mut.)           -60       -50       -40       -30       -20
HCPA1            DFWRGPAHFGSPIDVRMPFPSIQAVKIFLESHGISYETMIEDVQSLLDEE
HCPA2            :::KS:TTS:ETAH::V::VNV::::V::::Q::A:SI::::::V:::K:

(mut.)           -10       1         11        21        31
HCPA1            QEQMFAFRSRARSTDTFNYATYHTLEEIYDFLDLLVAENPHLVSKIQIGN
HCPS2            N:E:LFN:R:E:-SGN::FGA:::::::SQEM:N::::H:G::::VN::S (mut.)           41        51        61        71        81
HCPA1            TYEGRPIYVLKFSTGGSKRPAIWIDTGIHSREWVTQASGVWFAKKITQDY
HCPA2            SF:N::MN:::::::::-DK::::L:A:::A::::::::TAL:T:N::VS::

(mut.)           91        101       111       121       131
HCPA1            GQDAAFTAILDTLDIFLEIVTNPDGFAFTHSTNRMWRKTRSHTAGSLCIG
HCPA2            :K:PSI:S:::A:::::LP::::::YV:SQTK::::::::::KVS:::V:

(mut.)           141       151       161       171       181
HCPA1            VDPNRNWDAGFGLSGASSNPCSETYHGKFANSEVEVKSIVDFVKDHGNIK
HCPA2            :::::::::::GP:A::::::DS:::PS::::::::::::I:S::KV:

(mut.)           191       201       211       221       231
HCPA1            AFISIHSYSQLLMYPYGYKTEPVPDQDELDQLSKAAVTALASLYGTKFNY
HCPA2            :::TL:::::::::F:::::CTKLD:F:::SEVAQK:AQS:R::H:::YKV (mut.)           241       251       261       271       281
HCPA1            GSIIKAIYQASGSTIDWTYSQGIKYSFGFELRDTGRYGFLLPASQIIPTA
HCPA2            :P:CSV::::::GS:::S:DY::::::G::::::::::::::R::L:::

(mut.)                 291       301
HCPA1 (SEQ ID NO:17)   KETWLALLTIMEHTLNHPY
HCPA2 (SEQ ID NO:19)   E::::G:KA::::VRD:::
```

*Numbering scheme for CPA1 is used. Dashes at positions 3 and 57 indicate a gap in the A2 sequence required for optimal alignment with A1.
Colons indicate identity between A1 and A2.

We claim:

1. A conjugate comprising a cell targeting molecule and a mutant human carboxypeptidase A enzyme wherein the enzyme possesses amino acid substitutions at one or more of residues 203, 210, 242, 244, 250, 253, 255, 267, 268, 269 and 305.

2. A conjugate according to claim 1 wherein the amino acid substitutions are selected from the following:
Gly at 250 and 268,
Gly at 253 and 268,
Gly at 250 and His at 268,
Gly at 250,
Ala at 255 and His 268,
His at 268, and
Gly at 268.

3. A conjugate according to claim 2 wherein the targetting molecule is one of an antibody, a hormone, a ligand, a cytokine, an antigen, an oligonucleotide and a peptidomimetic.

4. A conjugate according to claim 2 wherein the substitution is Gly at 268.

5. A conjugate according to claim 4 wherein the targetting molecule is one of an antibody, a hormone, a ligand, a cytokine, an antigen, an oligonucleotide and a peptidomimetic.

6. A conjugate according to claim 1 wherein the targetting molecule is one of an antibody, a hormone, a ligand, a cytokine, an antigen, an oligonucleotide and a peptidomimetic.

7. A conjugate according to claim 6 wherein the antibody is a polyclonal antibody, a monoclonal antibody or a fragment thereof.

8. A conjugate according to claim 7 wherein the antibody of fragment thereof is humanised.

9. A conjugate according to claim 6, wherein the targeting molecule is joined to the enzyme by a linker molecule.

10. An enzyme comprising a mutant human caboxypeptidase A enzyme wherein the enzyme possesses amino acid substitutions at one or more of residues 203, 210, 242, 244, 250, 253, 255, 267, 268, 269 and 305.

11. An enzyme according to claim 10 wherein the amino acid substitutions are selected from the following:
Gly at 250 and 268,
Gly at 253 and 268,
Gly at 250 and His at 268,
Gly at 250,
Ala at 255 and His 268,
His at 268, and
Gly at 268.

12. An enzyme according to claim 11 wherein the substitution is Gly at 268.

* * * * *

SEQUENCE LISTING

<160> NUMBER OF SEQ ID NOS: 22

<210> SEQ ID NO 1
<211> LENGTH: 1257
<212> TYPE: DNA
<213> ORGANISM: Homo sapiens
<220> FEATURE:
<221> NAME/KEY: CDS
<222> LOCATION: (1)..(1257)

<400> SEQUENCE: 1

| | | | | | | | | | | | | | | | | |
|---|---|---|---|---|---|---|---|---|---|---|---|---|---|---|---|---|
| atg | cgc | ggg | ttg | ctg | gtg | ttg | agt | gtc | ctg | ttg | ggg | gct | gtc | ttt | ggc | 48 |
| Met | Arg | Gly | Leu | Leu | Val | Leu | Ser | Val | Leu | Leu | Gly | Ala | Val | Phe | Gly | |
| 1 | | | | 5 | | | | | 10 | | | | | 15 | | |

| aag | gag | gac | ttt | gtg | ggg | cat | cag | gtg | ctc | cga | atc | tct | gta | gcc | gat | 96 |
|---|---|---|---|---|---|---|---|---|---|---|---|---|---|---|---|---|
| Lys | Glu | Asp | Phe | Val | Gly | His | Gln | Val | Leu | Arg | Ile | Ser | Val | Ala | Asp | |
| | | | 20 | | | | | 25 | | | | | 30 | | | |

| gag | gcc | cag | gta | cag | aag | gtg | aag | gag | ctg | gag | gac | ctg | gag | cac | ctg | 144 |
|---|---|---|---|---|---|---|---|---|---|---|---|---|---|---|---|---|
| Glu | Ala | Gln | Val | Gln | Lys | Val | Lys | Glu | Leu | Glu | Asp | Leu | Glu | His | Leu | |
| | | 35 | | | | | 40 | | | | | 45 | | | | |

| cag | ctg | gac | ttc | tgg | cgg | ggc | cct | gcc | cac | cct | ggc | tcc | ccc | atc | gac | 192 |
|---|---|---|---|---|---|---|---|---|---|---|---|---|---|---|---|---|
| Gln | Leu | Asp | Phe | Trp | Arg | Gly | Pro | Ala | His | Pro | Gly | Ser | Pro | Ile | Asp | |
| | 50 | | | | | 55 | | | | | 60 | | | | | |

| gtc | cga | atg | ccc | ttc | ccc | agc | atc | cag | gcg | gtc | aag | atc | ttt | ctg | gag | 240 |
|---|---|---|---|---|---|---|---|---|---|---|---|---|---|---|---|---|
| Val | Arg | Met | Pro | Phe | Pro | Ser | Ile | Gln | Ala | Val | Lys | Ile | Phe | Leu | Glu | |
| 65 | | | | | 70 | | | | | 75 | | | | | 80 | |

| tcc | cac | ggc | atc | agc | tat | gag | acc | atg | atc | gag | gac | gtg | cag | tcg | ctg | 288 |
|---|---|---|---|---|---|---|---|---|---|---|---|---|---|---|---|---|
| Ser | His | Gly | Ile | Ser | Tyr | Glu | Thr | Met | Ile | Glu | Asp | Val | Gln | Ser | Leu | |
| | | | | 85 | | | | | 90 | | | | | 95 | | |

| ctg | gac | gag | gag | cag | gag | cag | atg | ttc | gcc | ttc | cgg | tcc | cgg | gcg | cgc | 336 |
|---|---|---|---|---|---|---|---|---|---|---|---|---|---|---|---|---|
| Leu | Asp | Glu | Glu | Gln | Glu | Gln | Met | Phe | Ala | Phe | Arg | Ser | Arg | Ala | Arg | |
| | | | 100 | | | | | 105 | | | | | 110 | | | |

| tcc | acc | gac | act | ttt | aac | tac | gcc | acc | tac | cac | acc | ctg | gag | gag | atc | 384 |
|---|---|---|---|---|---|---|---|---|---|---|---|---|---|---|---|---|
| Ser | Thr | Asp | Thr | Phe | Asn | Tyr | Ala | Thr | Tyr | His | Thr | Leu | Glu | Glu | Ile | |
| | | 115 | | | | | 120 | | | | | 125 | | | | |

| tat | gac | ttc | ctg | gac | ctg | ctg | gtg | gcg | gag | aac | ccg | cac | ctt | gtc | agc | 432 |
|---|---|---|---|---|---|---|---|---|---|---|---|---|---|---|---|---|
| Tyr | Asp | Phe | Leu | Asp | Leu | Leu | Val | Ala | Glu | Asn | Pro | His | Leu | Val | Ser | |
| | 130 | | | | | 135 | | | | | 140 | | | | | |

| aag | atc | cag | att | ggc | aac | acc | tat | gaa | ggg | cgt | ccc | att | tac | gtg | ctg | 480 |
|---|---|---|---|---|---|---|---|---|---|---|---|---|---|---|---|---|
| Lys | Ile | Gln | Ile | Gly | Asn | Thr | Tyr | Glu | Gly | Arg | Pro | Ile | Tyr | Val | Leu | |
| 145 | | | | | 150 | | | | | 155 | | | | | 160 | |

| aag | ttc | agc | acg | ggg | ggc | agt | aag | cgt | cca | gcc | atc | tgg | atc | gac | acg | 528 |
|---|---|---|---|---|---|---|---|---|---|---|---|---|---|---|---|---|
| Lys | Phe | Ser | Thr | Gly | Gly | Ser | Lys | Arg | Pro | Ala | Ile | Trp | Ile | Asp | Thr | |
| | | | | 165 | | | | | 170 | | | | | 175 | | |

| ggc | atc | cat | tcc | cgg | gag | tgg | gtc | acc | cag | gcc | agt | ggg | gtc | tgg | ttt | 576 |
|---|---|---|---|---|---|---|---|---|---|---|---|---|---|---|---|---|
| Gly | Ile | His | Ser | Arg | Glu | Trp | Val | Thr | Gln | Ala | Ser | Gly | Val | Trp | Phe | |
| | | | 180 | | | | | 185 | | | | | 190 | | | |

| gca | aag | aag | atc | act | caa | gac | tat | ggg | cag | gat | gca | gct | ttc | acc | gcc | 624 |
|---|---|---|---|---|---|---|---|---|---|---|---|---|---|---|---|---|
| Ala | Lys | Lys | Ile | Thr | Gln | Asp | Tyr | Gly | Gln | Asp | Ala | Ala | Phe | Thr | Ala | |
| | | 195 | | | | | 200 | | | | | 205 | | | | |

| att | ctc | gac | acc | ttg | gac | atc | ttc | ctg | gag | atc | gtc | acc | aac | cct | gat | 672 |
|---|---|---|---|---|---|---|---|---|---|---|---|---|---|---|---|---|
| Ile | Leu | Asp | Thr | Leu | Asp | Ile | Phe | Leu | Glu | Ile | Val | Thr | Asn | Pro | Asp | |
| | 210 | | | | | 215 | | | | | 220 | | | | | |

| ggc | ttt | gcc | ttc | acg | cac | agc | acg | aat | cgc | atg | tgg | cgc | aag | act | cgg | 720 |
|---|---|---|---|---|---|---|---|---|---|---|---|---|---|---|---|---|
| Gly | Phe | Ala | Phe | Thr | His | Ser | Thr | Asn | Arg | Met | Trp | Arg | Lys | Thr | Arg | |
| 225 | | | | | 230 | | | | | 235 | | | | | 240 | |

| tcc | cac | aca | gca | ggc | tcc | ctc | tgt | att | ggc | gtg | gac | ccc | aac | agg | aac | 768 |
|---|---|---|---|---|---|---|---|---|---|---|---|---|---|---|---|---|
| Ser | His | Thr | Ala | Gly | Ser | Leu | Cys | Ile | Gly | Val | Asp | Pro | Asn | Arg | Asn | |
| | | | | 245 | | | | | 250 | | | | | 255 | | |

-continued

```
tgg gac gct ggc ttt ggg ttg tcc gga gcc agc agt aac ccc tgc tcg         816
Trp Asp Ala Gly Phe Gly Leu Ser Gly Ala Ser Ser Asn Pro Cys Ser
        260                 265                 270 gag act tac cac ggc aag ttt gcc aat tcc gaa gtg gag gtc aag tcc         864
Glu Thr Tyr His Gly Lys Phe Ala Asn Ser Glu Val Glu Val Lys Ser
    275                 280                 285 att gta gac ttt gtg aag gac cat ggg aac atc aag gcc ttc atc tcc        912
Ile Val Asp Phe Val Lys Asp His Gly Asn Ile Lys Ala Phe Ile Ser
290                 295                 300 atc cac agc tac tcc cag ctc ctc atg tat ccc tat ggc tac aaa aca        960
Ile His Ser Tyr Ser Gln Leu Leu Met Tyr Pro Tyr Gly Tyr Lys Thr
305                 310                 315                 320 gaa cca gtc cct gac cag gat gag ctg gat cag ctt tcc aag gct gct       1008
Glu Pro Val Pro Asp Gln Asp Glu Leu Asp Gln Leu Ser Lys Ala Ala
            325                 330                 335 gtg aca gcc ctg gcc tct ctc tac ggg acc aag ttc aac tat ggc agc       1056
Val Thr Ala Leu Ala Ser Leu Tyr Gly Thr Lys Phe Asn Tyr Gly Ser
        340                 345                 350 atc atc aag gca att tat caa gcc agt gga agc act att gac tgg acc       1104
Ile Ile Lys Ala Ile Tyr Gln Ala Ser Gly Ser Thr Ile Asp Trp Thr
    355                 360                 365 tac agc cag ggc atc aag tac tcc ttc acc ttc gag ctc cgg gac act       1152
Tyr Ser Gln Gly Ile Lys Tyr Ser Phe Thr Phe Glu Leu Arg Asp Thr
370                 375                 380 ggg cgc tat ggc ttc ctg ctg cca gcc tcc cag atc atc ccc aca gcc       1200
Gly Arg Tyr Gly Phe Leu Leu Pro Ala Ser Gln Ile Ile Pro Thr Ala
385                 390                 395                 400 aag gag acg tgg ctg gcg ctt ctg acc atc atg gag cac acc ctg aat       1248
Lys Glu Thr Trp Leu Ala Leu Leu Thr Ile Met Glu His Thr Leu Asn
            405                 410                 415 cac ccc tac                                                            1257
His Pro Tyr
```

<210> SEQ ID NO 2
<211> LENGTH: 419
<212> TYPE: PRT
<213> ORGANISM: Homo sapiens

<400> SEQUENCE: 2

```
Met Arg Gly Leu Leu Val Leu Ser Val Leu Gly Ala Val Phe Gly
 1               5                  10                  15

Lys Glu Asp Phe Val Gly His Gln Val Leu Arg Ile Ser Val Ala Asp
                20                  25                  30

Glu Ala Gln Val Gln Lys Val Lys Glu Leu Glu Asp Leu Glu His Leu
            35                  40                  45

Gln Leu Asp Phe Trp Arg Gly Pro Ala His Pro Gly Ser Pro Ile Asp
        50                  55                  60

Val Arg Met Pro Phe Pro Ser Ile Gln Ala Val Lys Ile Phe Leu Glu
65                  70                  75                  80

Ser His Gly Ile Ser Tyr Glu Thr Met Ile Glu Asp Val Gln Ser Leu
                85                  90                  95

Leu Asp Glu Glu Gln Glu Gln Met Phe Ala Phe Arg Ser Arg Ala Arg
            100                 105                 110

Ser Thr Asp Thr Phe Asn Tyr Ala Thr Tyr His Thr Leu Glu Glu Ile
        115                 120                 125

Tyr Asp Phe Leu Asp Leu Leu Val Ala Glu Asn Pro His Leu Val Ser
    130                 135                 140

Lys Ile Gln Ile Gly Asn Thr Tyr Glu Gly Arg Pro Ile Tyr Val Leu
```

```
               145                 150                 155                 160
      Lys Phe Ser Thr Gly Gly Ser Lys Arg Pro Ala Ile Trp Ile Asp Thr
                      165                 170                 175

Gly Ile His Ser Arg Glu Trp Val Thr Gln Ala Ser Gly Val Trp Phe
                      180                 185                 190

Ala Lys Lys Ile Thr Gln Asp Tyr Gly Gln Asp Ala Ala Phe Thr Ala
                      195                 200                 205

Ile Leu Asp Thr Leu Asp Ile Phe Leu Glu Ile Val Thr Asn Pro Asp
                  210                 215                 220

Gly Phe Ala Phe Thr His Ser Thr Asn Arg Met Trp Arg Lys Thr Arg
      225                 230                 235                 240

Ser His Thr Ala Gly Ser Leu Cys Ile Gly Val Asp Pro Asn Arg Asn
                      245                 250                 255

Trp Asp Ala Gly Phe Gly Leu Ser Gly Ala Ser Ser Asn Pro Cys Ser
                      260                 265                 270

Glu Thr Tyr His Gly Lys Phe Ala Asn Ser Glu Val Glu Val Lys Ser
                      275                 280                 285

Ile Val Asp Phe Val Lys Asp His Gly Asn Ile Lys Ala Phe Ile Ser
                  290                 295                 300

Ile His Ser Tyr Ser Gln Leu Leu Met Tyr Pro Tyr Gly Tyr Lys Thr
      305                 310                 315                 320

Glu Pro Val Pro Asp Gln Asp Glu Leu Asp Gln Leu Ser Lys Ala Ala
                      325                 330                 335

Val Thr Ala Leu Ala Ser Leu Tyr Gly Thr Lys Phe Asn Tyr Gly Ser
                      340                 345                 350

Ile Ile Lys Ala Ile Tyr Gln Ala Ser Gly Ser Thr Ile Asp Trp Thr
                      355                 360                 365

Tyr Ser Gln Gly Ile Lys Tyr Ser Phe Thr Phe Glu Leu Arg Asp Thr
                      370                 375                 380

Gly Arg Tyr Gly Phe Leu Leu Pro Ala Ser Gln Ile Ile Pro Thr Ala
      385                 390                 395                 400

Lys Glu Thr Trp Leu Ala Leu Leu Thr Ile Met Glu His Thr Leu Asn
                      405                 410                 415

His Pro Tyr

<210> SEQ ID NO 3
<211> LENGTH: 1251
<212> TYPE: DNA
<213> ORGANISM: Homo sapiens
<220> FEATURE:
<221> NAME/KEY: CDS
<222> LOCATION: (1)..(1251)

<400> SEQUENCE: 3 atg agg ttg atc ctg ttt ttt ggt gcc ctt ttt ggg cat atc tac tgt        48
Met Arg Leu Ile Leu Phe Phe Gly Ala Leu Phe Gly His Ile Tyr Cys
  1               5                  10                  15 cta gaa aca ttt gtg gga gac caa gtt ctt gag att gta cca agc aat        96
Leu Glu Thr Phe Val Gly Asp Gln Val Leu Glu Ile Val Pro Ser Asn
                 20                  25                  30 gaa gaa caa att aaa aat ctg cta caa ttg gag gct caa gaa cat ctc       144
Glu Glu Gln Ile Lys Asn Leu Leu Gln Leu Glu Ala Gln Glu His Leu
             35                  40                  45 cag ctt gat ttt tgg aaa tca ccc acc acc tca ggg gag aca gcc cac       192
Gln Leu Asp Phe Trp Lys Ser Pro Thr Thr Ser Gly Glu Thr Ala His
         50                  55                  60
```

-continued

| | |
|---|---|
| gtc cga gtt ccc ttc gtc aac gtc cag gca gtc aaa gtg ttc ttg gag<br>Val Arg Val Pro Phe Val Asn Val Gln Ala Val Lys Val Phe Leu Glu<br>65                      70                      75                      80 | 240 |
| tcc cag gga att gcc tat tcc atc atg att gaa gac gtg cag gtc ctg<br>Ser Gln Gly Ile Ala Tyr Ser Ile Met Ile Glu Asp Val Gln Val Leu<br>85                      90                      95 | 288 |
| ttg gac aaa gag aat gaa gaa atg ctt ttt aat agg aga aga gaa cgg<br>Leu Asp Lys Glu Asn Glu Glu Met Leu Phe Asn Arg Arg Arg Glu Arg<br>100                      105                      110 | 336 |
| agt ggt aac ttc aat ttt ggg gcc tac cat acc ctg gaa gag att tcc<br>Ser Gly Asn Phe Asn Phe Gly Ala Tyr His Thr Leu Glu Glu Ile Ser<br>115                      120                      125 | 384 |
| caa gaa atg gat aac ctc gtg gct gag cac cct ggt cta gtg agc aaa<br>Gln Glu Met Asp Asn Leu Val Ala Glu His Pro Gly Leu Val Ser Lys<br>130                      135                      140 | 432 |
| gtg aat att ggc tct tct ttt gag aac cgg cct atg aac gtg ctc aag<br>Val Asn Ile Gly Ser Ser Phe Glu Asn Arg Pro Met Asn Val Leu Lys<br>145                      150                      155                      160 | 480 |
| ttc agc acc gga gga gac aag cca gct atc tgg ctg gat gcg ggg atc<br>Phe Ser Thr Gly Gly Asp Lys Pro Ala Ile Trp Leu Asp Ala Gly Ile<br>165                      170                      175 | 528 |
| cat gct cga gag tgg gtt aca caa gct acg gca ctt tgg aca gca aat<br>His Ala Arg Glu Trp Val Thr Gln Ala Thr Ala Leu Trp Thr Ala Asn<br>180                      185                      190 | 576 |
| aag att gtt tct gat tat gga aag gac cca tcc atc act tcc att ctg<br>Lys Ile Val Ser Asp Tyr Gly Lys Asp Pro Ser Ile Thr Ser Ile Leu<br>195                      200                      205 | 624 |
| gac gcc ctg gat atc ttc ctc ctg cca gtc aca aac cct gat gga tac<br>Asp Ala Leu Asp Ile Phe Leu Leu Pro Val Thr Asn Pro Asp Gly Tyr<br>210                      215                      220 | 672 |
| gtg ttc tct caa acc aaa aat cgt atg tgg cgg aag acc cgg tcc aag<br>Val Phe Ser Gln Thr Lys Asn Arg Met Trp Arg Lys Thr Arg Ser Lys<br>225                      230                      235                      240 | 720 |
| gta tct gga agc ctc tgt gtt ggt gtg gat cct aac cgg aac tgg gat<br>Val Ser Gly Ser Leu Cys Val Gly Val Asp Pro Asn Arg Asn Trp Asp<br>245                      250                      255 | 768 |
| gca ggt ttt gga gga cct gga gcc agc agc aac cct tgc tct gat tca<br>Ala Gly Phe Gly Gly Pro Gly Ala Ser Ser Asn Pro Cys Ser Asp Ser<br>260                      265                      270 | 816 |
| tac cac gga ccc agt gcc aac tct gaa gtt gaa gtg aaa tcc ata gtg<br>Tyr His Gly Pro Ser Ala Asn Ser Glu Val Glu Val Lys Ser Ile Val<br>275                      280                      285 | 864 |
| gac ttc atc aag agt cat gga aaa gtc aag gcc ttc att acc ctc cac<br>Asp Phe Ile Lys Ser His Gly Lys Val Lys Ala Phe Ile Thr Leu His<br>290                      295                      300 | 912 |
| agc tat tcc cag ctg ctg atg ttc ccc tat ggg tac aaa tgt acc aag<br>Ser Tyr Ser Gln Leu Leu Met Phe Pro Tyr Gly Tyr Lys Cys Thr Lys<br>305                      310                      315                      320 | 960 |
| tta gat gac ttt gat gag ctg agt gaa gtg gcc caa aag gct gcc caa<br>Leu Asp Asp Phe Asp Glu Leu Ser Glu Val Ala Gln Lys Ala Ala Gln<br>325                      330                      335 | 1008 |
| tct ctg aga agc ctg cat ggc acc aag tac aaa gtg gga cca atc tgc<br>Ser Leu Arg Ser Leu His Gly Thr Lys Tyr Lys Val Gly Pro Ile Cys<br>340                      345                      350 | 1056 |
| tct gtc atc tac caa gcc agt gga gga agc att gac tgg tcc tat gat<br>Ser Val Ile Tyr Gln Ala Ser Gly Gly Ser Ile Asp Trp Ser Tyr Asp<br>355                      360                      365 | 1104 |
| tat ggc atc aag tac tca ttt gcc ttt gaa ctg aga gac aca ggg cgc<br>Tyr Gly Ile Lys Tyr Ser Phe Ala Phe Glu Leu Arg Asp Thr Gly Arg<br>370                      375                      380 | 1152 |

-continued

```
tac ggc ttc ctc ttg cca gcc cgt cag atc ctg ccc aca gcc gag gag      1200
Tyr Gly Phe Leu Leu Pro Ala Arg Gln Ile Leu Pro Thr Ala Glu Glu
385                 390                 395                 400 acc tgg ctt ggc ttg aag gca atc atg gag cat gtg cga gac cac ccc      1248
Thr Trp Leu Gly Leu Lys Ala Ile Met Glu His Val Arg Asp His Pro
            405                 410                 415 tat                                                                  1251
Tyr
```

<210> SEQ ID NO 4
<211> LENGTH: 417
<212> TYPE: PRT
<213> ORGANISM: Homo sapiens

<400> SEQUENCE: 4

```
Met Arg Leu Ile Leu Phe Phe Gly Ala Leu Phe Gly His Ile Tyr Cys
  1               5                  10                  15

Leu Glu Thr Phe Val Gly Asp Gln Val Leu Glu Ile Val Pro Ser Asn
                 20                  25                  30

Glu Glu Gln Ile Lys Asn Leu Gln Leu Glu Ala Gln Glu His Leu
             35                  40                  45

Gln Leu Asp Phe Trp Lys Ser Pro Thr Thr Ser Gly Glu Thr Ala His
         50                  55                  60

Val Arg Val Pro Phe Val Asn Val Gln Ala Val Lys Val Phe Leu Glu
 65                  70                  75                  80

Ser Gln Gly Ile Ala Tyr Ser Ile Met Ile Glu Asp Val Gln Val Leu
                 85                  90                  95

Leu Asp Lys Glu Asn Glu Glu Met Leu Phe Asn Arg Arg Arg Glu Arg
            100                 105                 110

Ser Gly Asn Phe Asn Phe Gly Ala Tyr His Thr Leu Glu Glu Ile Ser
        115                 120                 125

Gln Glu Met Asp Asn Leu Val Ala Glu His Pro Gly Leu Val Ser Lys
    130                 135                 140

Val Asn Ile Gly Ser Ser Phe Glu Asn Arg Pro Met Asn Val Leu Lys
145                 150                 155                 160

Phe Ser Thr Gly Gly Asp Lys Pro Ala Ile Trp Leu Asp Ala Gly Ile
                165                 170                 175

His Ala Arg Glu Trp Val Thr Gln Ala Thr Ala Leu Trp Thr Ala Asn
            180                 185                 190

Lys Ile Val Ser Asp Tyr Gly Lys Asp Pro Ser Ile Thr Ser Ile Leu
        195                 200                 205

Asp Ala Leu Asp Ile Phe Leu Leu Pro Val Thr Asn Pro Asp Gly Tyr
    210                 215                 220

Val Phe Ser Gln Thr Lys Asn Arg Met Trp Arg Lys Thr Arg Ser Lys
225                 230                 235                 240

Val Ser Gly Ser Leu Cys Val Gly Val Asp Pro Asn Arg Asn Trp Asp
                245                 250                 255

Ala Gly Phe Gly Gly Pro Gly Ala Ser Ser Asn Pro Cys Ser Asp Ser
            260                 265                 270

Tyr His Gly Pro Ser Ala Asn Ser Glu Val Glu Val Lys Ser Ile Val
        275                 280                 285

Asp Phe Ile Lys Ser His Gly Lys Val Lys Ala Phe Ile Thr Leu His
    290                 295                 300

Ser Tyr Ser Gln Leu Leu Met Phe Pro Tyr Gly Tyr Lys Cys Thr Lys
305                 310                 315                 320
```

```
Leu Asp Asp Phe Asp Glu Leu Ser Glu Val Ala Gln Lys Ala Ala Gln
                325                 330                 335

Ser Leu Arg Ser Leu His Gly Thr Lys Tyr Lys Val Gly Pro Ile Cys
            340                 345                 350

Ser Val Ile Tyr Gln Ala Ser Gly Gly Ser Ile Asp Trp Ser Tyr Asp
        355                 360                 365

Tyr Gly Ile Lys Tyr Ser Phe Ala Phe Glu Leu Arg Asp Thr Gly Arg
    370                 375                 380

Tyr Gly Phe Leu Leu Pro Ala Arg Gln Ile Leu Pro Thr Ala Glu Glu
385                 390                 395                 400

Thr Trp Leu Gly Leu Lys Ala Ile Met Glu His Val Arg Asp His Pro
                405                 410                 415

Tyr

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:nucleotide
      primer from rat cDNA

<400> SEQUENCE: 5
cctgttattg gctgccctac tt                                            22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 6
aagccaggtc tcttctgctg tc                                            22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 7
ggtccagtca gcagtgcttc c                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
gagctcgaag gcgaaggagt a                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer
```

-continued

```
<400> SEQUENCE: 9
gagctcgaag ccgaaggagt a                                              21

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 10
tcccccgggc tgcaggatat cgatagctgg gctgtgt                             37

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 11
atcaagtact cctcccagct ccgggac                                        27

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 12
tttatcaagc cagtggaggt attgactgga cc                                  32

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 13
aaggcaattt atcaaggcag tggaagcact att                                 33

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 14
tcccccgggc tgcaggatat cgatagctgg gctgtgt                             37

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 15
gctgaagctt cggaggactt t                                              21

<210> SEQ ID NO 16
```

-continued

```
<211> LENGTH: 20
<212> TYPE: DNA
<213> ORGANISM: Artificial Sequence

<400> SEQUENCE: 16
tcttgaccgc ctggatgctg                                                    20

<210> SEQ ID NO 17
<211> LENGTH: 419
<212> TYPE: PRT
<213> ORGANISM: Homo sapiens

<400> SEQUENCE: 17

Met Arg Gly Leu Leu Val Leu Ser Val Leu Gly Ala Val Phe Gly
  1               5                  10                  15

Lys Glu Asp Phe Val Gly His Gln Val Leu Arg Ile Ser Val Ala Asp
                 20                  25                  30

Glu Ala Gln Val Gln Lys Val Lys Glu Leu Glu Asp Leu Glu His Leu
             35                  40                  45

Gln Leu Asp Phe Trp Arg Gly Pro Ala His Pro Gly Ser Pro Ile Asp
         50                  55                  60

Val Arg Met Pro Phe Pro Ser Ile Gln Ala Val Lys Ile Phe Leu Glu
 65                  70                  75                  80

Ser His Gly Ile Ser Tyr Glu Thr Met Ile Glu Asp Val Gln Ser Leu
                 85                  90                  95

Leu Asp Glu Glu Gln Glu Gln Met Phe Ala Phe Arg Ser Arg Ala Arg
            100                 105                 110

Ser Thr Asp Thr Phe Asn Tyr Ala Thr Tyr His Thr Leu Glu Glu Ile
        115                 120                 125

Tyr Asp Phe Leu Asp Leu Leu Val Ala Glu Asn Pro His Leu Val Ser
    130                 135                 140

Lys Ile Gln Ile Gly Asn Thr Tyr Glu Gly Arg Pro Ile Tyr Val Leu
145                 150                 155                 160

Lys Phe Ser Thr Gly Gly Ser Lys Arg Pro Ala Ile Trp Ile Asp Thr
                165                 170                 175

Gly Ile His Ser Arg Glu Trp Val Thr Gln Ala Ser Gly Val Trp Phe
            180                 185                 190

Ala Lys Lys Ile Thr Gln Asp Tyr Gly Gln Asp Ala Ala Phe Thr Ala
        195                 200                 205

Ile Leu Asp Thr Leu Asp Ile Phe Leu Glu Ile Val Thr Asn Pro Asp
    210                 215                 220

Gly Phe Ala Phe Thr His Ser Thr Asn Arg Met Trp Arg Lys Thr Arg
225                 230                 235                 240

Ser His Thr Ala Gly Ser Leu Cys Ile Gly Val Asp Pro Asn Arg Asn
                245                 250                 255

Trp Asp Ala Gly Phe Gly Leu Ser Gly Ala Ser Ser Asn Pro Cys Ser
            260                 265                 270

Glu Thr Tyr His Gly Lys Phe Ala Asn Ser Glu Val Glu Val Lys Ser
        275                 280                 285

Ile Val Asp Phe Val Lys Asp His Gly Asn Ile Lys Ala Phe Ile Ser
    290                 295                 300

Ile His Ser Tyr Ser Gln Leu Leu Met Tyr Pro Tyr Gly Tyr Lys Thr
305                 310                 315                 320

Glu Pro Val Pro Asp Gln Asp Glu Leu Asp Gln Leu Ser Lys Ala Ala
                325                 330                 335
```

```
Val Thr Ala Leu Ala Ser Leu Tyr Gly Thr Lys Phe Asn Tyr Gly Ser
            340                 345                 350

Ile Ile Lys Ala Ile Tyr Gln Ala Ser Gly Ser Thr Ile Asp Trp Thr
            355                 360                 365

Tyr Ser Gln Gly Ile Lys Tyr Ser Phe Gly Phe Glu Leu Arg Asp Thr
            370                 375                 380

Gly Arg Tyr Gly Phe Leu Leu Pro Ala Ser Gln Ile Ile Pro Thr Ala
385                 390                 395                 400

Lys Glu Thr Trp Leu Ala Leu Leu Thr Ile Met Glu His Thr Leu Asn
                405                 410                 415

His Pro Tyr

<210> SEQ ID NO 18
<211> LENGTH: 417
<212> TYPE: PRT
<213> ORGANISM: Homo sapiens

<400> SEQUENCE: 18

Met Arg Leu Ile Leu Phe Phe Gly Ala Leu Phe Gly His Ile Tyr Cys
 1                5                  10                  15

Leu Glu Thr Phe Val Gly Asp Gln Val Leu Glu Ile Val Pro Ser Asn
            20                  25                  30

Glu Glu Gln Ile Lys Asn Leu Leu Gln Leu Glu Ala Gln Glu His Leu
        35                  40                  45

Gln Leu Asp Phe Trp Lys Ser Pro Thr Thr Ser Gly Glu Thr Ala His
    50                  55                  60

Val Arg Val Pro Phe Val Asn Val Gln Ala Val Lys Val Phe Leu Glu
65                  70                  75                  80

Ser Gln Gly Ile Ala Tyr Ser Ile Met Ile Glu Asp Val Gln Val Leu
                85                  90                  95

Leu Asp Lys Glu Asn Glu Glu Met Leu Phe Asn Arg Arg Arg Glu Arg
            100                 105                 110

Ser Gly Asn Phe Asn Phe Gly Ala Tyr His Thr Leu Glu Glu Ile Ser
        115                 120                 125

Gln Glu Met Asp Asn Leu Val Ala Glu His Pro Gly Leu Val Ser Lys
    130                 135                 140

Val Asn Ile Gly Ser Ser Phe Glu Asn Arg Pro Met Asn Val Leu Lys
145                 150                 155                 160

Phe Ser Thr Gly Gly Asp Lys Pro Ala Ile Trp Leu Asp Ala Gly Ile
                165                 170                 175

His Ala Arg Glu Trp Val Thr Gln Ala Thr Ala Leu Trp Thr Ala Asn
            180                 185                 190

Lys Ile Val Ser Asp Tyr Gly Lys Asp Pro Ser Ile Thr Ser Ile Leu
        195                 200                 205

Asp Ala Leu Asp Ile Phe Leu Leu Pro Val Thr Asn Pro Asp Gly Tyr
    210                 215                 220

Val Phe Ser Gln Thr Lys Asn Arg Met Trp Arg Lys Thr Arg Ser Lys
225                 230                 235                 240

Val Ser Gly Ser Leu Cys Val Gly Val Asp Pro Asn Arg Asn Trp Asp
                245                 250                 255

Ala Gly Phe Gly Gly Pro Gly Ala Ser Ser Asn Pro Cys Ser Asp Ser
            260                 265                 270

Tyr His Gly Pro Ser Ala Asn Ser Glu Val Glu Val Lys Ser Ile Val
        275                 280                 285
```

```
Asp Phe Ile Lys Ser His Gly Lys Val Lys Ala Phe Ile Thr Leu His
    290                 295                 300

Ser Tyr Ser Gln Leu Leu Met Phe Pro Tyr Gly Tyr Lys Cys Thr Lys
305                 310                 315                 320

Leu Asp Asp Phe Asp Glu Leu Ser Glu Val Ala Gln Lys Ala Ala Gln
                325                 330                 335

Ser Leu Arg Ser Leu His Gly Thr Lys Tyr Lys Val Gly Pro Ile Cys
            340                 345                 350

Ser Val Ile Tyr Gln Ala Ser Gly Ser Ile Asp Trp Ser Tyr Asp
        355                 360                 365

Tyr Gly Ile Lys Tyr Ser Phe Gly Phe Glu Leu Arg Asp Thr Gly Arg
    370                 375                 380

Tyr Gly Phe Leu Leu Pro Ala Arg Gln Ile Leu Pro Thr Ala Glu Glu
385                 390                 395                 400

Thr Trp Leu Gly Leu Lys Ala Ile Met Glu His Val Arg Asp His Pro
                405                 410                 415

Tyr

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: primer
      sequence

<400> SEQUENCE: 19
gcagaagctt cagaaacgtt tgtgggagat caagttcttg agattgtacc          50

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 20
ctctttgtcc aacaggacct g                                         21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 21
tcctccactg ccttggtaga t                                         21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 22
cagttcaaag ccaaatgagt a                                         21
```